United States Patent
Davidson et al.

(10) Patent No.: US 8,148,531 B2
(45) Date of Patent: Apr. 3, 2012

(54) QUINOLINE AND QUINOXALINE DERIVATIVES AS INHIBITORS OF KINASE ENZYMATIC ACTIVITY

(75) Inventors: Alan Hornsby Davidson, Abingdon (GB); Stephen John Davies, Abingdon (GB); David Festus Charles Moffat, Abingdon (GB)

(73) Assignee: Chroma Therapeutics Ltd. (GB)

( * ) Notice: Subject to any disclaimer, the term of this patent is extended or adjusted under 35 U.S.C. 154(b) by 1047 days.

(21) Appl. No.: 11/918,898

(22) PCT Filed: May 4, 2006

(86) PCT No.: PCT/GB2006/001609
§ 371 (c)(1),
(2), (4) Date: Oct. 19, 2007

(87) PCT Pub. No.: WO2006/117552
PCT Pub. Date: Nov. 9, 2006

(65) Prior Publication Data
US 2009/0131461 A1    May 21, 2009

(30) Foreign Application Priority Data
May 5, 2005    (GB) .................................... 0509227.5

(51) Int. Cl.
C07D 215/00    (2006.01)
(52) U.S. Cl. ........................................ 546/153
(58) Field of Classification Search ............ 546/153
See application file for complete search history.

(56) References Cited

U.S. PATENT DOCUMENTS

| | | | |
|---|---|---|---|
| 6,143,764 A | 11/2000 | Kubo et al. | |
| 6,448,256 B1 | 9/2002 | Wright et al. | |
| 7,732,613 B2 * | 6/2010 | Kim .............................. | 546/159 |

FOREIGN PATENT DOCUMENTS

| | | | |
|---|---|---|---|
| WO | WO 02/00649 A | 1/2002 | |
| WO | WO 2004/105765 A | 12/2004 | |
| WO | WO 2005/030757 A | 4/2005 | |
| WO | WO 2005/097134 | * 10/2005 | |

OTHER PUBLICATIONS

West, Solid State Chemistry and Its Applications, John Wiley & Sons, 1984.*
Wolff, Burger's medicinal Chemistry and Drug Discovery, vol. 1, Principles and Practice, John Wiley & sons, New York, 1997.*
Waterbeemd et al, "Property—Based Design: Optimization of Drug Absorption and Pharmacokinetics", Journal of Medicinal Chemistry, 2001, vol. 44, No. 9, pp. 1313-1333.

* cited by examiner

*Primary Examiner* — Nizal Chandrakumar
(74) *Attorney, Agent, or Firm* — Banner & Witcoff, Ltd.

(57) ABSTRACT

Compounds of formula (IA) or (IB), are inhibitors of aurora kinase activity: Formula (IA), (IB) wherein -L1Y1-[CH2]z- is a linker radical wherein $Y^1$, $L^1$ and z are as defined in the claims; $R_6$ is $C_1$-$C_4$alkoxy, hydrogen or halo; W represents a bond, $-CH_2-$, $-O-$, $-S-$, $-S(=O)_2-$, or $-NR_5-$ where $R_5$ is hydrogen or $C_1$-$C_4$ alkyl; Q is $=N-$, $=CH-$ or $=C(X^1)-$ wherein $X^1$ is cyano, cyclopropyl or halo; linker radicals $L^2$ are as defined in the claims; R is a radical of formula (X) or (Y): wherein $R_1$ is a carboxylic acid group ($-COOH$), or an ester group which is hydrolysable by one or more intracellular carboxylesterase enzymes to a carboxylic acid group; $R_4$ is hydrogen; or optionally substituted $C_1$-$C_6$ alkyl, $C_3$-$C_7$ cycloalkyl, aryl, aryl($C_1$-$C_6$ alkyl)-, heteroaryl, heteroaryl($C_1$-$C_6$ alkyl)-, $-(C=O)R_3$, $-(C=O)OR_3$, or $-(C=O)NR_3$ wherein $R_3$ is hydrogen or optionally substituted ($C_1$-$C_6$)alkyl, $C_3$-$C_7$ cycloalkyl, aryl, aryl($C_1$-$C_6$ alkyl)-, heteroaryl, or heteroaryl($C_1$-$C_6$ alkyl)-; $R_4^1$ is hydrogen or optionally substituted $C_1$-$C_6$ alkyl; and D is a monocyclic heterocyclic ring of 5 or 6 ring atoms.

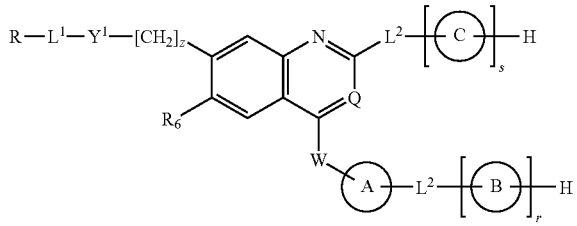

(IA)

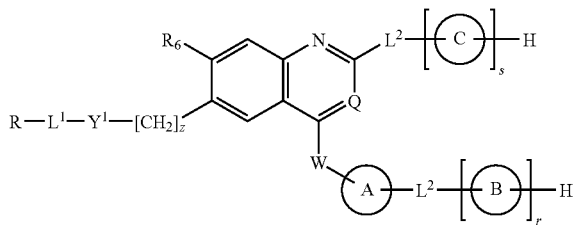

(IB)

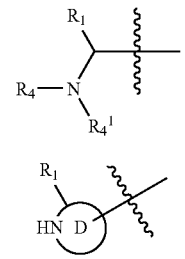

(X)

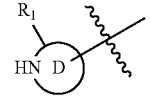

(Y)

21 Claims, No Drawings

QUINOLINE AND QUINOXALINE DERIVATIVES AS INHIBITORS OF KINASE ENZYMATIC ACTIVITY

CROSS REFERENCE TO RELATED APPLICATIONS

This application is a National Stage application of co-pending PCT application PCT/GB2006/001609 filed May 4, 2006, which claims the benefit of Great Britain application number 0509227.5 filed May 5, 2005. These applications are incorporated herein by reference in their entireties.

This invention relates to compounds which inhibit members of the Aurora Kinase family of enzymes and to their use in the treatment of cell proliferative diseases, including cancer.

BACKGROUND TO THE INVENTION

In eukaryotic cells DNA is packaged with histones, to form chromatin. Approximately 150 base pairs of DNA are wrapped twice around an octamer of histones (two each of histones 2A, 2B, 3 and 4) to form a nucleosome, the basic unit of chromatin. The ordered structure of chromatin needs to be modified in order to allow transcription of the associated genes. Transcriptional regulation is key to differentiation, proliferation and apoptosis, and is, therefore, tightly controlled. Control of the changes in chromatin structure (and hence of transcription) is mediated by covalent modifications to histones, most notably of the N-terminal tails. Covalent modifications (for example methylation, acetylation, phosphorylation and ubiquitination) of the side chains of amino acids are enzymatically mediated (A review of the covalent modifications of histones and their role in transcriptional regulation can be found in Berger SL 2001 Oncogene 20, 3007-3013; See Grunstein, M 1997 Nature 389, 349-352; Wolffe A P 1996 Science 272, 371-372; and Wade P A et al 1997 Trends Biochem Sci 22, 128-132 for reviews of histone acetylation and transcription).

The Aurora kinases are a family of serine/threonine kinases which have been identified as key regulators of the mitotic cell division process (Bischoff and Plowman, 1999 Trends Cell Biol 9, 454-459) which may become deregulated in cancer and other hyperproliferative diseases (Warner et al, 2003, Mol Can Ther 2, 589-595). The three members of this family identified so far are referred to as Aurora-A, Aurora-B and Aurora-C. Higher eukaryotic cells typically express two or more Aurora kinases. It has been shown that inhibition of Aurora B affects several facets of mitosis including histone H3 phosphorylation, chromosome segregation and cytokinesis. Aurora A and C localise to spindle poles with Aurora A being required for bipolar spindle formation in a number of systems (Giet and Prigent, 1999, J. Cell. Sci 11, 3591-3601). They have been identified as homologues of Ip11, a prototypic yeast kinase and the Drosophila aurora kinases. Aurora A and B have been shown to be overexpressed in a number of human cancers and their overexpression in cells in vitro leads to transformation, centrosome abnormalities and aneuploidy (Bischoff et al, 1998, EMBO J. 17, 3052). Cells which overexpress Aurora A have been shown to form tumours in aythymic mice. The observations contained in these manuscripts suggest that increase in Aurora kinase activity may serve to promote tumour development by providing growth advantage or by inducing genetic instability and that Aurora Kinase inhibition should have therapeutic benefit in cancer, and other proliferative diseases.

Aurora Kinase Inhibitors.

The following patent publications relate to Aurora kinase inhibitors and their preparation: WO 02/00649, WO 2004/000833, WO 03/055491, WO 2004/058752, WO 2004/058781, U.S. Pat. No. 6,143,764 and US 2004/0049032. Many of the known inhibitors are quinolines and quinazolines which conform to the general structural template:

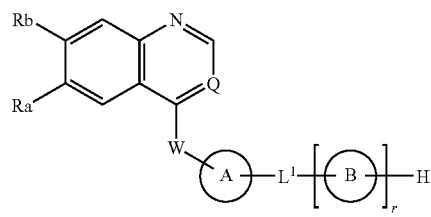

wherein Q is =CH—, =C(CN), =C(Br), =C(cyclopropyl) or =N—, the group Ra is variable but often a small alkoxy group such as methoxy, the group Rb is a solubilising group, W is a hetero radical such as NH or O, A is an aromatic or heteroaromatic ring, L1 is a linker radical, usually containing nitrogen and carbonyl, and ring B is an optional (r=0 or 1) aromatic or heteroaromatic ring. The —W-A-L$^1$-(B)$_r$—H can be thought of as the side chain of the quinoline/quinazoline ring system, and it is the quinoline/quinazoline plus side chain which plays the major role in binding to the Aurora kinase enzyme. The substituent Rb appears to be oriented away from the bound enzyme, and is therefore a suitable location for modification to improve properties such as solubility.

The present invention is based on the finding that certain novel modifications of the substituent in the Rb position (referred to above) of quinoline- and quinazoline-type Aurora kinase inhibitors lead to desirable pharmacokinetic improvements relative to known inhibitors. In particular, it has been found that incorporating an alpha amino acid ester moiety in that substituent facilitates transport into the cell, where the Aurora kinase is of course located. There, the ester is cleaved by intracellular esterases, releasing the parent acid, which is not readily transported out of the cell. The accumulation of the ester and its esterase hydrolysis product within the cell results in concentration of Aurora kinase inhibitory activity where it is needed.

DETAILED DESCRIPTION OF THE INVENTION

According to the present invention there is provided compound of formula (IA) or (IB), or a salt, N-oxide, hydrate or solvate thereof:

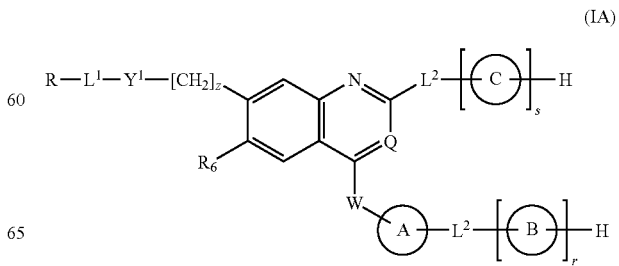

(IA)

-continued (IB)

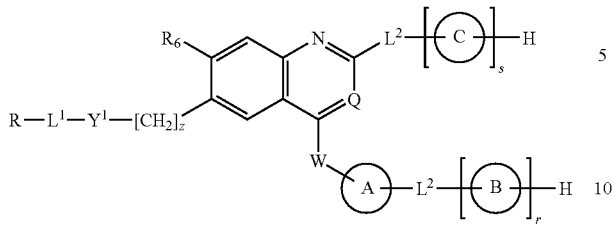

wherein $Y^1$ is a bond, —C(=O)—, —S(=O)$_2$—, —C(=O)O—, —C(=O)NR$_3$—, —C(=S)NR$_3$, —C(=NH)NR$_3$ or —S(=O)$_2$NR$_3$— wherein R$_3$ is hydrogen or optionally substituted C$_1$-C$_6$ alkyl;

$L^1$ is a divalent radical of formula -(Alk$^1$)$_m$(Q$^1$)$_n$(Alk$^2$)$_p$- wherein m, n and p are independently 0 or 1, Q$^1$ is (i) an optionally substituted divalent mono- or bicyclic carbocyclic or heterocyclic radical having 5-13 ring members, or (ii), in the case where p is 0, a divalent radical of formula -Q$^2$-X$^2$— wherein X$^2$ is —O—, —S— or NR$^A$— wherein R$^A$ is hydrogen or optionally substituted C$_1$-C$_3$ alkyl, and Q$^2$ is an optionally substituted divalent mono- or bicyclic carbocyclic or heterocyclic radical having 5-13 ring members, Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;

z is 0 or 1;

R$_6$ is C$_1$-C$_4$ alkoxy, hydrogen or halo;

W represents a bond, —CH$_2$—, —O—, —S—, —S(=O)$_2$—, or —NR$_5$— where R$_5$ is hydrogen or C$_1$-C$_4$ alkyl;

Q is =N—, =CH— or =C(X$^1$)— wherein X$^1$ is cyano, cyclopropyl or halo;

each $L^2$ independently represents a radical of formula -(Alk$^3$)$_a$-Z-(Alk$^4$)$_b$- wherein a and b are independently 0 or 1;

Alk$^3$ and Alk$^4$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;

Z represents a bond or an —O—, —S—, —S(=O)$_2$—, —C(=O)—, —NR$^B$, —CONR$^B$—NR$^B$CO—, —SO$_2$NR$^B$—, NR$^B$SO$_2$—, —NR$^B$CONR$^B$— or —NR$^B$CSNR$^B$— radical, wherein R$^B$ is hydrogen or C$_1$-C$_3$ alkyl;

r and s are independently 0 or 1; and rings A, B and C are mono- or bi-cyclic carbocyclic or heterocyclic rings or ring systems having up to 12 ring atoms;

R is a radical of formula (X) or (Y):

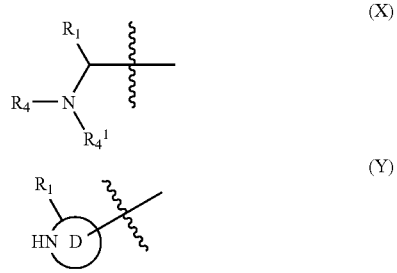

wherein

R$_1$ is a carboxylic acid group (—COOH), or an ester group which is hydrolysable by one or more intracellular carboxylesterase enzymes to a carboxylic acid group;

R$_4$ is hydrogen; or optionally substituted C$_1$-C$_6$ alkyl, C$_3$-C$_7$ cycloalkyl, aryl, aryl(C$_1$-C$_6$ alkyl)-, heteroaryl, heteroaryl (C$_1$-C$_6$ alkyl)-, —(C=O)R$_3$, —(C=O)OR$_3$, or —(C=O)NR$_3$ wherein R$_3$ is hydrogen or optionally substituted (C$_1$-C$_6$)alkyl, C$_3$-C$_7$ cycloalkyl, aryl, aryl(C$_1$-C$_6$ alkyl)-, heteroaryl, or heteroaryl(C$_1$-C$_6$ alkyl)-;

R$_4^1$ is hydrogen or optionally substituted C$_1$-C$_6$ alkyl; and

D is a monocyclic heterocyclic ring of 5 or 6 ring atoms wherein R$_1$ is linked to a ring carbon adjacent the ring nitrogen shown, and ring D is optionally fused to a second carbocyclic or heterocyclic ring of 5 or 6 ring atoms in which case the bond shown intersected by a wavy line may be from a ring atom in said second ring.

Although the above definition potentially includes molecules of high molecular weight, it is preferable, in line with general principles of medicinal chemistry practice, that the compounds with which this invention is concerned should have molecular weights of no more than 600.

In another broad aspect the invention provides the use of a compound of formula (IA) or (IB) as defined above, or an N-oxide, salt, hydrate or solvate thereof in the preparation of a composition for inhibiting the activity of an aurora kinase enzyme, particularly aurora-A.

The compounds with which the invention is concerned may be used for the inhibition of aurora kinase activity, particularly aurora-A activity, ex vivo or in vivo.

In one aspect of the invention, the compounds of the invention may be used in the preparation of a composition for the treatment of cell-proliferation disease, for example cancer cell proliferation and autoimmune diseases.

In another aspect, the invention provides a method for the treatment of the foregoing disease types, which comprises administering to a subject suffering such disease an effective amount of a compound of formula (IA) or (IB) as defined above.

The term "ester" or "esterified carboxyl group" means a group R$_9$O(C=O)— in which R$_9$ is the group characterising the ester, notionally derived from the alcohol R$_9$OH.

As used herein, the term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

As used herein the term "divalent (C$_a$-C$_b$)alkylene radical" wherein a and b are integers refers to a saturated hydrocarbon chain having from a to b carbon atoms and two unsatisfied valences.

As used herein the term "(C$_a$-C$_b$)alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent ($C_a$-$C_b$)alkenylene radical" means a hydrocarbon chain having from a to b carbon atoms, at least one double bond, and two unsatisfied valences.

As used herein the term "$C_a$-$C_b$ alkynyl" wherein a and b are integers refers to straight chain or branched chain hydrocarbon groups having from two to six carbon atoms and having in addition one triple bond. This term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent ($C_a$-$C_b$)alkynylene radical" wherein a and b are integers refers to a divalent hydrocarbon chain having from 2 to 6 carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic or bridged monocyclic saturated carbocyclic radical having from 3-8 carbon atoms and includes, for example, cyclopropyl, cyclobutyl, cyclopentyl, cyclohexyl, cycloheptyl, cyclooctyl and bicyclo[2.2.1]hept-1-yl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with up to four compatible substituents, each of which independently may be, for example, ($C_1$-$C_6$) alkyl, ($C_1$-$C_6$)alkoxy, hydroxy, hydroxy($C_1$-$C_6$)alkyl, mercapto, mercapto($C_1$-$C_6$)alkyl, ($C_1$-$C_6$)alkylthio, phenyl, halo (including fluoro, bromo and chloro), trifluoromethyl, trifluoromethoxy, nitro, nitrile (—CN), oxo, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, NHCOR$^A$, —NHCOOR$^A$, —NRBCOOR$^A$, —NHSO$_2$OR$^A$, —NR$^B$SO$_2$OH, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are independently a ($C_1$-$C_6$)alkyl, ($C_3$-$C_6$) cycloalkyl, phenyl or monocyclic heteroaryl having 5 or 6 ring atoms. An "optional substituent" may be one of the foregoing substituent groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like.

Compounds of the invention which contain one or more actual or potential chiral centres, because of the presence of asymmetric carbon atoms, can exist as enantiomers or as a number of diastereoisomers with R or S stereochemistry at each chiral centre. The invention includes all such enantiomers and diastereoisomers and mixtures thereof.

The esters of the invention are converted by intracellular esterases to the carboxylic acid. Both the esters and carboxylic acids may have aurora kinase inhibitory activity in their own right. The compounds of the invention therefore include not only the ester, but also the corresponding carboxylic acid hydrolysis products.

In the compounds with which the invention is concerned:

Regioisomers (IA) and (IB)

Compounds of formulae (IA) and (IB) are regioisomers. Presently the regioisomer class (IA) is preferred.

The Ester Group $R_1$, in the Radical R

The ester group $R_1$ must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will, subject to the N-carbonyl dependence of hCE-2 and hCE-3 discussed above, also hydrolyse the ester motif when covalently conjugated to the modulator. Hence, the broken cell assay described herein provide a straightforward, quick and simple first screen for esters which have the required hydrolysis profile. Ester motifs selected in that way may then be reassayed in the same carboxylesterase assay when conjugated to the aurora kinase inhibitor via the chosen conjugation chemistry, to confirm that it is still a carboxylesterase substrate in that background.

Subject to the requirement that they be hydroysable by intracellular carboxylesterase enzymes, examples of particular ester groups $R_1$ include those of formula —(C=O)OR$_9$ wherein R$_9$ is (i) R$_7$R$_8$CH— wherein R$_7$ is optionally substituted (C$_1$-C$_3$)alkyl-(Z$^1$)$_a$-(C$_1$-C$_3$)alkyl- or (C$_2$-C$_3$)alkenyl-(Z$^1$)$_a$-(C$_1$-C$_3$)alkyl- wherein a is 0 or 1 and Z$^1$ is —O—, —S—, or —NH—, and R$_8$ is hydrogen or (C$_1$-C$_3$)alkyl- or R$_7$ and R$_8$ taken together with the carbon to which they are attached form an optionally substituted C$_3$-C$_7$ cycloalkyl ring or an optionally substituted heterocyclic ring of 5- or 6-ring atoms; or (ii) optionally substituted phenyl or monocyclic heterocyclic having 5 or 6 ring atoms. Within these classes, R$_9$ may be, for example, methyl, ethyl, n- or iso-propyl, n- or sec-butyl, cyclohexyl, allyl, phenyl, benzyl, 2-, 3- or 4-pyridylmethyl, N-methylpiperidin-4-yl, tetrahydrofuran-3-yl or methoxyethyl. Currently preferred is where R$_9$ is cyclopentyl.

Macrophages are known to play a key role in inflammatory disorders through the release of cytokines in particular TNFα and IL-1 (van Roon et al Arthritis and Rheumatism, 2003, 1229-1238). In rheumatoid arthritis they are major contributors to the maintenance of joint inflammation and joint destruction. Macrophages are also involved in tumour growth and development (Naldini and in Carraro Curr Drug Targets Inflamm Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting aurora kinase inhibitors to macrophages which is based on the observation that the way in which the esterase motif is linked to the inhibitor determines whether it is hydrolysed, and hence whether or not it accumulates in different cell types. Specifically it has been found that macrophages contain the human carboxylesterase hCE-1 whereas other cell types do not. In the general formula (I) when the nitrogen of the esterase motif is substituted but not directly bonded to a carbonyl group the ester will only be hydrolysed by hCE-1 and hence the inhibitors will only accumulate in macrophages.

The Amino or Substituted Amino Group R$_4$, in the Radical R

The group R$_4$ is present in the compounds of the invention when R in formula (IA) or (IB) is a radical of formula (X)

As mentioned above, if the modulator is intended to act only in cell types where hCE-1 is present and not hCE-2 or hCE-3, such as macrophages, the amino group of the carboxylesterase motif should be directly linked to a group other than carbonyl. In such cases R$_4$ may be, inter alia, optionally substituted C$_1$-C$_6$ alkyl, C$_3$-C$_7$ cycloalkyl, aryl or heteroaryl, for example methyl, ethyl, n- or isopropyl, cyclopropyl, cyclopentyl, cyclohexyl, phenyl, or pyridyl. In cases where macrophage specificity is not required, R$_4$ may be, for example, optionally substituted C$_1$-C$_6$ alkyl such as methyl, ethyl, n- or isopropyl, or n-, iso- or sec-butyl, C$_3$-C$_7$ cycloalkyl such as cyclopropyl, cyclopentyl, cyclohexyl, phenyl, pyridyl, thienyl, phenyl(C$_1$-C$_6$ alkyl)-, thienyl(C$_1$-C$_6$ alkyl)- or pyridyl(C$_1$-C$_6$ alkyl)- such as benzyl, thienylmethyl or pyridylmethyl; or —(C═O)R$_3$, wherein R$_3$ is optionally substituted C$_1$-C$_6$ alkyl such as methyl, ethyl, n- or isopropyl, or n-, iso- or sec-butyl, C$_3$-C$_7$ cycloalkyl such as cyclopropyl, cyclopentyl, cyclohexyl, phenyl, pyridyl, thienyl, phenyl(C$_1$-C$_6$ alkyl)-, thienyl(C$_1$-C$_6$ alkyl)- or pyridyl(C$_1$-C$_6$ alkyl)- such as benzyl, 4-methoxyphenylmethylcarbonyl, thienylmethyl or pyridylmethyl.

R$_4$ may also be, for example —(C═O)OR$_3$, or —(C═O)NHR$_3$ wherein R$_3$ is hydrogen or optionally substituted (C$_1$-C$_6$)alkyl such as methyl, ethyl, or n-or isopropyl.

R$_4^1$ may be, for example, methyl, ethyl, n-or isopropyl, but hydrogen is presently preferred.

Of course, R$_4$ and R$_4^1$ may independently be hydrogen, and in one subset of the compounds of the invention both are hydrogen.

For compounds of the invention which are to be administered systemically, esters with a slow rate of esterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. If a carbon atom to which the group R is attached is unsubstituted, ie R is attached to a methylene (—CH$_2$)— radical, then the esters tend to be cleaved more rapidly than if that carbon is substituted, or is part of a ring system such as a phenyl or cyclohexyl ring.

The Ring or Ring System D

Ring or ring system D is present in the compounds of the invention when R is a radical of formula (Y) above In such cases, the ring or ring system D is preferably one chosen from the following:

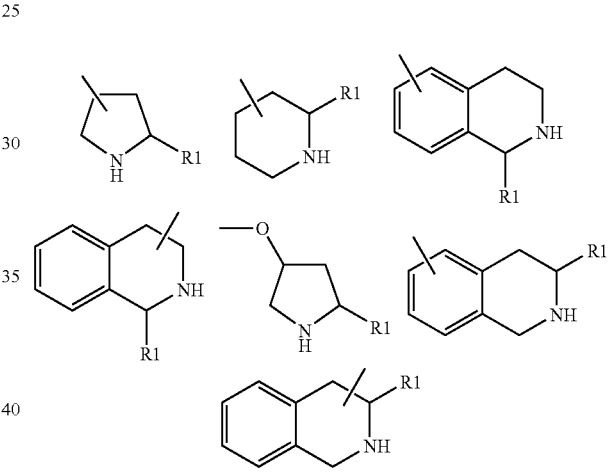

The radical -L$^1$-Y$^1$—[CH$_2$]$_z$—

This radical (or bond) arises from the particular chemistry strategy chosen to link the amino acid ester motif R to the rest of the molecule. Clearly the chemistry strategy for that coupling may vary widely, and thus many combinations of the variables Y$^1$, L$^1$, and z are possible. Hence the precise combination of variable making up the linking chemistry between the amino acid ester motif and the rest of the molecule will often be irrelevant to the primary binding mode of the compound as a whole. On the other hand, that linkage chemistry may in some cases pick up additional binding interactions with the enzyme at the top of, or adjacent to, the metal ion-containing pocket, thereby enhancing binding.

With the foregoing general observations in mind, taking the variables making up the radical -L$^1$-Y$^1$—[CH$_2$]$_z$— in turn:

z may be 0 or 1, so that a methylene radical linked to the rest of the molecule is optional; However, in a preferred subclass of compounds of the invention z is 0.

Y$^1$ may be, for example, —NR$_3$—, —S—, —O—, —C(═O)NR$_3$—, —NR$_3$C(═O)—, or —C(═O)O—, wherein R$_3$ is hydrogen or optionally substituted C$_1$-C$_6$ alkyl such as —CH$_2$CH$_2$OH; In a preferred subclass of compounds of the invention, $Y^1$ os —O—, especially when z is 0;

In another subclass of compounds of the invention $Y^1$ is a bond.

In the radical $L^1$, examples of $Alk^1$ and $Alk^2$ radicals, when present, include —$CH_2$—, —$CH_2CH_2$—, —$CH_2CH_2CH_2$—, —$CH_2CH_2CH_2CH_2$—, —CH=CH—, —CH=CHCH$_2$—, —$CH_2$CH=CH—, $CH_2$CH=CHCH$_2$—, —C≡C—, —C≡CCH$_2$—, $CH_2$C≡C—, and $CH_2$C≡CCH$_2$. Additional examples of $Alk^1$ and $Alk^2$ include —$CH_2$W—, —$CH_2CH_2$W— —$CH_2CH_2$WCH$_2$—, —$CH_2CH_2$WCH(CH$_3$)—, —$CH_2$WCH$_2CH_2$—, —$CH_2$WCH$_2CH_2$WCH$_2$—, and —WCH$_2CH_2$— where W is —O—, —S—, —NH—, —N(CH$_3$)—, or —$CH_2CH_2$N(CH$_2CH_2$OH)CH$_2$—. Further examples of $Alk^1$ and $Alk^2$ include divalent cyclopropyl, cyclopentyl and cyclohexyl radicals. At present it is preferred that $Alk^1$ and $Alk^2$ radicals, when present, are selected from —$CH_2$—, —$CH_2CH_2$—, —$CH_2CH_2CH_2$—, and divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclic radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention, $L^1$, m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from —$CH_2$—, —$CH_2CH_2$—, and —$CH_2CH_2CH_2$— and Q may be 1,4-phenylene.

Examples of the radical -$L^1$-$Y^1$—[CH$_2$]$_z$— include —(CH$_2$)$_3$NH—, —$CH_2$C(=O)NH—, —$CH_2CH_2$C(=O)NH—, —$CH_2$C(O)O—, —$CH_2$S—, —$CH_2CH_2$C(O)O—, —(CH$_2$)$_4$NH—, —$CH_2CH_2$S—, —$CH_2$O, —$CH_2CH_2$O—, —$CH_2CH_2CH_2$O—

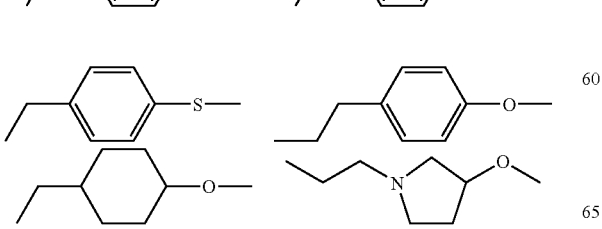

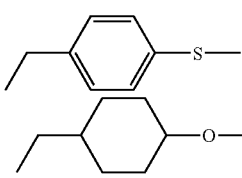

The Group $R_6$ $R_6$ is hydrogen; halogen, for example fluoro or chloro; or $C_1$-$C_4$ alkoxy for example methoxy, ethoxy or n- or iso-propoxy. Presently it is preferred that it be methoxy.

The Radical W

When W is —NR$_5$—, $R_5$ may be hydrogen (currently preferred) or $C_1$-$C_4$ alkyl, for example methyl, ethyl or n- or iso-propyl. Of all the permitted options for the hetero radical W, —O— or —NH— is currently preferred.

The Ring A

Ring A may be, for example a piperidine, piperazine, pyridine, pyrimidine, pyrazoline, triazoline, furan, thophene, pyrrole, thiazole, isothiazole, oxazole, isoxazole, or thiadiazole ring. Examples of rings A include those of formulae A-V below. Currently preferred rings A are 1,4-phenylene, 1,3-phenylene and 5-membered heterocycles such as A-K and 9-membered heterocycles such as M-O:

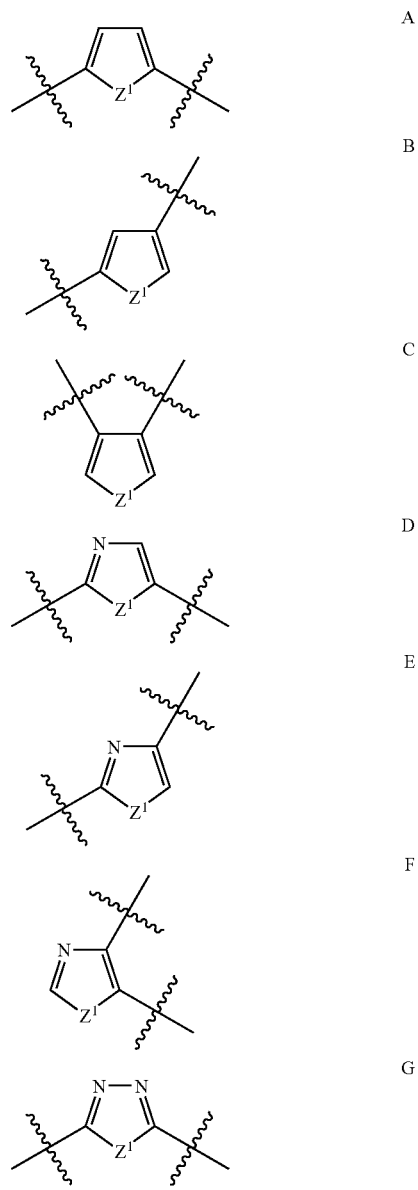

H 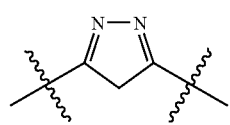

I 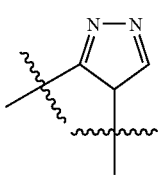

K

L 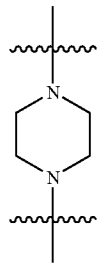

M 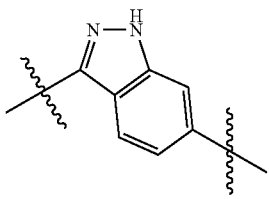

N 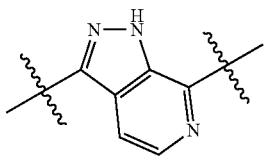

O 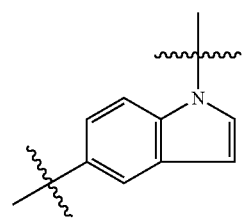

P 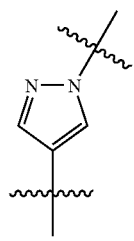

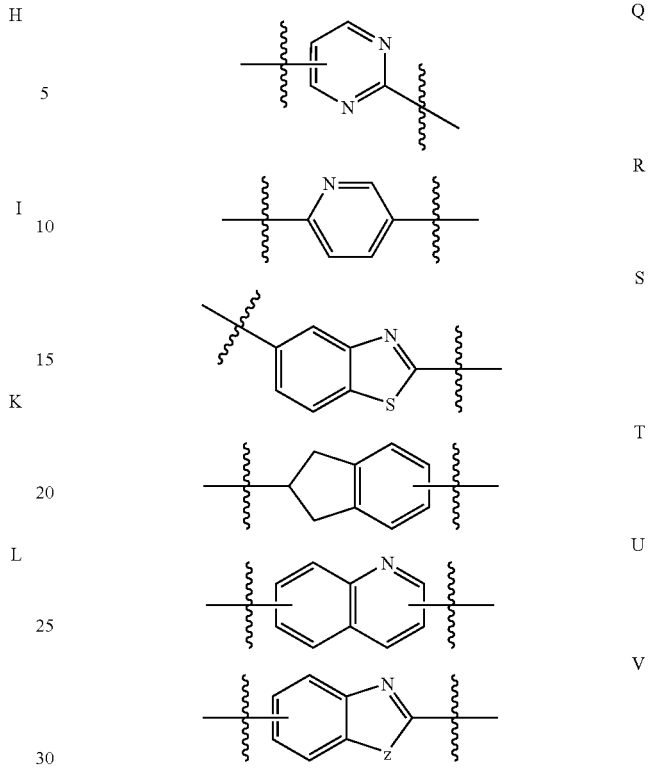

wherein $Z^1$ is NH, S or O, especially NH or S. Any of these rings A may contain optional substitutents such as, halo, nitrile, trifluoromethyl, $C_1$-$C_6$ alkoxy such as methoxy and ethoxy, $C_1$-$C_6$ alkyl such as methyl, ethyl and n- and isopropyl, although presently it is preferred that ring A be unsubstituted (except for the radicals -$L^2$[B]r and -$L^2$[C]$_r$, if present).

The Rings B and C

Rings B and C may be present in the compounds (IA) and (IB), or absent, according to whether the integers r and s are 1 or 0. In a preferred subclass of compounds of the invention s is 0.

When present, ring B (and ring C when present) may be any of the ring options discussed above in relation to ring A, for example optionally substituted phenyl, and can also be optionally substituted pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,3,4-triazolyl, 1,2,5-triazolyl, 1,2,3-oxadiazolyl, 1,2,4-oxadiazolyl, 1,2,5-oxadiazolyl, 1,3,4-oxadiazolyl, 1,3,4-thiadiazole, 2-, 3-, or 4-pyridyl, pyrimidinyl, pyridazinyl, pyrazinyl, 1,3,5-triazinyl, 1,2,4-triazinyl, 1,2,3-triazinyl, benzofuryl, [2,3-dihydro]benzofuryl, isobenzofuryl, benzothienyl, benzotriazolyl, isobenzothienyl, indanyl, indolyl, isoindolyl, 3H-indolyl, benzimidazolyl, indazolyl, imidazo[1,2-a]pyridyl, benzothiazolyl, benzoxazolyl, quinolizinyl, quinazolinyl, phthalazinyl, quinoxalinyl, cinnolinyl, naphthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl, and cycloalkyl rings such as cyclopropyl, cyclopentyl, and cyclohexyl. Preferred rings B are: 1,4-phenylene, 1,3-phenylene, pyridyl, pyrimidinyl and pyrazinyl. Substituents which may be present in rings B and C include halo such as fluoro and chloro, nitrile, trifluoromethyl, trifluoromethoxy, $C_1$-$C_6$ alkoxy such as methoxy and ethoxy, $C_1$-$C_6$ alkyl such as methyl, ethyl and n- and isopropyl, and phenyl, although presently it is preferred that rings B and C be unsubstituted.

The Linker Radical $L^2$

In the linker radical $L^2$ represents a radical of formula -(Alk$^3$)$_a$-Z-(Alk$^4$)$_b$- wherein Alk$^3$ and Alk$^4$ when present represent optionally substituted, straight or branched, $C_1$-$C_3$ alkylene, $C_2$-$C_3$ alkenylene or $C_2$-$C_3$ alkynylene radicals. Presently methylene (—CH$_2$—) is preferred for Alk$^3$, when present, and for Alk$^4$, when present. However, both a and b may be 0, so that both Alk$^3$ and Alk$^4$ are absent, or a may be 1 and b may be 0 so that only Alk$^3$ is present, or a may be 0 and b may be 1 so that only Alk$^4$ is present.

In the linker radical $L^2$, Z preferably represents an amido (—CONH—) link, in either orientation, or a ureido (—NHCONH—) link.

The Ring Atom Q

Although Q may be =N—, =CH— or =C(CN)—, =CH— is presently preferred.

A particular subclass of compounds of the invention has the formula (IC):

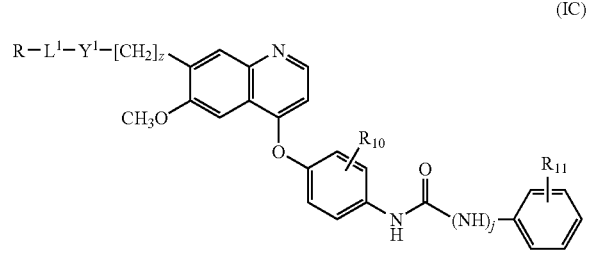

(IC)

wherein j is 0 or 1; $R_{10}$ and $R_{11}$ independently represent hydrogen or one or more substituents in their respective rings selected from fluoro, chloro, methyl, methoxy trifluoromethyl and trifluoromethoxy; and R, $L^1$, $Y^1$ and z are as defined and discussed above.

Another subclass of compounds of the invention has the formula (ID):

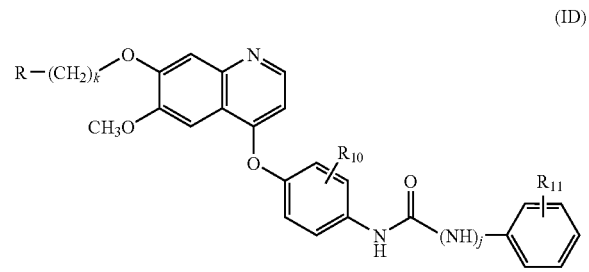

(ID)

wherein j is 0 or 1; $R_{10}$ and $R_{11}$ independently represent hydrogen or one or more substituents in their respective rings selected from fluoro, chloro, methyl, methoxy trifluoromethyl and trifluoromethoxy; k is 1, 2 or 3; and R is as defined and discussed above.

A narrow subclass of compounds of the invention has the formula (IE):

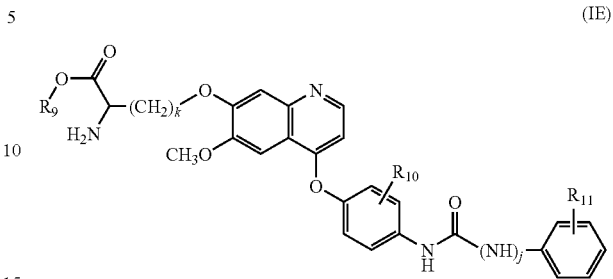

(IE)

wherein j is 0 or 1; $R_{10}$ and $R_{11}$ independently represent hydrogen or one or more substituents in their respective rings selected from fluoro, chloro, methyl, methoxy trifluoromethyl and trifluoromethoxy; k is 1, 2 or 3; and $R_9$ is (i) $R_7R_8$CH— wherein $R_7$ is optionally substituted ($C_1$-$C_3$) alkyl-($Z^1$)$_a$-($C_1$-$C_3$)alkyl- or ($C_2$-$C_3$)alkenyl-($Z^1$)$_a$-($C_1$-$C_3$)alkyl- wherein a is 0 or 1 and $Z^1$ is —O—, —S—, or —NH—, and $R_8$ is hydrogen or ($C_1$-$C_3$)alkyl- or $R_7$ and $R_8$ taken together with the carbon to which they are attached form an optionally substituted $C_3$-$C_7$ cycloalkyl ring or an optionally substituted heterocyclic ring of 5- or 6-ring atoms; or (ii) Optionally substituted phenyl or monocyclic heterocyclic having 5 or 6 ring atoms, In compounds (1E) it is currently preferred that $R_9$ be cyclopentyl, but other examples include methyl, ethyl, n- or iso-propyl, n- or sec-butyl, t-butyl, cyclohexyl, allyl, phenyl, benzyl, 2-, 3- or 4-pyridylmethyl, N-methylpiperidin-4-yl, tetrahydrofuran-3-yl or methoxyethyl.

Specific examples of compounds of the invention include those of the examples herein. They include:
(S)-2-Amino-4-[4-(4-benzoylamino-phenoxy)-6-methoxy-quinolin-7-yloxy]-butyric acid cyclopentyl ester
(R)-2-Amino-5-(6-methoxy-4-{4-[3-(4-trifluoromethyl-phenyl)-ureido]-phenoxy}-quinolin-7-yloxy)-pentanoic acid cyclopentyl ester
(R)-2-Amino-5-[4-(4-benzoylamino-phenoxy)-6-methoxy-quinolin-7-yloxy]-pentanoic acid cyclopentyl ester
(S)-2-Amino-4-{6-methoxy-4-[4-(3-phenyl-ureido)-phenoxy]-quinolin-7-yloxy}-butyric acid cyclopentyl ester
(R)-2-Amino-4-[4-(4-benzoylamino-phenoxy)-6-methoxy-quinolin-7-yloxy]-butyric acid cyclopentyl ester
(S)-2-Amino-4-(4-{2-fluoro-4-[3-(4-trifluoromethyl-phenyl)-ureido]-phenoxy}-6-methoxy-quinolin-7-yloxy)-butyric acid cyclopentyl ester
(R)-2-Amino-4-(6-methoxy-4-{4-[3-(4-trifluoromethyl-phenyl)-ureido]-phenoxy}-quinolin-7-yloxy)-butyric acid cyclopentyl ester
(S)-2-Amino-5-[4-(4-benzoylamino-phenoxy)-6-methoxy-quinolin-7-yloxy]-pentanoic acid cyclopentyl ester
(S)-2-Amino-4-{4-[4-(4-chloro-benzoylamino)-phenoxy]-6-methoxy-quinolin-7-yloxy}-butyric acid cyclopentyl ester
(R)-2-Amino-5-(6-methoxy-4-{4-[3-(4-trifluoromethyl-phenyl)-ureido]-phenylsulfanyl}-quinolin-7-yloxy)-pentanoic acid cyclopentyl ester Synthesis There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "*Advanced organic chemistry*", 4*th* Edition (Wiley), J March, "*Comprehensive Organic Transformation*", 2*nd* Edition (Wiley), R. C. Larock, "*Handbook of Heterocyclic Chemistry*", 2*nd* Edition (Pergamon), A. R. Katritzky), review articles such as found in "*Synthesis*", "*Acc. Chem. Res.*", "*Chem. Rev*", or primary literature sources identified by standard literature searches online or from secondary sources such as "*Chemical Abstracts*" or "*Beilstein*".

The routes to compounds of the invention described in the Examples below are typical of those derived from known chemistry as described in the literature. Those reoutes may be adapted for the preparation of other compounds of the invention.

In general, the compounds of the invention may be synthesised by reaction of a compound R-L-J$^2$ with a compound (IIIA) or (IIIB)

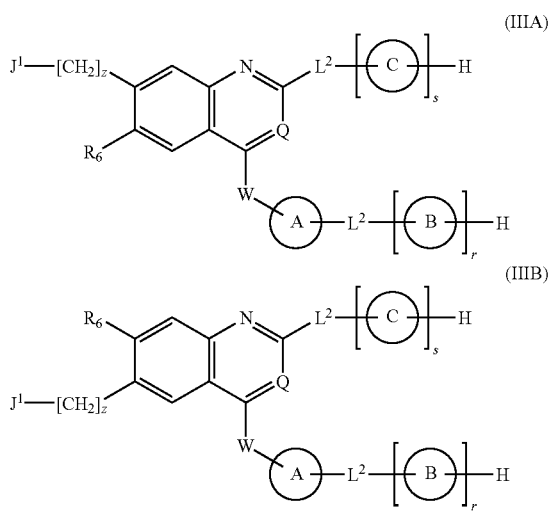

wherein J$^1$ and J$^2$ are mutually reactive to form the radical Y$^1$, or the desired compound where Y$^1$ is a bond and L$^1$ terminates in an ether or amino link. For example when J$^2$ is an acid chloride and J$^1$ is amino, amide formation results in the desired compound wherein Y$^1$ is —CONH$_2$—. Likewise when J$^2$ is an acid chloride and J$^1$ is hydroxy, ester formation results in the desired compound wherein Y$^1$ is —COO—. Similarly, when L$^1$ is alkyl and J$^1$ are J$^2$ both hydroxy, a condensation reaction results in the desired compound (IA) or (IB) wherein -L-Y$^1$—[CH$_2$]$_z$— is -Alk-O—[CH$_2$]$_z$—.

As mentioned above, the compounds with which the invention is concerned are inhibitors of the Aurora kinase family, namely Aurora kinases A and/or B and/or C, and are therefore of use in the treatment of cell proliferative disease, such as cancer, and in treatment of inflammation, in humans and other mammals.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

The following Examples illustrate the invention:
Abbreviations
The following Examples illustrate the invention:
Abbreviations
MeOH=methanol
EtOH=ethanol
EtOAc=ethyl acetate
Boc=tert-butoxycarbonyl
DCM=dichloromethane
DMF=dimethylformamide
DMSO=dimethyl sulfoxide
DMAP=dimethylamino pyridine
TFA=trifluoroacetic acid
THF=tetrahydrofuran
$Na_2CO_3$=sodium carbonate
HCl=hydrochloric acid
DIPEA=diisopropylethylamine
NaH=sodium hydride
NaOH=sodium hydroxide
$NaHCO_3$=sodium hydrogen carbonate
HCl=hydrochloric acid
Pd/C=palladium on carbon
EDC=1-ethyl-3-(3-dimethylaminopropyl)carbodiimide
ml=milliliter
g=gram(s)
mg=milligram(s)
mol=moles
mmol=millimole(s)
Sat=saturated LC/MS=high performance liquid chromatography/mass spectrometry
NMR=nuclear magnetic resonance Commercially available reagents and solvents (HPLC grade) were used without further purification. Solvents were removed using a Buchi rotary evaporator. Purification of compounds by flash chromatography column was performed using silica gel, particle size 40-63 μm (230-400 mesh) obtained from Silicycle. Purification of compounds by preparative HPLC was performed on Gilson systems using reverse phase ThermoHypersil-Keystone Hyperprep HS C18 columns (12 μm, 100×21.2 mm), gradient 20-100% B (A=water/0.1% TFA, B=acetonitrile/0.1% TFA) over 9.5 min, flow=30 ml/min, injection solvent 2:1 DMSO:acetonitrile (1.6 ml), UV detection at 215 nm.

$^1$H NMR spectra were recorded on a Bruker 300 MHz AV spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLC/MS was performed on an Agilent HP1100 LC system using reverse phase Hypersil BDS C18 columns (5 μm, 2.1×50 mm), gradient 0-95% B (A=water/0.1% TFA, B=acetonitrile/0.1% TFA) over 2.10 min, flow=1.0 ml/min. UV spectra were recorded at 215 nm using a G1214A single wavelength UV detector. Mass spectra were obtained over the range m/z 150 to 850 at a sampling rate of 2 scans per second or 1 scan per 1.2 seconds using LC/MSD Quad SW ESI interface. Data were integrated and reported using OpenLynx and OpenLynx Browser software.

The following Examples illustrate the preparation of specific compounds of the invention, and the Aurora Kinase inhibitory properties thereof:

In Scheme 1 below, the 4-chloroquinoline derivative (A) can be synthesized by methods described in Org. Synth. Col. Vol. 3, 272 (1955) and US006143764A (Kirin Beer Kabushiki Kaisha).

Scheme 1

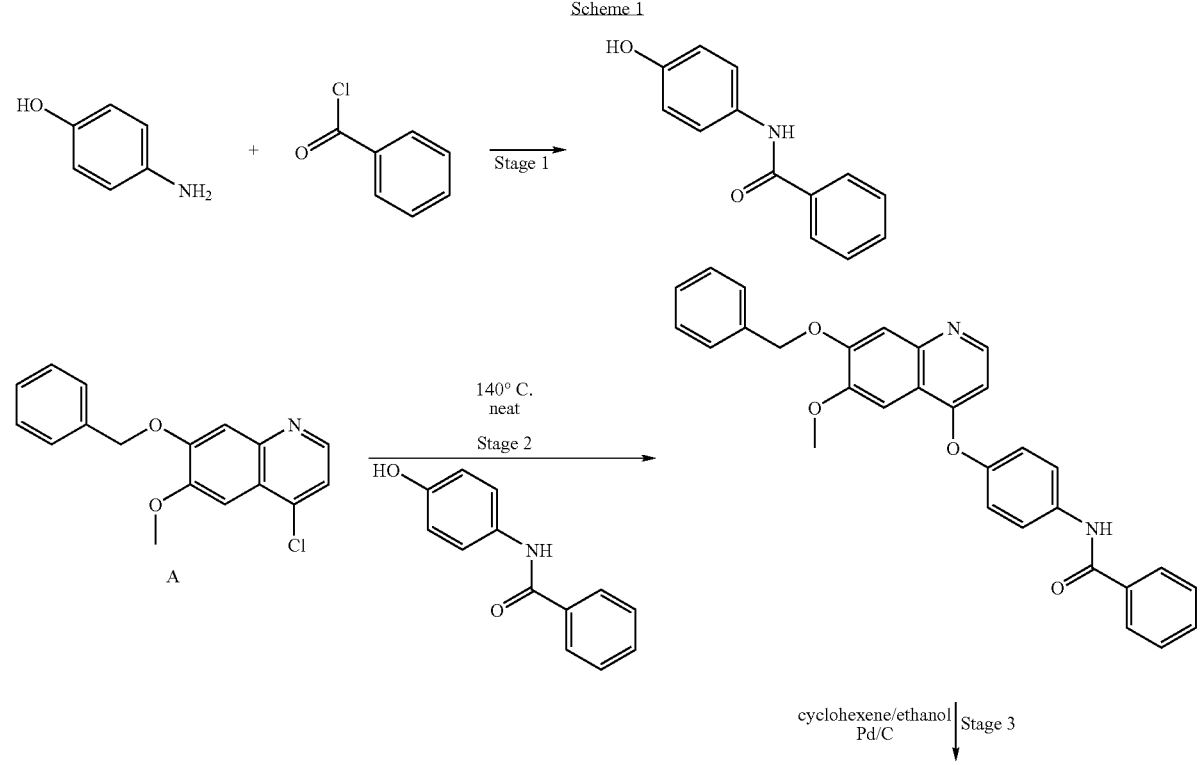

-continued
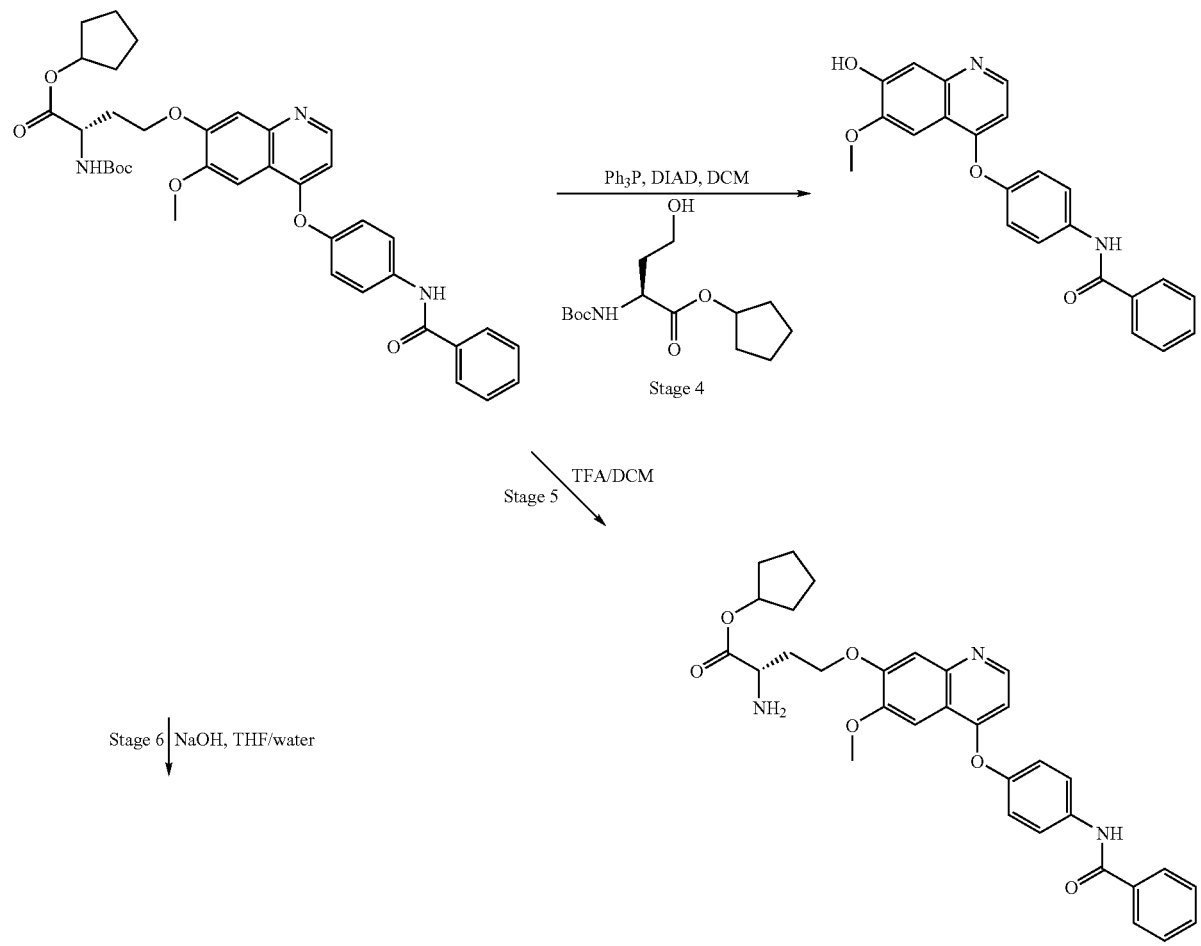
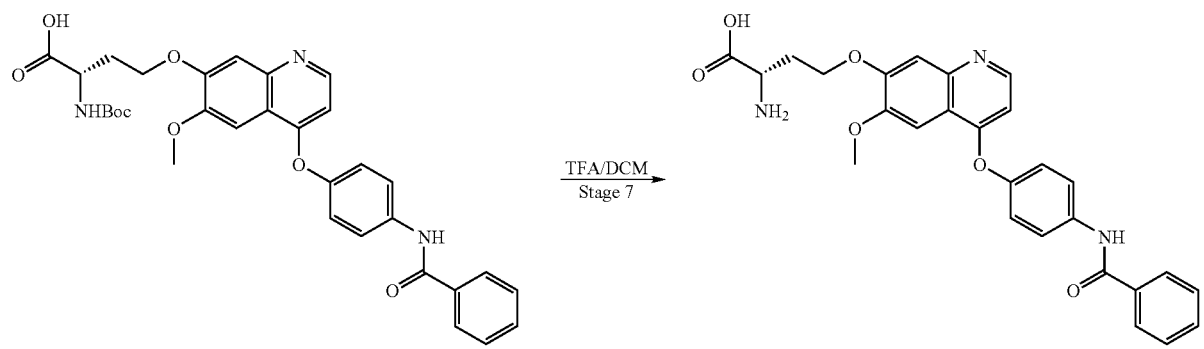

EXAMPLE 1

(S)-4-[4-(4-Benzoylamino-phenoxy)-6-methoxy-quinolin-7-yloxy]-2-tert-butoxycarbonylamino-butyric acid cyclopentyl ester

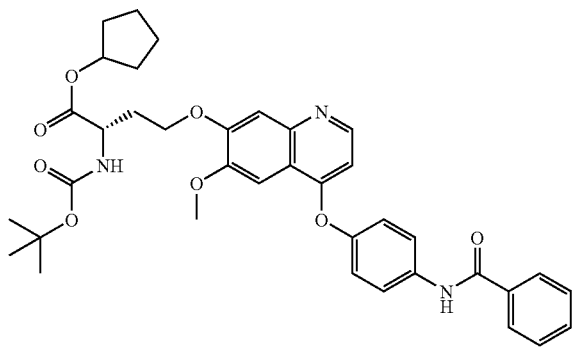

LC/MS purity: 99%, m/z 656 [M+H]⁺. ¹H NMR (300 MHz, DMSO-d$_6$), δ: 10.4 (1H, s), 8.5 (1H, d, J=7.8 Hz), 8.0 (4H, m), 7.6 (4H, m), 7.35 (4H, m), 6.45 (1H, d, J=7.5 Hz), 5.1 (1H, m), 4.2 (3H, m), 3.9 (3H, s), 2.1 (2H, m), 1.80-1.50 (8H, br m), 1.35 (9H, s).

Stage 1-N-(4-Hydroxy-phenyl)-benzamide

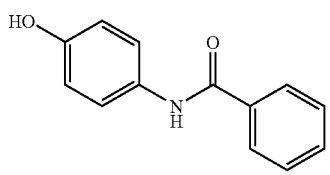

To a solution of 4-aminophenol (4.27 g, 39.1 mmol) in DMF (50 ml) at 0° C. under an atmosphere of argon was added triethylamine (7.44 ml, 53.4 mmol, 1.5 eq). The reaction mixture was stirred for 10 minutes before slow addition of benzoyl chloride (5 g, 35.6 mmol, 1 eq) over a period of 5 minutes. The reaction mixture was allowed to warm to room temperature and stirred over 18 hours. The DMF was removed under reduced pressure and the mixture was treated with ethyl acetate/water. Precipitation of a white solid resulted, which was filtered off and dried under reduced pressure. The title compound (8.0 g) was isolated in 96% yield.

¹H NMR (300 MHz, DMSO-d$_6$), δ: 10.0 (1H, s), 9.35 (1H, s), 7.9 (2H, d, J=7.2 Hz), 7.5 (5H, m), 6.75 (2H, d, J=7.4 Hz).

Stage 2-N-[4-(7-Benzyloxy-6-methoxy-quinolin-4-yloxy)-phenyl]-benzamide

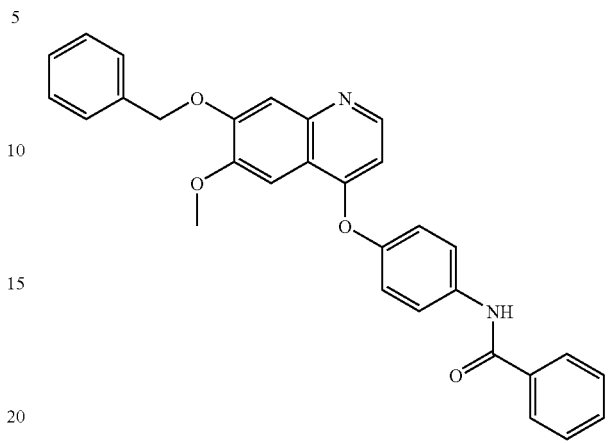

To a round bottomed flask charged with 4-chloro-6-methoxy, 7-benzyloxyquinoline (A) (1.09 g, 3.6 mmol) was added N-(4-hydroxy-phenyl)-benzamide (2.33 g, 10.9 mmol, 3 eq). The reaction mixture was heated to 140° C. for 3 hours. After cooling to room temperature, water was added to the reaction mixture and the mixture was extracted 3 times with ethyl acetate. The combined ethyl acetate extracts were washed with 5% aqueous NaOH, brine and dried over magnesium sulphate. The solvent was removed under reduced pressure and the crude mixture was purified by column chromatography eluting with ethyl acetate/heptane (2:1) to obtain 0.56 g of the title compound (Yield=32%).

LC/MS: m/z 477 [M+H]⁺.

Stage 3-N-[4-(7-Hydroxy-6-methoxy-quinolin-4-yloxy)-phenyl]-benzamide

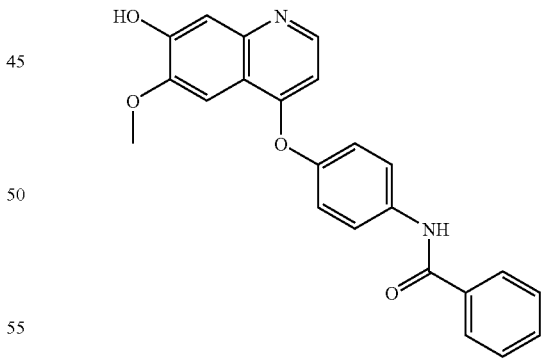

A mixture of stage 2 product (0.56 g, 1.17 mmol) and 10% Pd/C (80 mg) in 10% cyclohexene/ethanol (80 ml) was heated under reflux for 3 hours. The Pd/C catalyst was filtered off through a pad of Celite, washing twice with methanol. The filtrate was concentrated under reduced pressure to afford the title compound as a yellow solid (0.34 g, 75% yield).

LC/MS: m/z 387 [M+H]⁺.

Stage 4-(S)-4-[4-(4-Benzoylamino-phenoxy)-6-methoxy-quinolin-7-yloxy]-2-tert-butoxycarbonylamino-butyric acid cyclopentyl ester

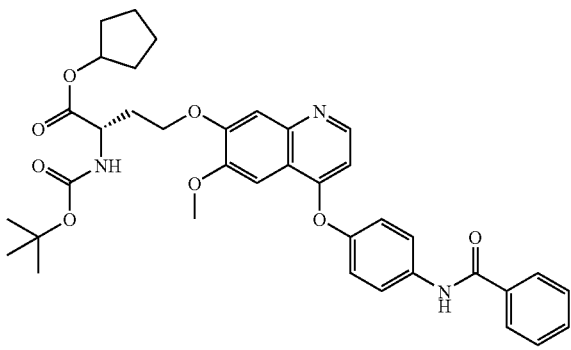

To a solution of N-[4-(7-hydroxy-6-methoxy-quinolin-4-yloxy)-phenyl]-benzamide (0.2 g, 0.52 mmol) in anhydrous DCM (30 ml) at 0° C. was added (S)-2-tert-butoxycarbonylamino-4-hydroxy-butyric acid cyclopentyl ester* (223 mg, 0.78 mmol, 1.5 eq) in 5 ml of DCM. Triphenylphosphine (557 mg, 2.1 mmol, 4.1 eq) and diisopropyl azodicarboxylate (0.41 ml, 2.1 mmol, 4.1 eq) were then added and the reaction mixture was allowed to warm to room temperature and stirred for 16 hours. The crude reaction mixture was concentrated under reduced pressure and purified by column chromatography to give the title compound (135 mg) in 46% yield.

LC/MS purity: 99%, m/z 656.3 [M+H]$^+$. $^1$H NMR (300 MHz, DMSO-d$_6$), δ: 10.4 (1H, s), 8.5 (1H, d, J=7.8 Hz), 8.0 (4H, m), 7.6 (4H, m), 7.35 (4H, m), 6.45 (1H, d, J=7.5 Hz), 5.1 (1H, m), 4.2 (3H, m), 3.9 (3H, s), 2.1 (2H, m), 1.8-1.5 (8H, br m), 1.35 (9H, s).

*The synthesis of (S)-2-tert-Butoxycarbonylamino-4-hydroxy-butyric acid cyclopentyl ester is outlined below in Scheme 2.

Scheme 2

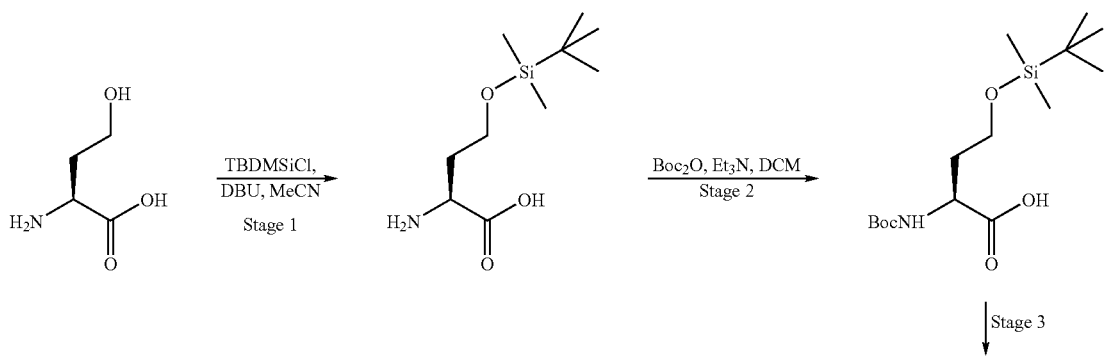

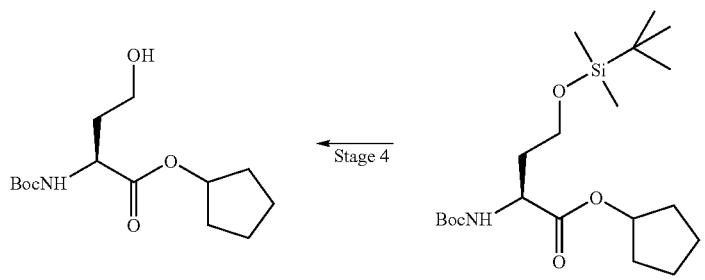

Stage 1-(S)-2-Amino-4-(tert-butyl-dimethyl-silanyloxy)-butyric acid

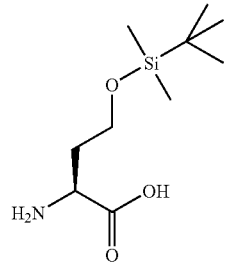

To a suspension of L-homoserine (1 g, 8.4 mmol) in acetonitrile (10 ml) at 0° C. was added 1,8-diazabicyclo[5.4.0]undec-7-ene (1.32 ml, 8.8 mmol, 1.05 eq). Tert-butyl-dimethyl-silyl chloride (1.33 g, 8.8 mmol, 1.05 eq) was then added portionwise over 5 minutes and the reaction mixture allowed to warm to room temperature and stirred for 16 hours. A white precipitate had formed, which was filtered off and washed with acetonitrile before drying under reduced pressure. The title compound was isolated as a white solid (1.8 g, 92% yield).

$^1$H NMR (500 MHz, DMSO-$d_6$), δ: 7.5 (1H, br s), 3.7 (1H, m), 3.35 (4H, br m), 1.95 (1H, m), 1.70 (1H, m), 0.9 (9H, s), 0.1 (6H, s).

Stage 2-(S)-2-tert-Butoxycarbonylamino-4-(tert-butyl-dimethyl-silanyloxy)-butyric acid

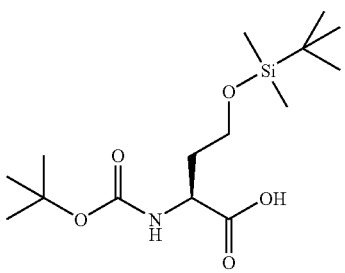

A suspension of stage 1 product (1.8 g, 7.7 mmol) in DCM (100 ml) at 0° C. was treated with triethylamine (2.15 ml, 15.4 mmol, 2 eq) and di-tert-butyl dicarbonate (1.77 g, 8.1 mmol, 1.05 eq). The reaction mixture was stirred at room temperature for 16 hours. The DCM was removed under reduced pressure and the mixture was treated with ethyl acetate/brine. The ethyl acetate layer was dried over magnesium sulphate and evaporated under reduced pressure. The crude product was taken forward without further purification (2.53 g, 99% yield).

$^1$H NMR (500 MHz, CDCl$_3$), δ: 7.5 (1H, br s), 5.85 (1H, d, J=6.5 Hz), 4.3 (1H, m), 3.75 (2H, m), 1.95 (2H, m), 1.40 (9H, s), 0.85 (9H, s), 0.1 (6H, s).

Stage 3-(S)-2-tert-Butoxycarbonylamino-4-(tert-butyl-dimethyl-silanyloxy)-butyric acid cyclopentyl ester

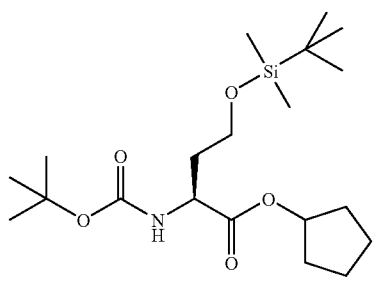

To a solution of (S)-2-tert-butoxycarbonylamino-4-(tert-butyl-dimethyl-silanyloxy)-butyric acid (2.53 g, 7.6 mmol) in DCM (50 ml) at 0° C. was added cyclopentanol (1.39 ml, 15.3 mmol, 2 eq), EDC (1.61 g, 8.4 mmol, 1.1 eq) and DMAP (93 mg, 0.76 mmol, 0.1 eq). The reaction mixture was stirred for 16 hours at room temperature before evaporation under reduced pressure. The crude residue was dissolved in ethyl acetate (100 ml) and washed with 1M HCl, 1M Na$_2$CO$_3$ and brine. The organic layer was then dried over magnesium sulphate and evaporated under reduced pressure. The product was purified by column chromatography using ethyl acetate/heptane (1:4) to give 2.24 g, 73% yield of title compound.

LC/MS purity: 100%, m/z 402 [M+H]$^+$. $^1$H NMR (250 MHz, CDCl$_3$), δ: 5.2 (1H, d, J=6.3 Hz), 5.15 (1H, m), 4.2 (1H, m), 3.6 (2H, m), 2.0 (1H, m), 1.95-1.55 (9H, br m), 1.4 (9H, s), 0.85 (9H, s), 0.1 (6H, s).

Stage 4-(S)-2-tert-Butoxycarbonylamino-4-hydroxy-butyric acid cyclopentyl ester

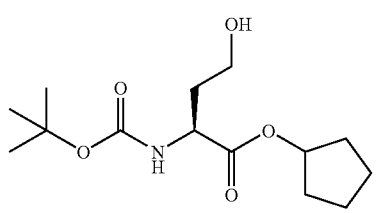

(S)-2-tert-Butoxycarbonylamino-4-(tert-butyl-dimethyl-silanyloxy)-butyric acid cyclopentyl ester (1.57 g, 3.9 mmol) was dissolved in acetic acid:THF:water (3:1:1, 100 ml). The reaction mixture was stirred at 30° C. for 16 hours. Ethyl acetate (200 ml) was added and washed with 1M Na$_2$CO$_3$, 1M HCl and brine. The ethyl acetate layer was dried over magnesium sulphate and concentrated under reduced pressure to give the product as a clear oil which crystallised on standing (1.00 g, 95% yield).

LC/MS purity: 100%, m/z 310 [M+Na]$^+$. $^1$H NMR (250 MHz, CDCl$_3$), δ: 5.4 (1H, d, J=6.5 Hz), 5.2 (1H, m), 4.4 (1H, m), 3.65 (2H, m), 2.15 (1H, m), 1.9-1.55 (9H, br m), 1.45 (9H, s).

EXAMPLE 2

Stage 5-(S)-2-Amino-4-[4-(4-benzoylamino-phenoxy)-6-methoxy-quinolin-7-yloxy]-butyric acid cyclopentyl ester

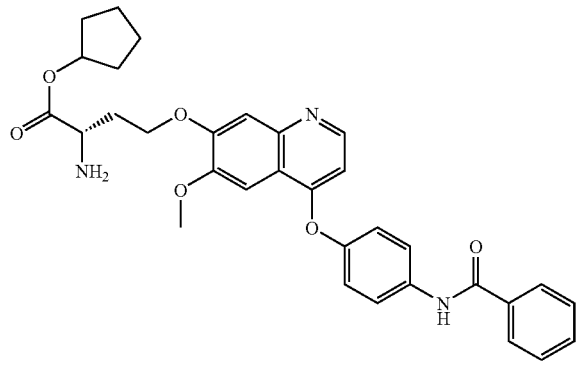

Stage 5: To a solution of (S)-4-[4-(4-benzoylamino-phenoxy)-6-methoxy-quinolin-7-yloxy]-2-tert-butoxycarbonylamino-butyric acid cyclopentyl ester (5.8 mg, 0.009 mmol) in DCM (1 ml) was added TFA (1 ml). The reaction mixture was allowed to stir for 16 hours before evaporation under reduced pressure, azeotroping with toluene to remove the traces of TFA.

The title compound was isolated as an off-white solid (4.7 mg).

LC/MS purity: 95%, m/z 556.2 [M+H]$^+$. $^1$H NMR (300 MHz, DMSO-d$_6$), δ: 10.40 (1H, s), 8.80 (1H, d, J=6.5 Hz), 8.55 (2H, br s), 8.01 (4H, m), 7.65 (4H, m), 7.35 (1H, d, J=7.6 Hz), 6.75 (1H, d, J=6.5 Hz), 5.25 (1H, m), 4.35 (3H, m), 4.00 (3H, s), 2.4 (2H, m), 1.85-1.40 (8H, br m).

An alternative route is shown in Scheme 3 for the preparation of the compound of Example 2 using (S)-4-bromo-2-tert-butoxycarbonylamino-butyric acid cyclopentyl ester at Stage 4.

Scheme 3

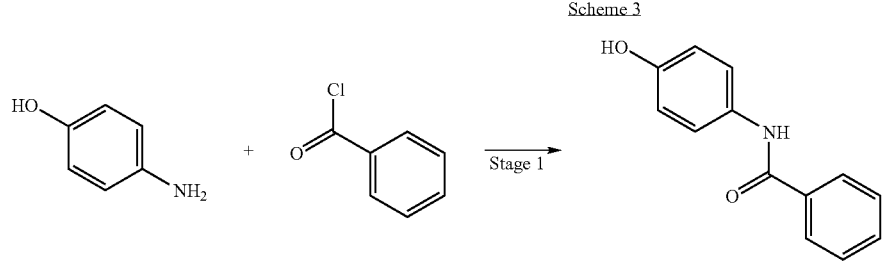

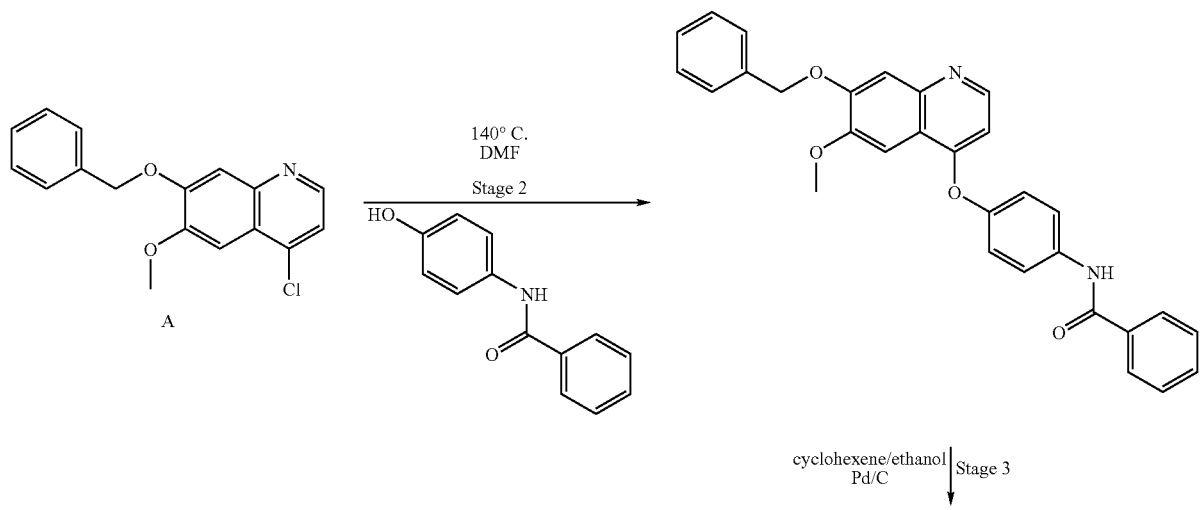

-continued

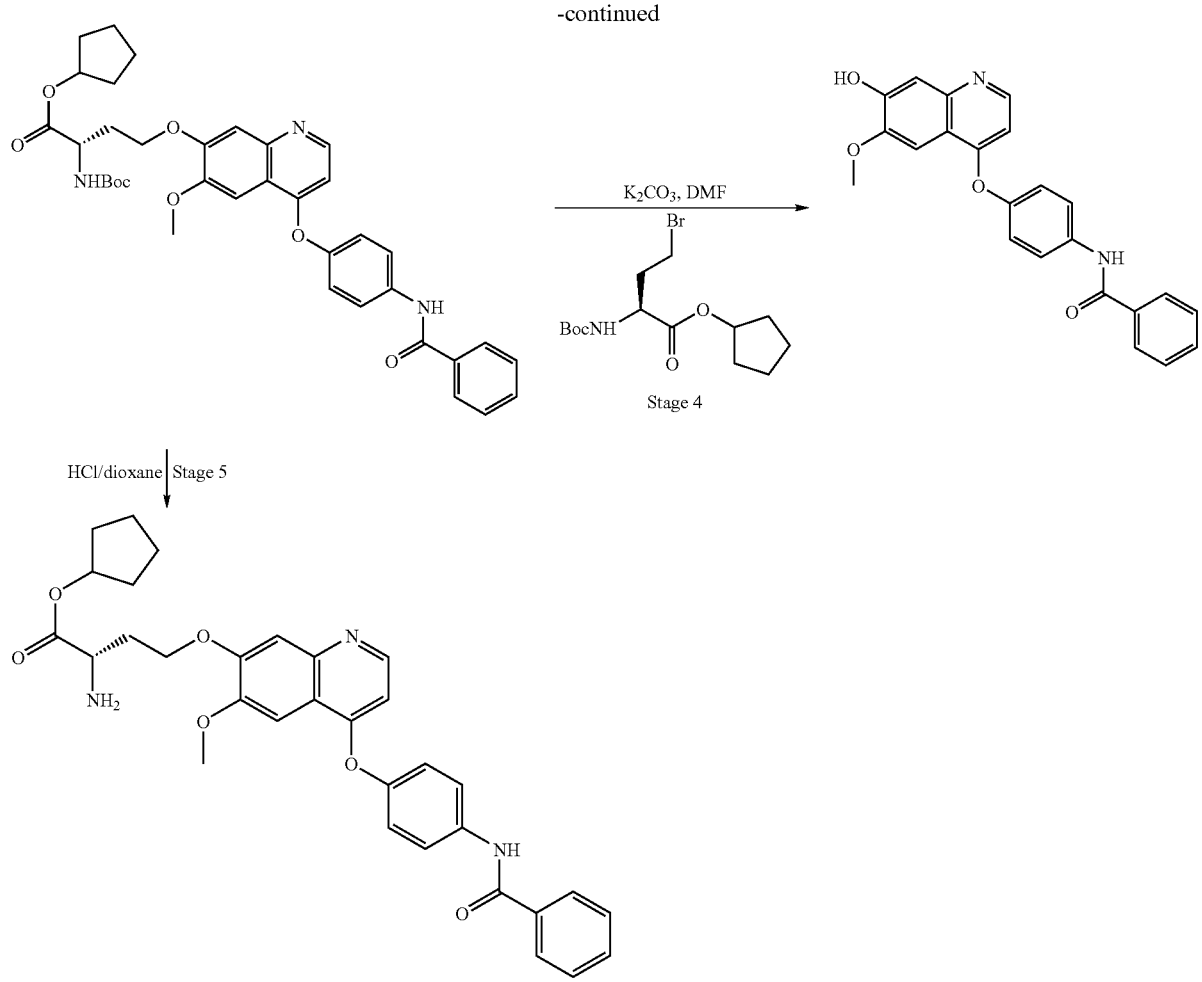

Stage 1-N-(4-Hydroxy-phenyl)-benzamide

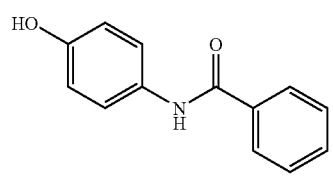

To a solution of 4-aminophenol (30.00 g, 275 mmol) in DMF (120 ml) at 0° C. under an atmosphere of nitrogen was added triethylamine (42.5 ml, 302 mmol, 1.2 eq). The reaction mixture was stirred for 10 minutes before dropwise addition of benzoyl chloride (31.9 ml, 275 mmol, 1.0 eq) over a period of 20 minutes. The reaction mixture was allowed to warm to room temperature and stirred for 18 hours. The reaction mixture was poured in ice cold water (800 ml) with vigorous stirring. A precipitate was collected by filtration and washed with water (2×500 ml). The precipitate was slurried in diethyl ether (1.5 L) and vigorously stirred for 30 minutes. The precipitate was collected by filtration and allowed to dry under reduced pressure to afford the title compound as an off-white solid (41.56 g, 71% yield).

LC/MS: m/z 214 [M+H]$^+$ and 449 [2M+Na]$^+$. $^1$H NMR (300 MHz, DMSO-d$_6$) δ: 10.01 (1H, s), 9.24 (1H, s), 7.83 (2H, d, J=6.3 Hz), 7.55-7.49 (5H, m), 6.74 (2H, d, J=8.7 Hz).

Stage 2-N-[4-(7-Benzyloxy-6-methoxy-quinolin-4-yloxy)-phenyl]-benzamide

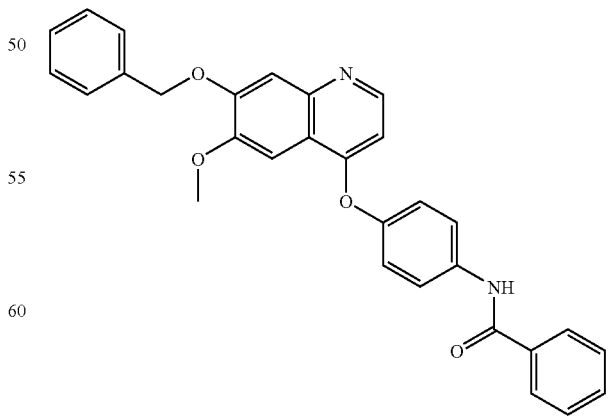

Ten reaction tubes were charged with 4-chloro-6-methoxy, 7-benzyloxyquinoline (A) (10×2.08 g, 10×6.9 mmol) in anhydrous DMF (10×6 ml). N-(4-Hydroxy-phenyl)-benzamide (10×4.44 g, 10×20.8 mmol, 3.0 eq) was added and the reaction mixtures were heated to 145° C. for 7 hours. DMF (10×30 ml) was added and the combined reaction mixtures were poured in ice cold water (1.5 L). The aqueous mixture was extracted with ethyl acetate (3×1.5 L). The combined organic extracts were washed with 2N NaOH (5×1.0 L) to remove excess N-(4-hydroxy-phenyl)-benzamide, brine (2.0 L), dried (MgSO$_4$), filtered and concentrated under reduced pressure to leave a pale brown solid. Purification by column chromatography (50-100% EtOAc in heptane) afforded the title compound as a pale yellow solid (6.30 g) and unreacted 4-chloro-6-methoxy-7-benzyloxyquinoline (A) (14.11 g). The recovered 4-chloro-6-methoxy-7-benzyloxyquinoline (A) was treated as described above in 12×1.18 g batches to afford an additional 4.72 g of title compound. Overall, the title compound was isolated as a pale yellow solid (11.02 g, 28% yield).

LC/MS: m/z 477 [M+H]$^+$. $^1$H NMR (300 MHz, CDCl$_3$) δ: 8.39 (1H, d, J=5.4 Hz), 7.89 (1H, s), 7.83 (2H, d, J=8.6 Hz), 7.69 (2H, d, J=9.0 Hz), 7.54-7.42 (7H, m), 7.35-7.23 (2H, m), 7.19 (1H, s), 7.14 (2H, d, J=8.6 Hz), 6.41 (1H, d, J=5.4 Hz), 5.26 (2H, s), 3.99 (3H, s).

Stage 3-N-[4-(7-Hydroxy-6-methoxy-quinolin-4-yloxy)-phenyl]-benzamide

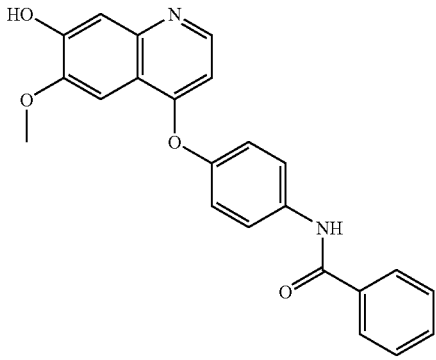

A mixture of N-[4-(7-Benzyloxy-6-methoxy-quinolin-4-yloxy)-phenyl]-benzamide (6.30 g, 13.2 mmol) and 10% Pd(OH)$_2$/C (600 mg) in cyclohexene/ethanol (1:9, 120 ml) was heated under reflux for 18 hours. The Pd(OH)$_2$/C catalyst was filtered off through a pad of Celite, washing with methanol/DCM (1:1, 3×1 L). The combined filtrates were concentrated under reduced pressure to afford the title compound as a yellow solid (4.93 g, 97% yield).

LC/MS: m/z 387 [M+H]$^+$. $^1$H NMR (300 MHz, DMSO-d$_6$) δ: 10.40 (1H, s), 8.41 (1H, d, J=5.4 Hz), 7.99-7.91 (4H, m), 7.62-7.50 (4H, m), 7.28-7.26 (3H, m), 6.40 (1H, d, J=5.4 Hz), 3.97 (3H, s).

Stage 4-(S)-4-[4-(4-Benzoylamino-phenoxy)-6-methoxy-quinolin-7-yloxy]-2-tert-butoxycarbonylamino-butyric acid cyclopentyl ester

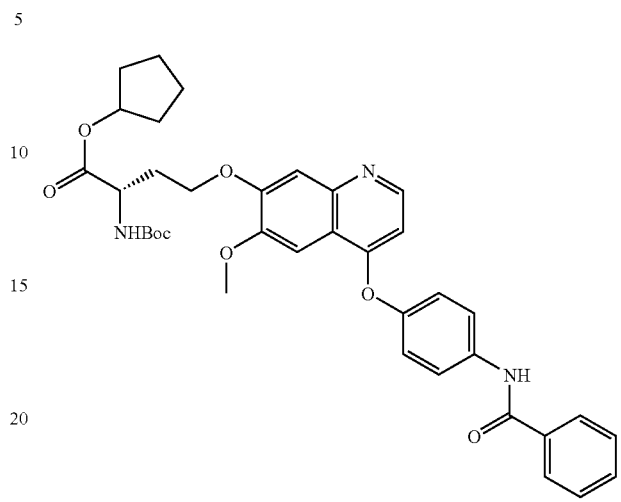

A mixture of N-[4-(7-Hydroxy-6-methoxy-quinolin-4-yloxy)-phenyl]-benzamide (4.93 g, 12.8 mmol), (S)-4-bromo-2-tert-butoxycarbonylamino-butyric acid cyclopentyl ester** (4.92 g, 14.0 mmol, 1.1 eq) and potassium carbonate (2.12 g, 15.3 mmol, 1.2 eq) in anhydrous DMF (50 ml) was stirred at 35° C. under an atmosphere of nitrogen for 20 hours. The reaction mixture was poured in water (200 ml). A yellow precipitate was collected by filtration, taken up in ethyl acetate (500 ml), washed with water (2×300 ml), brine (300 ml), dried (MgSO$_4$), filtered and concentrated under reduced pressure to leave a pale brown solid (8.52 g). A second batch of stage 3 product (3.94 g, 10.2 mmol) was treated has described above to afford an additional 7.16 g of crude material. Purification by column chromatography (60% EtOAc in heptane) of the combined crude mixtures afforded the title compound as a pale yellow solid (12.87 g, 86% yield).

LC/MS: m/z 656 [M+H]$^+$. $^1$H NMR (300 MHz, CD$_3$OD) δ: 8.43 (1H, d, J=5.4 Hz), 7.99-7.96 (2H, m), 7.88 (2H, d, J=9.0 Hz), 7.66 (1H, s), 7.62-7.52 (3H, m), 7.34 (1H, s), 7.27 (2H, d, J=9.3 Hz), 6.58 (1H, d, J=5.4 Hz), 5.24-5.17 (1H, m), 4.47-4.40 (1H, m), 4.39-4.28 (1H, m), 4.27-4.16 (1H, m), 4.05 (3H, s), 2.49-2.36 (1H, m), 2.35-2.21 (1H, m), 1.93-1.76 (2H, m), 1.75-1.51 (6H, m), 1.47 (9H, s).

Stage 5-(S)-2-Amino-4-[4-(4-benzoylamino-phenoxy)-6-methoxy-quinolin-7-yloxy]-butyric acid cyclopentyl ester

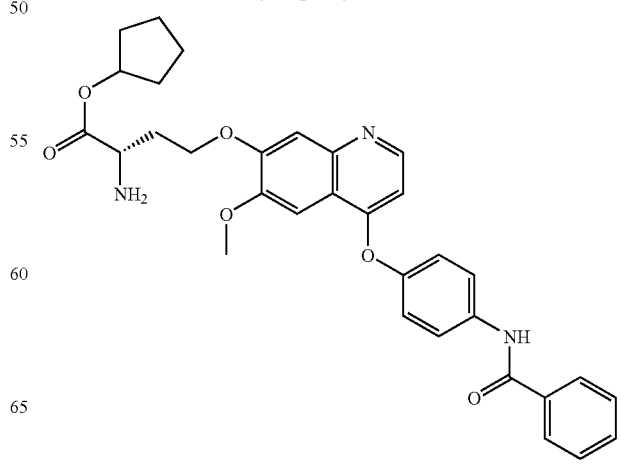

To a suspension of (S)-4-[4-(4-Benzoylamino-phenoxy)-6-methoxy-quinolin-7-yloxy]-2-tert-butoxycarbonylamino-butyric acid cyclopentyl ester (12.69 g, 19.4 mmol) in diethyl ether (20 ml) was added a 2N HCl solution in dioxane (100 ml). The mixture was stirred at room temperature for 18 hours. A precipitate was collected by filtration, thoroughly washed with diethyl ether and recrystallised from EtOH/EtOAc to afford the di-HCl salt of the title compound as an off-white solid (7.72 g, 72% yield).

LC/MS: m/z 556 [M+H]$^+$. $^1$H NMR (300 MHz, DMSO-d$_6$) δ: 10.55 (1H, s), 8.75-8.72 (4H, m), 8.02-7.94 (4H, m), 7.73 (2H, d, J=6.9 Hz), 7.58-7.42 (3H, m), 7.37 (2H, d, J=9.0 Hz), 6.80 (1H, d, J=6.6 Hz), 5.16-5.13 (1H, m), 4.41-4.29 (2H, m), 4.10 (1H, br s), 3.98 (3H, s), 2.44-2.38 (2H, m), 1.79-1.73 (2H, m), 1.63-1.47 (6H, m).

**The synthesis of (S)-4-Bromo-2-tert-butoxycarbonylamino-butyric acid cyclopentyl ester is outlined below in Scheme 4.

Scheme 4

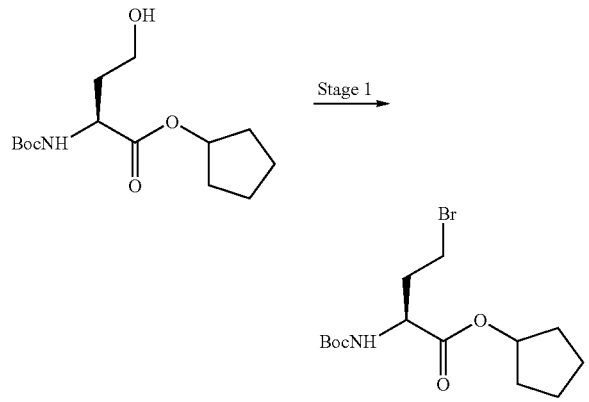

Stage 1-(S)-4-Bromo-2-tert-butoxycarbonylamino-butyric acid cyclopentyl ester

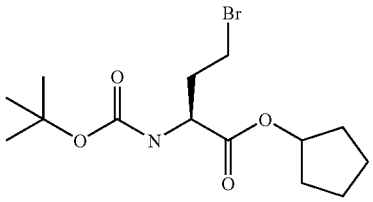

To a slurry of N-bromo succinimide (1.86 g, 10.4 mmol) in DCM (16.2 ml) was added a solution of triphenyl phosphine (2.56 g, 9.74 mmol) in DCM (7.2 ml). The solution was stirred for a further 5 minutes after addition. Pyridine (338 μl, 4.18 mmol) was added, followed by a solution of (S)-2-tert-butoxycarbonylamino-4-hydroxy-butyric acid cyclopentyl ester (1.00 g, 3.48 mmol) in DCM (8.8 ml). The solution was stirred for 18 hours, concentrated under reduced pressure and the residual solvent azeotroped with toluene (3×16 ml). The residue was triturated with diethyl ether (10 ml) and ethyl acetate:heptane (1:9, 2×10 ml). The combined ether and heptane solutions was concentrated onto silica and purified by column chromatography using ethyl acetate/heptane (1:9 to 2:8) to provide 1.02 g (84% yield) of title compound.

$^1$H NMR (300 MHz, CDCl$_3$), δ: 5.30-5.05 (2H, m), 4.45-4.30 (1H, m), 3.45 (2H, t, J=7.3 Hz), 2.50-2.30 (1H, m), 2.25-2.10 (1H, m), 1.95-1.60 (8H, br m), 1.47 (9H, s).

EXAMPLE 3

(S)-4-[4-(4-benzoylamino-phenoxy)-6-methoxy-quinolin-7-yloxy]-2-tert-butylcarbonylamino-butyric Acid

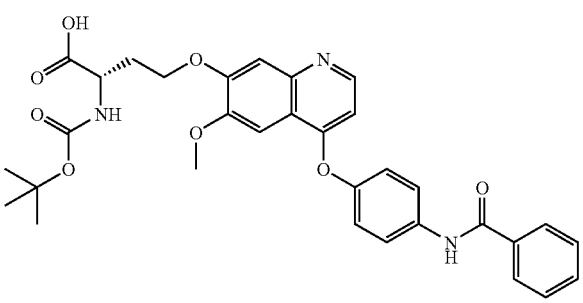

Stage 6: To a solution of (S)-4-[4-(4-benzoylamino-phenoxy)-6-methoxy-quinolin-7-yloxy]-2-tert-butoxycarbonylamino-butyric acid cyclopentyl ester (17 mg, 0.02 mmol) in THF (1 ml) was added 2M NaOH (0.026 ml, 0.046 mmol, 2 eq). After 16 hours reaction was incomplete so an additional 2 equivalents of NaOH was added. The reaction was completed after 6 hours and the THF was removed under reduced pressure. The aqueous layer was diluted with 3 ml of water and acidified to pH 6 with 1M HCl. The title compound was extracted into ethyl acetate, dried over magnesium sulphate and isolated as a white solid (13.8 mg, 91% yield).

LC/MS purity: 100%, m/z 588 [M+H]$^+$.

EXAMPLE 4

(S)-2-Amino-4-[4-(4-benzoylamino-phenoxy)-6-methoxy-quinolin-7-yloxy]-butyric acid

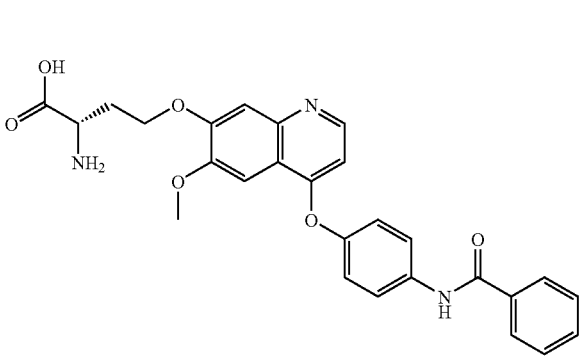

Stage 7: To a solution of (S)-4-[4-(4-benzoylamino-phenoxy)-6-methoxy-quinolin-7-yloxy]-2-tert-butylcarbonylamino-butyric acid (6.5 mg, 0.011 mmol) in DCM (1 ml) was added TFA (1 ml). The reaction was allowed to stir for 6 hours and then evaporated under reduced pressure to afford the title compound as an off-white solid (6.0 mg, 90% yield).

LC/MS purity: 100%, m/z 488 [M+H]$^+$. $^1$H NMR (300 MHz, CD$_3$OD), δ: 8.75 (1H, d, J=7.8 Hz), 8.00 (4H, m), 7.65

(4H, m), 7.40 (1H, d, J=7.6 Hz), 6.95 (1H, d, J=8.0 Hz), 4.60 (2H, m), 4.30 (1H, m), 4.20 (3H, s), 2.60 (2H, m).

Examples 5-14 were prepared by utilizing the appropriate substituted phenol intermediate at Stage 2 of Scheme 3.

EXAMPLE 5

(S)-2-Amino-4-[4-(3-fluoro-phenoxy)-6-methoxy-quinolin-7-yloxy]-butyric acid cyclopentyl ester

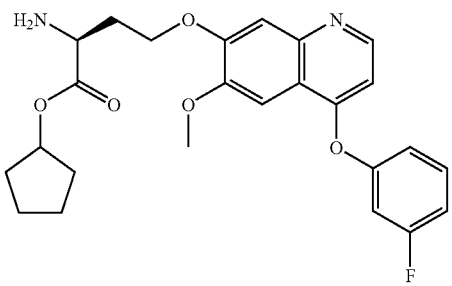

LC/MS purity: 97% (254 nm), m/z 455 [M+H]⁺. ¹H NMR (300 MHz, CD₃OD), δ: 8.71 (1H, d, J=6.7 Hz), 7.87 (1H, s), 7.70-7.60 (2H, m), 7.32-7.20 (3H, m), 6.98 (1H, d, J=6.7H), 4.55-4.47 (2H, m), 4.37-4.29 (1H, m), 4.12 (3H, s), 2.65-2.49 (2H, m), 2.01-1.52 (9H, m).

EXAMPLE 6

(S)-2-Amino-4-[4-(3-fluoro-phenoxy)-6-methoxy-quinolin-7-yloxy]-butyric acid

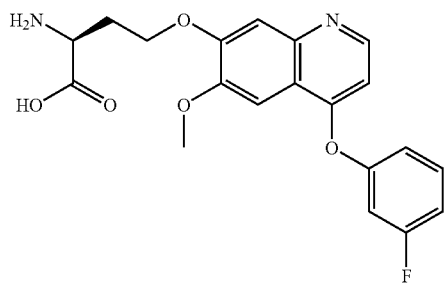

LC/MS purity: 92% (254 nm), m/z 387 [M+H]⁺. ¹H NMR (300 MHz, CD₃OD), δ: 8.71 (1H, d, J=6.6 Hz), 7.86 (1H, s), 7.71-7.60 (2H, m), 7.31-7.21 (3H, m), 6.97 (1H, d, J=6.8 Hz), 4.54 (2H, t, J=5.6 Hz) 4.34-4.27 (1H, m), 4.12 (3H, s), 2.73-2.46 (2H, m).

EXAMPLE 7

(S)-2-Amino-4-(6-methoxy-4-phenoxy-quinolin-7-yloxy)-butyric acid cyclopentyl ester

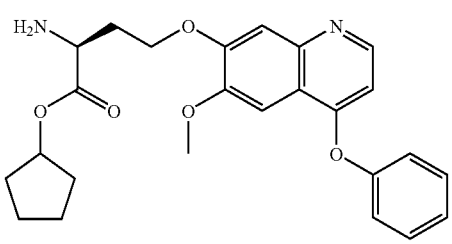

LC/MS purity: 97% (254 nm), m/z 437 [M+H]⁺. ¹H NMR (300 MHz, CD₃OD), δ: 8.67 (1H, d, J=6.6 Hz), 7.89 (1H, s), 7.67-7.59 (3H, m), 7.53-7.44 (1H, m), 7.41-7.34 (2H, m), 6.88 (1H, d, J=6.7 Hz), 5.39-5.30 (1H, m), 4.51 (2H, m), 4.36-4.30 (1H, m), 4.11 (3H, s), 2.66-2.48 (2H, m), 2.02-1.55 (9H, m).

EXAMPLE 8

(S)-2-Amino-4-(6-methoxy-4-phenoxy-quinolin-7-yloxy)-butyric acid

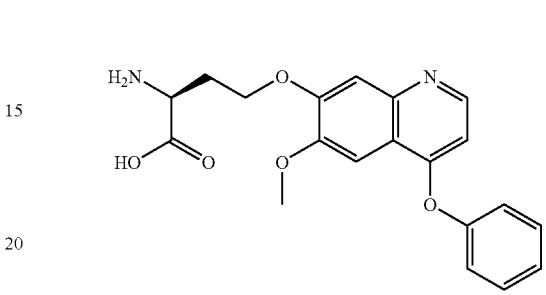

LC/MS purity: 98% (254 nm), m/z 369 [M+H]⁺. ¹H NMR (300 MHz, CD₃OD), δ: 8.66 (1H, d, J=5.7 Hz), 7.87 (1H, s), 7.67-7.54 (3H, m), 7.52-7.44 (1H, m), 7.41-7.34 (2H, m), 6.86 (1H, d, J=6.5 Hz), 4.59-4.48 (2H, m), 4.26-4.18 (1H, m), 4.12 (3H, s), 2.72-2.46 (2H, m).

EXAMPLE 9

(S)-2-Amino-4-[6-methoxy-4-(4-methoxy-phenoxy)-quinolin-7-yloxy]-butyric acid cyclopentyl ester

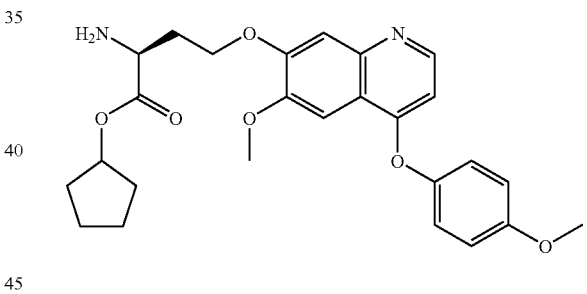

LC/MS purity: 97% (254 nm), m/z 467 [M+H]⁺. ¹H NMR (300 MHz, CD₃OD), δ: 8.68 (1H, d, J=6.8 Hz), 7.88 (1H, s), 7.63 (1H, s), 7.33-7.25 (2H, m), 7.18-7.11 (2H, m), 6.90 (1H, d, J=6.8 Hz), 5.39-5.30 (1H, m), 4.56-4.47 (2H, m), 4.37-4.30 (1H, m), 4.12 (3H, s), 3.88 (3H, s), 2.70-2.47 (2H, m), 2.02-1.56 (9H, m).

EXAMPLE 10

(S)-2-Amino-4-[6-methoxy-4-(4-methoxy-phenoxy)-quinolin-7-yloxy]-butyric acid

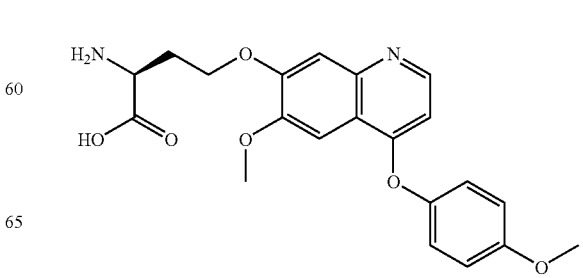

LC/MS purity: 98% (254 nm), m/z 399 [M+H]⁺. ¹H NMR (300 MHz, CD₃OD), δ: 8.67 (1H, d, J=6.8 Hz), 7.88 (1H, s), 7.57 (1H, s), 7.32-7.26 (2H, m), 7.18-7.12 (2H, m), 6.89 (1H, d, J=6.7 Hz), 4.54 (2H, t, J=5.7 Hz), 4.33-4.26 (1H, m), 4.13 (3H, s), 3.88 (3H, s), 2.71-2.49 (2H, m).

EXAMPLE 11

(S)-2-Amino-4-[4-(biphenyl-4-yloxy)-6-methoxy-quinolin-7-yloxy]-butyric acid cyclopentyl ester

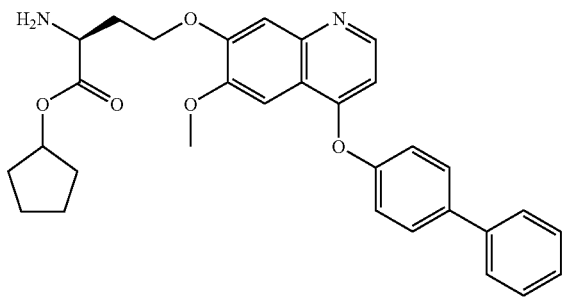

LC/MS purity: 99% (254 nm), m/z 513 [M+H]⁺. ¹H NMR (300 MHz, DMSO-d₆) δ: 8.80 (1H, d, J=6.3 Hz), 8.71 (3H, s), 7.92 (2H, d, J=8.7 Hz), 7.77 (4H, m), 7.51 (4H, m), 7.42 (1H, m), 6.92 (1H, d, J=6.6 Hz), 5.22 (1H, t, J=5.9 Hz), 4.42 (2H, m), 4.19 (1H, br s), 4.05 (3H, s), 2.46 (2H, m), 1.91-1.81 (2H, m), 1.65-1.56 (6H, m)

EXAMPLE 12

(S)-2-Amino-4-[6-methoxy-4-(2-methyl-benzothiazol-5-yloxy)-quinolin-7-yloxy]-butyric acid cyclopentyl ester

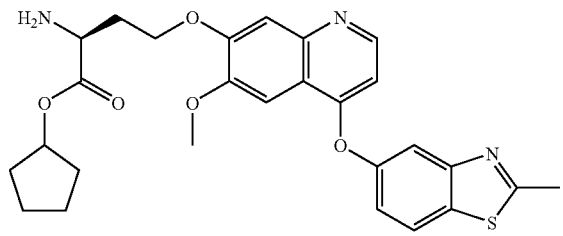

LC/MS purity: 93% (254 nm), m/z 508 [M+H]⁺. ¹H NMR (300 MHz, DMSO-d₆) δ: 8.79 (1H, d, J=6.6 Hz) 8.72 (3H, br s), 8.30 (1H, d, J=8.7 Hz), 8.03 (1H, d, J=2.1 Hz), 7.84 (1H, s), 7.80 (1H, s), 7.49 (1H, dd, J=2.1, 8.7 Hz), 6.91 (1H, d, J=6.6 Hz), 5.22 (1H, br s), 4.42 (2H, br s), 4.18 (1H, br s), 4.06 (3H, s), 2.86 (3H, s), 2.53-2.45 (2H, m), 1.87-1.81 (2H, m), 1.75-1.52 (6H, m).

EXAMPLE 13

(S)-2-Amino-4-[6-methoxy-4-(2-methyl-benzothiazol-5-yloxy)-quinolin-7-yloxy]-butyric acid

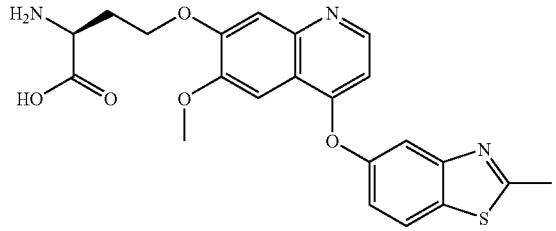

LC/MS purity: 99% (254 nm), m/z 440 [M+H]⁺. ¹H NMR (300 MHz, DMSO-d₆) δ: 8.48 (1H, d, J=5.2 Hz), 8.18 (1H, d, J=8.7 Hz), 7.82 (1H, d, J=2.1 Hz), 7.57 (1H, s), 7.43 (1H, s), 7.34 (1H, dd, J=8.7, 2.1 Hz), 6.50 (1H, d, J=5.2 Hz), 4.34 (2H, t, J=6.5 Hz), 4.02 (3H, s), 3.72 (1H, t, J=6.3 Hz), 2.83 (3H, s), 2.43-2.36 (1H, m), 2.26-2.17 (1H, m).

EXAMPLE 14

(S)-2-Amino-4-[6-methoxy-4-(quinolin-7-yloxy)-quinolin-7-yloxy]-butyric acid cyclopentyl ester

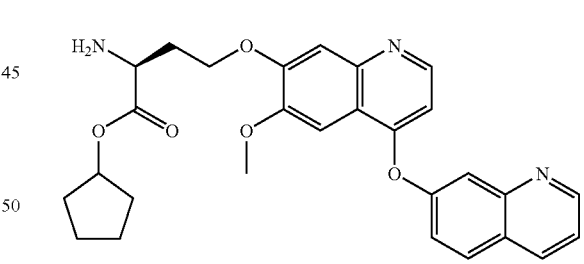

LC/MS purity: 95% (254 nm), m/z 488 [M+H]⁺. ¹H NMR (300 MHz, DMSO-d₆) δ: 8.11 (1H, d, J=3.0 Hz), 8.74 (3H, br s), 8.67 (1H, d, J=6.6 Hz), 8.61 (1H, d, J=8.1 Hz), 8.17 (1H, d, J=7.8 Hz), 7.95 (2H, m), 7.84 (2H, m), 7.67 (1H, m), 6.62 (1H, d, J=6.6 Hz), 5.30 (1H, br s), 4.44 (2H, br s), 4.18 (1H, br s), 4.07 (3H, s), 2.51 (2H, m), 1.84 (2H, m), 1.66-1.57 (6H, m)

The N-(4-amino-phenyl)-benzamide building block used in the synthesis of examples 15 and 16 was prepared as detailed below in Scheme 5.

Scheme 5

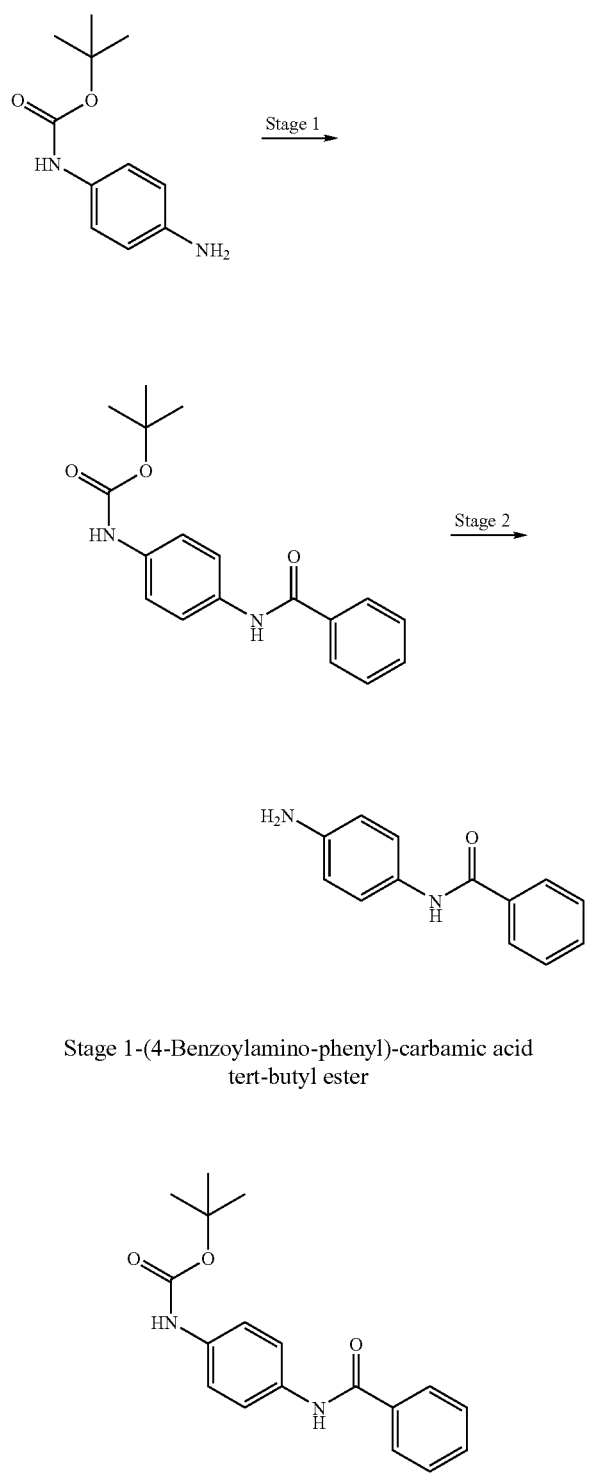

Stage 1-(4-Benzoylamino-phenyl)-carbamic acid tert-butyl ester

To a solution of (4-amino-phenyl)-carbamic acid tert-butyl ester (10 g, 48 mmol) in DCM (500 ml) at 0° C. under an atmosphere of argon was added triethylamine (7.44 ml, 53.4 mmol, 1.1 eq). The reaction mixture was stirred for 10 minutes before slow addition of benzoyl chloride (5.6 ml, 48 mmol, 1 eq) over a period of 5 minutes. The reaction mixture was allowed to warm to room temperature and stirred over 4 hours.

To the reaction mixture was added 200 ml of saturated NaHCO$_3$ solution and the biphasic mixture filtered to give an off-white solid which was dried under vacuum. The title compound (14.9 g) was isolated in 99% yield.

Stage 2-N-(4-Amino-phenyl)-benzamide

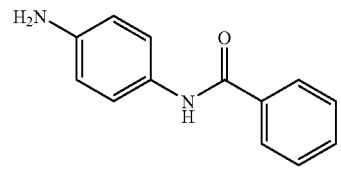

To a solution of (4-Benzoylamino-phenyl)-carbamic acid tert-butyl ester (14.92 g) in DCM (200 ml) was added TFA (100 ml). The reaction was stirred at room temperature for 30 minutes before concentration under reduced pressure. The crude residue was dissolved in water (200 ml) and adjusted to pH 11 with sodium carbonate. The aqueous mixture was extracted with ethyl acetate, the organic extracts were combined and dried over magnesium sulphate. The solvent was removed under reduced pressure to obtain 9.63 g of the title compound in 95% yield.

EXAMPLE 15

(S)-2-Amino-4-[4-(4-benzoylamino-phenylamino)-6-methoxy-quinolin-7-yloxy]-butyric acid cyclopentyl ester

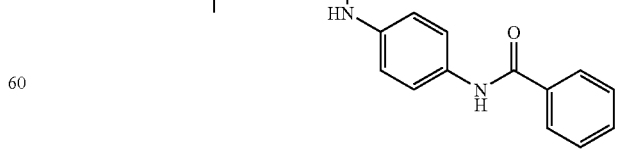

LC/MS purity: 97% (254 nm), m/z 554 [M+H]$^+$. $^1$H NMR (300 MHz, CD$_3$OD), δ: 8.22 (1H, d, J=7.8 Hz), 7.98-7.91 (5H, m), 7.61-7.44 (5H, m), 7.34 (1H, s), 6.45 (1H, d, J=7.8

Hz), 5.33 (1H, m), 4.44 (1H, m), 4.31 (1H, m), 4.08 (3H, s), 2.53 (2H, m), 1.89 (1H, m), 1.76-1.64 (8H, m).

EXAMPLE 16

(S)-2-Amino-4-[4-(4-benzoylamino-phenylamino)-6-methoxy-quinolin-7-yloxy]-butyric acid

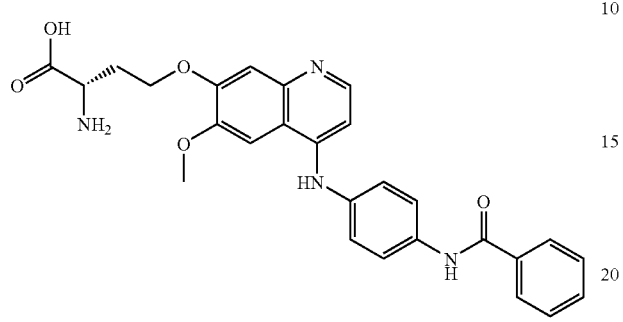

LC/MS purity: 95% (254 nm), m/z 487 [M+H]$^+$. $^1$H NMR (300 MHz, CD$_3$OD), δ: 8.22 (1H, d, J=6.8 Hz), 8.00-7.83 (5H, m), 7.28-7.17 (6H, m), 6.76 (1H, d, J=6.8 Hz), 4.84 (1H, m), 4.59 (1H, m), 4.39 (1H, m), 3.94 (3H, s), 2.57 (1H, br s), 2.43 (2H, m), 0.80 (2H, m).

EXAMPLE 17

(S)-2-Amino-4-[6-methoxy-4-(5-methyl-1H-pyrazol-3-ylamino)-quinolin-7-yloxy]-butyric acid cyclopentyl ester

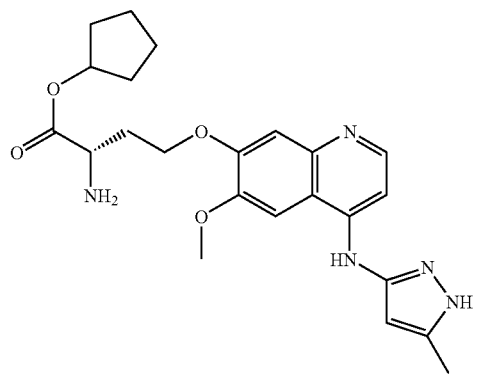

LC/MS purity: 97% (254 nm), m/z 440 [M+H]$^+$. $^1$H NMR (300 MHz, DMSO-d$_6$) δ: 10.76 (1H, s), 8.70 (3H, br s), 8.45 (1H, t, J=6.6 Hz), 8.27 (1H, s), 7.70 (1H, d, J=7.0 Hz), 7.54 (1H, s), 6.23 (1H, s), 5.21 (5H, br s), 4.33 (2H, br s), 4.21-4.11 (1H, m), 4.02 (3H, s), 2.47-2.36 (2H, m), 2.31 (3H, s), 1.93-1.74 (2H, m), 1.73-1.45 (6H, m)

EXAMPLE 18

(S)-2-Amino-4-[4-(4-benzoylamino-phenylsulfanyl)-6-methoxy-quinolin-7-yloxy]-butyric acid cyclopentyl ester

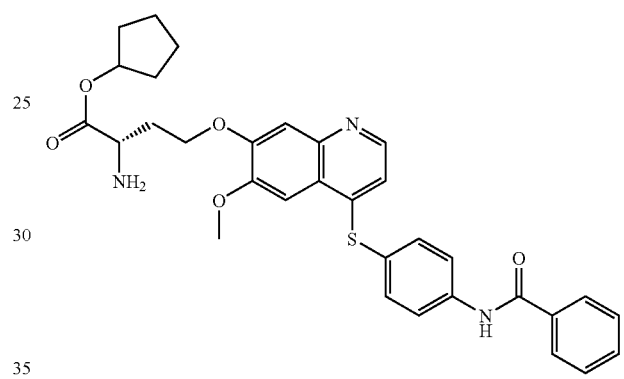

LC/MS: m/z 572 [M+H]$^+$. $^1$H NMR (300 MHz, CD$_3$OD) δ: 8.24 (1H, d, J=5.1 Hz), 7.88-7.80 (4H, m), 7.54-7.39 (5H, m), 7.34 (1H, s), 7.24 (1H, s), 6.70 (1H, d, J=5.1 Hz), 5.13-5.09 (1H, m), 4.22 (2H, t, J=5.9 Hz), 3.91 (3H, s), 3.65 (1H, t, J=6.3 Hz), 2.28-2.19 (1H, m), 2.15-2.04 (1H, m), 1.78-1.72 (2H, m), 1.61-1.48 (6H, m).

The preparation of Example 18 is shown below in Scheme 6.

Scheme 6

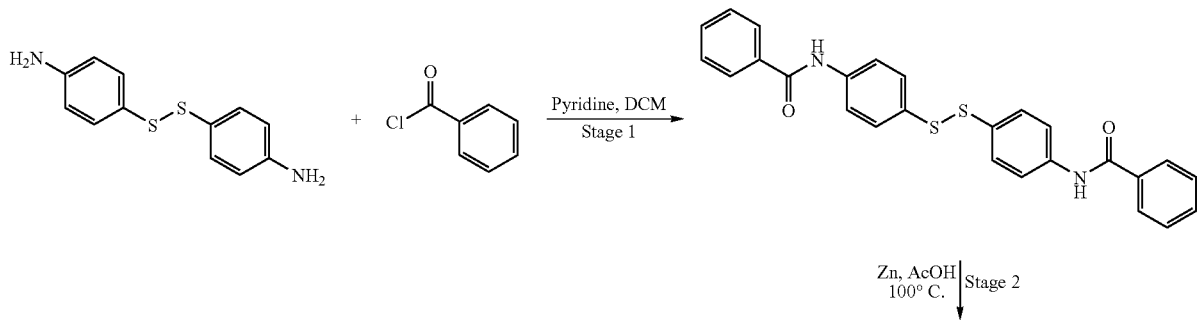

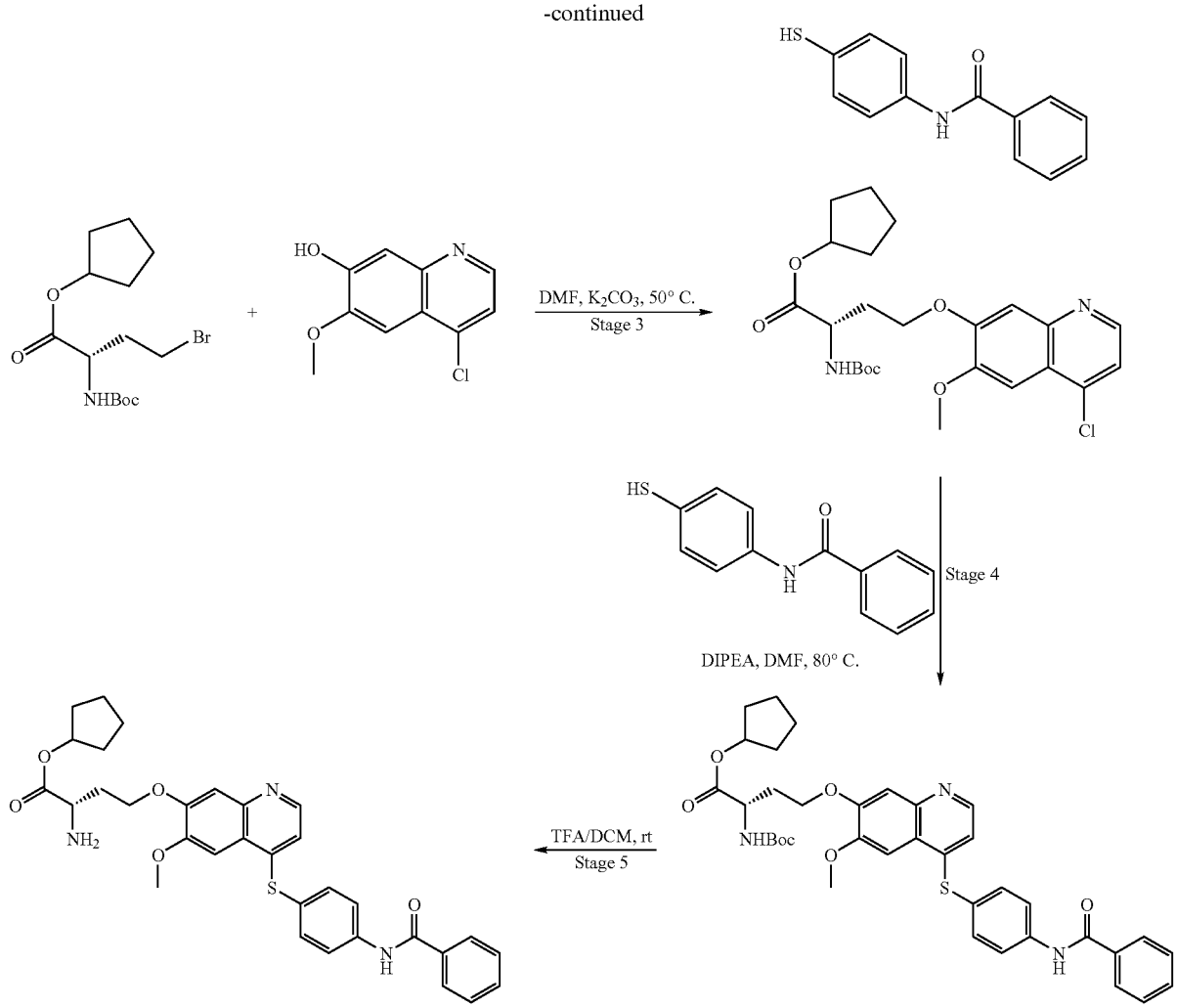

Stage 1-bis-(4-Benzoylamino-phenyl)-disulfide $^1$H NMR (300 MHz, DMSO-d$_6$) δ: 10.40 (2H, s), 7.95 (4H, d, J=6.9 Hz), 7.83 (4H, d, J=8.7 Hz), 7.63-7.51 (10H, m)

Stage 2-N-(4-Mercapto-phenyl)-benzamide

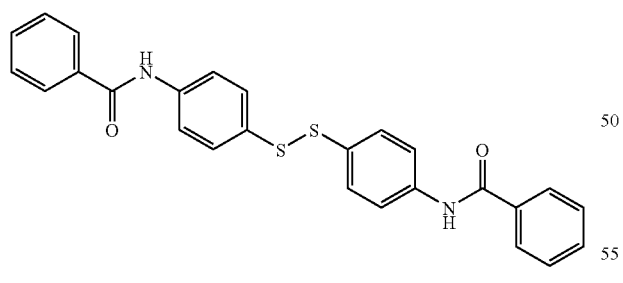

To a solution of bis-(4-aminophenyl)-disulfide (5.45 g, 21.9 mmol) in DCM (110 ml) under an atmosphere of nitrogen was added pyridine (3.9 ml, 48.3 mmol, 2.2 eq). The reaction mixture was cooled to 0° C. and benzoyl chloride (5.1 ml, 23.9 mmol, 2.0 eq) was added dropwise over 5 minutes. The reaction mixture was allowed to warm to room temperature and stirred for 30 minutes. A solid was collected by filtration, washed with DCM and allowed to dry under reduced pressure to afford the title compound as white solid (10.01 g, 100% yield).

To a solution of bis-(4-benzoylamino-phenyl)-disulfide (10.01 g, 21.9 mmol) in glacial acetic acid (55 ml) was added zinc powder (3.15 g, 48.2 mmol, 2.2 eq) and the reaction mixture was stirred at 100° C. for 4 hours. The hot reaction mixture was filtered through a short pad of Celite. Upon cooling a solid precipitated. The liquid was discarded and the solid was triturated with water, dried under reduced pressure to afford the title compound as a pale yellow solid (8.81 g, 88% yield).

LC/MS: m/z 230 [M+H]⁺ and 481 [2M+Na]⁺. ¹H NMR (300 MHz, DMSO-d₆) δ: 10.06 (1H, s), 7.96 (2H, d, J=6.6 Hz), 7.73-7.45 (5H, m), 7.32 (2H, d, J=8.4 Hz).

Stage 3-(S)-2-tert-Butoxycarbonylamino-4-(4-chloro-6-methoxy-quinolin-7-yloxy)-butyric acid cyclopentyl ester

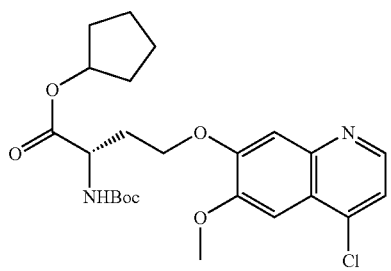

To a solution of 4-cloro-6-methoxy-quinolin-7-ol (300 mg, 1.43 mmol) and (S)-4-bromo-2-tert-butoxycarbonylamino-butyric acid cyclopentyl ester (551 mg, 1.57 mmol, 1.1 eq) in DMF (10 ml) was added potassium carbonate (237 mg, 1.72 mmol, 1.2 eq). The reaction mixture was stirred at 50° C. for 22 hours, allowed to cool to room temperature and diluted with water (50 ml). The aqueous suspension was extracted with ethyl acetate (3×50 ml). The combined organic extracts were washed with water (2×50 ml), brine (50 ml), dried (MgSO₄), filtered and concentrated under reduced pressure to leave a brown oil. Purification by column chromatography (50% ethyl acetate in heptane) afforded the title compound as a pale yellow solid (497 mg, 73% yield).

LC/MS: m/z 479 [M+H]⁺. ¹H NMR (300 MHz, CDCl₃) δ: 8.60 (1H, d, J=5.4 Hz), 7.43 (1H, s), 7.39-7.35 (2H, m), 6.06 (1H, d, J=5.4 Hz), 5.23-5.19 (1H, m), 4.58 (1H, br s), 4.39-4.33 (1H, m), 4.22-4.14 (1H, m), 4.09 (3H, s), 2.49-2.42 (2H, m), 1.89-1.72 (2H, m), 1.71-1.51 (8H, m), 1.50 (9H, s).

Stage 4-(S)-4-[4-(4-Benzoylamino-phenylsulfanyl)-6-methoxy-quinolin-7-yloxy]-2-tert-butoxycarbonyl-amino-butyric acid cyclopentyl ester

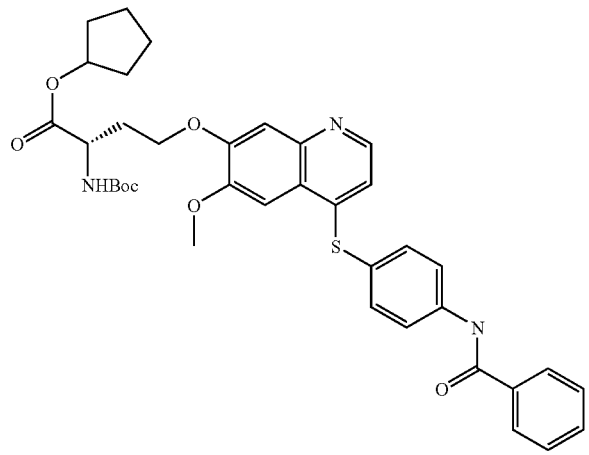

A mixture of (S)-2-tert-butoxycarbonylamino-4-(4-chloro-6-methoxy-quinolin-7-yloxy)-butyric acid cyclopen- tyl ester (250 mg, 0.52 mmol), N-(4-mercapto-phenyl)-benzamide (132 mg, 0.57 mmol, 1.1 eq), and diisopropylethylamine (0.10 ml, 0.63 mmol, 1.2 eq) in anhydrous DMF (2 ml) was stirred at 80° C. under an atmosphere of nitrogen for 24 hours. The reaction mixture was allowed to cool to room temperature and diluted with ethyl acetate (25 ml). The organic solution was washed with water (2×25 ml), brine (25 ml), dried (MgSO₄), filtered and concentrated under reduced pressure to leave a yellow oil. Purification by column chromatography (70-100% ethyl acetate in heptane) afforded the title compound as a white solid (275 mg, 78% yield).

LC/MS: m/z 672 [M+H]⁺.

Stage 5-(S)-2-Amino-4-[4-(4-benzoylamino-phenyl-sulfanyl)-6-methoxy-quinolin-7-yloxy]-butyric acid cyclopentyl ester

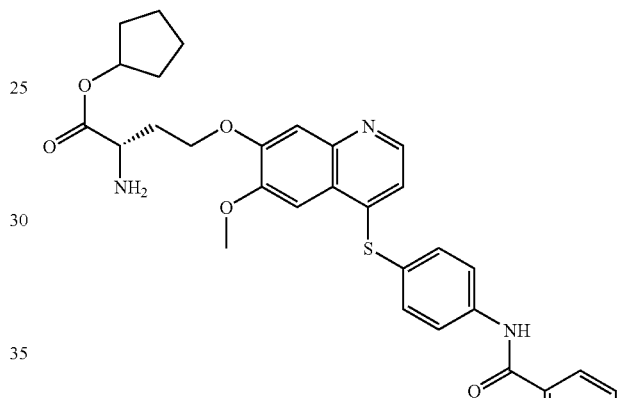

A solution of (S)-4-[4-(4-benzoylamino-phenylsulfanyl)-6-methoxy-quinolin-7-yloxy]-2-tert-butoxycarbonylamino-butyric acid cyclopentyl ester (275 mg, 0.41 mmol) in DCM/TFA (2:1, 15 ml) was stirred at room temperature for 2.5 hours. The reaction mixture was concentrated under reduce pressure. The residue was taken up in DCM (50 ml), washed with a saturated solution of NaHCO₃ (2×50 ml), brine (50 ml), dried (MgSO₄), filtered and concentrated under reduced pressure to afford the title compound as an off-white solid (230 mg, 98% yield).

LC/MS: m/z 572 [M+H]⁺. ¹H NMR (300 MHz, CD₃OD) 8.24 (1H, d, J=5.1 Hz), 7.88-7.80 (4H, m), 7.54-7.39 (5H, m), 7.34 (1H, s), 7.24 (1H, s), 6.70 (1H, d, J=5.1 Hz), 5.13-5.09 (1H, m), 4.22 (2H, t, J=5.9 Hz), 3.91 (3H, s), 3.65 (1H, t, J=6.3 Hz), 2.28-2.19 (1H, m), 2.15-2.04 (1H, m), 1.78-1.72 (2H, m), 1.61-1.48 (6H, m).

The ester hydrolysis of Example 18 follows the same protocol as Stage 6 of Scheme 1.

EXAMPLE 19

(S)-2-Amino-4-[4-(4-benzoylamino-phenylsulfanyl)-6-methoxy-quinolin-7-yloxy]-butyric acid

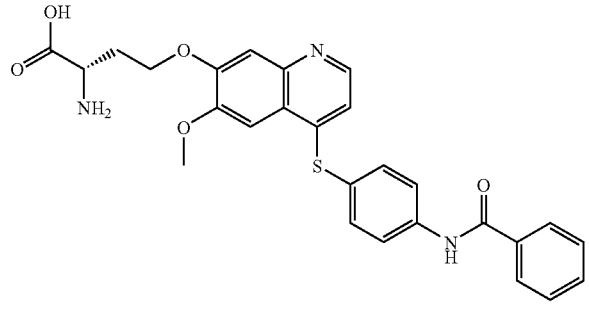

LC/MS: m/z 504 [M+H]⁺. ¹H NMR (300 MHz, DMSO-d₆) δ: 10.56 (1H, s), 8.44 (1H, d, J=4.8 Hz), 8.01-7.98 (4H, m), 7.64-7.54 (5H, m), 7.39 (1H, s), 7.35 (1H, s), 6.69 (1H, d, J=4.8 Hz), 4.32 (2H, t, J=6.5 Hz), 3.96 (3H, s), 3.49-3.45 (1H, m), 2.39-2.32 (1H, m), 2.15-2.08 (1H, m).

EXAMPLE 20

(S)-2-Amino-4-{4-[4-(cyclopropanecarbonyl-amino)-phenylsulfanyl]-6-methoxy-quinolin-7-yloxy}-butyric acid cyclopentyl ester

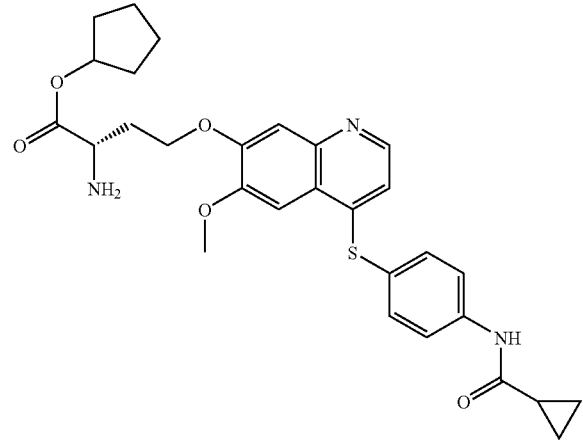

LC/MS: m/z 536 [M+H]⁺. ¹H NMR (300 MHz, DMSO-d₆) δ: 10.49 (1H, s), 8.42 (1H, d, J=4.8 Hz), 7.67 (2H, d, J=8.4 Hz), 7.55 (2H, d, J=8.4 Hz), 7.38 (1H, s), 7.32 (1H, s), 6.64 (1H, d, J=4.8 Hz), 5.12-5.08 (1H, m), 4.30-4.21 (1H, m), 3.93 (3H, s), 3.52-3.48 (1H, m), 2.17-2.08 (1H, m), 1.97-1.79 (6H, m), 1.71-1.49 (6H, m), 0.86-0.83 (4H, m).

EXAMPLE 21

(S)-2-Amino-4-{4-[4-(cyclopropanecarbonyl-amino)-phenylsulfanyl]-6-methoxy-quinolin-7-yloxy}-butyric acid

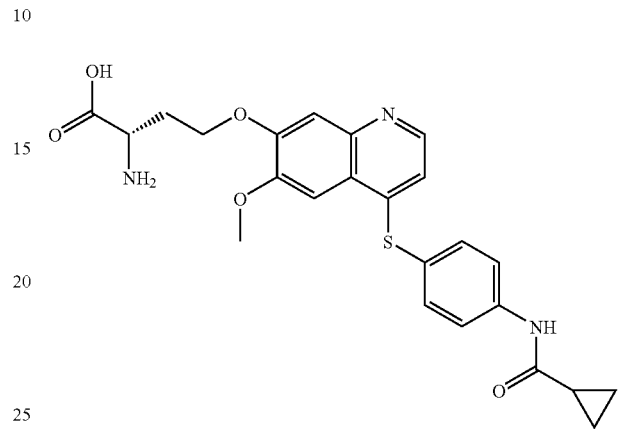

LC/MS: m/z 468 [M+H]⁺. ¹H NMR (300 MHz, CD₃OD) δ: 8.32 (1H, d, J=4.8 Hz), 7.78 (2H, d, J=8.6 Hz), 7.55 (2H, d, J=8.6 Hz), 7.43 (1H, s), 7.35 (1H, s), 6.73 (1H, d, J=4.8 Hz), 4.41 (2H, brs), 4.03 (3H, s), 3.91-3.72 (1H, m), 2.67-2.15 (2H, m), 1.90-1.83 (1H, m), 1.02-0.89 (4H, m).

EXAMPLE 22

(S)-2-Amino-4-[6-methoxy-4-(1-phenylcarbamoyl-methyl-1H-pyrazol-4-ylamino)-quinolin-7-yloxy]-butyric acid cyclopentyl ester

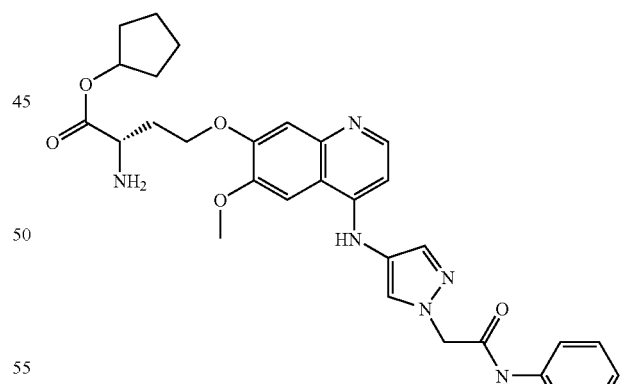

LC/MS purity: 97% (254 nm), m/z 559 [M+H]⁺. ¹H NMR (300 MHz, CD₃OD), δ: 8.30 (1H, d, J=10.5 Hz), 8.11 (1H, s), 8.06 (1H, s), 7.91 (1H, s), 7.45 (1H, s), 7.62 (2H, d), 7.39-7.35 (6H, m), 7.17 (1H, m), 7.00 (1H, d, J=10.5 Hz), 5.32 (1H, m), 5.15 (2H, s), 4.48 (2H, m), 4.09 (3H, s), 2.5 (2H, m), 1.90-1.56 (8H, m), 1.34 (1H, m).

The synthesis of 2-(4-Amino-pyrazol-1-yl)-N-phenyl-acetamide sidechain used in the synthesis of Example 22 is shown below in Scheme 7.

Scheme 7

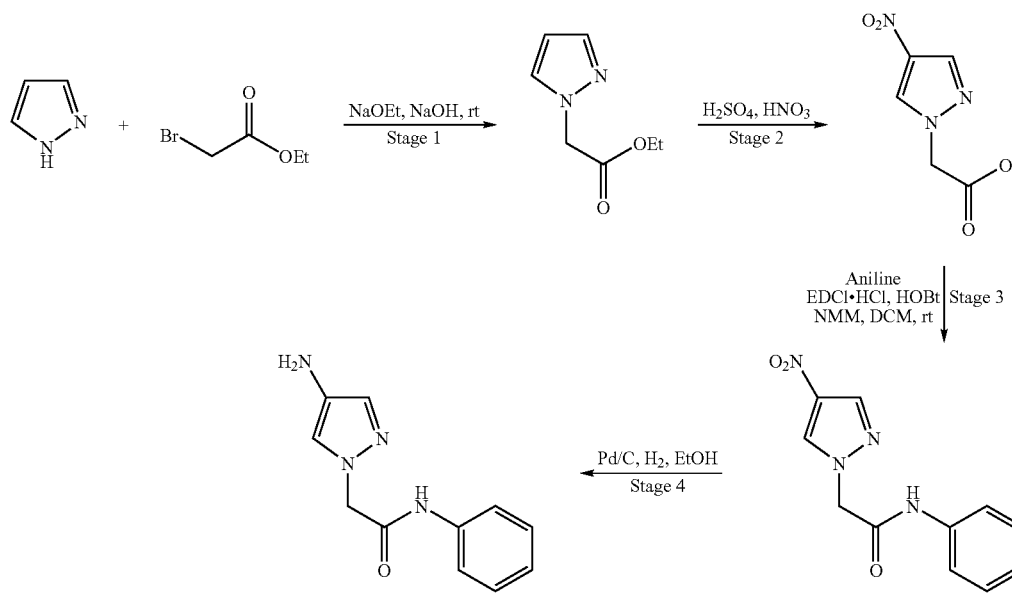

Stage 1-Pyrazol-1-yl-acetic acid ethyl ester

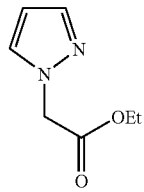

To a solution of pyrazole (38.85 g, 0.57 mol) in ethanol (300 ml) was added sodium ethoxide (46.60 g, 0.69 mol, 1.2 eq) followed by ethylbromoacetate (127 ml, 1.14 mol, 2.0 eq) dropwise over 1 hour. The reaction mixture was stirred at room temperature for 18 hours and concentrated under reduced pressure. The residue was taken up in 6 N HCl (400 ml) and the aqueous solution was washed with diethyl ether (2×400 ml). The diethyl ether extracts were discarded. The aqueous solution was basified to pH=11 with solid $Na_2CO_3$ and extracted with ethyl acetate (3×400 ml). The combined organic extracts were washed with brine (400 ml), dried ($MgSO_4$), filtered and concentrated under reduced pressure to leave a brown oil. Purification by distillation under reduced pressure afforded the title compound as a colourless oil (57.95 g, 66% yield).

$^1$H NMR (300 MHz, $CDCl_3$), δ: 7.51 (1H, d, J=1.2 Hz), 7.43 (1H, d, J=2.1 Hz), 6.28-6.26 (1H, m), 4.87 (2H, s), 4.17 (2H, q, J=7.2 Hz), 1.22 (3H, t, J=7.2 Hz).

Stage 2-(4-Nitro-pyrazol-1-yl)-acetic acid

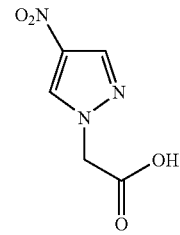

Six conical flasks were charged with pyrazol-1-yl-acetic acid ethyl ester (6×9.66 g, 6×62.6 mmol) and concentrated sulphuric acid (6×20 ml) was added. The solutions were cooled to 0° C. and concentrated nitric acid (6×10 ml) was added dropwise. The reaction mixtures were allowed to warm to room temperature and left standing for 18 hours. The combined organic mixtures were poured into ice (50 ml) and extracted with ethyl acetate (5×500 ml). The combined organic extracts were washed with brine (500 ml), dried ($MgSO_4$), filtered and concentrated under reduced pressure to leave a yellow solid. Recrystallisation from ethyl acetate afforded the title compound as an off-white solid (20.97 g, 33% yield).

$^1$H NMR (300 MHz, DMSO-$d_6$) δ: 13.33 (1H, br s), 8.87 (1H, s), 8.29 (1H, s), 5.08 (2H, s).

LC/MS: m/z 341 [2M−H]$^−$.

Stage 3-2-(4-Nitro-pyrazol-1-yl)-N-phenyl-acetamide

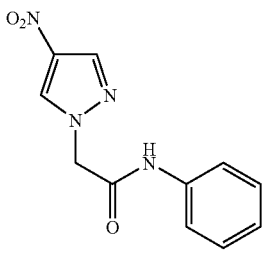

A solution of (4-nitro-pyrazol-1-yl)-acetic acid (10.00 g, 58 mmol), aniline (5.3 ml, 58 mmol, 1.0 eq), EDC (12.30 g, 64 mmol, 1.1 eq), HOBt (8.70 g, 64 mmol, 1.1 eq) and N-methylmorpholine (19.3 ml, 175 mmol, 3.0 eq) in DCM (100 ml) was stirred at room temperature 17 hours. The reaction mixture was washed with water (100 ml). The aqueous layer was separated and extracted with DCM (3×100 ml). The combined organic extracts were washed with 2N HCl (2×100 ml), brine (100 ml), dried (MgSO$_4$), filtered and concentrated under reduced pressure to leave a yellow solid. Purification by column chromatography (60% ethyl acetate in heptane) afforded the title compound as a pale yellow solid (7.28 g, 69% yield).

LC/MS: m/z 247 [M+H]$^+$. $^1$H NMR (300 MHz, CDCl$_3$), δ: 8.36 (1H, s), 8.25 (1H, s), 8.09 (1H, br s), 7.49 (2H, d, J=7.5 Hz), 7.36 (2H, t, J=7.5 Hz), 7.19 (1H, t, J=7.5 Hz), 4.99 (2H, s).

Stage 4-2-(4-Amino-pyrazol-1-yl)-N-phenyl-acetamide

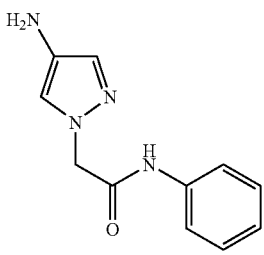

To a solution of 2-(4-nitro-pyrazol-1-yl)-N-phenyl-acetamide (7.28 g, 40 mmol) in ethanol (100 ml) was added Pd/C (1.5 g) and the reaction mixture was stirred at room temperature under an atmosphere of hydrogen for 24 hours. The reaction mixture was filtered through a short pad of Celite, which was then thoroughly washed with ethyl acetate. The combined filtrates were concentrated under reduced pressure to give the title compound as a purple solid (4.60 g, 72% yield).

LC/MS: m/z 217 [M+H]$^+$ and 455 [2M+Na]$^+$. $^1$H NMR (300 MHz, CDCl$_3$) δ: 8.17 (1H, br s), 7.47-7.44 (2H, m), 7.38-7.29 (3H, m), 7.15-7.10 (2H, m), 4.81 (2H, s), 3.03 (2H, br s).

EXAMPLE 23

(S)-2-Amino-4-[6-methoxy-4-(1-phenylcarbamoyl-methyl-1H-pyrazol-4-ylamino)-quinolin-7-yloxy]-butyric acid

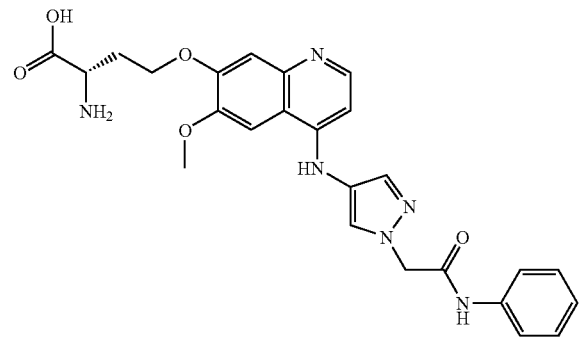

LC/MS purity: 97% (254 nm), m/z 492 [M+H]$^+$. $^1$H NMR (300 MHz, CD$_3$OD), δ: 8.26 (1H, d, J=6.9 Hz), 8.06 (1H, s), 7.89 (1H, s), 7.74 (1H, s), 7.60 (2H, d), 7.37-7.32 (3H, m), 7.14 (1H, m), 6.97 (1H, d, J=6.9 Hz), 5.15 (1H, s), 4.48 (2H, m), 4.24 (1H, m), 4.10 (3H, s), 2.62-2.52 (2H, m).

EXAMPLE 24

(S)-2-Amino-4-(4-{1-[(3-fluoro-phenylcarbamoyl)-methyl]-1H-pyrazol-4-ylamino}-6-methoxy-quinolin-7-yloxy)-butyric acid cyclopentyl ester LC/MS purity: 96%, m/z 602 [M+H]$^+$. $^1$H NMR (300 MHz, CD$_3$OD), δ: 8.80 (1H, s), 8.16 (1H, s), 7.95 (1H, s), 7.81 (1H, s), 7.55 (1H, d, J=11.1 Hz), 7.48 (1H, s), 7.37-7.27 (2H, m), 6.90-6.83 (1H, m), 5.35 (1H, m), 5.15 (2H, s), 4.49

(2H, t, J=5.6 Hz), 4.33 (1H, t, J=6.4 Hz), 4.09 (3H, s), 2.60-2.52 (2H, m), 1.96-1.56 (8H, m).

EXAMPLE 25

(S)-2-Amino-4-[4-(2-benzoylamino-pyrimidin-5-ylamino)-6-methoxy-quinolin-7-yloxy]-butyric acid cyclopentyl ester

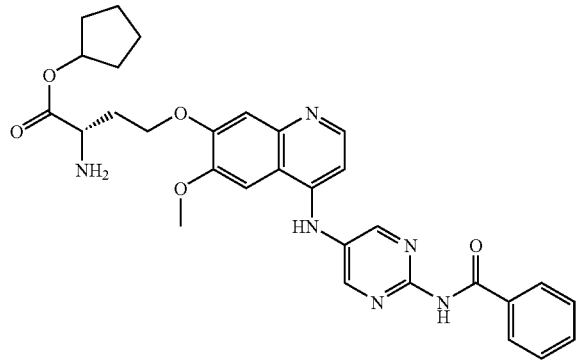

LC/MS purity: 99% (254 nm), m/z 557 [M+H]+. 1H NMR (300 MHz, CD3OD), δ: 8.85 (2H, s), 8.36 (1H, d, J=7.0 Hz), 8.03 (2H, d), 8.02 (1H, s), 7.69-7.55 (3H, m), 7.43 (1H, s), 6.95 (1H, d, J=7.2 Hz), 5.37-5.34 (1H, m), 4.50 (2H, m), 4.35 (1H, m), 4.13 (3H, s), 2.59-2.53 (2H, m), 1.96-1.92 (1H, m), 1.79-1.67 (8H, m).

The synthesis of N-(5-Amino-pyrimidin-2-yl)-benzamide sidechain used in the synthesis of Example 25 is shown below in Scheme 8.

Scheme 8

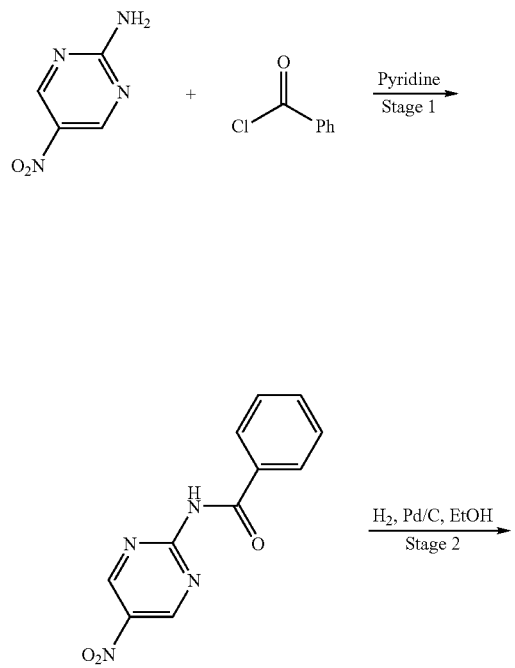

Stage 1-N-(5-Nitro-pyrimidin-2-yl)-benzamide

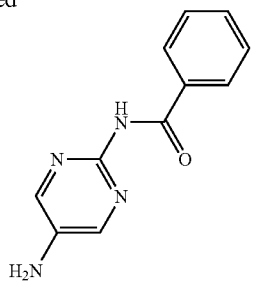

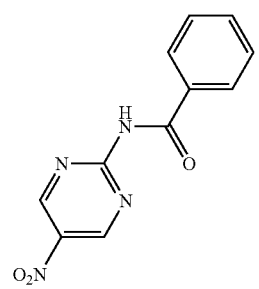

To a solution of 2-amino-5-nitropyrimidine (6.34 g, 45.3 mmol) in pyridine (100 ml) was added benzoyl chloride (5.8 ml, 49.8 mmol, 1.1 eq) dropwise over 10 minutes. The reaction mixture was refluxed for 6 hours, poured into ice (800 ml) and allowed to stand overnight. A brown solid was collected by filtration, washed with water and taken up in DCM (500 ml). The solution was washed with brine (3×200 ml), dried (MgSO4), filtered and concentrated under reduced pressure to leave a brown solid. Purification by column chromatography (1% methanol in DCM), afforded the title compound as a thick yellow oil (5.14 g, 47% yield).

LC/MS: m/z 245 [M+H]+ and 511 [2M+Na]+.

Stage 2-N-(5-Amino-pyrimidin-2-yl)-benzamide

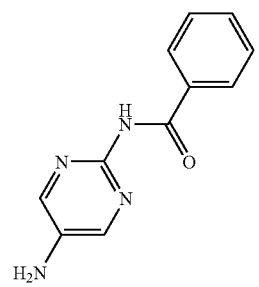

To a solution of N-(5-nitro-pyrimidin-2-yl)-benzamide (5.14 g, 21.0 mmol) in ethanol (250 ml) was added Pd/C (1.03 g) and the reaction mixture was stirred at room temperature under an atmosphere of hydrogen for 20 hours. The reaction mixture was filtered through Celite, which was then washed with ethyl acetate. The combined filtrates were concentrated under reduced pressure to leave a yellow solid. Purification by column chromatography (5-10% methanol in DCM) provided the title compound as a yellow solid (3.30 g, 73% yield).

LC/MS: m/z 215 [M+H]+.

EXAMPLE 26

(S)-2-Amino-4-[4-(2-benzoylamino-pyrimidin-5-ylamino)-6-methoxy-quinolin-7-yloxy]-butyric acid

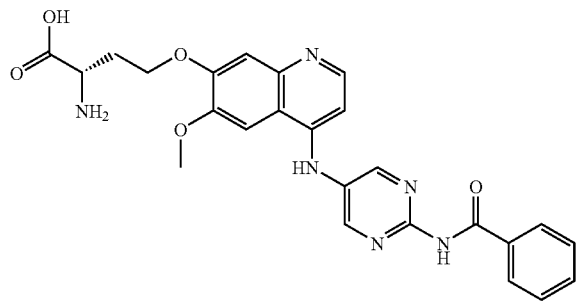

LC/MS purity: 94% (254 nm), m/z 489 [M+H]$^+$.

The following example was prepared by methods outlined in Scheme 9 in the preparation of intermediate B. Synthetic methods used are detailed in WO98/43960 and *J. Med. Chem.* 2004, 3 (17), 3244-3256.

This key intermediate is then used as detailed in Scheme 10 for the synthesis of Example 27.

EXAMPLE 27

(S)-2-Amino-4-[4-(4-benzoylamino-phenoxy)-3-cyano-6-methoxy-quinolin-7-yloxy]-butyric acid cyclopentyl ester

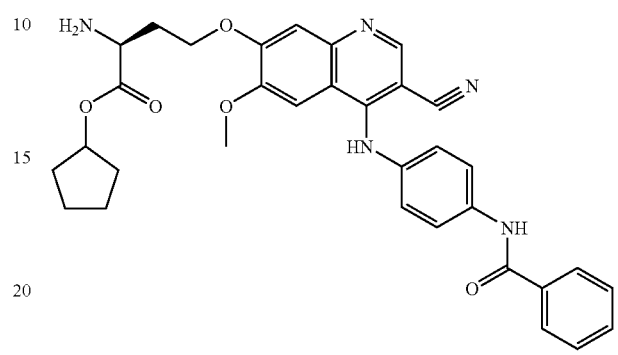

LC/MS purity: 98%, m/z 579 [M+H]$^+$. $^1$H NMR (300 MHz, CD$_3$OD), δ: 8.75 (1H, br s), 8.00-7.90 (6H, m), 7.65-7.42 (6H, m), 5.40-5.30 (1H, m), 4.47 (2H, br s), 4.31 (1H, br s), 4.06 (3H, s), 2.55 (2H, br s), 2.0-1.60 (8H, m).

Scheme 9

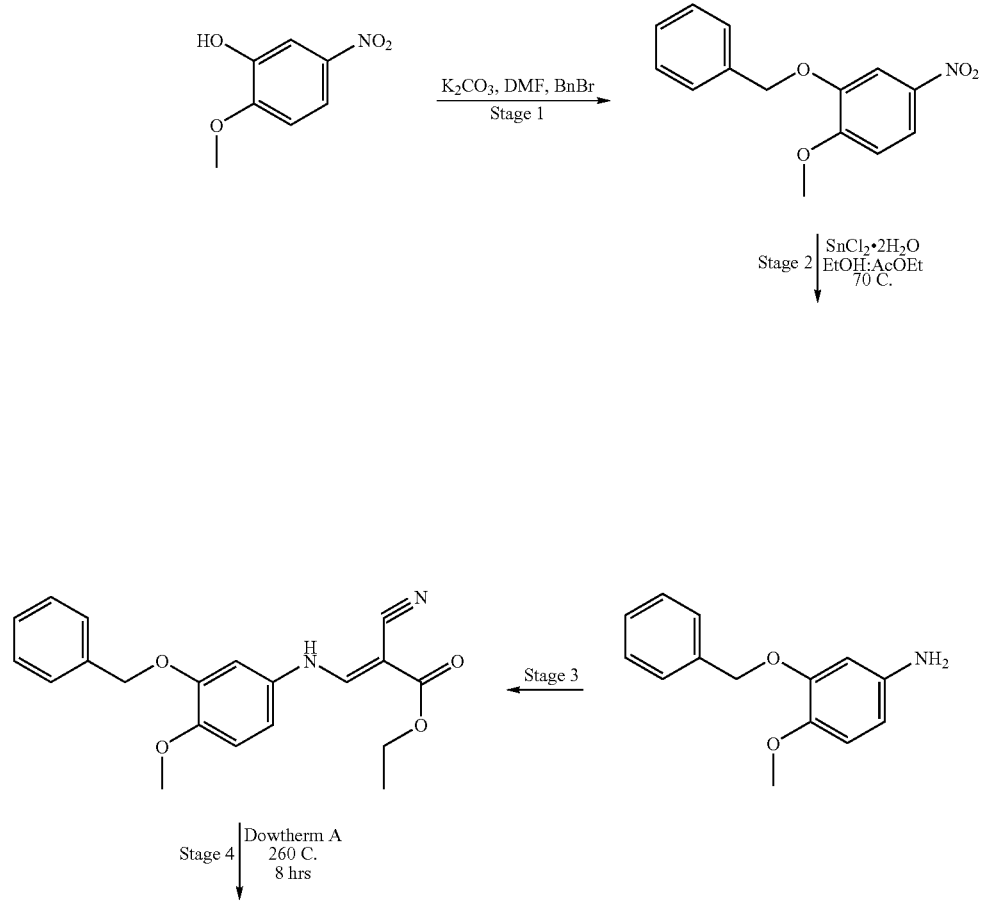

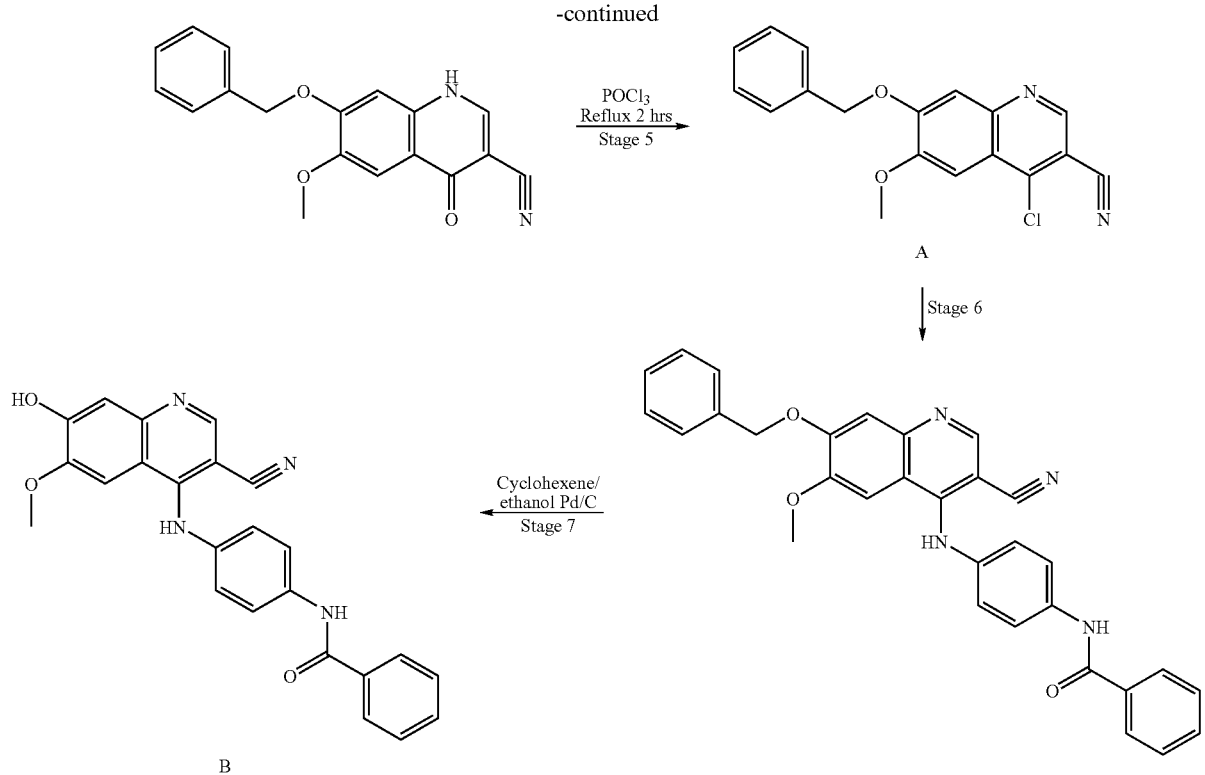

A

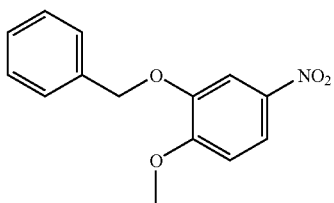

B

Stage 1-2-(Benzyloxy)-1-methoxy-4-nitrobenzene

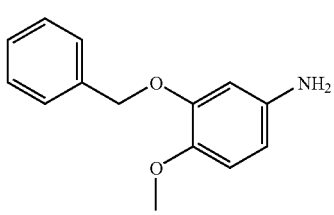

To a solution of 2-methoxy-5-nitrophenol (5.0 g, 29.6 mmol) in anhydrous DMF (60 ml) was added $K_2CO_3$ (4.49 g, 32.5 mmol) and benzyl bromide (3.87 ml, 32.5 mmol). The mixture was stirred at ambient temperature under argon atmosphere for 18 hours. The reaction mixture was poured into water (100 ml) and extracted with DCM (3×100 ml). The combined organic extracts were dried over magnesium sulphate and concentrated under reduced pressure. The residue was purified by flash column chromatography (2:8 EtOAc: Heptane) to provide the title compound as a yellow solid (7.46 g, 97% yield).

$^1$H NMR (300 MHz, DMSO-$d_6$), δ: 7.93 (1H, dd, J=2.6, 9.3 Hz), 7.85 (1H, d, J=2.6 Hz), 7.5-7.3 (5H, m), 7.2 (1H, d, J=9.3 Hz), 5.22 (2H, s), 3.91 (1H, s).

Stage 2-3-(Benzyloxy)-4-methoxy-phenylamine 2-(Benzyloxy)-1-methoxy-4-nitro benzene (7.45 g, 28.7 mmol) was dissolved in EtOH:EtOAc (150 ml). The solution was heated to 70° C., and $SnCl_2.2H_2O$ (28.5 g, 126 mmol) was added. The reaction mixture was stirred for 7 hours, cooled to room temperature, diluted with water (230 ml), and carefully neutralised by addition of solid $NaHCO_3$. The aqueous layer was extracted with ethyl acetate (2×400 ml) and the organic layer washed with water (300 ml), brine (300 ml), dried over magnesium sulphate and concentrated under reduced pressure. The residue was purified by column chromatography (1:1 EtOAc:Heptane) to provide the title compound as a brown solid (3.84 g, 59% yield).

LC/MS purity: 93%. $^1$H NMR (300 MHz, DMSO-$d_6$), δ: 7.5-7.25 (5H, m), 6.66 (1H, d, J=8.2 Hz), 6.34 (1H, d, J=2.6 Hz), 6.08 (1H, dd, J=8.1, 2.6 Hz), 4.97 (2H, s), 4.65 (2H, br s), 3.62 (3H, s).

Stage 3-(E)-3-(3-Benzyloxy-4-methoxy-phenylamino)-2-cyano-acrylic acid ethyl ester

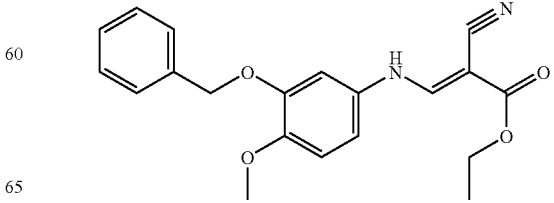

A mixture of 3-(benzyloxy)-4-methoxy-phenylamine (3.84 g, 16.7 mmol) and ethyl (ethoxymethylene) cyanoacetate (2.83 g, 16.7 mmol) in toluene (10.5 ml) was heated at 100° C. for 1 hour and 125° C. for 15 minutes. The reaction mixture was cooled and concentrated in vacuo. The residue was recrystallised from ethyl acetate (20 ml) and the solid washed with heptane. Further product was obtained by addition of heptane to the ethyl acetate filtrate.

The title compound was obtained as a brown solid (4.5 g, 90% yield).

LC/MS purity: 95%, m/z 353 [M+H]$^+$.

Stage 4-7-Benzyloxy-6-methoxy-4-oxo-1,4-dihydro-quinoline-3-carbonitrile

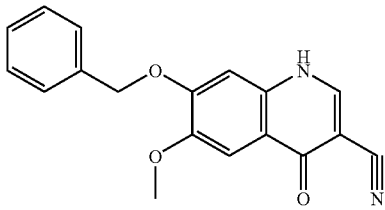

A mixture of (E)-3-(3-benzyloxy-4-methoxy-phenylamino)-2-cyano-acrylic acid ethyl ester (1.7 g, 4.82 mmol) and Dowtherm A (35 ml) was refluxed for 8 hours, cooled and diluted with heptane (35 ml). The precipitate was filtered, washed with heptane followed by DCM and dried under reduced pressure to provide the title compound as a black solid (1.44 g, 50% yield).

LC/MS purity: 66%, m/z 307 [M+H]$^+$. $^1$H NMR (300 MHz, DMSO-d$_6$), δ: 12.61 (1H, br s), 8.59 (1H, s), 7.55-7.35 (6H, m), 7.17 (1H, s), 5.22 (2H, s), 3.87 (3H, s).

Stage 5-7-Benzyloxy-4-chloro-6-methoxy-quinoline-3-carbonitrile

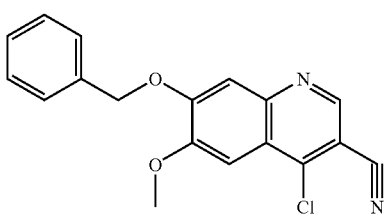

A stirred mixture of 7-benzyloxy-6-methoxy-4-oxo-1,4-dihydro-quinoline-3-carbonitrile (1.77 g, 5.78 mmol) and phosphorous oxylchloride (10 ml) was refluxed for 2 hours, cooled and concentrated in vacuo. The residue was stirred for 30 minutes in DCM-water at 0° C. and solid Na$_2$CO$_3$ was added. The organic layer was washed with H$_2$O (100 ml), dried and concentrated in vacuo to provide the title compound (1.1 g, 59% yield).

LC/MS purity: 89%, m/z 325 [M+H]$^+$. $^1$H NMR (300 MHz, DMSO-d$_6$), δ: 8.99 (1H, s), 7.68 (1H, s), 7.55-7.35 (6H, m), 5.38 (2H, s), 4.02 (3H, s).

Stage 6-N-[4-(7-Benzyloxy-3-cyano-6-methoxy-quinolin-4-ylamino)-phenyl]-benzamid

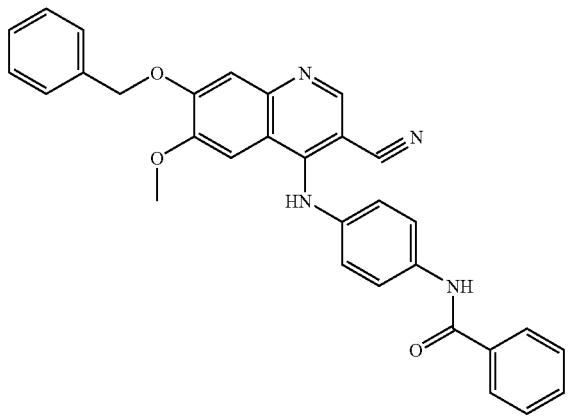

A mixture of 7-benzyloxy-4-chloro-6-methoxy-quinoline-3-carbonitrile (1.1 g, 3.39 mmol), N-(4-amino-phenyl)-benzamide* (Scheme 3) (0.79 g, 3.73 mmol) and pyridine (274 μL, 33.39 mmol) in EtOH (20 ml) was refluxed for 4 hours. The reaction mixture was cooled, concentrated under reduced pressure and the residue partitioned between DCM and saturated aqueous NaHCO$_3$. The aqueous layer was extracted several times with DCM and the combined organic extracts were dried over magnesium sulphate and concentrated under reduced pressure. The residue was purified by column chromatography (1:1 EtOAc:Heptane) to provide the title compound (743 mg). The aqueous layer was filtered to provide further material (526 mg).

LC/MS purity: 92%, m/z 501 [M+H]$^+$. $^1$H NMR (300 MHz, DMSO-d$_6$), δ: 10.35 (1H, s), 9.55 (1H, br s), 8.37 (1H, s), 8.02-7.93 (2H, m), 7.88-7.78 (2H, m), 7.60-7.32 (10H, m), 7.24 (2H, d, J=8.5 Hz), 5.30 (2H, s), 3.93 (3H, s).

Stage 7-N-[4-(3-Cyano-7-hydroxy-6-methoxy-quinolin-4-ylamino)-phenyl]-benzamide

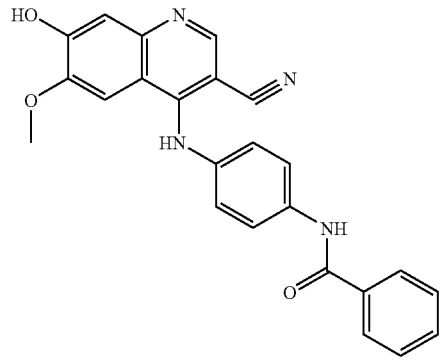

A mixture of N-[4-(7-benzyloxy-3-cyano-6-methoxy-quinolin-4-ylamino)-phenyl]-benzamide (100 mg, 0.200 mmol) and 10% Pd/C (20 mg) in 10% cyclohexene (100 μl) in EtOH (900 μl) was refluxed for 18 hours. The mixture was cooled, filtered through Celite and washed several times with EtOH and MeCN. The solution was concentrated under reduced pressure to provide the title compound as a yellow solid (842 mg, 89% yield).

LC/MS purity: 93%, m/z 411 [M+H]$^+$. $^1$H NMR (300 MHz, DMSO-d$_6$), δ: 10.35 (1H, s), 9.40 (1H, br s), 8.33 (1H, s), 8.01-7.94 (2H, m), 7.88-7.80 (2H, m), 7.74 (1H, s), 7.62-7.47 (3H, m), 7.28-7.18 (2H, m), 7.15 (1H, s), 3.91 (3H, s).

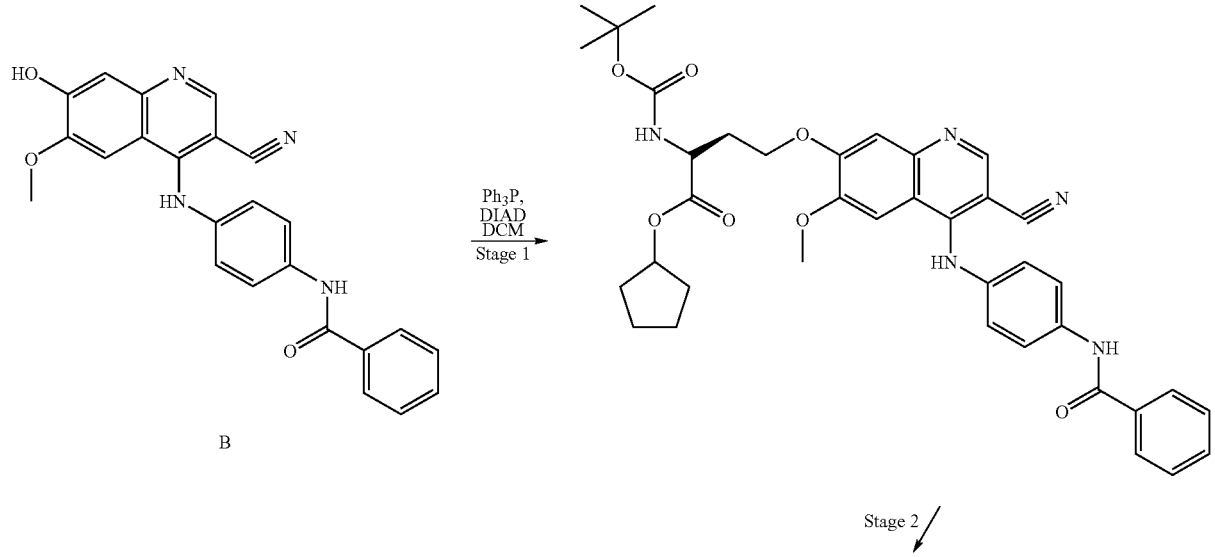

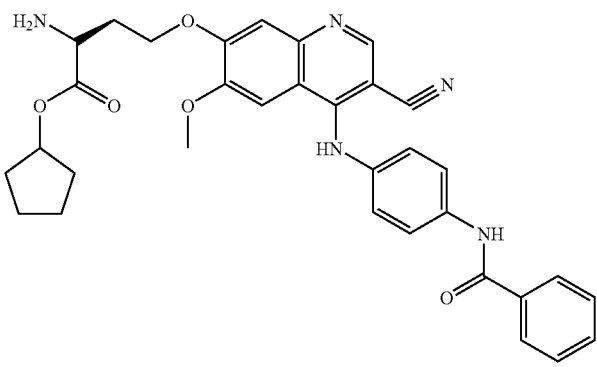

EXAMPLE 28

(S)-4-[(4-(4-Benzoylamino-phenylamino)-3-cyano-6-methoxy-quinolin-7-yloxy]-2-tert-butoxycarbonylamino-butyric acid cyclopentyl ester

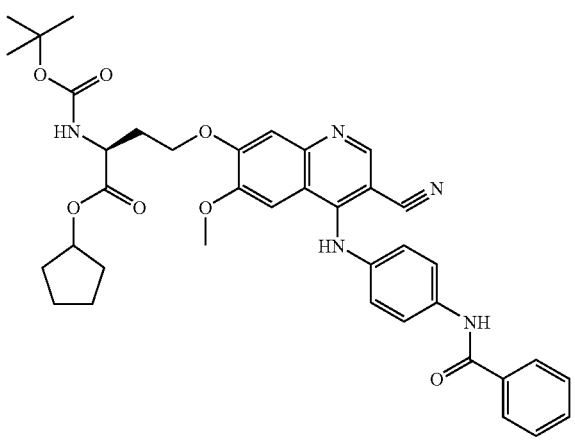

Stage 1-(S)-4-[4-(4-Benzoylamino-phenylamino)-3-cyano-6-methoxy-quinolin-7-yloxy]-2-tert-butoxycarbonylamino-butyric acid cyclopentyl ester To a mixture of N-[4-(3-cyano-7-hydroxy-6-methoxy-quinolin-4-ylamino)-phenyl]-benzamide mg, 0.244 mmol), triphenylphosphine (262 mg, 0.999 mmol), (S)-2-tert-butoxycarbonylamino-4-hydroxy-butyric acid cyclopentyl ester (105 mg, 0.365 mmol) in DCM, at 0° C., was added DIAD (194 µl, 0.999 mmol). The reaction mixture was stirred at 0° C. for 30 minutes, then warmed to room temperature over 18 hours. The reaction was concentrated in vacuo and the residue purified by column chromatography (1:1 to 2:1 EtOAc:Heptane) to provide the title compound as a white solid (25 mg).

LC/MS purity: 98%, m/z 680 [M+H]$^+$. $^1$H NMR (300 MHz, CD$_3$OD), δ: 8.41 (1H, s), 7.90-7.87 (2H, m), 7.82 (2H, d, J=8.8 Hz), 7.66 (1H, s), 7.61-7.49 (3H, m), 7.33 (2H, d, J=8.8 Hz), 7.27 (1H, br s), 5.25-5.15 (1H, m), 4.46-4.14 (3H, m), 4.00 (3H, s), 2.49-2.33 (1H, m), 2.31-2.18 (1H, m), 1.88-1.77 (2H, m), 1.72-1.54 (6H, m), 1.46 (9H, s).

Stage 2-(S)-2-Amino-4-[4-(4-benzoylamino-phenylamino)-3-cyano-6-methoxy-quinolin-7-yloxy]-butyric acid cyclopentyl ester

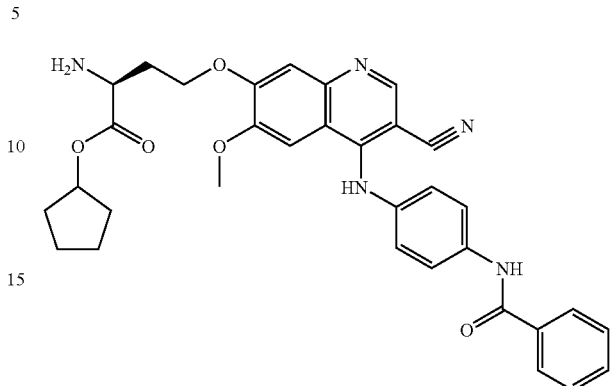

A mixture of (S)-4-[4-(4-benzoylamino-phenylamino)-3-cyano-6-methoxy-quinolin-7-yloxy]-2-tert-butoxycarbonylamino-butyric acid cyclopentyl ester in 50% TFA/DCM (10 ml) was stirred at room temperature for 18 hours. The reaction was concentrated in vacuo and residual TFA removed by azeotroping with DCM to provide the title compound (example 27) as a yellow solid (22 mg).

Example 29 was prepared by methods outlined in Scheme 11 for the synthesis of the key 7-benzyloxy-4-chloro-6-methoxy-quinazoline intermediate. This intermediate was then used as detailed in Scheme 12.

EXAMPLE 29

(S)-2-Amino-4-[4-(4-benzoylamino-phenylamino)-6-methoxy-quinazolin-7-yloxy]-butyric acid cyclopentyl ester

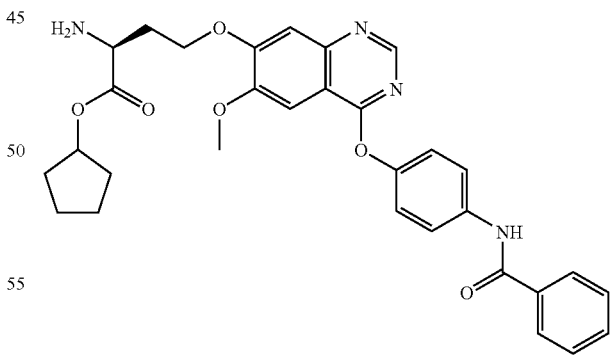

LC/MS purity: 96%, m/z 556 [M+H]$^+$. $^1$H NMR (300 MHz, CD$_3$OD) δ: 8.69 (1H, br s), 7.99-7.96 (2H, m), 7.93-7.85 (2H, m), 7.77 (1H, s), 7.66-7.51 (3H, m), 7.44 (1H, s), 7.36-7.31 (2H, m), 5.37-5.32 (1H, m), 4.82 (2H, t, J=5.6 Hz), 4.35 (1H, t, J=6.5 Hz), 4.11 (3H, s), 2.64-2.49 (2H, m), 2.01-1.89 (2H, m), 1.79-1.64 (6H, m).

Scheme 11

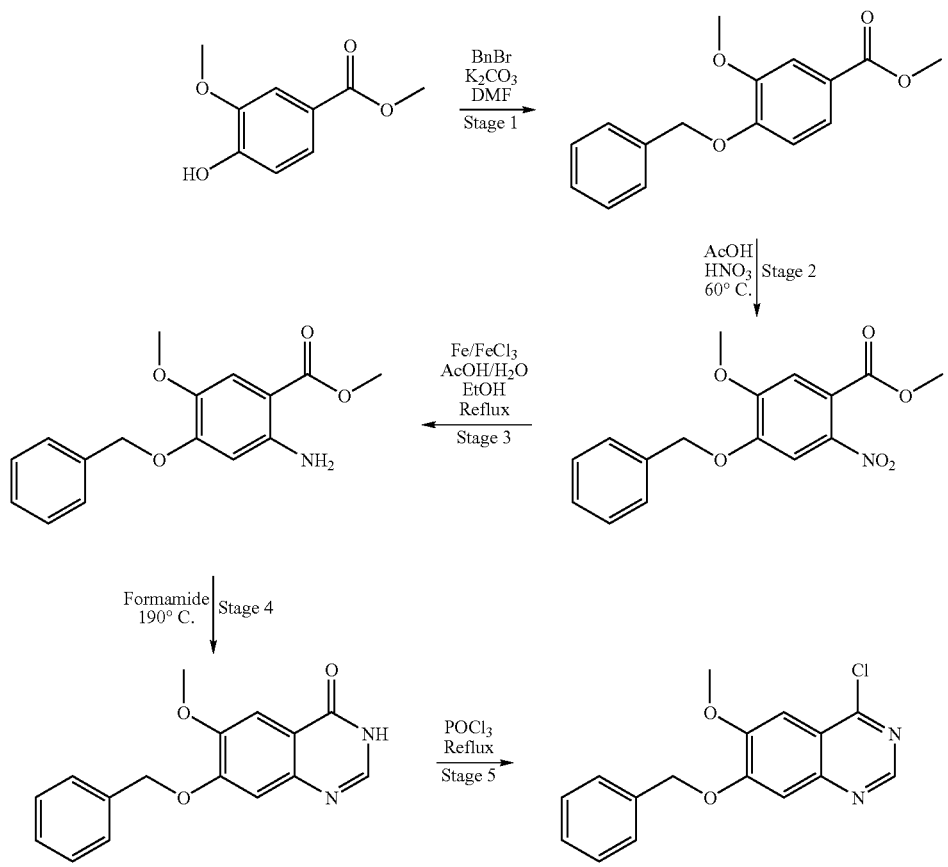

Stage 1-4-Benzyloxy-3-methoxy-benzoic acid methyl ester

To a solution of methyl vanillate (5.0 g, 27.4 mmol) in DMF (50 ml) was added K$_2$CO$_3$ (4.92 g, 35.6 mmol) and benzyl bromide (3.9 ml, 32.9 mmol). The reaction was stirred at room temperature, under nitrogen, for 4 hours, poured into water (100 ml) and stirred for 30 minutes. The aqueous layer was extracted with EtOAc and the organic washed with saturated aqueous NaHCO$_3$, water, brine, dried (MgSO$_4$) and concentrated. The residue was recrystallised from heptane to provide the title compound as a cream coloured solid (6.35 g).

LC/MS purity: 100%, m/z 566 [M+H]$^+$. $^1$H NMR (400 MHz, CDCl$_3$) δ: 7.60 (1H, dd, J=8.2, 8.5 Hz), 7.56 (1H, d, J=2.2 Hz), 7.45-7.41 (2H, m), 7.40-7.35 (2H, m), 7.34-7.29 (1H, m), 6.89 (1H, d, J=8.5 Hz), 5.22 (2H, s), 3.94 (3H, s), 3.88 (3H, s).

Stage 2-4-Benzyloxy-5-methoxy-2-nitro-benzoic acid methyl ester

To a solution of 4-benzyloxy-3-methoxy-benzoic acid methyl ester (7.08 g, 26 mmol) in acetic acid (50 ml), at 0° C., was added dropwise nitric acid (7 ml) over 10 minutes. The reaction mixture was warmed to room temperature and then stirred at 60° C. for 1 hour. The reaction mixture was poured into water, extracted with DCM (3×125 ml) and the combined organic extracts were washed with water, saturated aqueous NaHCO$_3$, brine, dried (MgSO$_4$) and concentrated to provide the title compound as a pale yellow solid (7.5 g).

LC/MS purity: 95%, m/z 318 [M+H]$^+$. $^1$H NMR (300 MHz, CDCl$_3$) δ: 7.55 (1H, s), 7.53-7.39 (5H, m), 7.11 (1H, s), 5.23 (2H, s), 3.99 (3H, s), 3.92 (3H, s).

Stage 3-2-Amino-4-benzyloxy-5-methoxy-benzoic acid methyl ester

A mixture of 4-benzyloxy-5-methoxy-2-nitro-benzoic acid methyl ester (6.00 g, 18.91 mmol), iron powder (5.91 g, 105.9 mmol) and iron (III) chloride (307 mg, 1.89 mmol) in EtOH (12 ml), acetic acid (48 ml) and water (2.4 ml) was heated at reflux for 4 hours. The reaction mixture was cooled, filtered and the solids washed with EtOAc. The filtrate was concentrated and the residue purified by column chromatography (15-70% EtOAc:Heptane) to provide the title compound as a pale yellow solid (5.09 g).

LC/MS purity: 92%, m/z 288.1 [M+H]$^+$. $^1$H NMR (300 MHz, CDCl$_3$) δ: 7.53-7.31 (6H, m), 6.33 (1H, s), 5.10 (2H, s), 3.94 (3H, s), 3.90 (3H, s).

Stage 4-7-Benzyloxy-6-methoxy-3H-quinazolin-4-one

A mixture of 2-amino-4-benzyloxy-5-methoxy-benzoic acid methyl ester (5.09 g, 17.7 mmol) in formamide (50 ml) was heated at 190° C. for 5 hours. The reaction mixture was cooled, poured into water and NaCl was added. The precipitate was filtered, washed with water and dried under reduced pressure to provide the title compound as a tan brown solid (4.0 g).

LC/MS purity: 98%, m/z 283 [M+H]⁺. ¹H NMR (300 MHz, DMSO-d₆) δ: 12.10 (1H, br s), 7.98 (1H, s), 7.51-7.33 (5H, m), 7.23 (1H, s), 5.26 (2H, s), 3.88 (3H, s).

Stage 5-7-Benzyloxy-4-chloro-6-methoxy-quinazoline

A mixture of 7-benzyloxy-6-methoxy-3H-quinazolin-4-one (1.60 g, 5.67 mmol) in POCl₃ (16 ml) was refluxed for 3 hours, cooled, concentrated under reduced pressure and azeotroped with toluene (2×30 ml). The residue was dissolved in EtOAc/DCM (1:1), washed with brine, dried (MgSO₄) and concentrated to provide the title compound as an orange solid (1.02 g).

LC/MS purity: 95%, m/z 301 [M+H]⁺. ¹H NMR (300 MHz, DMSO-d₆) δ: 8.88 (1H, s), 7.58-7.36 (6H, m), 5.38 (2H, s), 4.00 (3H, s).

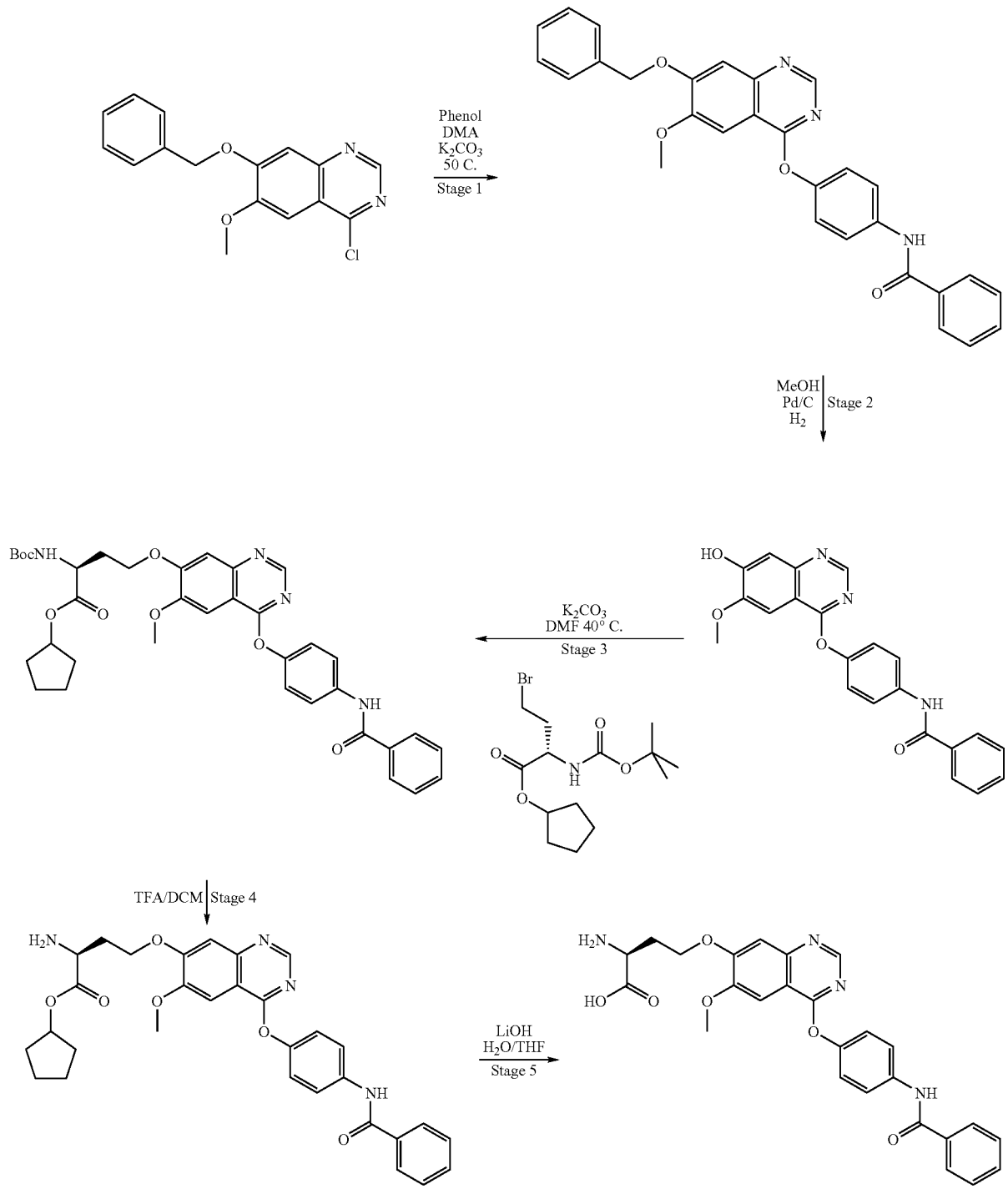

Scheme 12

Stage 1-N-[4-(7-Benzyloxy-6-methoxy-quinazolin-4-yloxy)-phenyl]-benzamide

A mixture of 7-benzyloxy-4-chloro-6-methoxy-quinazoline (100 mg, 0.333 mmol), K₂CO₃ (345 mg, 2.49 mmol) and N-(4-hydroxy-phenyl)-benzamide (106 mg, 0.499 mmol) in DMA was heated at 50° C. for 18 hours. The reaction was cooled and partitioned between ice water and EtOAc. The aqueous was extracted twice with EtOAc and the combine organic washed with water, brine, dried and concentrated. The residue was purified by column chromatography (30-100% EtOAc:Heptane) to provide the title compound as a cream solid (120 mg).

LC/MS purity: 98%, m/z 478 [M+H]⁺. ¹H NMR (300 MHz, DMSO-d₆) δ: 10.37 (1H, s), 8.55 (1H, s), 8.00 (2H, d, J=6.2 Hz), 7.88 (2H, d, J=9.0 Hz), 7.66-7.35 (12H, m), 7.31 (2H, d, J=9.0 Hz), 5.36 (2H, s), 3.93 (3H, s).

Stage 2-N-[4-(7-Hydroxy-6-methoxy-quinazolin-4-yloxy)-phenyl]-benzamide

A mixture of N-[4-(7-benzyloxy-6-methoxy-quinazolin-4-yloxy)-phenyl]-benzamide (120 mg, 0.251 mmol) and 10% Pd/C was stirred under H₂ atmosphere for 1 hour, filtered through celite, washed with MeOH and concentrated in vacuo to provide the title compound as a pale yellow solid (81 mg).

LC/MS purity: 90%, m/z 388 [M+H]⁺. ¹H NMR (300 MHz, DMSO-d₆) δ: 10.36 (1H, s), 8.46 (1H, s), 8.00-7.90 (2H, m), 7.87 (2H, d, J=9.0 Hz), 7.62-7.52 (5H, m), 7.28 (2H, d, J=9.0 Hz), 7.20 (1H, br s), 3.99 (3H, s).

Stage 3-(S)-4-[4-(4-benzoylamino-phenoxy)-6-methoxy-quinazolin-7-yloxy]-2-tert-butoxycarbonylamino-butyric acid cyclopentyl ester A mixture of N-[4-(7-hydroxy-6-methoxy-quinazolin-4-yloxy)-phenyl]-benzamide (71 mg, 0.183 mmol), K₂CO₃ (33 mg, 0.238 mmol) and (S)-4-bromo-2-tert-butoxycarbonylamino-butyric acid cyclopentyl ester (71 mg, 0.202 mmol) in DMF (5 ml) was heated at 40° C. for 18 hours. The reaction mixture was cooled, partitioned between EtOAc/H₂O and the organic dried and concentrated. The residue was purified by column chromatography (60-90% EtOAc:Heptane) to provide the title compound as a white solid (102 mg).

¹H NMR (300 MHz, CDCl₃) δ: 8.64 (1H, s), 8.00-7.90 (3H, m), 7.85-7.76 (2H, m), 7.65-7.50 (4H, m), 7.35-7.25 (3H, m), 6.10-6.00 (1H, m), 5.30-5.20 (1H, m), 4.65-4.50 (1H, m), 4.45-4.30 (1H, m), 4.25-4.15 (1H, m), 4.02 (3H, s), 2.55-2.35 (2H, m), 1.90-1.50 (17H, m).

Stage 4-(S)-2-Amino-4-[4-(4-benzoylamino-phenoxy)-6-methoxy-quinazolin-7-yloxy]-butyric acid cyclopentyl ester To a solution of (S)-4-[4-(4-benzoylamino-phenoxy)-6-methoxy-quinazolin-7-yloxy]-2-tert-butoxycarbonylamino-butyric acid cyclopentyl ester (100 mg, 0.152 mmol) in DCM (5 ml) was added TFA (5 ml). The reaction was stirred for 3 hours, concentrated, azeotroped with DCM (2×20 ml). The resulting solid was partitioned between EtOAc/H₂O. The organic layer was separated, dried (MgSO₄) and concentrated under reduced pressure. The residue was purified by preparative HPLC to provide the title compound as a yellow oil (33 mg).

EXAMPLE 30

(S)-2-Amino-4-[4-(4-benzoylamino-phenoxy)-6-methoxy-quinazolin-7-yloxy]-butyric acid

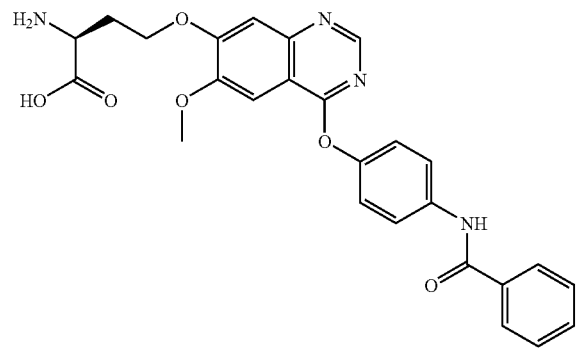

Stage 5: To a mixture of (S)-2-amino-4-[4-(4-benzoylamino-phenoxy)-6-methoxy-quinazolin-7-yloxy]-butyric acid cyclopentyl ester (25 mg, 0.045 mmol) in THF/H₂O (4 ml, 1:1) was added lithium hydroxide (5.4 mg, 0.225 mmol) and the mixture was stirred for 18 hours, acidified and concentrated under reduced pressure. The residue was purified by preparative HPLC to provide the title compound as a white solid (8 mg).

LC/MS purity: 90%, m/z 488 [M+H]⁺.

Example 31 was synthesised according to the procedure shown in Scheme 13.

EXAMPLE 31

(S)-2-Amino-4-[4-(2-benzoylamino-pyrimidin-5-ylamino)-6-methoxy-quinazolin-7-yloxy]-butyric acid cyclopentyl ester

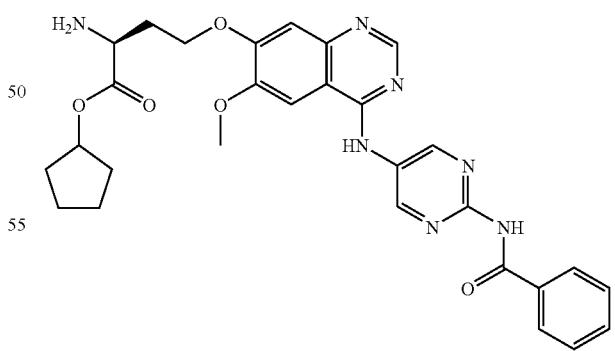

LC/MS purity: 98%, m/z 558 [M+H]⁺. ¹H NMR (300 MHz, DMSO-d₆) δ: 11.0 (1H, br s), 9.81 (1H, br s), 9.14 (2H, s), 8.51 (1H, s), 8.00 (2H, d, J=7.2 Hz), 7.85 (1H, s), 7.62-7.50 (3H, m), 7.23 (1H, s), 5.11-5.06 (1H, m), 4.29-4.23 (2H, m), 3.99 (3H, s), 3.50 (1H, dd, J=3.6, 5.1 Hz), 2.20-2.05 (1H, m), 1.93-1.72 (3H, m), 1.70-1.48 (6H,m).

Scheme 13

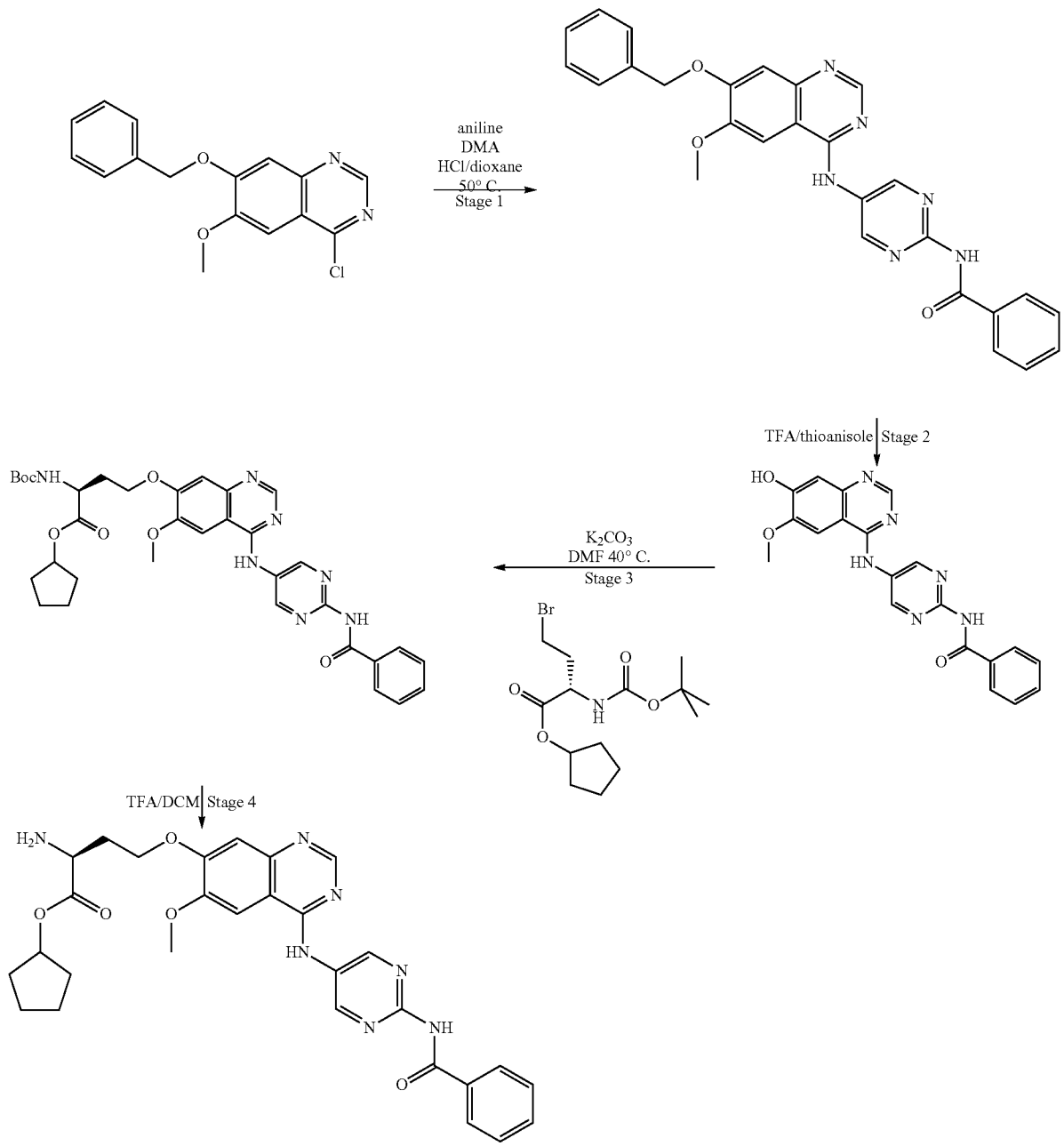

Stage 1-N-[5-(7-Benzyloxy-6-methoxy-quinazolin-4-ylamino)-pyrimidin-2-yl]-benzamide Dihydrochloride To a solution of 7-benzyloxy-4-chloro-6-methoxy-quinazoline (760 mg, 2.53 mmol) and N-(5-amino-pyrimidin-2-yl)-benzamide (542 mg, 2.53 mmol) in DMA was added 4N HCl in dioxane (822 µl, 3.29 mmol) and the reaction heated at 50° C. for 4 hours under nitrogen. The reaction was cooled and filtered. The precipitate was washed with Et$_2$O and dried under reduced pressure to provide the title compound as a light tan brown solid (706 mg).

LC/MS purity: 95%, m/z 479 [M+H]$^+$.

Stage 2-N-[5-(7-Hydroxy-6-methoxy-quinazolin-4-ylamino)-pyrimidin-2-yl]-benzamide dihydrochloride A mixture of N-[5-(7-benzyloxy-6-methoxy-quinazolin-4-ylamino)-pyrimidin-2-yl]-benzamide dihydrochloride (706 mg, 1.28 mmol) in TFA (20 ml) was refluxed for 2 hours, cooled and concentrated under reduced pressure and azeotroped with DCM. The resulting solid was stirred in Et$_2$O, filtered and dried to provide the title compound as a light tan brown solid (670 mg).

LC/MS purity: 90%, m/z 389 [M+H]$^+$.

Stage 3-(S)-4-[4-(2-Benzoylamino-pyrimidin-5-ylamino)-6-methoxy-quinazolin-7-yloxy]-2-tert-butoxycarbonylamino-butyric acid cyclopentyl ester To a mixture of N-[5-(7-hydroxy-6-methoxy-quinazolin-4-ylamino)-pyrimidin-2-yl]-benzamide dihyhydrochloride (100 mg, 0.162 mmol) and $K_2CO_3$ (90 mg, 0.649 mmol) in DMF (4 ml) was added (S)-4-bromo-2-tert-butoxycarbonylamino-butyric acid cyclopentyl ester (63 mg, 0.178 mmol) and the mixture heated at 40° C. for 18 hours. The reaction was cooled, diluted with water and the precipitate filtered. The solid was washed with water, $Et_2O$, dried and purified by column chromatography (4% MeOH in DCM) to provide the title compound as a yellow solid (102 mg).

LC/MS purity: 95%, m/z 658 [M+H]$^+$. $^1$H NMR (300 MHz, CDCl$_3$) δ: 9.16 (2H, s), 8.83 (1H, s), 8.45 (1H, s), 7.80 (2H, d, J=7.8 Hz), 7.63-7.44 (5H, m), 7.04 (1H, s), 5.95 (1H, br d, J=7.8 Hz), 5.20-5.10 (1H, m), 4.55-4.45 (1H, m), 4.20-4.15 (1H, m), 4.10-4.00 (1H, m), 3.66 (3H, s), 2.40-2.28 (2H, m), 1.90-1.50 (8H, m), 1.42 (9H, s).

Stage 4-(S)-2-Amino-4-[4-(2-benzoylamino-pyrimidin-5-ylamino)-6-methoxy-quinazolin-7-yloxy]-butyric acid cyclopentyl ester To a solution of (S)-4-[4-(2-benzoylamino-pyrimidin-5-ylamino)-6-methoxy-quinazolin-7-yloxy]-2-tert-butoxycarbonylamino-butyric acid cyclopentyl ester (102 mg, 0.155 mmol) in DCM (5 ml) was added TFA (5 ml). The reaction was stirred for 18 hours, concentrated, azeotroped with DCM and $Et_2O$. The resulting solid was dried under high vacuum to provide the title compound as a yellow solid (109 mg).

The synthesis of Example 32 is detailed in Scheme 14 using 7-Benzyloxy-6-methoxy-1H-quinolin-4 already described in US006143764A (Kirin Beer Kabushiki Kaisha).

EXAMPLE 32

(S)-4-[4-(4-Benzoylamino-phenoxy)-3-bromo-6-methoxy-quinolin-7-yloxy]-2-tert-butoxycarbonylamino-butyric acid cyclopentyl ester

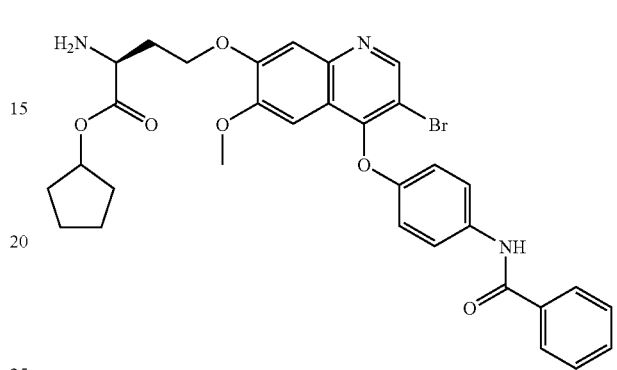

LC/MS purity: 96%, m/z 636 [M+H]$^+$. $^1$H NMR (300 MHz, DMSO-d$_6$) δ: 10.29 (1H, s), 8.92 (1H, s), 8.64 (3H, br s), 7.95 (2H, d, J=8.4 Hz), 7.75 (2H, d, J=9.3 Hz), 7.62-7.50 (5H, m), 7.15 (1H, s), 6.91 (2H, d, J=9.3 Hz), 5.25-5.10 (1H, m), 4.45-4.30 (2H, m), 3.78 (3H, s), 2.41-2.30 (2H, m), 1.90-1.40 (8H, m).

Scheme 14

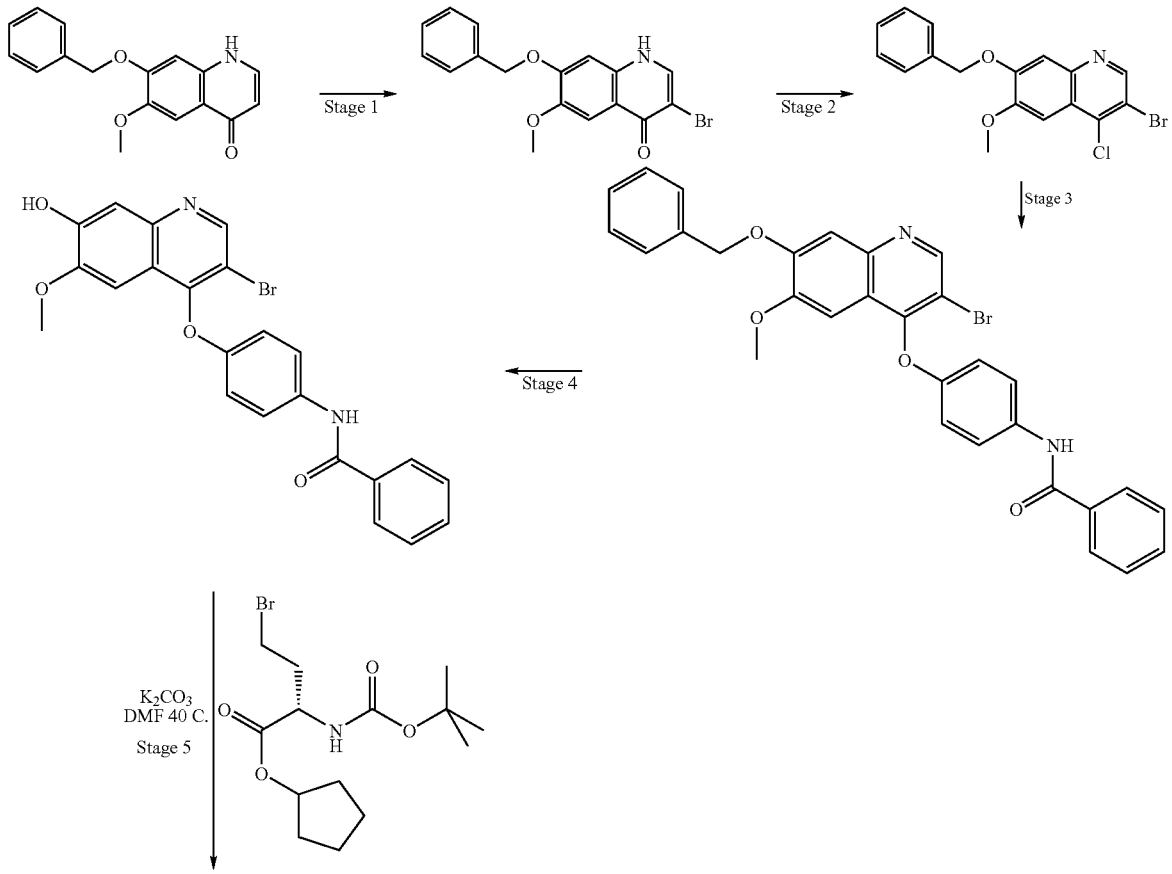

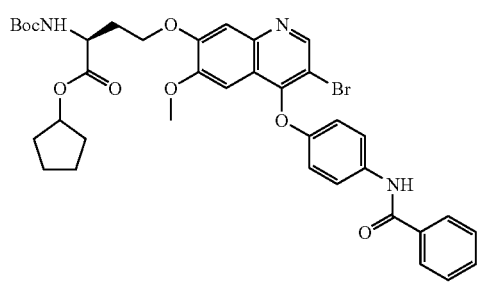
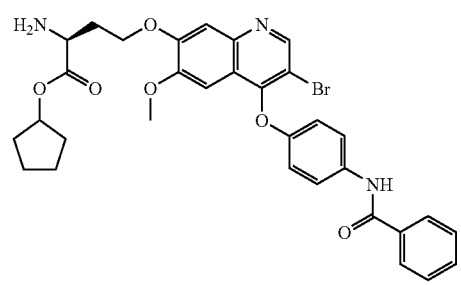

HCl/dioxane
Stage 6

Stage 1-7-Benzyloxy-3-bromo-6-methoxy-1H-quinolin-4-one

To a solution of 7-benzyloxy-6-methoxy-1H-quinolin-4-one (2.0 g, 7.11 mmol) in acetic acid (30 ml) was added bromine (364 µl, 7.11 mmol) dropwise at 70° C. The mixture was heated to 95° C. for 1 hour and cooled. The precipitate was filtered, washed with AcOH and dried. A slurry of the precipitate in water (50 ml) was neutralised with 2M aq. NaOH and the solid filtered, washed with Et$_2$O and dried (MgSO$_4$) to provide the title compound as a solid (3.24 g, 100% yield).

LC/MS purity: 100%, m/z 360 [M+H]$^+$. $^1$H NMR (300 MHz, DMSO-d$_6$) δ: 12.20 (1H, br s), 8.35 (1H, s), 7.51-7.34 (6H, m), 7.14 (1H, s), 5.20 (2H, s), 3.86 (3H, s).

Stage 2-7-Benzyloxy-3-bromo-4-chloro-6-methoxy-quinoline

To a stirred mixture of 7-benzyloxy-3-bromo-6-methoxy-1H-quinolin-4-one (2.0 g, 5.55 mmol) in phosphorous oxychloride (30 ml) was heated at reflux for 2 hours. The reaction mixture was cooled, concentrated in vacuo and a mixture of ice and water was added. The pH was adjusted to ~8 using aqueous ammonia. The aqueous layer was diluted further and extracted with EtOAc (2×100 ml). The combined organic layers were combined, dried (MgSO$_4$) and concentrated to provide the title compound as a pale yellow solid (1.7 g, 79% yield).

LC/MS purity: 95%, m/z 378 [M+H]$^+$. $^1$H NMR (300 MHz, DMSO-d$_6$) δ: 8.34 (1H, s), 7.58 (1H, s), 7.54-7.50 (2H, m), 7.46-7.37 (4H, m), 5.32 (2H, s), 3.99 (3H, s).

Stage 3-N-[4-(7-Benzyloxy-3-bromo-6-methoxy-quinolin-4-yloxy)-phenyl]-benzamide A mixture of 7-benzyloxy-3-bromo-4-chloro-6-methoxy-quinoline (200 mg, 0.528 mmol) and N-(4-hydroxy-phenyl)-benzamide (337 mg, 1.58 mmol) in DMF (3 ml) was heated at 150° C. for 4 hours. The mixture was cooled, concentrated to half volume and heated for a further 4 hours. The reaction mixture was cooled, concentrated and partitioned between EtOAc/H$_2$O/sat NaHCO$_3$. The organic layer was separated, dried and concentrated. The residue was purified by column chromatography (10-40% EtOAc/Heptane) then by preparative HPLC to provide the title compound (35 mg).

LC/MS m/z 555 [M+H]$^+$.

Stage 4-(S)-4-[4-(4-Benzoylamino-phenoxy)-3-bromo-6-methoxy-quinolin-7-ol

A mixture of N-[4-(7-benzyloxy-3-bromo-6-methoxy-quinolin-4-yloxy)-phenyl]-benzamide (35 mg, 0.063 mmol) in TFA (1 ml) and thioanisole (80 µl) was refluxed for 4 hours, cooled and concentrated under high vacuum.

Stage 5-(S)-4-[4-(4-Benzoylamino-phenoxy)-3-bromo-6-methoxy-quinolin-7-yloxy]-2-tert-butoxycarbonylamino-butyric acid cyclopentyl ester The residue from Stage 4 was dissolved in DMF (2 ml), K$_2$CO$_3$ (20 mg, 0.139 mmol) and (S)-4-bromo-2-tert-butoxycarbonylamino-butyric acid cyclopentyl ester (24 mg, 0.069 mmol) were added and the mixture heated at 40° C., under nitrogen for 18 hours. The reaction was concentrated under high vacuum and the residue partitioned between EtOAc/H$_2$O. The organic layer was separated, washed with brine, dried (MgSO$_4$) and concentrated under reduced pressure. The residue was purified by column chromatography (40-50% EtOAc/Heptane) to provide the title compound as a white solid (38 mg).

LC/MS purity: 99%, m/z 734 [M+H]$^+$. $^1$H NMR (300 MHz, DMSO-d$_6$) δ: 8.72 (1H, s), 7.80-7.75 (3H, m), 7.52-7.36 (5H, m), 7.19 (1H, s), 7.06 (1H, s), 6.81-6.78 (2H, m), 5.97 (1H, br d, J=8.4 Hz), 5.15-5.09 (1H, m), 4.50-4.40 (1H, m), 4.29-4.21 (1H, m), 4.12-4.03 (1H, m), 3.82 (3, s), 2.37-2.32 (2H, m), 1.80-1.45 (8H, m), 1.38 (9H, s).

Stage 6-(S)-2-Amino-4-(3-bromo-4-chloro-6-methoxy-quinolin-7-yloxy)-butyric acid cyclopentyl ester dihydrochloride To a slurry of (S)-4-[4-(4-benzoylamino-phenoxy)-3-bromo-6-methoxy-quinolin-7-yloxy]-2-tert-butoxycarbonylamino-butyric acid cyclopentyl ester (38 mg) in Et$_2$O (6 ml) was added 4M HCl/dioxane (2 ml) and the mixture was stirred for 24 hours. The mixture was concentrated under high vacuum to provide the title compound as a solid.

Example 33 was synthesised using N-(4-amino-phenyl)-benzamide at Stage 3 of scheme 14.

EXAMPLE 33

(S)-2-Amino-4-[4-(4-benzoylamino-phenoxy)-3-bromo-6-methoxy-quinolin-7-yloxy]-butyric acid cyclopentyl ester Dihydrochloride

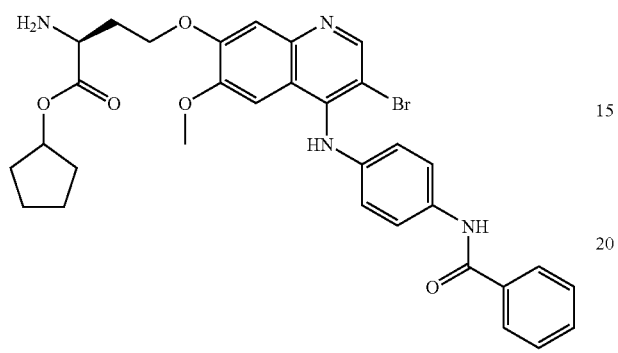

LC/MS purity: 95%, m/z 635 [M+H]$^+$. $^1$H NMR (300 MHz, DMSO-d$_6$) δ: 10.41 (1H, s), 10.16 (1H, br s), 8.92 (1H, s), 8.64 (3H, br s), 7.98 (2H, d, J=8.5 Hz), 7.85 (2H, d, J=9.0 Hz), 7.62-7.52 (5H, m), 7.21 (2H, d, J=8.5 Hz), 5.22-5.16 (1H, m), 4.40-4.30 (2H, m), 4.20-4.10 (1H, m), 3.76 (3H, s), 2.41-2.30 (2H, m), 1.90-1.40 (8H, m).

Example 34 was prepared by methods described in Scheme 15 below.

EXAMPLE 34

(S)-2-Amino-4-[4-(4-benzoylamino-phenoxy)-3-cyclopropyl-6-methoxy-quinolin-7-yloxy]-butyric acid cyclopentyl ester

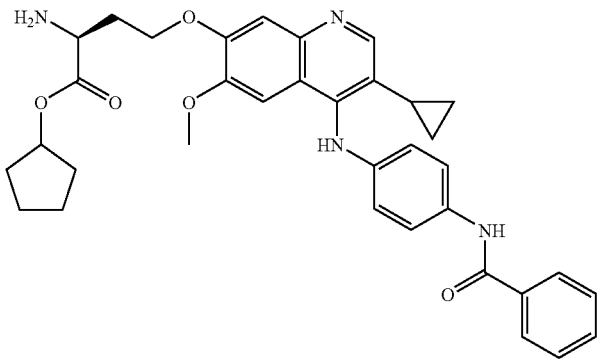

Scheme 15

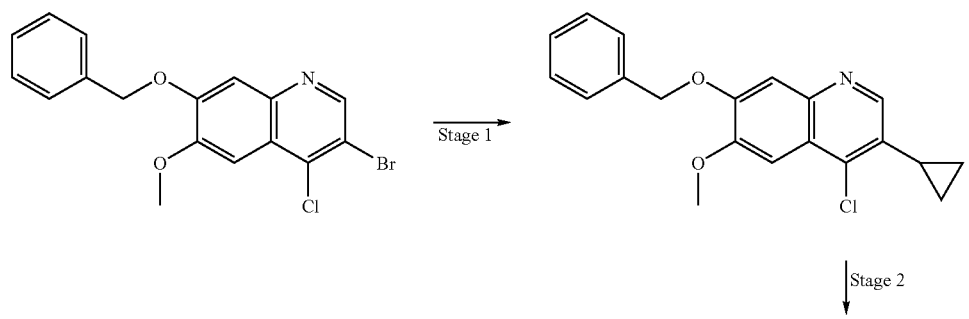

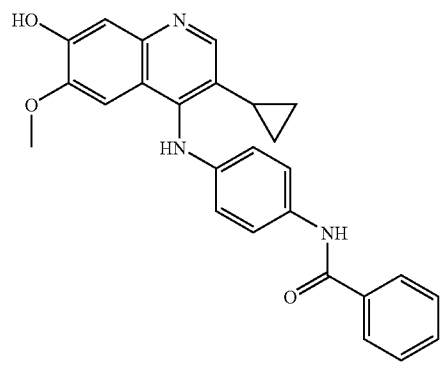

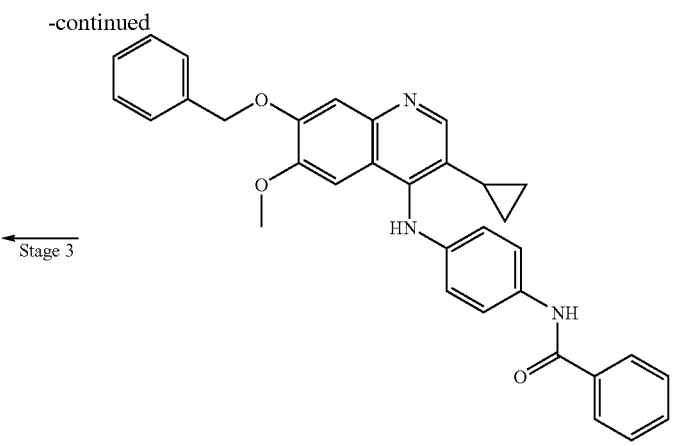

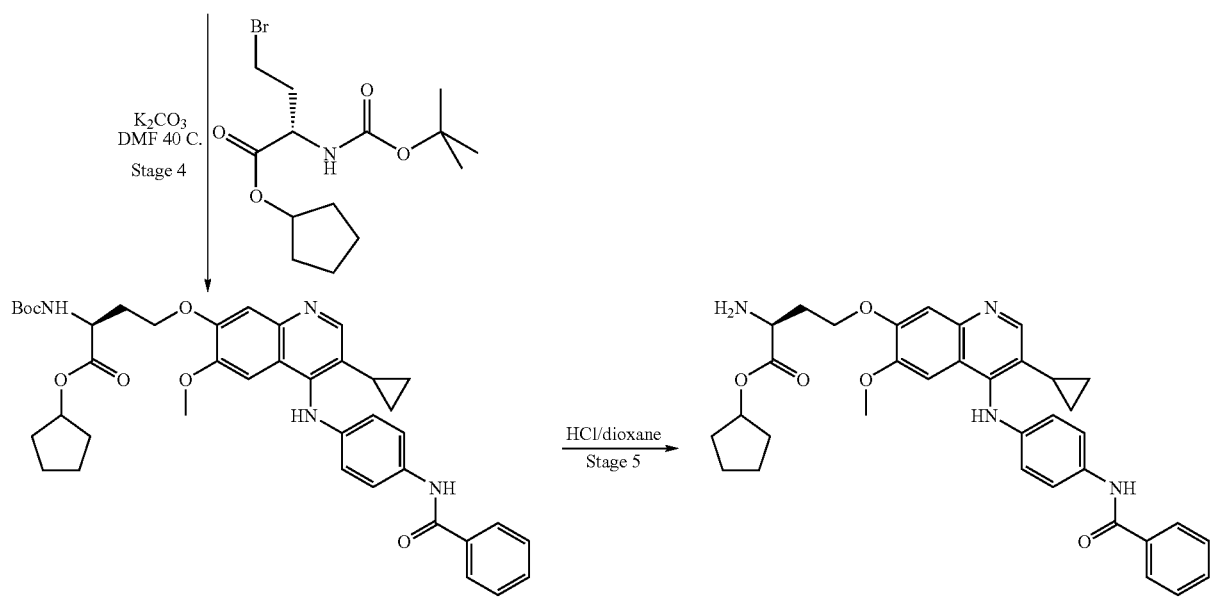

Stage 1-7-Benzyloxy-4-chloro-3-cyclopropyl-6-methoxy-quinoline

To a mixture of 7-benzyloxy-3-bromo-4-chloro-6-methoxy-quinoline (200 mg, 0.528 mmol), potassium phosphate (392 mg, 1.85 mmol), cyclopropyl boronic acid (60 mg, 0.687 mmol) and tricyclohexane phosphine (15 mg, 0.053 mmol) in $H_2O$ (165 μl) and toluene (3.3 ml) was added palladium diacetate (6 mg, 0.026 mmol). The reaction was heated at 100° C. for 2 hours, cooled, filtered through Celite and washed twice with EtOAc. The organic layer was washed with $H_2O$, dried ($MgSO_4$) and concentrated. The residue was purified by column chromatography (10-20% EtOAc/Heptane) to provide the title compound as a white solid (136 mg). LC/MS m/z 340.2 $[M+H]^+$.

Stage 2-N-[4-(7-Benzyloxy-3-cyclopropyl-6-methoxy-quinolin-4-yloxy)-phenyl]-benzamide A mixture of 7-benzyloxy-4-chloro-3-cyclopropyl-6-methoxy-quinoline (143 mg, 0.421 mmol) and N-(4-hydroxy-phenyl)-benzamide (269 mg, 1.26 mmol) in DMF (200 μl) was heated at 150° C. for 6 hours. The reaction was cooled, concentrated and partitioned between DCM and 5% aqueous NaOH. The aqueous layer was extracted with DCM twice and the combined organic extracts were washed with brine, dried ($MgSO_4$) and concentrated. The residue was purified by column chromatography (20-70% EtOAc/Heptane) to provide the title compound (50 mg).

LC/MS purity: 75%, m/z 554/556 $[M+H]^+$. $^1H$ NMR (300 MHz, $CDCl_3$) δ: 8.29 (1H, s), 7.91 (1H, br s), 7.80 (2H, d, J=6.6 Hz), 7.54-7.22 (10H, m), 7.19 (1H, s), 7.11 (1H, s), 6.85-6.79 (2H, m), 5.23 (2H, s), 3.83 (3H, s), 1.80-1.74 (1H, m), 0.85-0.78 (2H, m), 0.73-0.65 (2H, m).

Stage 3-4-[4-(4-Benzoylamino-phenoxy)-3-cyclopropyl-6-methoxy-quinolin-7-ol

A mixture of N-[4-(7-benzyloxy-3-cyclopropyl-6-methoxy-quinolin-4-yloxy)-phenyl]-benzamide (50 mg, 0.097 mmol) in TFA (750 μl) and thioanisole (90 μl) was refluxed for 1 hour, cooled and concentrated under high vacuum to use crude in the next stage.

Stage 4-4-[4-(4-Benzoylamino-phenoxy)-3-cyclopropyl-6-methoxy-quinolin-7-yloxy]-2-tert-butoxycarbonylamino-butyric acid cyclopentyl ester 4-[4-(4-Benzoylamino-phenoxy)-3-cyclopropyl-6-methoxy-quinolin-7-ol was dissolved in DMF (2 ml). $K_2CO_3$ (29 mg, 0.213 mmol) and (S)-4-bromo-2-tert-butoxycarbonylamino-butyric acid cyclopentyl ester (37 mg, 0.107 mmol) were added and the mixture heated at 40° C., under nitrogen, for 72 hours. The reaction was partitioned between EtOAc/H$_2$O. The organic layer was washed with H$_2$O, brine, dried (MgSO$_4$) and the residue purified by column chromatography (30-100% EtOAc/Heptane) to provide the title compound (23 mg).

LC/MS m/z 696 [M+H]$^+$.

Stage 5-2-Amino-4-[4-(4-benzoylamino-phenoxy)-3-cyclopropyl-6-methoxy-quinolin-7-yloxy]-butyric acid cyclopentyl ester To a slurry of 4-[4-(4-benzoylamino-phenoxy)-3-cyclopropyl-6-methoxy-quinolin-7-yloxy]-2-tert-butoxycarbonylamino-butyric acid cyclopentyl ester (23 mg) in Et$_2$O (3 ml) was added 4M HCl/dioxane (1 ml) and the mixture was stirred for 24 hours. The mixture was concentrated and purified by prep HPLC to provide the title compound as a brown oil.

LC/MS purity: 98%, m/z 596 [M+H]$^+$. $^1$H NMR (300 MHz, DMSO-d$_6$) δ: 10.31 (1H, br s), 8.69 (1H, s), 8.58 (3H, br s), 7.95 (2H, d, J=6.6 Hz), 7.77 (2H, d, J=9.3 Hz), 7.67 (1H, s), 7.02 (2H, d, J=9.3 Hz), 5.19 (1H, t, J=5.7 Hz), 4.35 (2H, t, J=5.6 Hz), 4.20-4.10 (1H, m), 3.82 (3H, s), 2.45-2.30 (2H, m), 1.93-1.75 (3H, m), 1.62-1.45 (6H, m), 0.92-0.88 (4H, m).

EXAMPLE 35

(S)-2-Amino-4-[4-(4-benzoylamino-phenoxy)-7-methoxy-quinolin-6-yloxy]-butyric acid cyclopentyl ester

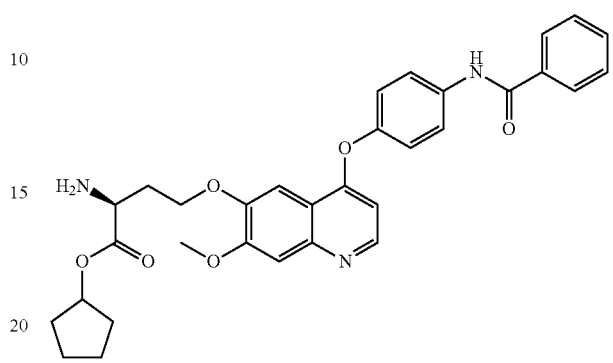

LC/MS: m/z 556 [M+H]$^+$. $^1$H NMR (300 MHz, CD$_3$OD) δ: 8.45 (1H, d, J=5.6 Hz), 7.98 (2H, d, J=8.7 Hz), 7.88 (2H, d, J=9.0 Hz), 7.67 (1H, s), 7.65-7.52 (4H, m), 7.38 (1H, s), 7.26 (2H, d, J=9.0 Hz), 5.24-4.94 (1H, m), 4.32 (2H, t, J=6.0 Hz), 4.04 (3H, s), 3.74 (1H, dd, J=7.1, 5.6 Hz), 2.39-2.15 (2H, m), 1.88-1.31 (8H, m).

The preparation of Example 35 (a regioisomer of Example 2) is detailed in Scheme 16 below.

Scheme 16

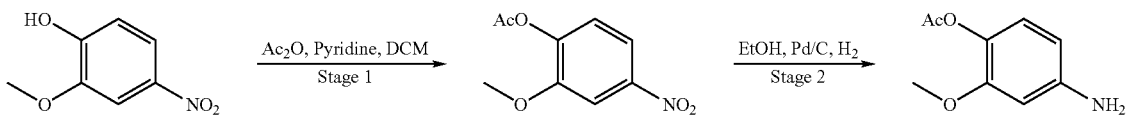

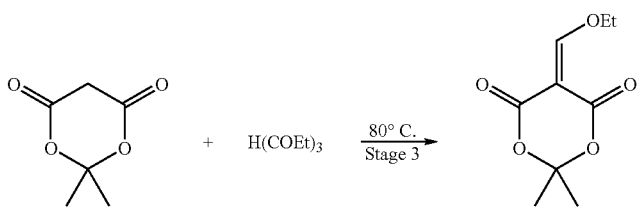

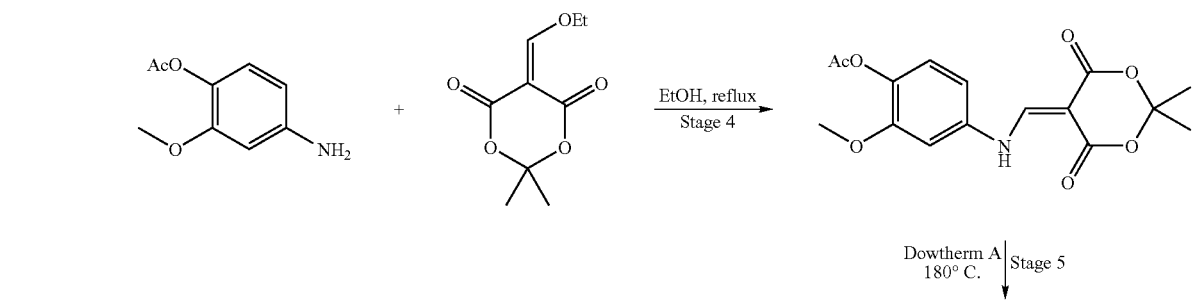

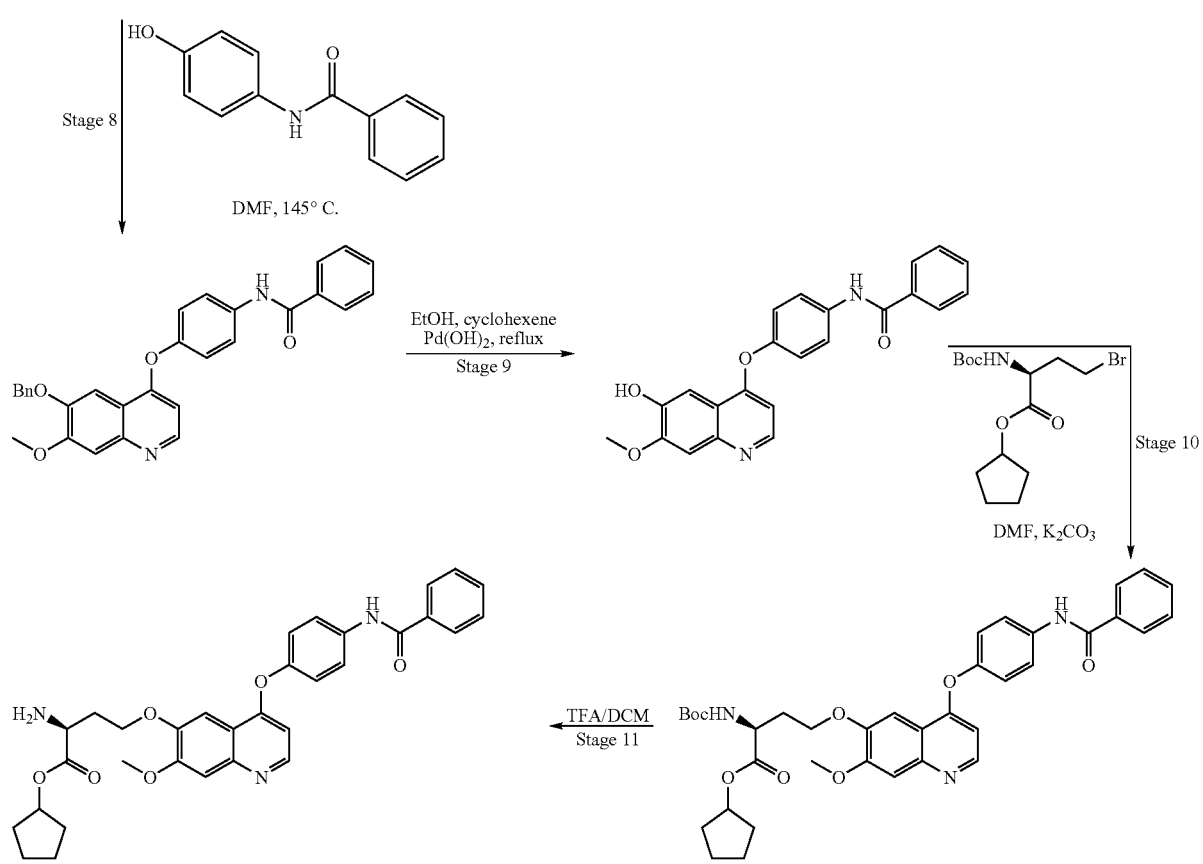

Stage 1-Acetic acid 4-nitro-2-methoxy-phenyl ester

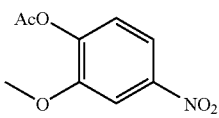

To a solution of 2-methoxy-4-nitro-phenol (9.96 g, 58.9 mmol) and pyridine (5.24 ml, 64.8 mmol, 1.1 eq) in DCM (50 ml) at 0° C. was added acetic anhydride (6.11 ml, 64.8 mmol, 1.1 eq) over 15 minutes. The reaction mixture was allowed to warm to room temperature and stirred for 4 hours and washed with water (50 ml). The aqueous layer was separated and extracted with DCM (3×50 ml). The combined organic extracts were washed with water (50 ml), 2N HCl (50 ml), 2N NaOH (50 ml), brine (50 ml), dried (MgSO$_4$), and concentrated under reduced pressure to provide the title compound as a pale yellow solid (12.22 g, 98% yield).

$^1$H NMR (300 MHz, CDCl$_3$) δ: 7.92-86 (2H, m), 7.21 (1H, d, J=8.7 Hz), 3.95 (3H, s), 2.37 (3H, s).

Stage 2-Acetic Acid 4-amino-2-methoxy-phenyl ester

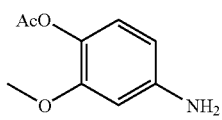

To a solution of acetic acid 4-amino-2-methoxy-phenyl ester (12.22 g, 57.9 mmol) in ethanol (100 ml) was added Pd/C (425 mg) and the reaction mixture was stirred at room temperature under an atmosphere of hydrogen for 17 hours. The reaction mixture was filtered through a pad of Celite. This was washed with methanol and the combined filtrates were concentrated under reduced pressure to afford the title compound as a thick yellow oil (10.16 g, 98% yield).

LC/MS: m/z 182 [M+H]⁺. ¹H NMR (300 MHz, CDCl₃) δ: 6.81 (1H, d, J=8.1 Hz), 6.32 (1H, d, J=2.4 Hz), 6.24 (1H, dd, J=2.4, 8.1 Hz), 3.82 (3H, s), 3.71 (2H, br s), 2.29 (3H, s).

Stage 3-5-Ethoxymethylene-2,2-dimethyl-[1,3]dioxane-4,6-dione

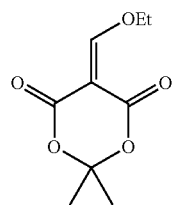

A mixture of cyclo-isopropylidene malonate (21.6 g, 150 mmol) and triethylorthoformate (75 ml, 450 mmol, 3.0 eq) was stirred at 80° C. for 3 hours and concentrated under reduced pressure to afford the title compound as a brown oil, which solidified on standing (30.01 g, 100% yield).
¹H NMR (300 MHz, CDCl₃), δ: 8.24 (1H, s), 4.51 (2H, q, J=7.2 Hz), 1.73 (6H, s), 1.53 (3H, t, J=7.2 Hz).

Stage 4-Acetic Acid 4-[(2,2-dimethyl-4,6-dioxo-[1,3]dioxan-5-ylidenemethyl)-amino]-2-methoxy-phenyl ester

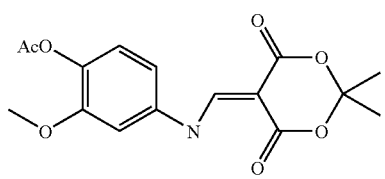

A mixture of acetic acid 4-amino-2-methoxy-phenyl ester (12.22 g, 93 mmol) and 5-ethoxymethylene-2,2-dimethyl-[1,3]dioxane-4,6-dione (18.65 g, 93 mmol, 1.0 eq) in ethanol (200 ml) was refluxed for 2 hours. The reaction mixture was cooled to 0° C. and a solid was collected by filtration. This was washed with ethanol and heptane and dried under reduced pressure to afford the title compound as a yellow solid (17.63 g, 78% yield).
LC/MS: m/z 358 [M+Na]⁺ and 693 [2M+Na]⁺. ¹H NMR (300 MHz, CDCl₃), δ: 11.28 (1H, d, J=14.1 Hz), 8.61 (1H, d, J=14.1 Hz), 7.11 (1H, d, J=8.4 Hz), 6.87-6.82 (2H, m), 3.90 (3H, s), 2.34 (3H, s), 1.78 (6H, S).

Stage 5-Acetic Acid 7-methoxy-4-oxo-1,4-dihydro-quinolin-6-yl ester

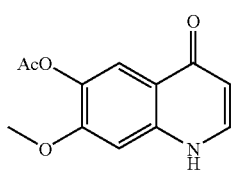

A mixture of acetic acid 4-[(2,2-dimethyl-4,6-dioxo-[1,3]dioxan-5-ylidenemethyl)-amino]-2-methoxy-phenyl ester (17.63 g, 52.6 mmol), diphenyl ether (220 g) and biphenyl (78 g) was heated to 190° C. for one hour. The reaction mixture was allowed to cool to 60° C. and poured in heptane (500 ml). A precipitate was collected by filtration, washed with heptane and diethyl ether and dried under reduced pressure to leave a yellow solid. Purification by column chromatography (5-10% methanol in DCM) afforded the title compound as a pale brown solid (8.34 g, 68% yield).
LC/MS: m/z 234 [M+H]⁺. ¹H NMR (300 MHz, DMSO-d₆) δ: 11.65 (1H, br s), 7.86 (1H, d, J=7.4 Hz), 7.68 (1H, s), 7.38 (1H, s), 5.96 (1H, d, J=7.4 Hz), 3.87 (3H, s), 2.29 (3H, s).

Stage 6-4-Chloro-7-methoxy-quinolin-6-ol

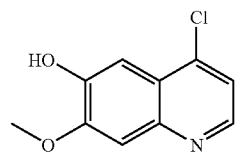

To a solution of acetic acid 7-methoxy-4-oxo-1,4-dihydroquinolin-6-yl ester (8.34 g, 36 mmol) in chloroform (150 ml) was slowly added POCl₃ (17 ml, 179 mmol, 5 eq). The reaction mixture was refluxed for 6 hours and concentrated under reduced pressure. The residue was taken up in water (200 ml) and the pH was adjusted to 6 with solid NaOH. A solid was collected by filtration, washed with water, a small amount of ethanol and diethyl ether and subsequently dried under reduced pressure to afford the title compound as a yellow solid (5.47 g, 73% yield).
LC/MS: m/z 210 [M+H]⁺. ¹H NMR (300 MHz, DMSO-d₆) δ: 10.22 (1H, br s), 8.54 (1H, d, J=4.7 Hz), 7.49 (1H, d, J=4.7 Hz), 7.43 (1H, s), 7.410 (1H, s), 3.97 (3H, s).

Stage 7-6-Benzyloxy-4-chloro-7-methoxy-quinoline

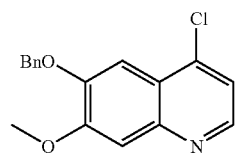

To a solution of 4-chloro-7-methoxy-quinolin-6-ol (5.47 g, 26.1 mmol) and benzyl bromide (3.4 ml, 28.8 mmol, 1.1 eq) in DMF (50 ml) was added potassium carbonate (7.23 g, 52.3 mmol, 2.0 eq). The reaction mixture was stirred at room temperature for 18 hours and poured in water (300 ml). The aqueous solution was extracted with ethyl acetate (3×300 ml). The combined organic extracts were washed with water (2×300 ml), brine (300 ml), dried (MgSO-4) and concentrated under reduced pressure to leave a brown solid. Purification by column chromatography (60-80% EtOAc in heptane) afforded the title compound as a pale yellow solid (4.60 g, 59% yield).

LC/MS: m/z 300 [M+H]+. 1H NMR (300 MHz, DMSO-d6) δ: 8.62 (1H, d, J=4.8 Hz), 7.62-7.34 (8H, m), 5.32 (2H, s), 3.97 (3H, s).

Stage 8-N-[4-(6-Benzyloxy-7-methoxy-quinolin-4-yloxy)-phenyl]-benzamide

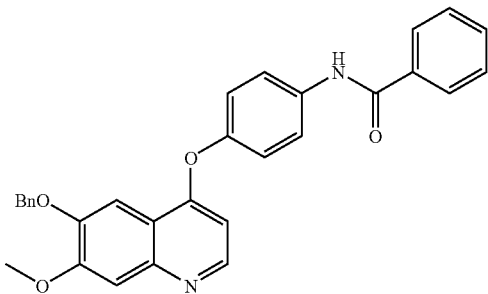

A mixture of 6-benzyloxy-4-chloro-7-methoxy-quinoline (1.00 g, 3.3 mmol) and N-(4-hydroxy-phenyl)-benzamide (2.13 g, 10,0 mmol, 3.0 eq) in DMF (2 ml) was stirred at 145° C. under an atmosphere of nitrogen for 7 hours. The reaction mixture was allowed to cool to room temperature, diluted with water (150 ml) and extracted with ethyl acetate (3×150 ml). The combined organic extracts were washed with brine (100 ml), dried (MgSO4) and concentrated under reduced pressure to leave a brown oil. Purification by column chromatography (100% EtOAc) afforded the title compound as a beige solid (1.10 g, 69% yield).

LC/MS: m/z 477 [M+H]+.

Stage 9-N-[4-(6-Hydroxy-7-methoxy-quinolin-4-yloxy)-phenyl]-benzamide

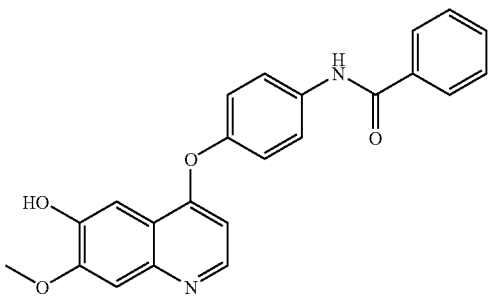

To a solution of N-[4-(6-benzyloxy-7-methoxy-quinolin-4-yloxy)-phenyl]-benzamide (1.20 g, 2.52 mmol) in cyclohexene/ethanol (1:4, 25 ml) was added Pd(OH)2/C and the reaction mixture was refluxed under an atmosphere of nitrogen for 7 hours. The reaction mixture was filtered through a pad of Celite, which was washed with ethyl acetate (150 ml). The combined filtrates were concentrated under reduced pressure to provide the title compound as a yellow solid (880 mg, 90% yield).

LC/MS: m/z 387 [M+H]+.

Stage 10-(S)-4-[4-(4-Benzoylamino-phenoxy)-7-methoxy-quinolin-6-yloxy]-2-tert-butoxycarbonylamino-butyric acid cyclopentyl ester

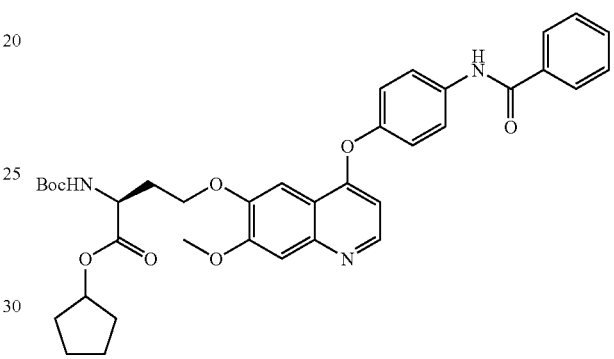

To a solution of (S)-4-[4-(4-benzoylamino-phenoxy)-7-methoxy-quinolin-6-yloxy]-2-tert-butoxycarbonylamino-butyric acid cyclopentyl ester (300 mg, 0.78 mmol) and (S)-4-bromo-2-tert-butoxycarbonylamino-butyric acid cyclopentyl ester (300 mg, 0.85 mmol, 1.1 eq) in DMF (3 ml) was added potassium carbonate (129 mg, 0.93 mmol, 1.2 eq). The reaction mixture was stirred at 40° C. for 17 hours and diluted with water (20 ml). A solid was collected by filtration and taken up in ethyl acetate (50 ml). This solution was washed with water (2×25 ml), brine (25 ml), dried (MgSO4), filtered and concentrated under reduced pressure to leave a thick yellow oil. Purification by column chromatography (ethyl acetate) afforded the title compound as a colourless oil (268 mg, 53% yield).

LC/MS: m/z 656 [M+H]+. 1H NMR (300 MHz, CDCl3) δ: 8.74 (1H, s), 8.45 (1H, d, J=5.2 Hz), 7.92 (2H, d, J=6.9 Hz), 7.78 (2H, d, J=9.0 Hz), 7.54-7.28 (5H, m), 7.14 (2H, d, J=9.0 Hz), 6.44 (1H, d, J=5.2 Hz), 6.18 (1H, d, J=8.7 Hz), 5.17 (1H, br s), 4.55-4.48 (1H, m), 4.35-4.29 (1H, m), 4.19-4.08 (1H, m), 4.01 (3H, s), 2.42-2.36 (2H, m) <1.80-1.26 (17H, m).

Stage 11-(S)-2-Amino-4-[4-(4-benzoylamino-phenoxy)-7-methoxy-quinolin-6-yloxy]-butyric acid cyclopentyl ester

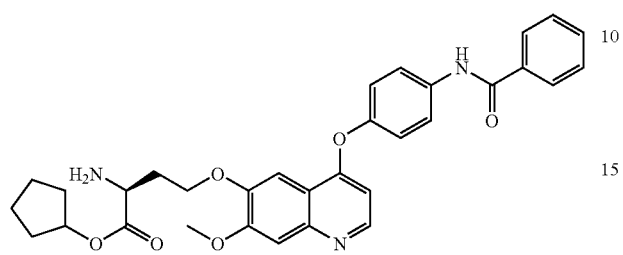

A solution of (S)-4-[4-(4-benzoylamino-phenoxy)-7-methoxy-quinolin-6-yloxy]-2-tert-butoxycarbonylamino-butyric acid cyclopentyl ester (268 mg, 0.41 mmol) in TFA/DCM (1:2, 15 ml) was stirred at room temperature for 1 hour. The reaction mixture was concentrated under reduced pressure and the residue taken up in DCM (20 ml). This solution was washed with saturated NaHCO$_3$ (2×20 ml), brine (20 ml), dried (MgSO$_4$) and concentrated under reduced pressure to leave a thick yellow oil. Purification by column chromatography (5% methanol in DCM) afforded the title compound as a white solid (161 mg, 71% yield).

LC/MS: m/z 556 [M+H]$^+$. $^1$H NMR (300 MHz, CD$_3$OD) δ: 8.45 (1H, d, J=5.6 Hz), 7.98 (2H, d, J=8.7 Hz), 7.88 (2H, d, J=9.0 Hz), 7.67 (1H, s), 7.65-7.52 (4H, m), 7.38 (1H, s), 7.26 (2H, d, J=9.0 Hz), 5.24-4.94 (1H, m), 4.32 (2H, t, J=6.0 Hz), 4.04 (3H, s), 3.74 (1H, dd, J=7.1, 5.6 Hz), 2.39-2.15 (2H, m), 1.88-1.31 (8H, m).

EXAMPLE 36

(S)-2-Amino-4-[4-(4-benzoylamino-phenoxy)-7-methoxy-quinolin-6-yloxy]-butyric acid

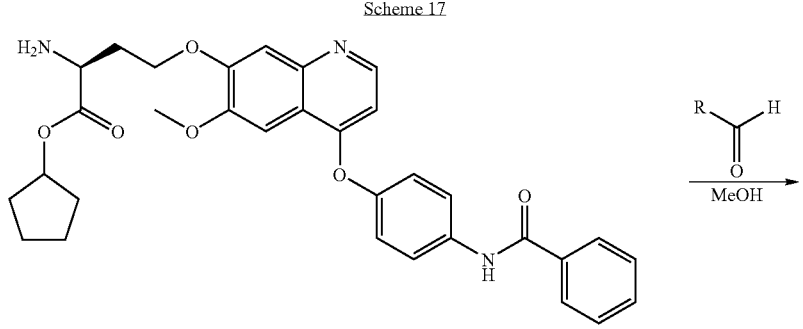

LC/MS: m/z 488 [M+H]$^+$. $^1$H NMR (300 MHz, CD$_3$OD) δ: 8.61 (1H, d, J=5.8 Hz), 8.00-7.93 (4H, m), 7.82 (1H, s), 7.63-7.50 (4H, m), 7.34 (2H, d, J=8.7 Hz), 7.82 (1H, d, J=5.8 Hz), 4.54-4.45 (2H, m), 4.14 (3H, s), 4.11-4.03 (1H, m), 2.70-2.58 (1H, m), 2.51-2.38 (1H, m).

Examples 37-41 were prepared by methods shown in Scheme 17 below.

Scheme 17

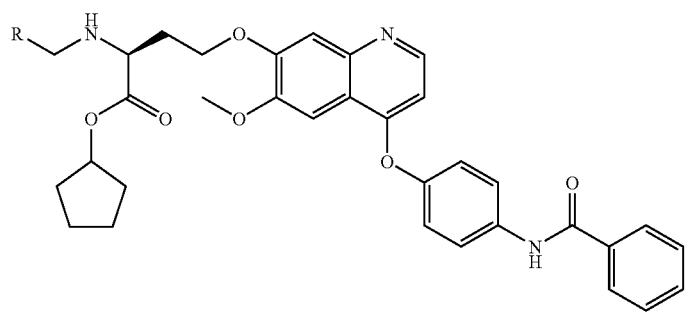

EXAMPLE 37

(S)-4-[4-(4-Benzoylamino-phenoxy)-6-methoxy-quinolin-7-yloxy]-2-isobutylamino-butyric acid cyclopentyl ester

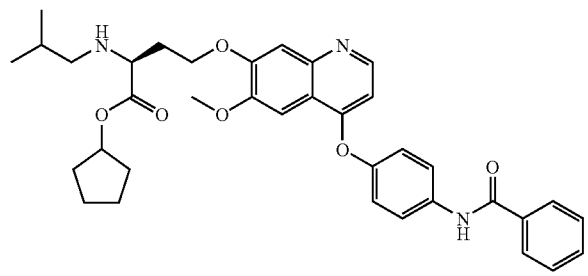

To (S)-2-Amino-4-[4-(4-benzoylamino-phenoxy)-6-methoxy-quinolin-7-yloxy]-butyric acid cyclopentyl ester (37 mg, 0.066 mmol) in anhydrous methanol (1 ml) were added 100 μL of a 1 M solution of isobutyraldehyde in methanol and 1 drop of acetic acid. The reaction mixture was stirred at room temperature for 3 hours. Sodium cyanoborohydride (10.3 mg, 0.165 mmol) was then added and the reaction was left stirring 4 hours at room temperature, prior to concentration under vacuum. Purification by preparative HPLC afforded the title compound as a di-TFA salt (40 mg, 72% yield).

LC/MS: m/z 612 [M+H]$^+$. $^1$H NMR (300 MHz, CD$_3$OD) δ: 8.72 (1H, d, J=6.7 Hz), 8.04-7.95 (4H, m), 7.92 (1H, s), 7.71-7.51 (4H, m), 7.41 (2H, d, J=6.6 Hz), 6.99 (1H, d, J=6.7 Hz), 5.44-5.35 (1H, m), 4.53 (2H, t, J=5.3 Hz), 4.36 (1H, t, J=6.2 Hz), 4.13 (3H, s), 3.15-3.06 (1H, m), 3.05-2.95 (1H, m), 2.68 (2H, s), 2.21-1.56 (9H, m), 1.12 (6H, dd, J=4.4, 6.6 Hz).

EXAMPLE 38

(S)-4-[4-(4-Benzoylamino-phenoxy)-6-methoxy-quinolin-7-yloxy]-2-ethylamino-butyric acid cyclopentyl ester

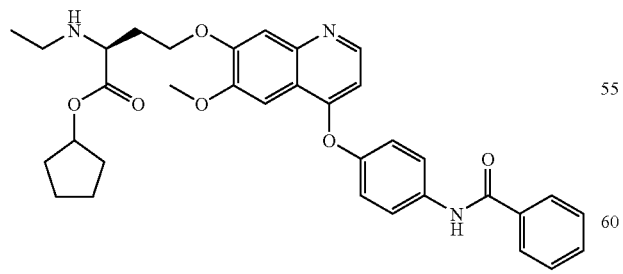

LC/MS: m/z 584 [M+H]$^+$. $^1$H NMR (300 MHz, CD$_3$OD) δ: 8.71 (1H, d, J=6.6 Hz), 7.99 (4H, dd, J=2.1, 7.2 Hz), 7.92 (1H, s), 7.61 (4H, m), 7.40 (2H, dd, J=2.4, 7.2 Hz), 6.99 (1H, d, J=6.6 Hz), 5.38 (1H, m), 4.50 (2H, t, J=5.4 Hz), 4.36 (1H, t, J=6.9 Hz), 4.14 (3H, s), 3.27 (2H, m), 2.65 (2H, m), 1.92 (2H, m), 1.76-1.67 (6H, m), 1.43 (3H, t, J=6.9 Hz).

EXAMPLE 39

(S)-4-[4-(4-Benzoylamino-phenoxy)-6-methoxy-quinolin-7-yloxy]-2-cyclohexylamino-butyric acid cyclopentyl ester

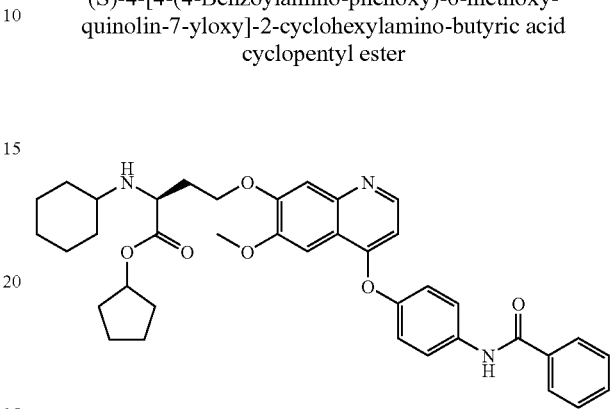

LC/MS: m/z 638 [M+H]$^+$. $^1$H NMR (300 MHz, CD$_3$OD) δ: 8.72 (1H, d, J=6.8 Hz), 8.02-7.98 (4H, m), 7.93 (1H, s), 7.67 (1H, s), 7.66-7.53 (3H, m), 7.42 (2H, m), 6.99 (1H, d, J=6.8 Hz), 5.38 (1H, m), 4.49 (3H, m), 4.14 (3H, s), 3.27 (11H, m), 2.66 (2H, m), 2.20 (2H, m), 12.05-1.46 (16H, m).

EXAMPLE 40

(S)-4-[4-(4-Benzoylamino-phenoxy)-6-methoxy-quinolin-7-yloxy]-2-benzylamino-butyric acid cyclopentyl ester

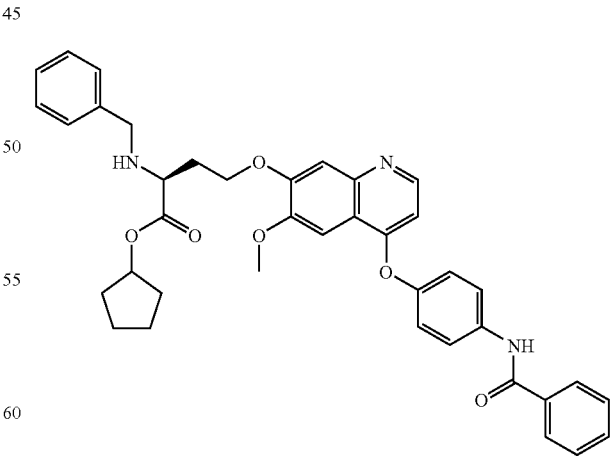

LC/MS purity: 94%, m/z 646 [M+H]$^+$. $^1$H NMR (300 MHz, CD$_3$OD), δ: 8.43 (1H, d, J=7.1 Hz), 7.97 (2H, m), 7.87 (2H, d, J=9.0 Hz), 7.55 (4H, m), 7.35-7.22 (8H, m), 6.58 (1H, d, J=7.1 Hz), 5.23 (1H, m), 4.30 (2H, m), 3.89 (3H, s), 3.84 (1H, m), 3.72-3.57 (2H, m), 2.33-2.20 (2H, m), 1.84 (2H, m), 1.68 (6H, m).

EXAMPLE 41

(S)-4-[4-(4-Benzoylamino-phenoxy)-6-methoxy-quinolin-7-yloxy]-2-diethylamino-butyric acid cyclopentyl ester

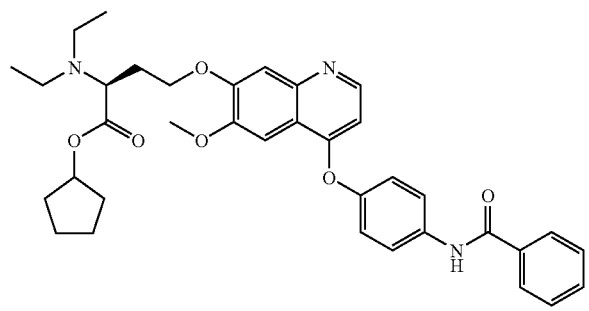

To (S)-2-Amino-4-[4-(4-benzoylamino-phenoxy)-6-methoxy-quinolin-7-yloxy]-butyric acid cyclopentyl ester (37 mg, 0.066 mmol) in anhydrous methanol (1 ml) were added acetaldehyde (4.1 μL, 0.073 mmol) and 1 drop of acetic acid. The reaction mixture was stirred at room temperature for 3 hours. Sodium cyanoborohydride (10.3 mg, 0.165 mmol) was then added and the reaction was left stirring overnight at room temperature, prior to concentration under vacuum. Purification was achieved on a prepacked Si-column followed by preparative HPLC, to provide the title compound as a di-TFA salt (10 mg, 18% yield)

LC/MS purity: 89%, m/z 612 [M+H]$^+$. $^1$H NMR (300 MHz, CD$_3$OD) δ: 8.71 (1H, d, J=6.8 Hz), 7.99 (4H, dd, J=1.8 Hz, J=6.9 Hz), 7.91 (1H, s), 7.61 (4H, m), 7.40 (2H, d, J=9 Hz), 6.99 (1H, d, J=6.8 Hz), 5.39 (1H, m), 4.61 (2H, m), 4.50 (1H, m), 4.12 (3H, s), 3.55 (2H, m), 3.39 (2H, m), 2.65 (2H, m), 1.95 (2H, m), 1.82-1.69 (6H, m), 1.49 (6H, t, J=6.9 Hz).

Examples 42-45 were prepared by the method shown in Scheme 18 below.

Scheme 18

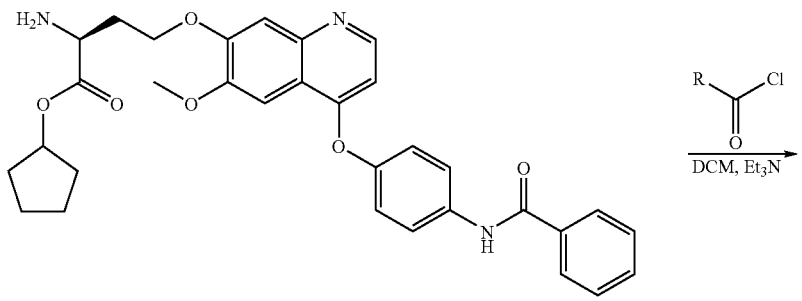

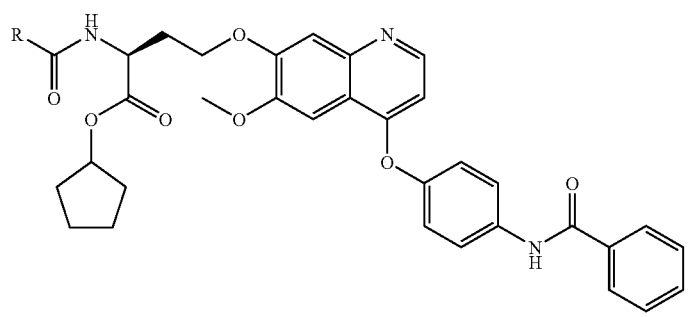

EXAMPLE 42

(S)-2-Acetylamino-4-[4-(4-benzoylamino-phenoxy)-6-methoxy-quinolin-7-yloxy]-butyric acid cyclopentyl ester

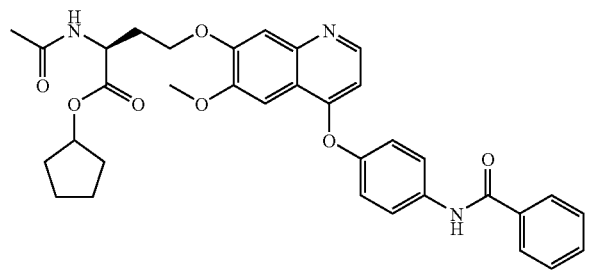

To (S)-2-Amino-4-[4-(4-benzoylamino-phenoxy)-6-methoxy-quinolin-7-yloxy]-butyric acid cyclopentyl ester (120 mg, 0.216 mmol) in DCM (2 ml) were added acetyl chloride (15 μL, 0.216 mmol) and triethylamine (33 μL, 0.238 mmol) at 0° C. The reaction mixture was stirred at 0° C. for 30 min. then at room temperature for 1 hour. The crude mixture was concentrated under vacuum and purified by preparative HPLC to provide the title compound as a mono-TFA salt (67 mg, 52% yield).

LC/MS purity: 97%, m/z 598 [M+H]$^+$. $^1$H NMR (300 MHz, CD$_3$OD) δ: 8.68 (1H, d, J=6.8 Hz), 8.02-7.94 (4H, m), 7.87 (1H, s), 7.67-7.50 (4H, m), 7.44-7.36 (2H, m), 6.96 (1H, d, J=6.6 Hz), 5.28-5.19 (1H, m), 4.66 (1H, dd, J=5.4, 8.4 Hz), 4.47-4.30 (2H, m), 4.12 (3H, s), 2.57-2.43 (1H, m), 2.39-2.25 (1H, m), 2.02 (3H, s), 1.94-1.81 (2H, m), 1.80-1.57 (6H, m).

EXAMPLE 43

(S)-2-Acetylamino-4-[4-(4-benzoylamino-phenoxy)-6-methoxy-quinolin-7-yloxy]-butyric acid

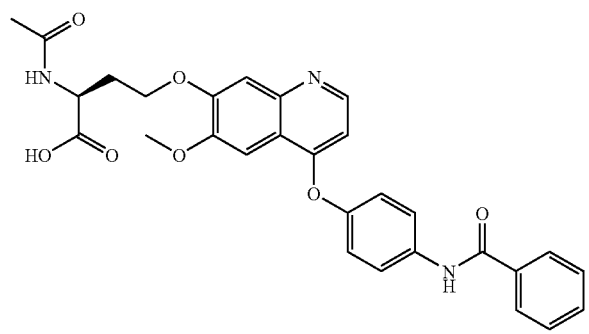

LC/MS: m/z 530 [M+H]$^+$. $^1$H NMR (300 MHz, CD$_3$OD), δ: 8.44 (1H, d, J=5.3 Hz), 8.00-7.97 (2H, m), 7.92-7.84 (2H, m), 7.68-7.65 (1H, m), 7.64-7.51 (3H, m), 7.36 (1H, s), 7.31-7.25 (2H, m), 6.59 (1H, d, J=5.5 Hz), 4.63 (1H, dd, J=4.2, 7.8 Hz), 4.36-4.27 (2H, m), 4.04 (3H, s), 2.55-2.42 (1H, m), 2.37-2.25 (1H, m), 2.05 (3H, s).

EXAMPLE 44

(S)-4-[4-(4-Benzoylamino-phenoxy)-6-methoxy-quinolin-7-yloxy]-2-[(thiophene-2-carbonyl)-amino]-butyric acid cyclopentyl ester

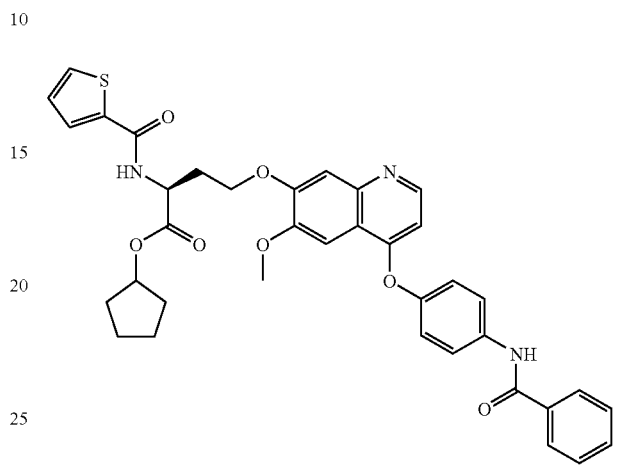

LC/MS purity: 95%, m/z 666 [M+H]$^+$. $^1$H NMR (300 MHz, CD$_3$OD) δ: 8.72 (1H, m), 8.66 (1H, d, J=6.6 Hz), 7.97 (4H, d, J=6.9 Hz), 7.84 (1H, s), 7.79 (1H, d, J=3.9 Hz), 7.69 (1H, d, J=5.1 Hz), 7.64 (1H, d, J=7.5 Hz), 7.61-7.53 (2H, m), 7.49 (1H, s), 7.39 (2H, d, J=9.0 Hz), 7.17 (1H, dd, J=3.9, 4.8 Hz), 6.95 (1H, d, J=6.6 Hz), 5.25 (1H, m), 4.82 (1H, m), 4.48 (2H, m), 4.07 (3H, s), 2.63 (1H, m), 2.49 (1H, m), 1.86 (2H, m), 1.75-1.64 (6H, m).

EXAMPLE 45

(S)-4-[4-(4-Benzoylamino-phenoxy)-6-methoxy-quinolin-7-yloxy]-2-[2-(3-methoxy-phenyl)-acetylamino]-butyric acid cyclopentyl ester

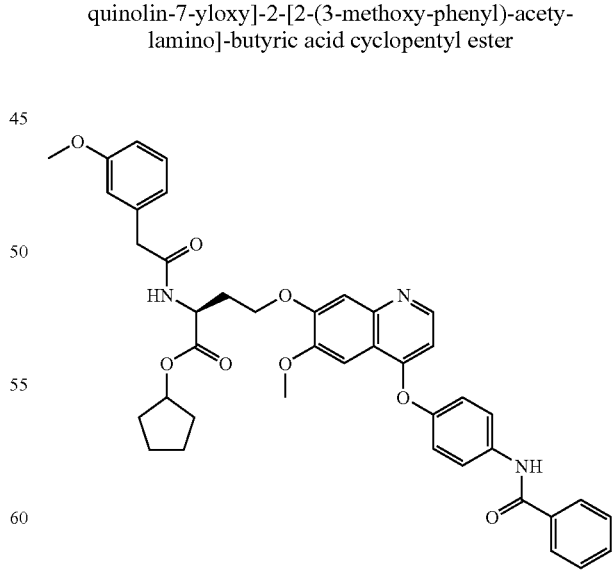

LC/MS purity: 98%, m/z 705 [M+H]$^+$. $^1$H NMR (300 MHz, CD$_3$OD), δ: 8.67 (1H, m), 8.50 (1H, d, J=7.5 Hz), 7.99 (4H, d, J=7.2 Hz), 7.84 (1H, s), 7.66-7.53 (3H, m), 7.42 (1H, s), 7.39 (2H, s), 7.13 (1H, t, J=8.1 Hz), 6.97 (1H, d, J=6.6 Hz), 6.85 (2H, s), 6.68 (1H, d, J=7.5 Hz), 5.21 (1H, m), 4.72 (1H, m), 4.37 (1H, m), 4.27 (1H, m), 4.09 (3H, s), 3.70 (3H, m), 3.53 (2H, s), 2.54 (1H, m), 2.33 (1H, m), 1.86 (2H, m), 1.78-1.61 (6H, m).
Examples 46-50 show modification to the cyclopentyl ester functionality and their preparation is detailed below in Scheme 19.
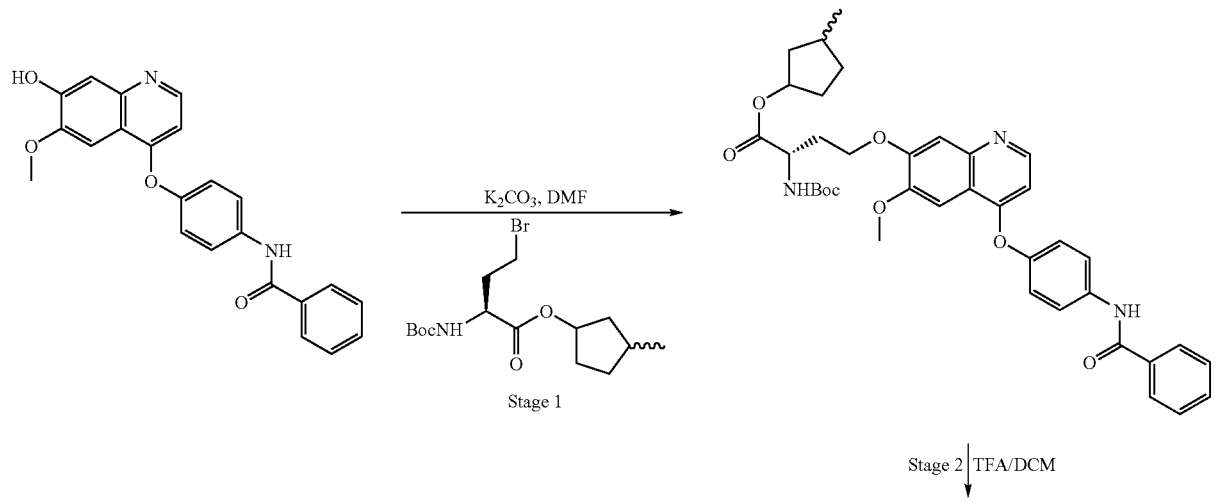
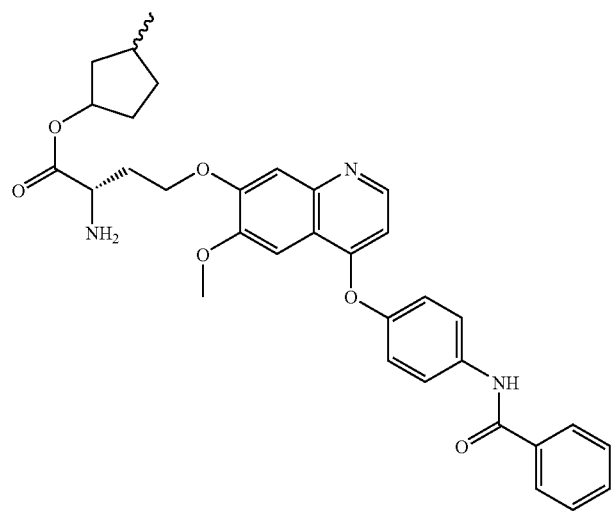

EXAMPLE 46

(S)-2-Amino-4-[4-(4-benzoylamino-phenoxy)-6-methoxy-quinolin-7-yloxy]-butyric acid 3-methyl-cyclopentyl ester

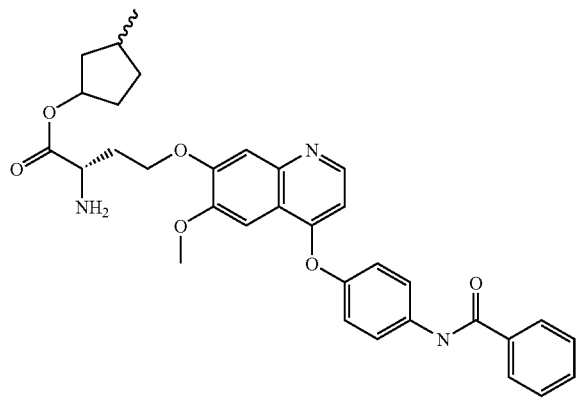

LC/MS purity: 93%, m/z 570 [M+H]+. ¹H NMR (300 MHz, CD₃OD), δ: 10.35 (1H, s), 8.71 (1H, d, J=6.6 Hz), 7.98 (4H, dd, J=1.3, 8.3 Hz), 7.91 (1H, s), 7.65-7.49 (5H, m), 7.39 (2H, d, J=8.9 Hz), 6.99 (1H, d, J=6.7 Hz), 5.41-5.26 (1H, m), 4.59-4.50 (2H, m), 4.39-4.31 (1H, m), 4.13 (3H, s), 2.65-2.54 (2H, m), 2.40-1.66 (6H, m), 1.57-1.10 (3H, m), 1.06-0.90 (4H, m)

Stage 1-(S)-4-[4-(4-Benzoylamino-phenoxy)-6-methoxy-quinolin-7-yloxy]-2-tert-butoxycarbonylamino-butyric acid 3-methyl cyclopentyl ester

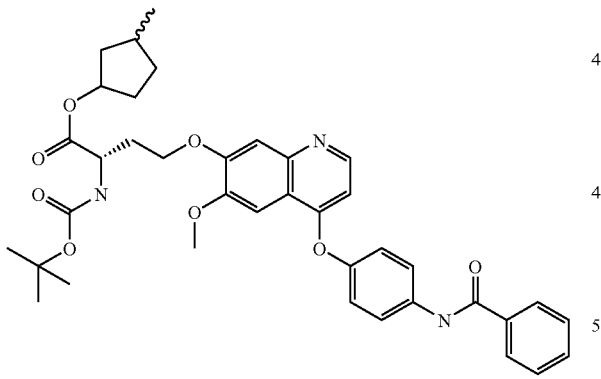

N-[4-(7-Hydroxy-6-methoxy-quinolin-4-yloxy)-phenyl]-benzamide (82 mg, 0.212 mmol, 1 eq), (S)-4-bromo-2-tert-butoxycarbonylamino-butyric acid 3-methyl-cyclopentyl ester* (Scheme 20) (85 mg, 0.233 mmol, 1.1 eq) and K₂CO₃ (59 mg, 0.424 mmol, 2 eq) were dissolved in anhydrous DMF (6 ml) under an atmosphere of nitrogen. The reaction was stirred at 35° C. overnight and the DMF was removed under reduced pressure. The residue was dissolved in DCM and washed with water followed by brine. The organic layer was dried over magnesium sulphate and evaporated under reduced pressure. The product was purified by column chromatography eluting with DCM/methanol to give the title compound (44 mg, 28% yield).
LC/MS: m/z 670 [M+H]+.

Stage 2-(S)-2-Amino-4-[4-(4-benzoylamino-phenoxy)-6-methoxy-quinolin-7-yloxy]-butyric acid 3-methyl-cyclopentyl ester

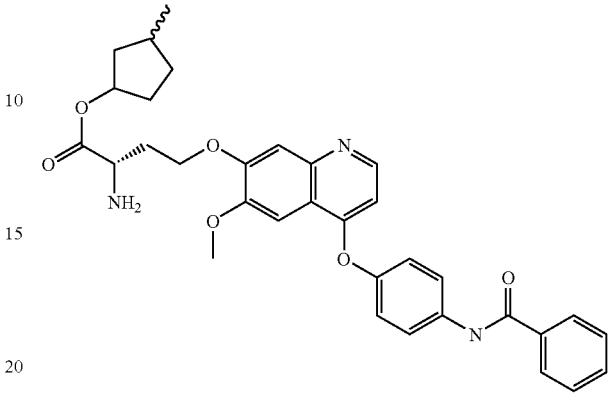

The product from stage 1 was treated with 4M HCl in dioxane (1.5 ml). The solution was stirred at room temperature overnight before evaporation under reduced pressure to give the title compound as a yellow powder (33 mg, 88% yield).

*The synthesis of (S)-4-Bromo-2-tert-butoxycarbonylamino-butyric acid 3-methyl cyclopentyl ester is outlined below in Scheme 20.

Scheme 20

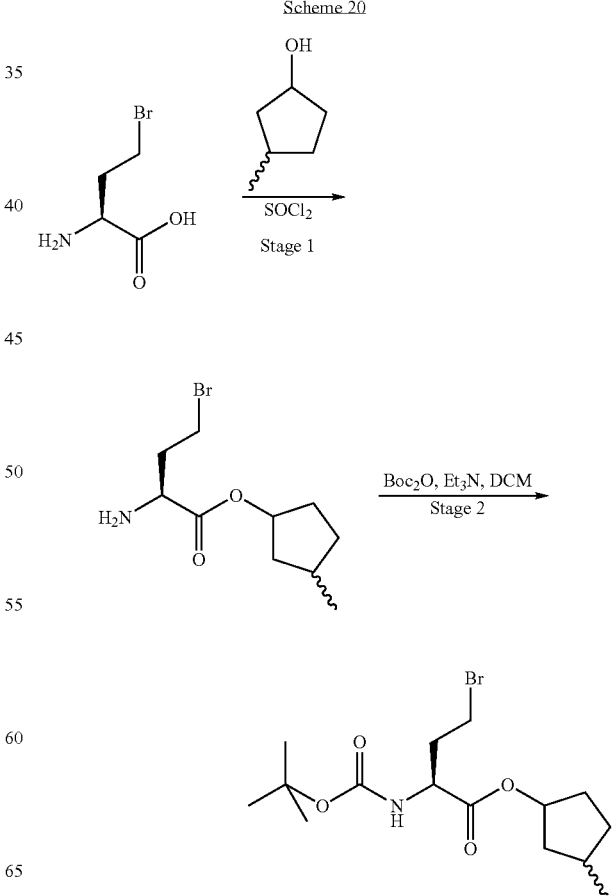

Stage 1-(S)-2-Amino-4-bromo-butyric acid 3-methyl cyclopentyl ester

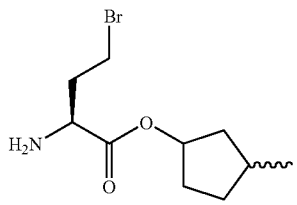

(S)-2-Amino-4-bromo-butyric acid (1.0 g, 3.8 mmol, 1 eq) was dissolved in 3-methylcyclopentanol (5 vol) and cooled to 0-5° C. under an atmosphere of nitrogen. Thionyl chloride (0.55 ml, 7.6 mmol, 2 eq) was added over approximately 15 minutes whilst maintaining the temperature below 10° C. (a red to brown colouration develops during the addition) before allowing to warm to 15-25° C. After stirring for 2.5 hours at room temperature the reaction mixture was heated to 60° C. and refluxed overnight. The reaction mixture was then concentrated under reduced pressure. Toluene (20 ml) was added to the residue and the concentration repeated to obtain 1.9 g of crude residue which was cooled to 15-25° C. before the addition of heptane (15 ml) to effect precipitation of the product. The resulting slurry was stirred at 15-25° C. for 2 hours before being filtered to provide the title compound as a brown solid (726 mg, 64% yield).

LC/MS: m/z 265 [M+H]$^+$.

Stage 2-(S)-4-Bromo-2-tert-butoxycarbonylamino-butyric acid cyclohexyl ester

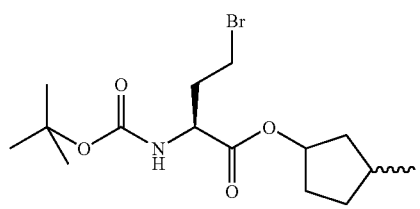

(S)-2-Amino-4-bromo-butyric acid 3-methyl cyclopentyl ester (726 mg, 2.42 mmol, 1 eq) was dissolved in THF (6 ml) and cooled to 0° C. before addition of triethylamine (0.74 ml) at 0-5° C. A solution of di-tert-butyl dicarbonate (580 mg, 2.66 mmol, 1.1 eq) was added keeping the temperature at 0-5° C. The reaction was then allowed to warm to room temperature and stirred overnight. The residue was partitioned between diethyl ether and water. The aqueous layer was extracted with diethyl ether and the organic extracts were combined and washed successively with 1M HCl, saturated aqueous sodium hydrogen carbonate solution and brine and then dried over magnesium sulphate. Diethyl ether was evaporated under reduced pressure and the residue purified by column chromatography using DCM/methanol to provide the title compound as a transparent oil (367 mg, 42% yield).

LC/MS: m/z 265 [M+H]$^+$.

EXAMPLE 47

(S)-2-Amino-4-[4-(4-benzoylamino-phenoxy)-6-methoxy-quinolin-7-yloxy]-butyric acid bicyclo[2.2.1]hept-1-yl ester

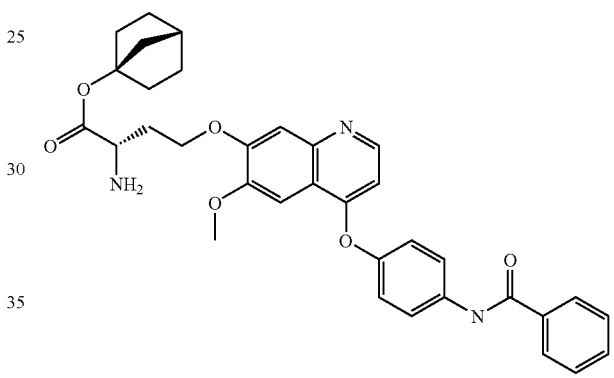

LC/MS purity: 99%, m/z 570 [M+H]$^+$. $^1$H NMR (300 MHz, CD$_3$OD) δ: 8.71 (1H, dd), 8.02-7.95 (4H, m), 7.92 (1H, s), 7.66-7.50 (4H, m), 7.43-7.36 (2H, m), 6.99 (1H, d, J=6.8 Hz), 4.59-4.50 (2H, m), 4.14 (3H, s), 2.67-2.53 (2H, m), 2.34-2.20 (1H, m), 2.16 (1H, s), 1.60-1.03 (10H, m)

Stage 1-(S)-4-[4-(4-Benzoylamino-phenoxy)-6-methoxy-quinolin-7-yloxy]-2-tert-butoxycarbonylamino-butyric acid bicyclo[2.2.1]hept-1-yl ester

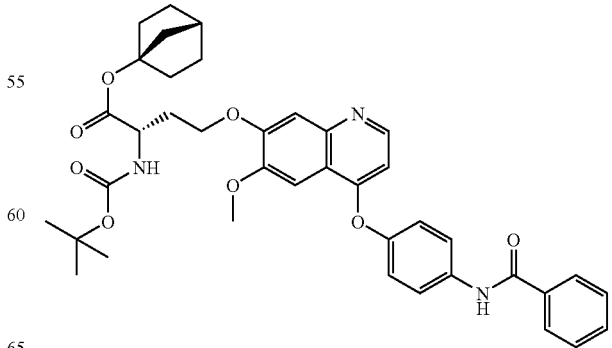

N-[4-(7-Hydroxy-6-methoxy-quinolin-4-yloxy)-phenyl]-benzamide (80 mg, 0.2 mmol, 1 eq), (S)-4-bromo-2-tert-butoxycarbonylamino-butyric acid bicyclo[2.2.1]hept-1-yl ester** (70 mg, 0.2 mmol, 1.1 eq) and $K_2CO_3$ (55 mg, 0.4 mmol, 2 eq) were dissolved in anhydrous DMF (5 ml) under an atmosphere of nitrogen. The reaction was stirred at 35° C. for 42 hours before the DMF was removed under reduced pressure. The residue was dissolved in DCM and washed with water followed by brine. The organic layer was dried over magnesium sulphate and evaporated under reduced pressure. The product was purified using column chromatography eluting with DCM/methanol to afford the title compound (94 mg, 14% yield).

LC/MS: m/z 682 [M+H]$^+$.

Stage 2-(S)-2-Amino-4-[4-(4-benzoylamino-phenoxy)-6-methoxy-quinolin-7-yloxy]-butyric acid bicyclo[2.2.1]hept-1-yl ester

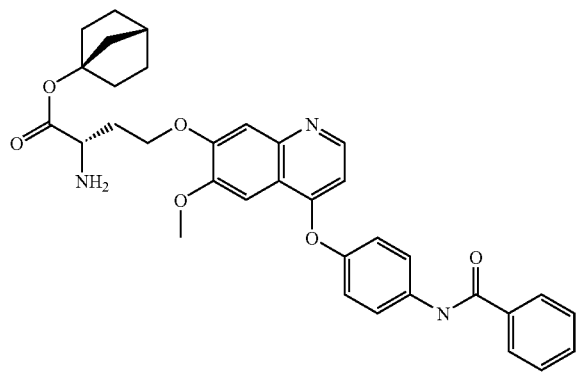

(S)-4-[4-(4-Benzoylamino-phenoxy)-6-methoxy-quinolin-7-yloxy]-2-tert-butoxycarbonylamino-butyric acid bicyclo[2.2.1]hept-1-yl ester was treated with 4M HCl in dioxane (3 ml). The solution was stirred at room temperature overnight before evaporation under reduced pressure to give the product as a pale yellow powder (100 mg, 100% yield).

LC/MS purity: 99%, m/z 570 [M+H]$^+$. $^1$H NMR (300 MHz, CD$_3$OD), δ: 8.71 (1H, dd), 8.02-7.95 (4H, m), 7.92 (1H, s), 7.66-7.50 (4H, m), 7.43-7.36 (2H, m), 6.99 (1H, d, J=6.8 Hz), 4.59-4.50 (2H, m), 4.14 (3H, s), 2.67-2.53 (2H, m), 2.34-2.20 (1H, m), 2.16 (1H, s), 1.60-1.03 (10H, m)

EXAMPLE 48

(S)-2-Amino-4-[4-(4-benzoylamino-phenoxy)-6-methoxyquinolin-7-yloxy]-butyric acid cyclohexyl ester

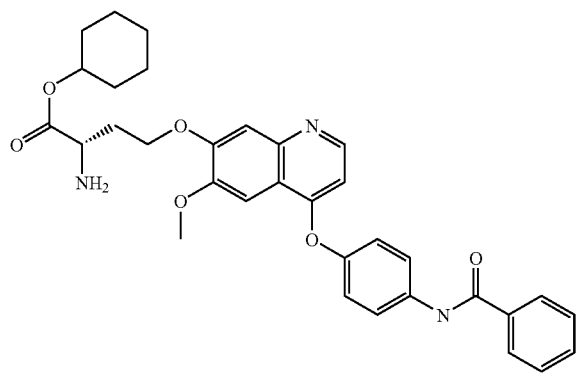

LC/MS purity: 99% (254 nm), m/z 570 [M+H]$^+$. $^1$H NMR (300 MHz, CD$_3$OD), δ: 8.71 (1H, d, J=6.8 Hz), 8.03-7.98 (2H,m), 7.98-7.95 (2H, m), 7.89 (1H, s), 7.69 (1H, s), 7.65-7.50 (3H, m), 7.43-7.37 (2H, m), 6.98 (1H, d, J=6.8 Hz), 5.02-4.97 (1H, m), 4.54 (2H, t, J=5.6 Hz), 4.38 (1H, t, J=6.4 Hz), 4.14 (3H, s), 2.73-2.51 (2H, m), 2.00-1.85 (2H, m), 1.83-1.70 (2H, m), 1.62-1.51 (2H, m), 1.50-1.28 (4H, m).

Stage 1-(S)-4-[4-(4-Benzoylamino-phenoxy)-6-methoxy-quinolin-7-yloxy]-2-tert-butoxycarbonylamino-butyric acid cyclohexyl ester

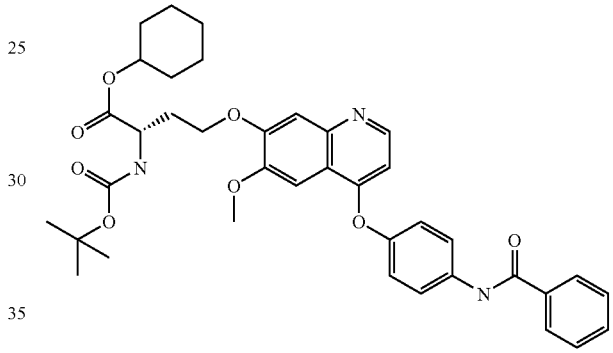

N-[4-(7-Hydroxy-6-methoxy-quinolin-4-yloxy)-phenyl]-benzamide (70 mg, 0.18 mmol, 1 eq), (S)-4-bromo-2-tert-butoxycarbonylamino-butyric acid cyclohexyl ester** (72 mg, 0.19 mmol, 1.1 eq) and $K_2CO_3$ (50 mg, 0.36 mmol, 2 eq) were dissolved in anhydrous DMF (5 ml) under an atmosphere of nitrogen. The reaction was stirred at 35° C. for 60 hours before the DMF was removed under reduced pressure. The residue was dissolved in DCM and washed with water followed by brine. The organic layer was dried over magnesium sulphate and evaporated under reduced pressure. The product was purified by column chromatography eluting with DCM/methanol to give the title compound as transparent crystals (80 mg, 62% yield).

LC/MS: m/z 760 [M+H]$^+$.

105

Stage 2-(S)-2-Amino-4-[4-(4-benzoylamino-phenoxy)-6-methoxy-quinolin-7-yloxy]-butyric acid cyclohexyl ester

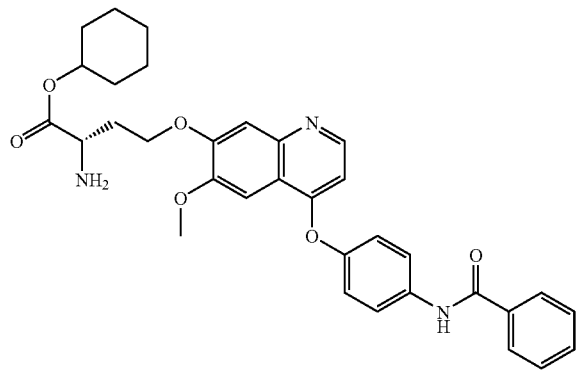

(S)-4-[4-(4-Benzoylamino-phenoxy)-6-methoxy-quinolin-7-yloxy]-2-tert-butoxycarbonylamino-butyric acid cyclohexyl ester was treated with a solution of 1:1 DCM/TFA (4 ml) and the solution was stirred at room temperature for 1 hour before evaporation under reduced pressure. The product was purified using preparative HPLC to provide the title compound as white crystals (46 mg, 68% yield)

** (S)-4-Bromo-2-tert-butoxycarbonylamino-butyric acid (1S,4R)-bicyclo [2.2.1]hept-2-yl-ester and (S)-4-bromo-2-tert butoxycarbonylamino-butyric acid cyclohexyl ester for the synthesis of Examples 47 and 48 were prepared following the route described in Scheme 20.

106

EXAMPLE 49

(S)-2-Amino-4-[4-(4-benzoylamino-phenoxy)-6-methoxy-quinolin-7-yloxy]-butyric acid 2-methyl-cyclopentyl ester

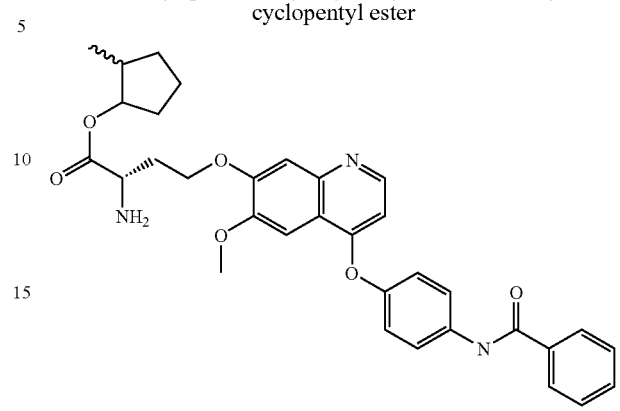

LC/MS purity: 99% (254 nm), m/z 570 [M+H]$^+$. $^1$H NMR (300 MHz, CD$_3$OD), δ: 8.69 (1H, d, J=4.3 Hz), 7.97 (4H,d, J=8.7 Hz), 7.89 (1H, s), 7.71-7.49 (4H, m), 7.39 (2H, d, J=8.9 Hz), 6.96 (1H, d, J=6.4 Hz), 4.58-4.47 (2H, m), 4.36 (1H, t, J=6.3 Hz), 4.12 (3H, s), 2.70-2.48 (2H, m), 2.18-1.85 (4H, m), 1.80-1.63 (3H, m), 1.36-1.17 (2H, m), 1.02 (3H, dd, J=5.6, 6.9 Hz).

The synthesis of Example 49 is outlined in Scheme 21.

Scheme 21

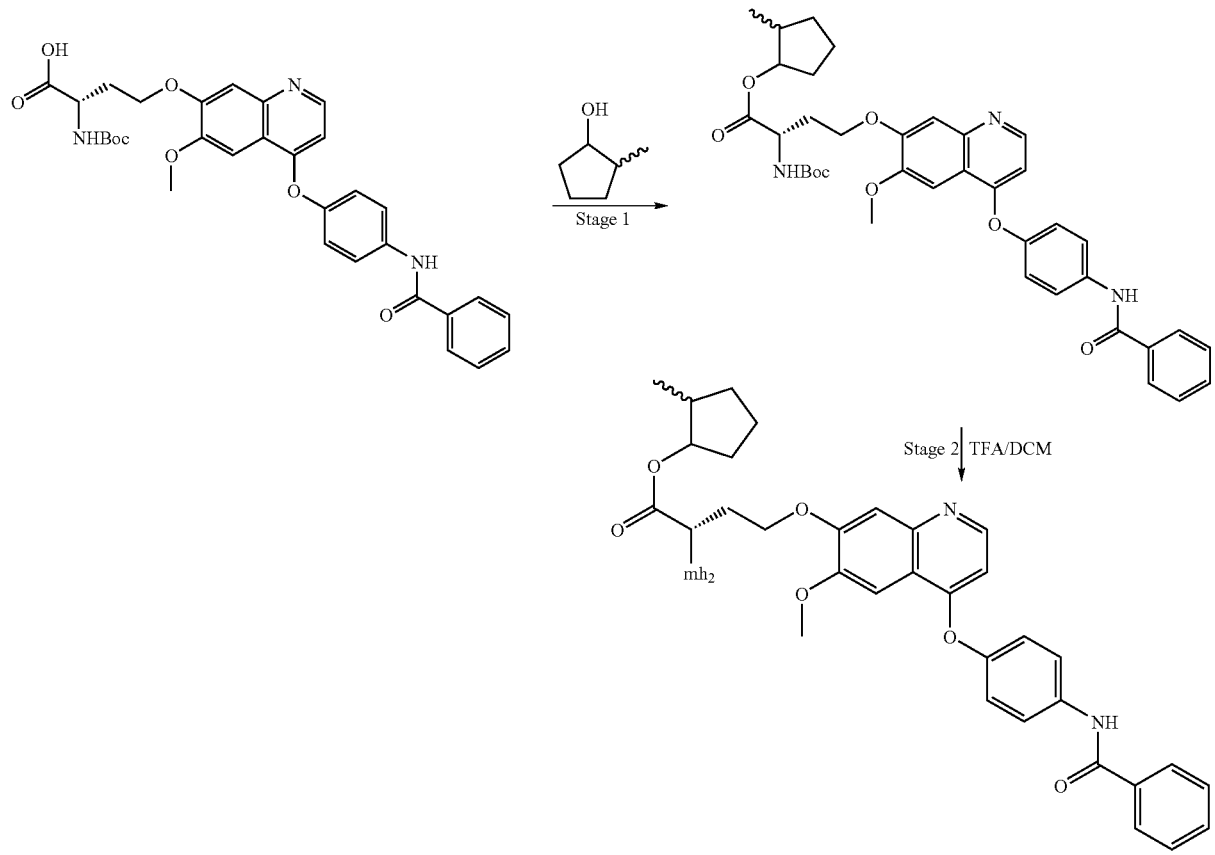

Stage 1 -(S)-4-[4-(4-Benzoylamino-phenoxy)-6-methoxy-quinolin-7-yloxy]-2-tert-butoxycarbonylamino-butyric acid 2-methyl-cyclopentyl ester

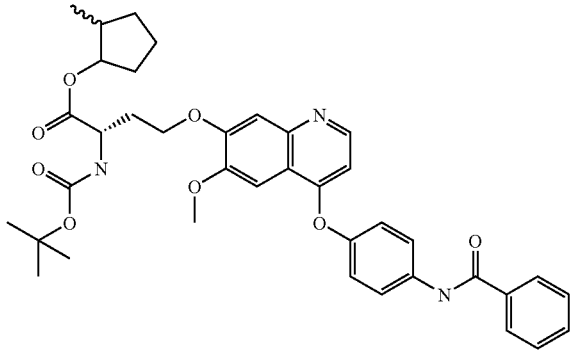

(S)-4-[4-(4-Benzoylamino-phenoxy)-6-methoxy-quinolin-7-yloxy]-2-tert-butoxycarbonylamino-butyric acid (150 mg, 0.255 mmol, 1 eq) was dissolved in DMF (5 ml) under an atmosphere of nitrogen and cooled to 0° C. DMAP (6.2 mg, 0.05 mmol, 0.2 eq), 2-methyl cyclopentanol (0.12 ml, 1.02 mmol, 4 eq) and EDC (100 mg, 0.52 mmol, 2 eq) were added portion wise. The mixture was stirred and warmed to room temperature for 84 hours before the DMF was evaporated under reduced pressure. The residue was dissolved in DCM and washed with 1M HCl (2×20 ml) followed by 1M Na₂CO₃ (2×20 ml) and brine. The organic layer was then dried over magnesium sulphate and evaporated under reduced pressure. The product was purified using column chromatography eluting with ethyl acetate/heptane (2:3) to afford the title compound as a white solid (30 mg, 16% yield)

LC/MS: m/z 670 [M+H]⁺.

Stage 2-(S)-2-Amino-4-[4-(4-benzoylamino-phenoxy)-6-methoxy-quinolin-7-yloxy]-butyric acid 2-methyl-cyclopentyl ester

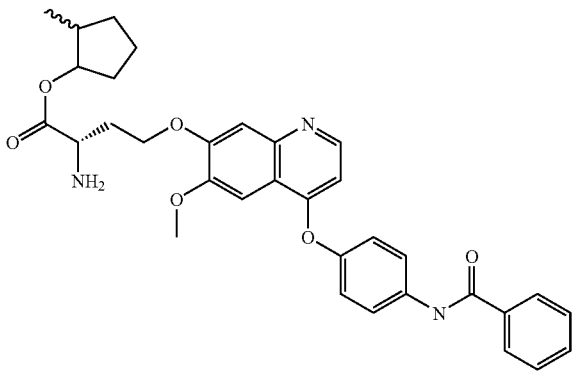

The product from stage 1 was dissolved in a solution of 1:1 DCM and TFA (4 ml). The reaction mixture was stirred at room temperature for 1 hour before evaporation under reduced pressure. The product was purified using preparative HPLC to obtain the title compound as a yellow solid (23 mg, 97% yield).

Example 50 was prepared using (S)-2-Benzyloxycarbonylamino-4-bromo-butyric acid tert-butyl ester* at Stage 1 of Scheme 19.

EXAMPLE 50

(S)-2-Amino-4-[4-(4-benzoylamino-phenoxy)-6-methoxy-quinolin-7-yloxy]-butyric acid tert-butyl ester

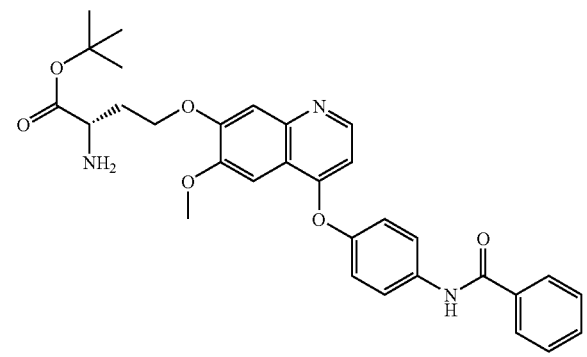

LC/MS purity: 97%. m/z 544 [M+H]⁺, ¹H NMR (300 MHz, CD₃OD), δ 8.67 (1H, d, J=6.8 Hz), 7.98 (4H,d, J=8.7 Hz), 7.90 (1H,s), 7.68-7.51 (4H, m), 7.42-7.36 (2H, m), 6.97 (1H, d, J=6.6 Hz), 4.52 (2H, t, J=5.7 Hz), 4.28 (1H, t, J=6.5 Hz), 4.13 (3H, s), 2.69-2.45 (2H,m), 1.53 (9H, s).

*The synthesis of (S)-2-Benzyloxycarbonylamino-4-bromo-butyric acid tert-butyl ester is outlined in Scheme 21a.

Scheme 21a

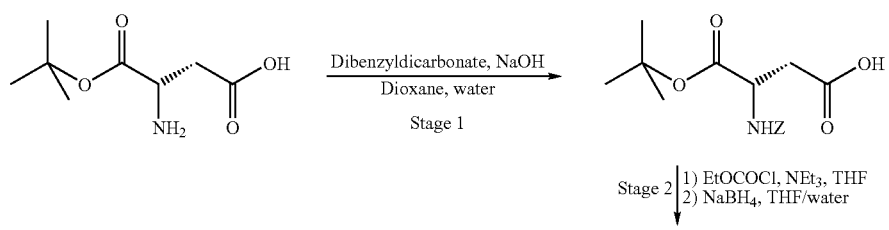

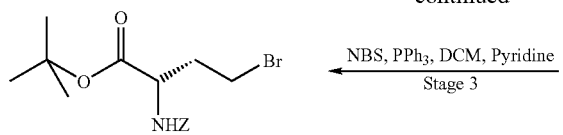 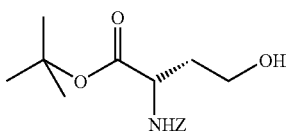

Stage 1 -(S)-2-Benzyloxycarbonylamino-succinic acid 1-tert-butyl ester

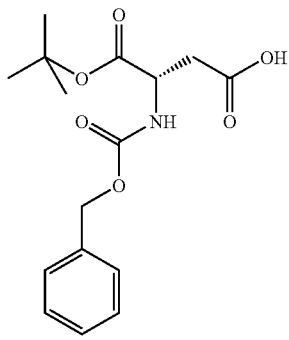

(S)-2-Amino-succinic acid 1-tert-butyl ester (0.9 g, 4.75 mmol) and sodium hydroxide (0.28 g, 7.13 mmol, 1.5 eq) were dissolved in 25% water in dioxane (50 ml). The solution was stirred at 5° C. and dibenzyldicarbonate (2 g, 4.13 mmol, 1.5 eq) in dioxane (10 ml) was added slowly. The mixture was stirred at 0° C. for 1 hour and then at room temperature overnight. Water (10 ml) was added and the mixture was extracted with ethyl acetate (2×20 ml). The organic phase was back extracted with a saturated aqueous solution of sodium bicarbonate (2×10 ml). The combined aqueous layers were acidified to pH 1 with 1M HCl, and extracted with ethyl acetate (3×10 ml). The combined organic fractions were dried over magnesium sulphate and concentrated under reduced pressure. The product was purified by column chromatography (35% ethyl acetate in heptane) to provide 0.76 g (50% yield) of title compound as a colourless oil.

LC/MS: m/z 346 [M+23]$^+$, $^1$H NMR (300 MHz, CDCl$_3$), δ 7.39-7.32 (5H, m), 5.72 (1H, d, J=8.1 Hz), 5.13 (2H, s), 4.58-4.50 (1H, m), 3.10-2.99 (1H, m), 2.94-2.83 (1H, m), 1.45 (9H, s).

Stage 2-(S)-2-Benzyloxycarbonylamino-4-hydroxy-butyric acid tert-butyl ester

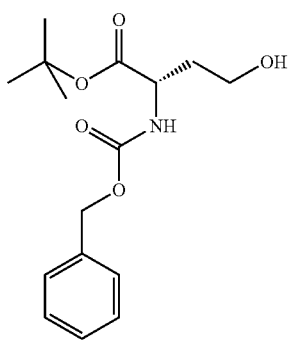

To a solution of (S)-2-(3-Phenyl-propionylamino)-succinic acid 1-tert-butyl ester (0.6 g, 1.87 mmol) in anhydrous THF (20 ml) at −20° C. was slowly added triethylamine (0.032 ml, 2.24 mmol, 1.2 eq) and ethyl chloroformate (0.021 ml, 2.24 mmol, 1.2 eq). The mixture was stirred at −20° C. for 2 hours. The solid formed was filtered off and washed with THF (2×10 ml). The filtrate was added drop wise to a solution of sodium borohydride (0.2 g, 5.61 mmol, 3 eq) at 0° C. and stirred at room temperature for 4 hours. The solvent was removed under reduced pressure, the residue was diluted with water (10 ml) acidified to pH 5 with 1M HCl and extracted with EtOAc. The organic fractions were combined washed with 10% aqueous sodium hydroxide, water, brine dried on magnesium sulphate and concentrated under reduced pressure to give the title compound as clear oil (0.3 g, 51% yield).

LC/MS: m/z 332 [M+23]$^+$.

Stage 3-(S)-2-Benzyloxycarbonylamino-4-bromo-butyric acid tert-butyl ester

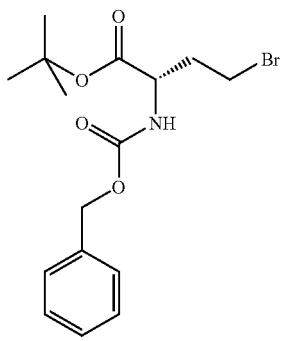

To a solution of N-bromosuccinimide (0.52 g, 2.91 mmol, 3 eq) in DCM (10 ml) was slowly added a solution of triphenylphosphine (0.71 g, 2.72 mmol, 2.8 eq) in DCM (10 ml). The mixture was stirred at room temperature for 5 minutes. Pyridine (0.094 ml, 1.16 mmol, 1.2 eq) and a solution of (S)-2-Benzyloxycarbonylamino-4-hydroxy-butyric acid tert-butyl ester (0.3 g, 0.97 mmol, 1 eq) in DCM (20 ml) were added drop wise and the mixture stirred at room temperature overnight. The solvent was removed under reduced pressure, the residue was azeotroped with toluene (2×15 ml) and triturated with diethyl ether (2×25 ml) and 10% ethyl acetate in heptanes. The solutions from the trituration were combined and evaporated to dryness. The crude product was purified by column chromatography (15% ethyl acetate in heptanes) to give the title compound as a clear oil (0.16 g, 44% yield).

LC/MS: m/z 395 [M+23]$^+$, $^1$H NMR (300 MHz, CDCl$_3$), δ 7.39-7.30 (5H, m), 5.40 (1H, d, J=6.8 Hz), 5.12 (2H, s), 4.38

(1H, q, J=7.7 Hz), 3.47-3.38 (2H, m), 2.49-2.33 (1H, m), 2.28-2.13 (1H, m), 1.48 (9H, s).

EXAMPLE 51

(S)-2-Amino-4-[4-(4-benzoylamino-phenoxy)-6-methoxy-quinolin-7-yloxy]-butyric acid Ethyl ester

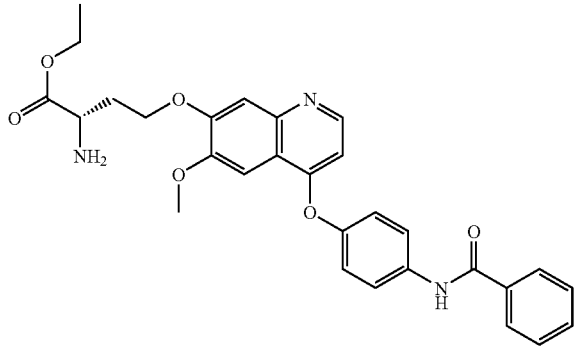

LC/MS purity: 98%, m/z 516.2 [M+H]+. 1H NMR (300 MHz, DMSO-d6), δ: 10.56 (1H, s), 8.80 (1H, d, J=6.6 Hz), 8.72 (3H, br s), 8.07-7.98 (3H, m), 7.75 (1H, s), 7.66 (1H, s), 7.64-7.53 (3H, m), 7.42 (2H, d, J=9 Hz), 6.97 (1H, d, J=6.6 Hz), 4.42 (2H, t, J=5.7 Hz), 4.24 (3H, q, J=6.9 Hz), 4.05 (3H, s), 1.24 (3H, t, J=7.1 Hz).

Example 51 was prepared using (S)-2-Benzyloxycarbonylamino-4-bromo-butyric acid ethyl ester* at Stage 1 of Scheme 19.

The synthesis of (S)-4-Bromo-2-tert-butoxycarbonylamino-butyric acid ethyl ester is outlined below in Scheme 21b.

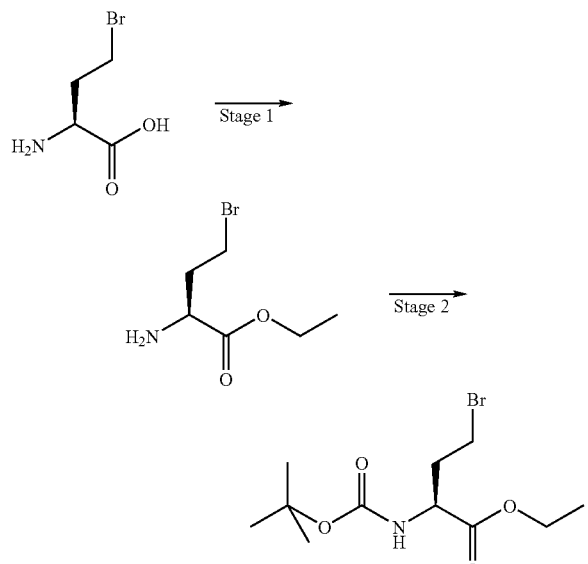

Stage 1-(S)-2-amino-4-bromo-butyric acid Ethyl ester Hydrochloride

To a solution of (S)-2-amino-4-bromo-butyric acid hydrobromide (2 g, 7.6 mmol) in ethanol (10 ml), at 0° C., was added thionyl chloride (1.11 ml, 15.21 mmol). The solution was stirred at 70° C. for 1 hour, cooled and concentrated in vacuo. Heptane added and mixture concentrated under high vac. Ether was added and the precipitate stirred for 1 hr, filter and dried in vacuo to provide (S)-2-amino-4-bromo-butyric acid ethyl ester hydrochloride as an sticky white solid (1.9 g).

1H NMR (300 MHz, DMSO), δ:8.46 (3H, bs), 4.24 (2H, q, J=6.9&7.2 Hz), 4.12 (1H, t, J=6.5 Hz), 3.85-3.55 (2H, m), 2.45-2.18 (2H, m), 1.26 (3H, t, J=7.2 Hz).

Stage 2-(S)-4-bromo-2-tert-butoxycarbonylamino-butyric acid Ethyl ester

To a slurry of (S)-2-amino-4-bromo-butyric acid ethyl ester hydrochloride (1.95 g, 9.28 mmol) in dioxane (16 ml), at 0° C., was added triethylamine (2.84 ml, 20.42 mmol) and a solution of BOC anhydride (2.03 g, 9.28 mmol) in dioxane (3.4 ml). The reaction was stirred at 50° C. for 1 hr then at room temperature for 18 hrs. The reaction was concentrated in vacuo, partitioned between EtOAc and water. The aqueous was extracted with EtOAc and the combined organics washed with 1H aq HCl, sat aq NaHCO3, brine and dried. The residue was purified by column chromatography (10-15% EtOAc/Heptane) to provide (S)-4-bromo-2-tert-butoxycarbonylamino-butyric acid ethyl ester as a viscous oil that solidified upon cooling (1.84 g).

1H NMR (300 MHz, CDCl3), δ: 5.15 (1H, bs), 4.50-4.40 (1H, m), 4.28 (2H, q, J=6.9&7.2 Hz), 3.70-3.40 (2H, m), 2.50-2.15 (2H, m), 1.51 (9H, s), 1.36 (3H, t, J=7.2 Hz).

EXAMPLE 52

(S)-2-Amino-4-[4-(4-benzoylamino-phenoxy)-6-methoxy-quinolin-7-yloxy]-butyric acid benzyl ester

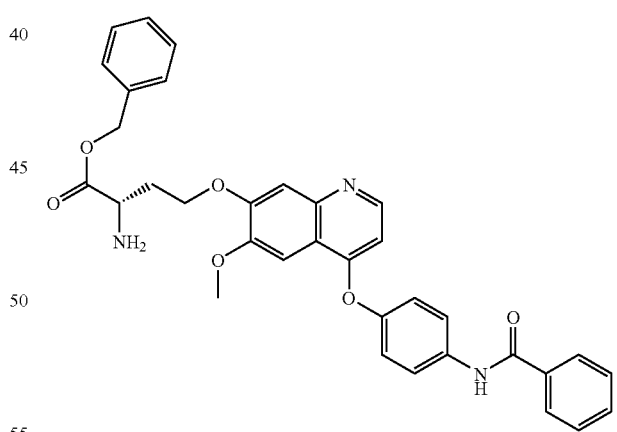

LC/MS purity: 98.6%, m/z 578.2 [M+H]+. 1H NMR (300 MHz, DMSO-d6), δ: 10.59 (1H,s), 9.00-8.70 (4H, br s), 8.08-8.00 (4H, m), 7.74 (2H, s), 7.67-7.54 (3H, m), 7.45-7.26 (7H, m), 6.87 (1H, d, J=6.6 Hz), 5.31-5.20 (2H, m), 4.50-4.25 (3H, m), 4.01 (3H, s).

Example 52 was prepared using (S)-2-Benzyloxycarbonylamino-4-bromo-butyric acid benzyl ester* at Stage 1 of Scheme 19.

The synthesis of (S)-4-Bromo-2-tert-butoxycarbonylamino-butyric acid benzyl ester follows a similar route to Scheme 21b using benzyl alcohol at Stage 1.

Stage 1-(S)-2-amino-4-bromo-butyric acid benzyl ester hydrochloride

To a solution of (S)-2-amino-4-bromo-butyric acid hydrobromide (2 g, 7.6 mmol) in benzyl alcohol (10 ml), at 0° C., was added thionyl chloride (1.11 ml, 15.21 mmol). The solution was stirred at 70° C. for 2 hour, cooled and concentrated in vacuo. Heptane was added and the mixture was concentrated. The oil was dissolved in toluene, ether added and initial precipitate filtered. The filtrate was allowed to stand overnight and the second precipitate filtered and dried in vacuo to provide (S)-2-amino-4-bromo-butyric acid benzyl ester hydrochloride as an off white solid (630 mg).

Stage 2-(S)-4-bromo-2-tert-butoxycarbonylamino-butyric acid benzyl ester

To a slurry of (S)-2-amino-4-bromo-butyric acid benzyl ester hydrochloride (630 mg, 2.04 mmol) in THF (10 ml), at 0° C., was added triethylamine (625 µl, 4.49 mmol) and a solution of BOC anhydride (445 mg, 2.04 mmol) in THF (3 ml). The reaction was stirred at 50° C. for 18 hrs. The reaction was partitioned between EtOAc and water. The aqueous was extracted with EtOAc and the combined organic washed with 1H aq HCl, sat aq NaHCO$_3$, brine and dried. The residue was purified by column chromatography (20-100% EtOAc/Heptane) to provide (S)-4-bromo-2-tert-butoxycarbonylamino-butyric acid benzyl ester as a viscous oil that solidified upon standing (460 mg).

$^1$H NMR (300 MHz, CDCl$_3$), δ: 7.40-7.35 (5H, m), 5.21 (2H, s), 5.18-5.10 (1H, m), 4.50-4.40 (1H, m), 3.61-3.40 (2H, m), 2.50-2.10 (2H, m), 1.46 (9H, s).

The following example was prepared by the route shown in Scheme 23 using N-(4-hydroxy-phenyl)-4-trifluoromethyl-benzamide* at Stage 4.

EXAMPLE 53

(S)-2-Amino-4-{6-methoxy-4-[4-(4-trifluoromethyl-benzoylamino)-phenoxy]-quinolin-7-yloxy}-butyric acid cyclopentyl ester

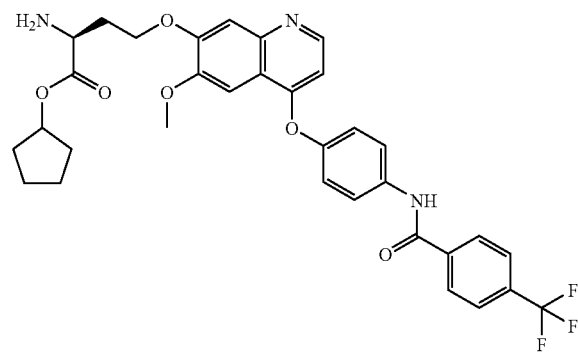

LC/MS purity: 98%, m/z 624 [M+H]$^+$. $^1$H NMR (300 MHz, CD$_3$OD), δ: 8.72 (1H, d, J=6.6 Hz), 8.16 (2H, d, J=7.9 Hz), 8.01 (2H, d, J=8.7 Hz), 7.92 (1H, s), 7.88 (2H, d, J=8.1 Hz), 7.64 (1H, s), 7.42 (2H, d, J=8.8 Hz), 7.00 (1H, d, J=6.6 Hz), 5.41-5.32 (1H, m), 4.53 (2H, t, J=4.8 Hz), 4.35 (1H, t, J=6.2 Hz), 4.14 (3H, s), 2.64-2.53 (2H, m), 2.02-1.87 (2H, m), 1.85-1.59 (6H, m).

*Synthesis of N-(4-hydroxy-phenyl)-4-trifluoromethyl-benzamide (Scheme 22 Below).

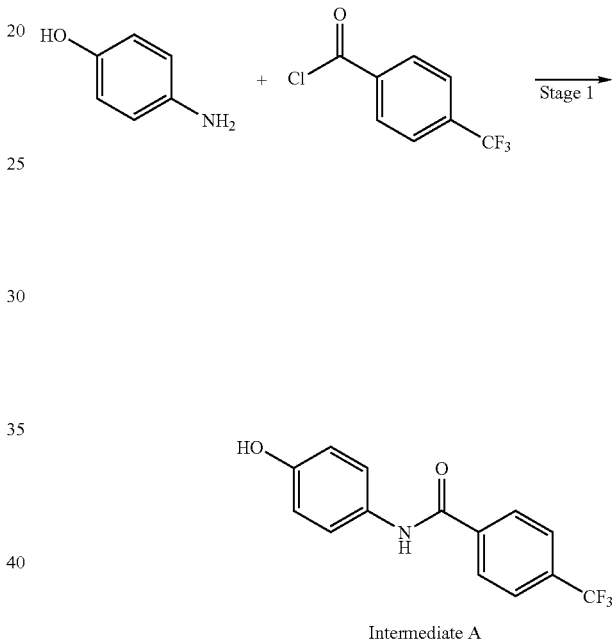

Intermediate A

A solution of 4-amino-phenol (1.00 g, 9.2 mmol) and triethylamine (1.42 ml, 10.1 mmol) was cooled to 0° C. and 4-trifluoromethyl-benzoyl chloride (1.36 ml, 9.2 mmol) was added dropwise. The reaction mixture was allowed to warm to room temperature and stirred for 6 hours. The reaction mixture was poured in water (50 ml). A precipitate was collected by filtration and taken up in ethyl acetate (200 ml). The organic solution was washed with 1N HCl (100 ml), water (100 ml), brine (100 ml), dried (MgSO$_4$), filtered and concentrated under reduced pressure to afford the title compound as a pale yellow solid (1.98 g, 77% yield).

$^1$H NMR (300 MHz, DMSO-d$_6$) δ: 10.24 (1H, s), 9.30 (1H, s), 8.13 (2H, d, J=8.0 Hz), 7.90 (2H, d, j+8.0 Hz), 7.54 (2H, d, J=8.9 Hz), 6.76 (2H, d, J=8.9 Hz).

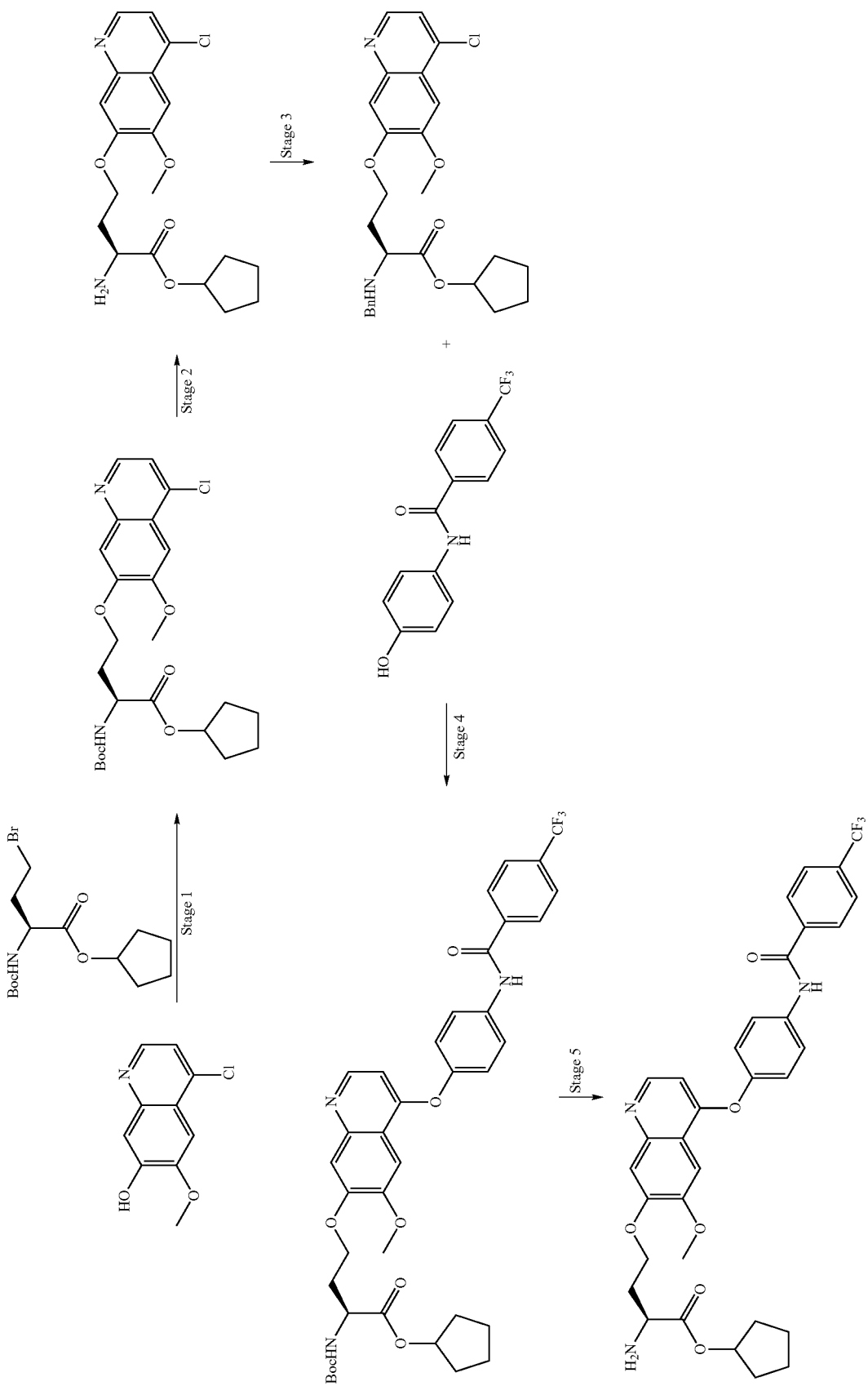

Stage 1-(S)-2-tert-Butoxycarbonylamino-4-(4-chloro-6-methoxy-quinolin-7-yloxy)-butyric acid cyclopentyl ester To a solution of 4-chloro-6-methoxy-quinolin-7-ol (2.18 g, 10.4 mmol) in DMF (80 ml) were added N-(4-hydroxy-phenyl)-4-trifluoromethyl-benzamide (4.0 g, 11.4 mmol) and $K_2CO_3$ (1.73 g, 12.5 mmol). The reaction mixture was stirred overnight at 40° C. The DMF was removed under reduced pressure. The remaining mixture was poured into EtOAc (200 ml) and $H_2O$ (200 ml), the organic layer was separated, washed with brine and DCM/MeOH 4/1 (100 ml) had to be added to break the emulsion formed. The organic layer was concentrated under vacuum and $Et_2O$/heptane 1/1 (100 ml) was added to allow a brown solid to form, which was filtered to give the title compound (4.41 g, 88% yield).

LC/MS: m/z 479/481 [M+H]$^+$. $^1$H NMR (300 MHz, DMSO-$d_6$) δ: 7.62 (1H, d, J=4.9 Hz), 6.59 (1H, d, J=5.1 Hz), 6.57 (1H, s), 6.45 (1H, s), 4.31-4.26 (1H, m), 3.96 (3H, s), 3.53-3.47 (1H, m), 3.42 (1H, dd, J=4.8, 7.9 Hz), 3.35-3.27 (1H, m), 1.54-1.44 (1H, m), 1.42-1.31 (1H, m), 0.97-0.85 (2H, m), 0.82-0.67 (6H, m), 0.54 (9H, s).

Stage 2-(S)-2-Amino-4-(4-chloro-6-methoxy-quinolin-7-yloxy)-butyric acid cyclopentyl ester To a solution of (S)-2-tert-butoxycarbonylamino-4-(4-chloro-6-methoxy-quinolin-7-yloxy)-butyric acid cyclopentyl ester (4.41 g, 9.2 mmol) in DCM (50 ml) was added TFA (50 ml) and the reaction mixture was stirred at room temperature for 2 hours. The solvent was removed under reduced pressure and the product poured into DCM (100 ml) and washed with a saturated aqueous solution of $NaHCO_3$ (100 ml). The organic layer was washed with brine (150 ml), dried over $MgSO_4$, filtered and concentrated under vacuum to provide the title compound (3.00 g, 86% yield).

LC/MS: m/z 379/381 [M+H]$^+$. $^1$H NMR (300 MHz, CDCl$_3$) δ: 8.62 (1H, d, J=6.0 Hz), 8.12 (1H, s), 7.66 (1H, d, J=6.0 Hz), 7.43 (1H, s), 5.22 (1H, m), 4.49 (2H, m), 4.29 (1H, m), 4.03 (3H, s), 2.62 (2H, m), 1.79 (2H, m), 1.68-1.65 (4H, m), 1.53 (2H, m).

Stage 3-(S)-2-Benzylamino-4-(4-chloro-6-methoxy-quinolin-7-yloxy)-butyric acid cyclopentyl ester To a solution of (S)-2-amino-4-(4-chloro-6-methoxy-quinolin-7-yloxy)-butyric acid cyclopentyl ester (3.0 g, 7.9 mmol) in DMF (150 ml) were added $K_2CO_3$ (1.64 g, 11.8 mmol) and benzyl bromide (942 μL, 7.9 mmol). The reaction mixture was stirred overnight at room temperature. The DMF was removed under reduced pressure. The crude product was dissolved in DCM (200 ml) and washed with water (200 ml) and brine (200 ml). The organic layer was dried over $MgSO_4$, filtered and concentrated under reduced pressure. The crude mixture was purified by flash chromatography using 1-2% MeOH in DCM to afford the title compound (1.50 g, 41% yield).

LC/MS: m/z 469/471 [M+H]$^+$.

Stage 4-(S)-2-Benzylamino-4-{6-methoxy-4-[4-(4-trifluoromethyl-benzoylamino)-phenoxy]-quinolin-7-yloxy}-butyric acid cyclopentyl ester To a mixture of (S)-2-benzylamino-4-(4-chloro-6-methoxy-quinolin-7-yloxy)-butyric acid cyclopentyl ester (97 mg, 0.21 mmol) and N-(4-hydroxy-phenyl)-4-trifluoromethyl-benzamide (141 mg, 0.62 mmol) was added DMF (200 μL). The reaction mixture was stirred in a sealed tube at 140° C. under nitrogen for 5 hours. The crude was poured into $H_2O$ (10 ml) and 1 M NaOH solution (10 ml) and the product was extracted with EtOAc (20 ml), washed with brine (10 ml), dried over $MgSO_4$ and concentrated under reduced pressure to give 135 mg of crude product, which was used without purification in the next step.

LC/MS: m/z 714 [M+H]$^+$.

Stage 5-(S)-2-Amino-4-{6-methoxy-4-[4-(4-trifluoromethyl-benzoylamino)-phenoxy]-quinolin-7-yloxy}-butyric acid cyclopentyl ester A solution of (S)-2-benzylamino-4-{6-methoxy-4-[4-(4-trifluoromethyl-benzoylamino)-phenoxy]-quinolin-7-yloxy}-butyric acid cyclopentyl ester in 4.4% formic acid/MeOH (8 ml) was degassed and put under nitrogen three times. Pd(OH)$_2$ (20 mg) was added and the reaction mixture was stirred at 70° C. for 2 hr. The suspension was left cooling, filtered through a pad of Celite and washed thoroughly with DCM (30 ml) and MeOH (30 ml), and the filtrate was concentrated under reduced pressure. The product was then purified by semi-preparative HPLC to give 17 mg of product (13% yield over 2 steps).

EXAMPLE 54

(S)-2-Amino-4-{6-methoxy-4-[4-(4-trifluoromethyl-benzoylamino)-phenoxy]-quinolin-7-yloxy}-butyric acid

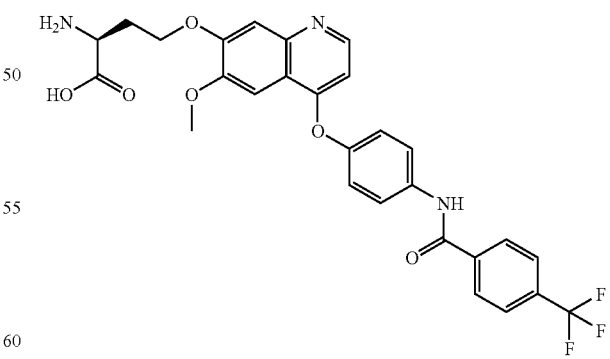

LC/MS purity: 100%, m/z 556 [M+H]$^+$. $^1$H NMR (300 MHz, CD$_3$OD), δ: 8.71 (1H, d, J=6.6 Hz), 8.16 (2H, d, J=8.1 Hz), 8.03-7.97 (2H, m), 7.90 (2H, d, J=3.6 Hz), 7.87 (1H, s), 7.58 (1H, s), 7.45-7.39 (2H, m), 6.98 (1H, d, J=6.6 Hz), 4.56 (2H, t, J=5.5 Hz), 4.31-4.25 (1H, m), 4.15 (3H, s), 2.72-2.61 (1H, m), 2.59-2.50 (1H, m).

Examples 55 to 72 were synthesised following the route shown in Scheme 23, using the appropriate acid chloride intermediate in Scheme 22.

EXAMPLE 55

(S)-2-Amino-4-{4-[4-(3-fluoro-benzoylamino)-phenoxy]-6-methoxy-quinolin-7-yloxy}-butyric acid cyclopentyl ester

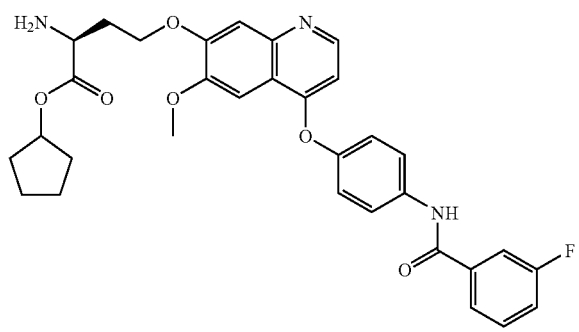

LC/MS purity: 98%, m/z 574 [M+H]⁺. ¹H NMR (300 MHz, CD₃OD), δ: 8.72 (1H, d, J=6.6 Hz), 8.03-7.94 (2H, m), 7.90 (1H, s), 7.83 (1H, d, J=7.7 Hz), 7.76-7.69 (1H, m), 7.67 (1H, s), 7.63-7.53 (1H, m), 7.43-7.39 (2H, m), 7.39-7.32 (1H, m), 6.99 (1H, d, J=6.8 Hz), 5.40-5.31 (1H, m), 4.53 (2H, t, J=5.6 Hz), 4.35 (1H, t, J=6.5 Hz), 4.14 (3H, s), 2.69-2.50 (2H, m), 2.06-1.87 (2H, m), 1.85-1.58 (6H, m).

EXAMPLE 56

(S)-2-Amino-4-{4-[4-(3-fluoro-benzoylamino)-phenoxy]-6-methoxy-quinolin-7-yloxy}-butyric acid

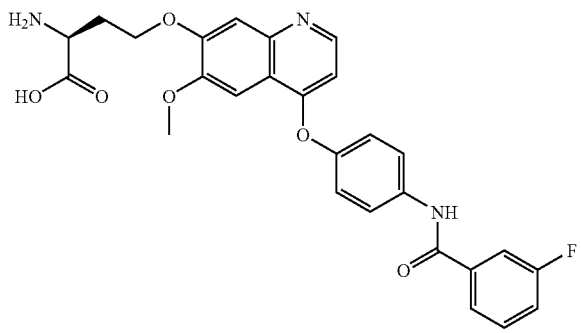

LC/MS purity: 93%, m/z 506 [M+H]⁺. ¹H NMR (300 MHz, CD₃OD), δ: 8.44 (1H, d, J=5.5 Hz), 7.88 (2H, d, J=8.9 Hz), 7.82 (1H, d, J=7.7 Hz), 7.76-7.70 (1H, m), 7.68 (1H, s), 7.63-7.53 (1H, m), 7.40-7.32 (2H, m), 7.27 (2H, d, J=8.9 Hz), 6.58 (1H, d, J=5.5 Hz), 4.52-4.37 (2H, m), 4.06 (3H, s), 3.94-3.84 (1H, m), 2.67-2.53 (1H, m), 2.46-2.32 (1H, m).

EXAMPLE 57

(S)-2-Amino-4-{6-methoxy-4-[4-(4-methoxy-benzoylamino)-phenoxy]-quinolin-7-yloxy}-butyric acid cyclopentyl ester

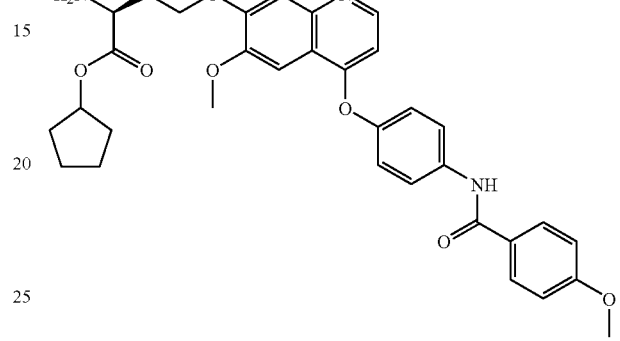

LC/MS purity: 95%, m/z 586 [M+H]⁺. ¹H NMR (300 MHz, CD₃OD) δ: 8.71 (1H, d, J=6.8 Hz), 8.01-7.93 (4H, m), 7.90 (1H, s), 7.66 (1H, s), 7.41-7.36 (2H, m), 7.11-7.04 (2H, m), 6.99 (1H, d, J=6.8 Hz), 5.40-5.31 (1H, m), 4.53 (2H, t, J=5.7 Hz), 4.35 (1H, t, J=6.4 Hz), 4.14 (3H, s), 3.90 (3H, s), 2.64-2.54 (2H, m), 2.00-1.86 (2H, m), 1.85-1.59 (6H, m).

EXAMPLE 58

(S)-2-Amino-4-{6-methoxy-4-[4-(4-methoxy-benzoylamino)-phenoxy]-quinolin-7-yloxy}-butyric acid

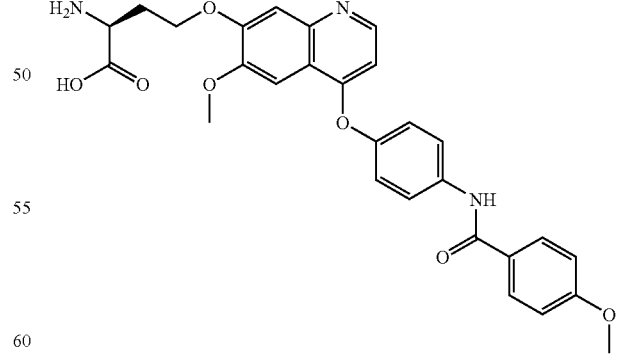

LC/MS purity: 94%, m/z 518 [M+H]⁺. ¹H NMR (300 MHz, CD₃OD) δ: 10.34 (1H, s), 8.49 (1H, d, J=5.3 Hz), 8.16 (1H, s), 7.99 (3H, dd, J=8.9, 20.1 Hz), 7.55 (1H, s), 7.41 (1H, s), 7.27 (2H, d, J=9.0 Hz), 7.08 (2H, d, J=8.9 Hz), 6.48 (1H, d, J=5.3 Hz), 4.49 (2H, s), 4.38-4.29 (2H, m), 3.96 (3H, s), 3.85 (3H, s), 3.69-3.58 (2H, m).

EXAMPLE 59

(S)-2-Amino-4-{4-[4-(cyclopropanecarbonyl-amino)-phenoxy]-6-methoxy-quinolin-7-yloxy}-butyric acid cyclopentyl ester

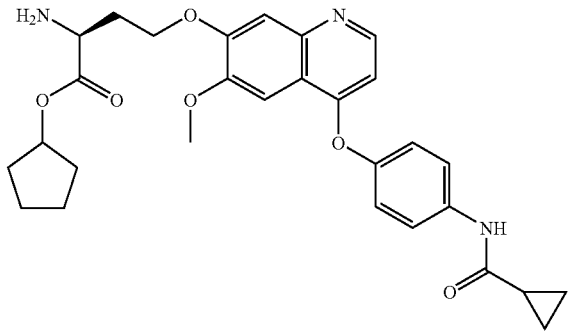

LC/MS purity: 93%, m/z 520 [M+H]⁺. ¹H NMR (300 MHz, CD₃OD) δ: 8.69 (1H, d, J=6.8 Hz), 7.88 (1H, s), 7.85-7.78 (2H, m), 7.66 (1H, s), 7.37-7.30 (2H, m), 6.94 (1H, d, J=6.8 Hz), 5.41-5.31 (1H, m), 4.52 (2H, t, J=5.6 Hz), 4.35 (1H, t, J=6.4 Hz), 4.13 (3H, s), 2.67-2.49 (2H, m), 1.92 (2H, dd, J=6.2, 13.9 Hz), 1.85-1.58 (7H, m), 1.03-0.96 (2H, m), 0.95-0.87 (2H, m).

EXAMPLE 60

(S)-2-Amino-4-{4-[4-(cyclopropanecarbonyl-amino)-phenoxy]-6-methoxy-quinolin-7-yloxy}-butyric acid

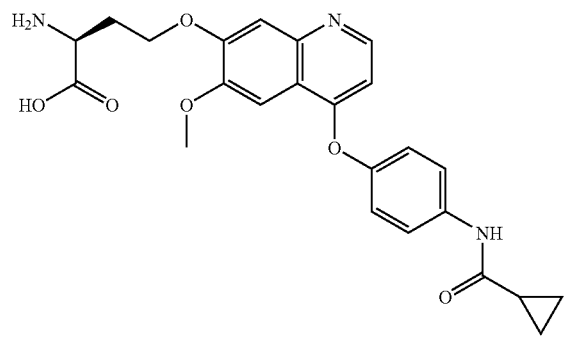

LC/MS purity: 94%, m/z 452 [M+H]⁺. ¹H NMR (300 MHz, CD₃OD) δ: 8.69 (1H, d, J=6.8 Hz), 7.89 (1H, s), 7.82 (2H, d, J=8.9 Hz), 7.62 (1H, s), 7.37-7.29 (2H, m), 6.94 (1H, d, J=6.8 Hz), 4.55 (2H, t, J=5.6 Hz), 4.33 (1H, dd, J=5.6, 7.1

Hz), 4.14 (3H, s), 2.75-2.61 (1H, m), 2.61-2.48 (1H, m), 1.88-1.76 (1H, m), 1.03-0.96 (2H, m), 0.95-0.87 (2H, m).

EXAMPLE 61

(S)-2-Amino-4-{4-[4-(2-fluoro-benzoylamino)-phenoxy]-6-methoxy-quinolin-7-yloxy}-butyric acid cyclopentyl ester

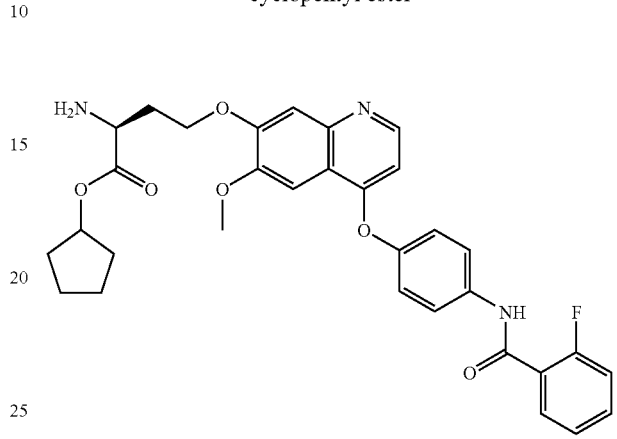

LC/MS purity: 93%, m/z 574 [M+H]⁺. ¹H NMR (300 MHz, CD₃OD) δ: 8.71 (1H, d, J=6.8 Hz), 8.00-7.94 (2H, m), 7.91 (1H, s), 7.82-7.75 (1H, m), 7.65 (1H, s), 7.64-7.57 (1H, m), 7.43-7.38 (2H, m), 7.37-7.32 (1H, m), 7.31-7.26 (1H, m), 6.98 (1H, d, J=6.8 Hz), 5.40-5.32 (1H, m), 4.53 (2H, t, J=5.6 Hz), 4.35 (1H, t, J=6.4 Hz), 4.14 (3H, s), 2.64-2.54 (2H, m), 2.01-1.85 (2H, m), 1.85-1.62 (6H, m).

EXAMPLE 62

(S)-2-Amino-4-{4-[4-(2-fluoro-benzoylamino)-phenoxy]-6-methoxy-quinolin-7-yloxy}-butyric acid

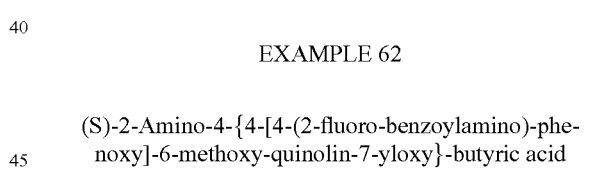

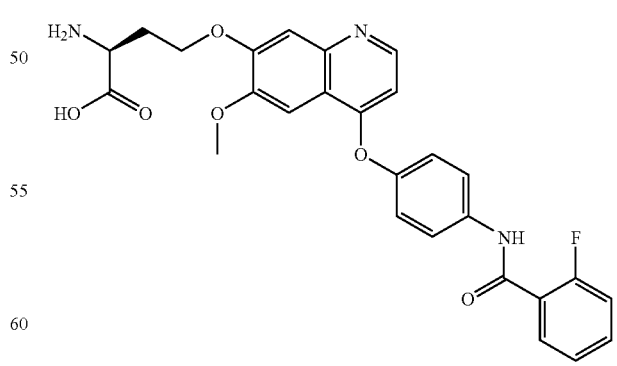

LC/MS purity: 94%, m/z 506 [M+H]⁺. ¹H NMR (300 MHz, CD₃OD) δ: 8.69 (1H, d, J=6.6 Hz), 7.97 (2H, d, J=9.0 Hz), 7.90 (1H, s), 7.82-7.74 (1H, m), 7.67-7.59 (1H, m), 7.57 (1H, s), 7.40 (2H, d, J=8.9 Hz), 7.37-7.24 (2H, m), 6.96 (1H, d, J=6.6 Hz), 4.60-4.51 (2H, m), 4.24 (1H, t, J=5.9 Hz), 4.14 (3H, s), 2.72-2.59 (1H, m), 2.58-2.49 (1H, m).

EXAMPLE 63

(S)-2-Amino-4-{4-[4-(4-fluoro-benzoylamino)-phenoxy]-6-methoxy-quinolin-7-yloxy}-butyric acid cyclopentyl ester

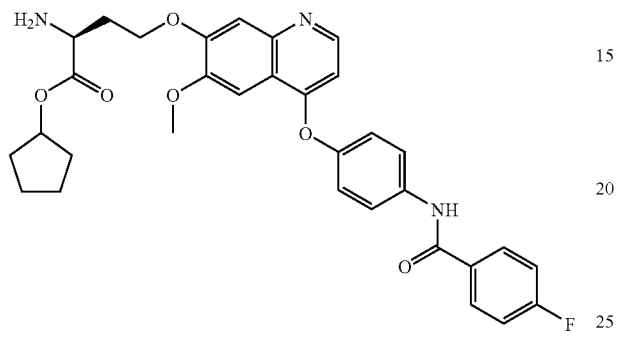

LC/MS purity: 93%, m/z 574 [M+H]⁺. ¹H NMR (300 MHz, CD₃OD) δ: 8.72 (1H, d, J=6.8 Hz), 8.09-8.02 (2H, m), 8.00-7.95 (2H, m), 7.91 (1H, s), 7.66 (1H, s), 7.44-7.37 (2H, m), 7.29 (2H, t, J=8.8 Hz), 6.99 (1H, d, J=6.6 Hz), 5.40-5.32 (1H, m), 4.53 (2H, t, J=5.5 Hz), 4.35 (1H, t, J=6.5 Hz), 4.14 (3H, s), 2.65-2.54 (2H, m), 1.99-1.86 (2H, m), 1.84-1.63 (6H, m).

EXAMPLE 64

(S)-2-Amino-4-{4-[4-(4-fluoro-benzoylamino)-phenoxy]-6-methoxy-quinolin-7-yloxy}-butyric acid

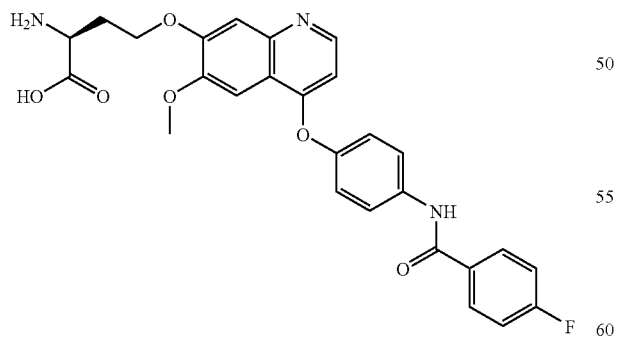

LC/MS purity: 95%, m/z 506 [M+H]⁺. ¹H NMR (300 MHz, CD₃OD) δ: 8.57 (1H, d, J=4.7 Hz), 8.06 (2H, dd, J=5.3, 8.7 Hz), 7.93 (2H, d, J=8.9 Hz), 7.77 (1H, s), 7.50 (1H, br. s), 7.38-7.22 (4H, m), 6.77 (1H, d, J=5.5 Hz), 4.59-4.45 (2H, m), 4.10 (3H, s), 4.04-3.93 (1H, m), 2.69-2.56 (1H, m), 2.55-2.41 (1H, m).

EXAMPLE 65

(S)-2-Amino-4-{4-[4-(2,4-difluoro-benzoylamino)-phenoxy]-6-methoxy-quinolin-7-yloxy}-butyric acid cyclopentyl ester

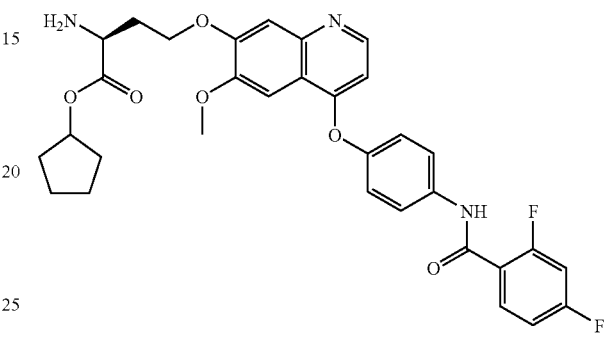

LC/MS purity: 96%, m/z 592 [M+H]⁺. ¹H NMR (300 MHz, CD₃OD) δ: 8.71 (1H, d, J=6.8 Hz), 7.96 (2H, d, J=8.9 Hz), 7.91 (1H, s), 7.90-7.81 (1H, m), 7.66 (1H, s), 7.41 (2H, d, J=8.9 Hz), 7.21-7.11 (2H, m), 6.98 (1H, d, J=6.8 Hz), 5.36 (1H, t, J=5.7 Hz), 4.53 (2H, t, J=5.4 Hz), 4.35 (1H, t, J=6.4 Hz), 4.14 (3H, s), 2.64-2.55 (2H, m), 1.93 (2H, dd, J=6.4, 13.6 Hz), 1.82-1.62 (6H, m).

EXAMPLE 66

(S)-2-Amino-4-{4-[4-(4-chloro-benzoylamino)-phenoxy]-6-methoxy-quinolin-7-yloxy}-butyric acid cyclopentyl ester

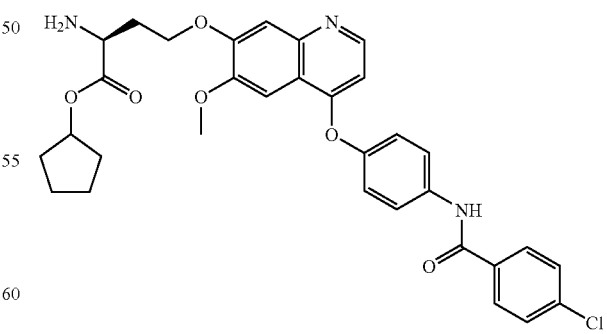

LC/MS purity: 93%, m/z 590 [M+H]⁺. ¹H NMR (300 MHz, CD₃OD) δ: 8.72 (1H, d, J=6.6 Hz), 7.98 (4H, d, J=8.7 Hz), 7.65 (1H, s), 7.57 (2H, d, J=8.5 Hz), 7.50-7.37 (3H, m), 6.99 (1H, d, J=6.6 Hz), 5.40-5.32 (1H, m), 4.53 (2H, t, J=5.4

Hz), 4.35 (1H, t, J=6.4 Hz), 4.14 (3H, s), 2.64-2.54 (2H, m), 2.00-1.86 (2H, m), 1.84-1.60 (6H, m).

EXAMPLE 67

(S)-2-Amino-4-{4-[4-(4-chloro-benzoylamino)-phenoxy]-6-methoxy-quinolin-7-yloxy}-butyric acid

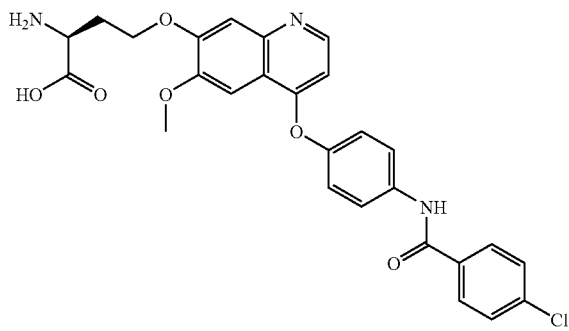

LC/MS purity: 95%, m/z 522 [M+H]$^+$. $^1$H NMR (300 MHz, CD$_3$OD) δ: 8.67 (1H, d, J=6.4 Hz), 8.01-7.93 (4H, m), 7.88 (1H, s), 7.62-7.55 (2H, m), 7.53 (1H, s), 7.42-7.36 (2H, m), 6.92 (1H, d, J=6.4 Hz), 4.60-4.50 (2H, m), 4.14 (3H, s), 3.58-3.43 (1H, m), 2.70-2.57 (1H, m), 2.56-2.44 (1H, m).

EXAMPLE 68

(S)-2-Amino-4-{4-[4-(2-fluoro-5-trifluoromethyl-benzoylamino)-phenoxy]-6-methoxy-quinolin-7-yloxy}-butyric acid cyclopentyl ester

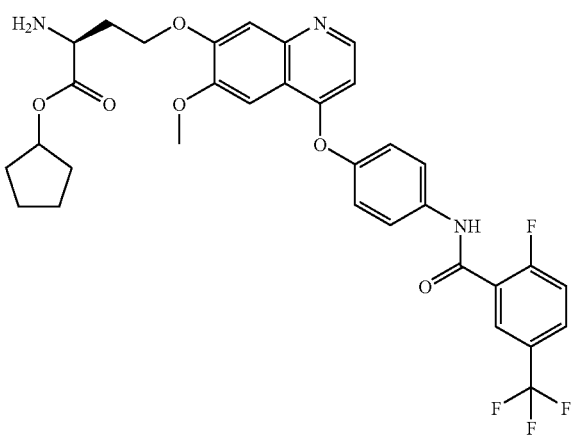

LC/MS purity: 94%, m/z 642 [M+H]$^+$. H NMR (300 MHz, CD$_3$OD) δ: 8.78-8.68 (1H, m), 8.11 (1H, dd, J=2.2, 6.1 Hz), 8.02-7.88 (4H, m), 7.71-7.63 (1H, m), 7.59-7.40 (3H, m), 7.04-6.95 (1H, m), 5.43-5.32 (1H, m), 4.53 (2H, t, J=5.6 Hz), 4.36 (1H, q, J=6.3 Hz), 4.14 (3H, s), 2.64-2.54 (2H, m), 1.95 (2H, d, J=6.2 Hz), 1.79-1.61 (6H, m).

EXAMPLE 69

(S)-2-Amino-4-{4-[4-(2-fluoro-5-trifluoromethyl-benzoylamino)-phenoxy]-6-methoxy-quinolin-7-yloxy}-butyric acid

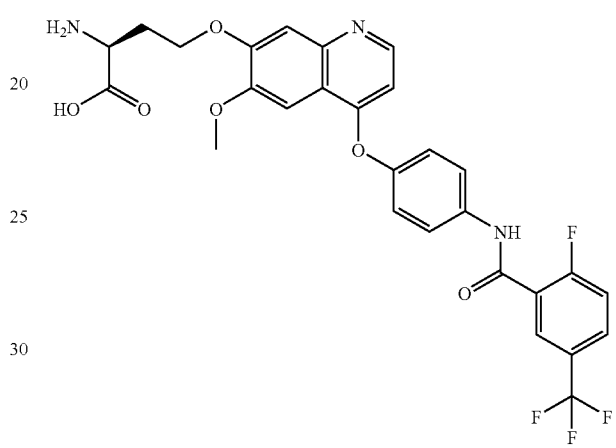

LC/MS purity: 95%, m/z 574 [M+H]$^+$. $^1$H NMR (300 MHz, CD$_3$OD) δ: 8.59-8.45 (1H, m), 8.09 (1H, br s), 7.92 (3H, d, J=8.3 Hz), 7.75 (1H, s), 7.62-7.41 (2H, m), 7.33 (2H, d, J=8.7 Hz), 6.71 (1H, d, J=4.0 Hz), 4.56-4.40 (2H, m), 4.10 (3H, s), 3.97 (1H, d, J=6.0 Hz), 2.70-2.54 (1H, m), 2.50-2.37 (1H, m).

EXAMPLE 70

(S)-2-Amino-4-{6-methoxy-4-[4-(4-trifluoromethoxy-benzoylamino)-phenoxy]-quinolin-7-yloxy}-butyric acid cyclopentyl ester

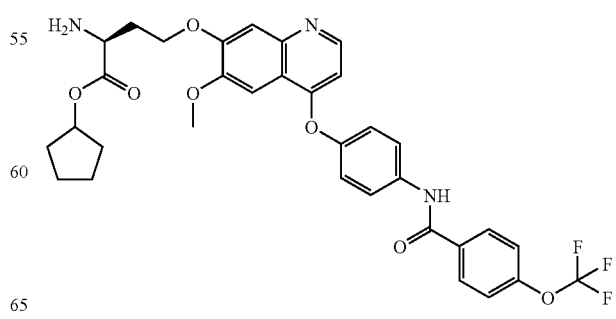

LC/MS purity: 95%, m/z 640 [M+H]$^+$. $^1$H NMR (300 MHz, CD$_3$OD) δ: 8.72 (1H, d, J=6.8 Hz), 8.17-8.08 (2H, m), 8.04-7.96 (2H, m), 7.91 (1H, s), 7.64 (1H, s), 7.52-7.38 (4H, m), 6.99 (1H, d, J=6.6 Hz), 5.41-5.32 (1H, m), 4.53 (2H, t, J=5.1 Hz), 4.35 (1H, t, J=6.6 Hz), 4.14 (3H, s), 2.65-2.53 (2H, m), 2.01-1.88 (2H, m), 1.84-1.63 (6H, m).

EXAMPLE 71

(S)-2-Amino-4-{6-methoxy-4-[4-(4-trifluoromethoxy-benzoylamino)-phenoxy]-quinolin-7-yloxy}-butyric acid

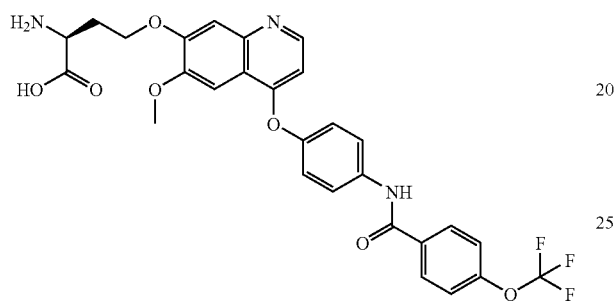

LC/MS purity: 94%, m/z 572 [M+H]$^+$. $^1$H NMR (300 MHz, CD$_3$OD) δ: 8.49-8.45 (1H, m), 8.14-8.07 (2H, m), 7.90 (2H, d, J=9.0 Hz), 7.72 (1H, s), 7.51-7.39 (3H, m), 7.29 (2H, d, J=8.9 Hz), 6.62 (1H, d, J=5.5 Hz), 4.72-4.57 (2H, m), 4.08 (3H, s), 3.98-3.90 (1H, m), 2.67-2.53 (1H, m), 2.49-2.31 (1H, m).

EXAMPLE 72

(S)-2-Amino-4-(6-methoxy-4-{4-[(3-methyl-1H-indene-2-carbonyl)-amino]-phenoxy}-quinolin-7-yloxy)-butyric acid cyclopentyl ester

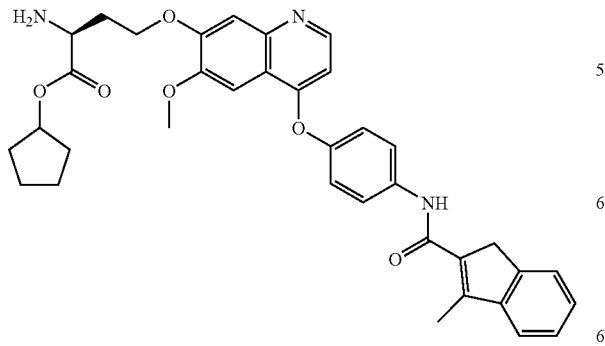

LC/MS purity: 99% (254 nm), m/z 610 [M+H]$^+$. $^1$H NMR (300 MHz, CD$_3$OD), δ: 8.69 (1H, d, J=4.6 Hz), 7.79-7.92 (3H, m), 7.53 (1H, s), 7.29-7.39 (2H, m), 7.11-7.27 (4H, m), 6.95 (1H, d, J=6.6 Hz), 4.52 (2H, t, J=5.5 Hz), 4.34 (1H, t, J=6.5 Hz), 4.13 (3H, s), 2.95-3.07 (1H, m), 2.52-2.66 (2H, m), 1.85-2.04 (2H, m), 1.57-1.83 (6H, m), 1.30 (2H, s), 1.20 (3H, d, J=7.1 Hz).

Examples 73 and 74 were synthesised following the route shown in Scheme 23, using benzenesulfonyl chloride in Scheme 22.

EXAMPLE 73

(S)-2-Amino-4-[4-(4-benzenesulfonylamino-phenoxy)-6-methoxy-quinolin-7-yloxy]-butyric acid cyclopentyl ester

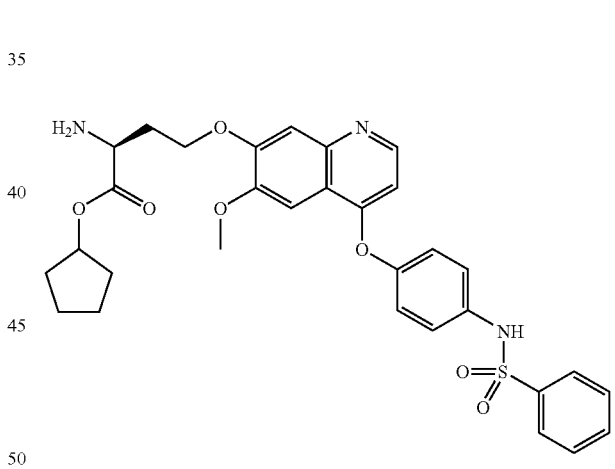

LC/MS purity: 95% (254 nm), m/z 592 [M+H]$^+$. $^1$H NMR (300 MHz, CD$_3$OD) δ: 8.68 (1H, d, J=6.6 Hz), 7.86-7.81 (3H, m), 7.67-7.59 (2H, m), 7.58-7.50 (2H, m), 7.37-7.30 (2H, m), 7.29-7.23 (2H, m), 6.82 (1H, d, J=6.8 Hz), 5.39-5.31 (1H, m), 4.51 (2H, t, J=5.6 Hz), 4.34 (1H, t, J=6.5 Hz), 4.10 (3H, s), 2.65-2.52 (2H, m), 2.00-1.86 (2H, m), 1.84-1.57 (6H, m).

EXAMPLE 74

(S)-2-Amino-4-[4-(4-benzenesulfonylamino-phenoxy)-6-methoxy-quinolin-7-yloxy]-butyric acid

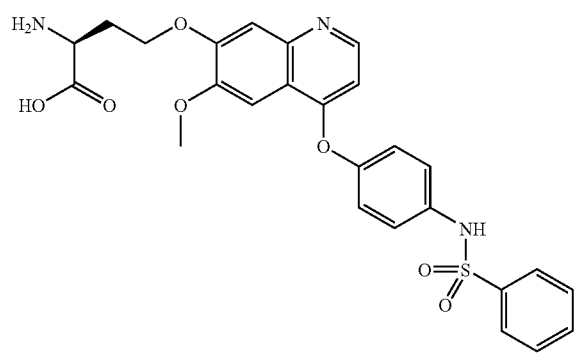

LC/MS purity: 93% (254 nm), m/z 524 [M+H]$^+$. $^1$H NMR (300 MHz, CD$_3$OD) δ: 8.46 (1H, d, J=5.7 Hz), 7.88-7.77 (2H, m), 7.69-7.59 (2H, m), 7.54 (2H, t, J=7.3 Hz), 7.40 (1H, br s), 7.30-7.21 (2H, m), 7.14 (2H, d, J=8.9 Hz), 6.50 (1H, d, J=5.3 Hz), 4.53-4.40 (2H, m), 4.05 (3H, s), 3.97-3.89 (1H, m), 2.67-2.54 (1H, m), 2.48-2.35 (1H, m).

EXAMPLE 75

(S)-2-Amino-4-(6-methoxy-4-{4-[(thiophene-2-carbonyl)-amino]-phenoxy}-quinolin-7-yloxy)-butyric acid cyclopentyl ester

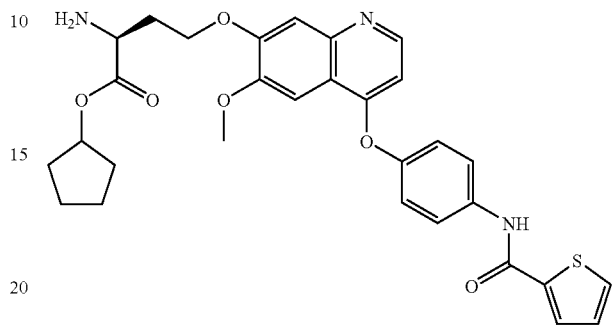

LC/MS: m/z 562 [M+H]$^+$. $^1$H NMR (300 MHz, DMSO-d$_6$) δ: 10.39 (1H, s), 8.48 (1H, d, J=5.3 Hz), 8.07-8.03 (1H, m), 7.90-7.88 (2H, m), 7.86 (1H, s), 7.52 (1H, s), 7.40 (1H, s), 7.30 (1H, s), 7.29-7.23 (2H, m), 6.49 (1H, d, J=5.1 Hz), 5.12 (1H, t, J=5.7 Hz), 4.35-4.16 (2H, m), 3.95 (3H, s), 3.56 (1H, dd, J=5.3, 8.3 Hz), 2.71-2.59 (2H, m), 2.21-2.09 (1H, m), 1.98-1.88 (1H, m), 1.87-1.73 (2H, m), 1.68-1.49 (6H, m).

The route to Example 75 is outlined below in Scheme 24.

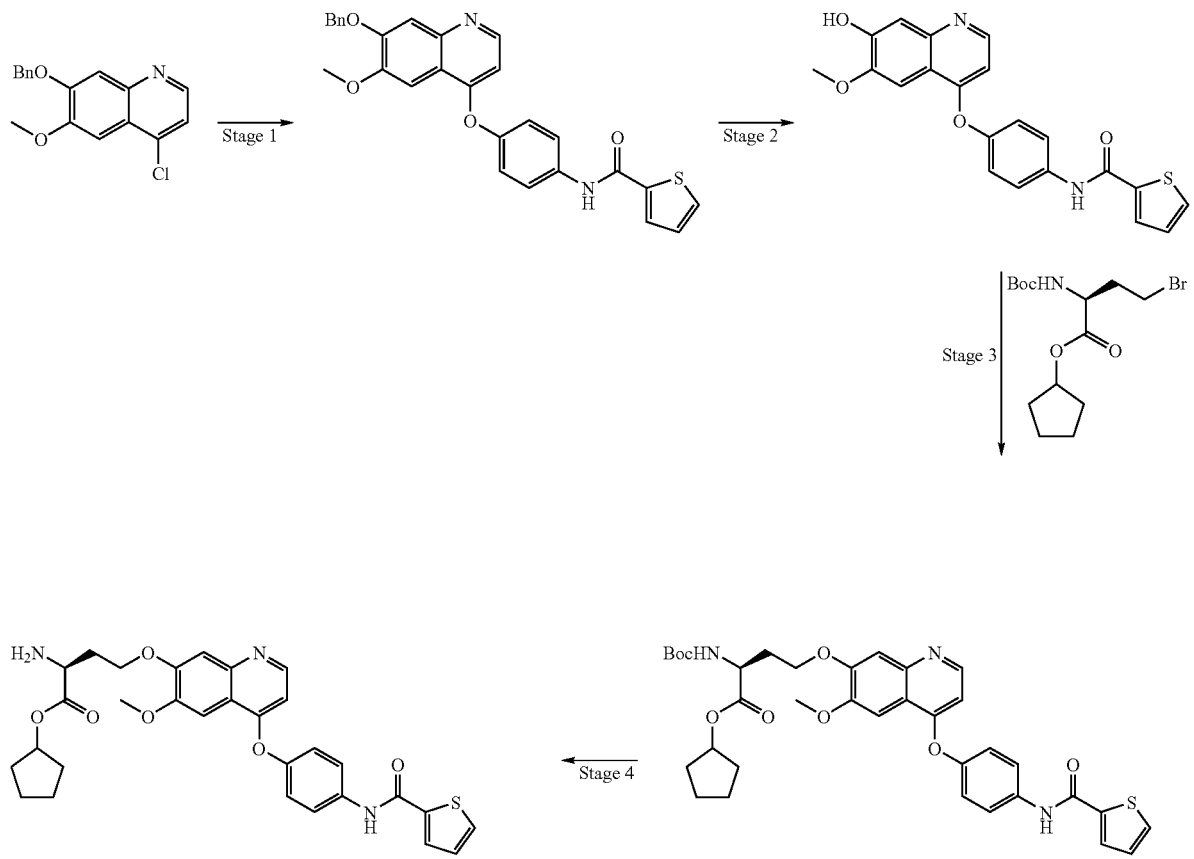

Scheme 24

Stage 1-Thiophene-2-carboxylic acid [4-(7-benzyloxy-6-methoxy-quinolin-4-yloxy)-phenyl]-amide A suspension of 7-benzyloxy-4-chloro-6-methoxy-quinoline (0.50 g, 1.67 mmol) and thiophene-2-carboxylic acid (4-hydroxy-phenyl)-amide (1.10 g, 5.01 mmol) in DMF (1 ml) was heated at 140° C. for 5 hours. The crude was poured into DCM (50 ml) and 1M NaOH (50 ml). The organic layer was separated, washed with brine, dried over MgSO$_4$, filtered and concentrated under reduced pressure. Purification was achieved by flash chromatography using DCM/MeOH 99/1 as eluent, to provide the title compound (289 mg, 36% yield).

LC/MS: m/z 483 [M+H]$^+$. $^1$H NMR (300 MHz, DMSO-d$_6$) δ: 10.37 (1H, s), 8.48 (1H, d, J=5.3 Hz), 8.06-8.02 (1H, m), 7.90-7.85 (3H, m), 7.55 (2H, s), 7.52 (2H, d, J=4.5 Hz), 7.47-7.41 (2H, m), 7.40-7.36 (1H, m), 7.32-7.26 (2H, m), 7.26-7.23 (1H, m), 6.49 (1H, d, J=5.3 Hz), 5.31 (2H, s), 3.96 (3H, s).

Stage 2-Thiophene-2-carboxylic acid [4-(7-hydroxy-6-methoxy-quinolin-4-yloxy)-phenyl]-amide To a solution of thiophene-2-carboxylic acid [4-(7-benzyloxy-6-methoxy-quinolin-4-yloxy)-phenyl]-amide (289 mg, 0.60 mmol) in TFA (5 ml) was added thioanisole (0.5 ml). The reaction mixture was heated at 80° C. for 3 hours, followed by concentration under reduced pressure. Heptane (10 ml) and diethyl ether (10 ml) were added and the product was triturated until it precipitated. The solid was filtered to afford the title compound (200 mg, 85% yield).

LC/MS: m/z 393 [M+H]$^+$. $^1$H NMR (300 MHz, DMSO-d$_6$) δ: 11.68 (1H, br s), 10.48 (1H, s), 8.73 (1H, d, J=6.6 Hz), 8.07 (1H, dd, J=0.9, 3.6 Hz), 7.96 (2H, d, J=9.0 Hz), 7.90 (1H, dd, J=1.2, 5.1 Hz), 7.73 (1H, s), 7.48 (1H, s), 7.41 (2H, d, J=9.0 Hz), 7.26 (1H, dd, J=3.9, 4. Hz), 6.79 (1H, d, J=6.6 Hz), 4.03 (3H, s).

Stage 3-(S)-2-tert-Butoxycarbonylamino-4-(6-methoxy-4-{4-[(thiophene-2-carbonyl)-amino]-phenoxy}-quinolin-7-yloxy)-butyric acid cyclopentyl ester To a solution of thiophene-2-carboxylic acid [4-(7-hydroxy-6-methoxy-quinolin-4-yloxy)-phenyl]-amide (200 mg, 0.51 mmol) in DMF (10 ml) under nitrogen were added (S)-4-bromo-2-tert-butoxycarbonylamino-butyric acid cyclopentyl ester (196 mg, 0.56 mmol) and K$_2$CO$_3$ (84 mg, 0.61 mmol). The reaction mixture was stirred overnight at room temperature. The crude was poured into DCM (30 ml), washed with H$_2$O (30 ml) and brine (30 ml), dried over MgSO$_4$ and concentrated under reduced pressure. Purification was performed by flash chromatography using DCM then DCM/MeOH 99/1 as eluent, to afford the title compound (210 mg, 62% yield).

LC/MS: m/z 662 [M+H]$^+$. $^1$H NMR (300 MHz, CDCl$_3$) δ: 8.50-8.45 (2H, m), 7.78 (1H, s), 7.74 (2H, s), 7.56 (2H, s), 7.34 (1H, s), 7.17 (2H, d, J=5.4 Hz), 7.14 (1H, m), 6.47 (1H, d, J=5.1 Hz), 6.20 (1H, d, J=8.9 Hz), 5.19 (1H, t, J=5.3 Hz), 4.61-4.53 (1H, m), 4.38-4.28 (1H, m), 4.19-4.09 (1H, m), 4.05 (3H, s), 2.51-2.33 (2H, m), 1.85-1.72 (2H, m), 1.71-1.53 (6H, m), 1.49 (9H, s).

Stage 4-(S)-2-Amino-4-(6-methoxy-4-{4-[(thiophene-2-carbonyl)-amino]-phenoxy}-quinolin-7-yloxy)-butyric acid cyclopentyl ester To a solution of (S)-2-tert-butoxycarbonylamino-4-(6-methoxy-4-{4-[(thiophene-2-carbonyl)-amino]-phenoxy}-quinolin-7-yloxy)-butyric acid cyclopentyl ester (210 mg, 0.32 mmol) in DCM (2.5 ml) was added TFA (2.5 ml) and the reaction mixture was stirred at room temperature for 3 hours, followed by concentration under reduced pressure. The crude was diluted in DCM (30 ml) and washed with a saturated aqueous solution of Na$_2$CO$_3$ (30 ml). The organic layer was washed with brine (20 ml) and dried over MgSO$_4$, filtered and concentrated under reduced pressure to provide the title compound as a white solid (179 mg, 100% yield).

EXAMPLE 76

(S)-2-Amino-4-(6-methoxy-4-{4-[(thiophene-2-carbonyl)-amino]-phenoxy}-quinolin-7-yloxy)-butyric acid

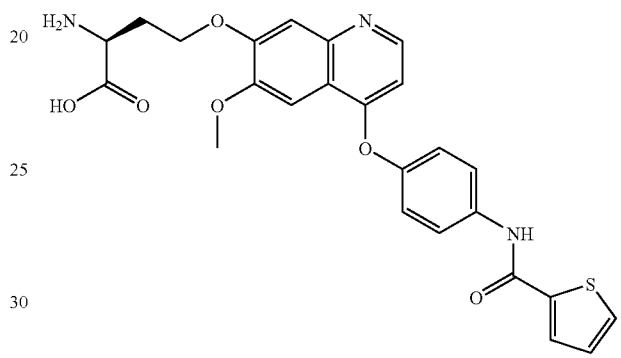

LC/MS: m/z 495 [M+H]$^+$. $^1$H NMR (300 MHz, CD$_3$OD) δ: 8.71 (1H, d, J=6.6 Hz), 8.00-7.93 (3H, m), 7.90 (1H, s), 7.78 (1H, dd, J=1.0, 5.0 Hz), 7.63 (1H, s), 7.43-7.36 (2H, m), 7.23 (1H, dd, J=3.9, 5.0 Hz), 6.98 (1H, d, J=6.6 Hz), 4.56 (2H, t, J=5.7 Hz), 4.34 (1H, dd, J=5.5, 7.2 Hz), 4.14 (3H, s), 2.75-2.62 (1H, m), 2.62-2.49 (1H, m).

EXAMPLE 77

(S)-2-Amino-4-[6-methoxy-4-(4-phenylcarbamoyl-phenoxy)-quinolin-7-yloxy]-butyric acid cyclopentyl ester

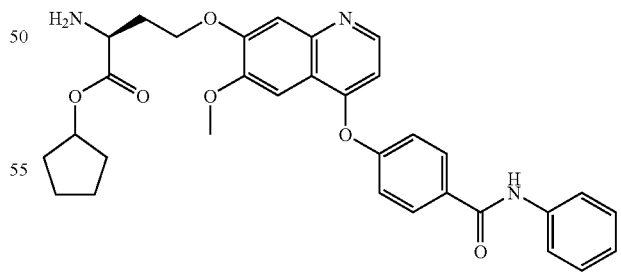

LC/MS: m/z 556 [M+H]$^+$. $^1$H NMR (300 MHz, CD$_3$OD) δ: 8.74 (1H, d, J=6.8 Hz), 8.24-8.18 (2H, m), 7.91 (1H, s), 7.74 (1H, s), 7.71 (2H, d, J=6.2 Hz), 7.58-7.52 (2H, m), 7.43-7.36 (2H, m), 7.19 (1H, t, J=7.4 Hz), 7.01 (1H, d, J=6.8 Hz), 5.40-5.33 (1H, m), 4.53 (2H, t, J=5.6 Hz), 4.35 (1H, t, J=6.4 Hz), 4.14 (3H, s), 2.67-2.51 (2H, m), 1.93 (2H, dd, J=6.1, 13.8 Hz), 1.84-1.59 (6H, m).

The Synthesis of 4-Hydroxy-N-phenyl-benzamide is outlined below in Scheme 25.

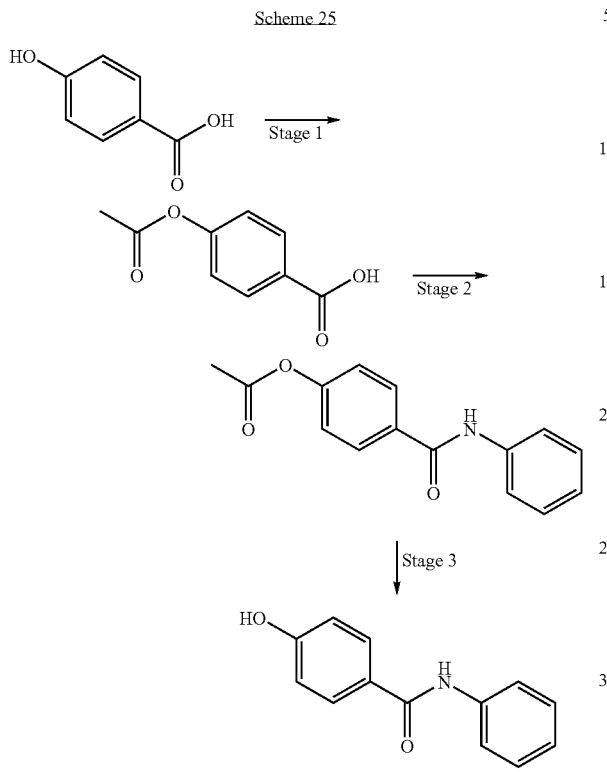

Scheme 25

Stage 1-4-Acetoxybenzoic acid

To a solution of 4-hydroxybenzoic acid (1 g, 7.24 mmol) in acetic anhydride (2 ml) were added 3 drops of concentrated sulfuric acid. The reaction mixture was heated at 80° C. for 2 h. After addition of H$_2$O (20 ml), a solid precipitated and was filtered and washed with heptane to provide the title compound (1.12 g, 86% yield).

LC/MS: m/z 181 [M+H]$^+$. $^1$H NMR (300 MHz, DMSO-d$_6$) δ: 13.0 (1H, br s), 7.99 (2H, d, J=6.6 Hz), 7.26 (2H, d, J=6.9 Hz), 2.33 (3H, s).

Stage 2-Acetic acid 4-phenylcarbamoyl-phenyl ester

To a suspension of 4-acetoxybenzoic acid (1.12 g, 6.2 mmol) in DMF (100 μL) was added a solution of oxalyl chloride (6.2 ml, 2 M in DCM) dropwise. After a few minutes stirring at room temperature, the solution became clear. After 2 hours, the reaction mixture was concentrated under reduced pressure and anhydrous DCM (8 ml) was added, followed by aniline (1.69 ml, 18.6 mmol). After 5 minutes of slow addition of aniline, the product precipitated. It was filtered and washed with DCM to give afford the title compound as a white solid (1.6 g, 100% yield).

LC/MS: m/z 256 [M+H]$^+$ and 533 [2M+Na]$^+$. $^1$H NMR (300 MHz, DMSO-d$_6$) δ: 10.2 (1H, s), 7.99 (2H, d, J=6.6 Hz), 7.78 (2H, d, J=6.9 Hz), 7.38-7.24 (4H, m), 7.12 (1H, m), 2.31 (3H, s).

Stage 3-4-Hydroxy-N-phenyl-benzamide

To a suspension of acetic acid 4-phenylcarbamoyl-phenyl ester (1.6 g, 6.2 mmol) in MeOH/H$_2$O 1/1 (60 ml) was added NaOH (0.5 g, 12.5 mmol). The reaction mixture was stirred at room temperature for 2 hours. A solution of 1M HCl was added until pH 6. A white solid precipitated which was filtered, washed with H$_2$O, redissolved in EtOAc and concentrated under reduced pressure to give the title compound (1.30 g, 100% yield).

LC/MS: m/z 214 [M+H]$^+$ and 449 [2M+Na]$^+$. $^1$H NMR (300 MHz, DMSO-d$_6$) δ: 10.13 (1H, s), 9.99 (1H, s), 7.86 (2H, m), 7.76 (2H, m), 7.34 (2H, m), 7.07 (1H, m), 6.87 (2H, m).

EXAMPLE 78

(S)-2-Amino-4-[6-methoxy-4-(4-phenylcarbamoyl-phenoxy)-quinolin-7-yloxy]-butyric acid

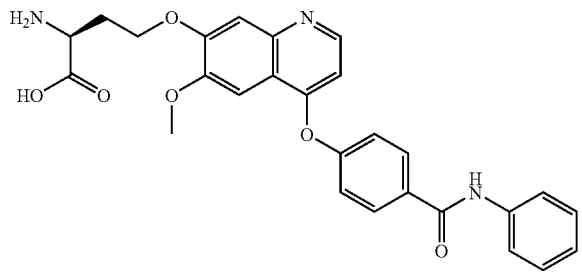

LC/MS: m/z 488 [M+H]$^+$. $^1$H NMR (300 MHz, CD$_3$OD) δ: 8.74 (1H, d, J=6.8 Hz), 8.25-8.19 (2H, m), 7.92 (1H, s), 7.76-7.71 (2H, m), 7.61-7.56 (2H, m), 7.56-7.53 (1H, m), 7.45-7.37 (2H, m), 7.24-7.17 (1H, m), 7.01 (1H, d, J=6.8 Hz), 4.57 (2H, t, J=5.7 Hz), 4.35-4.29 (1H, m), 4.15 (3H, s), 2.73-2.62 (1H, m), 2.62-2.50 (1H, m).

The following examples contain a methylene spacer unit in the sidechain substituent and were prepared via the route outlined in Scheme 26 below, using the appropriate aniline at Stage 3.

EXAMPLE 79

(S)-2-Amino-4-(6-methoxy-4-{4-[(4-trifluoromethyl-phenylcarbamoyl)-methyl]-phenoxy}-quinolin-7-yloxy)-butyric acid cyclopentyl ester

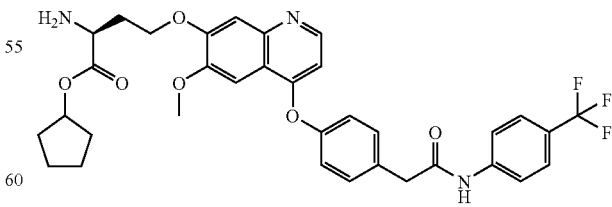

LC/MS: m/z 638 [M+H]$^+$. $^1$H NMR (300 MHz, CD$_3$OD) δ: 6.68 (1H, d, J=6.6 Hz), 7.89-7.82 (3H, m), 7.65-7.61 (5H, m), 7.38-7.32 (2H, m), 6.96 (1H, d, J=6.6 Hz), 5.42-5.30 (1H, m), 4.52 (2H, t, J=5.4 Hz), 4.35 (1H, t, J=6.5 Hz), 4.13 (3H, s), 3.87 (2H, s), 2.68-2.46 (2H, m), 2.02-1.52 (8H, m)

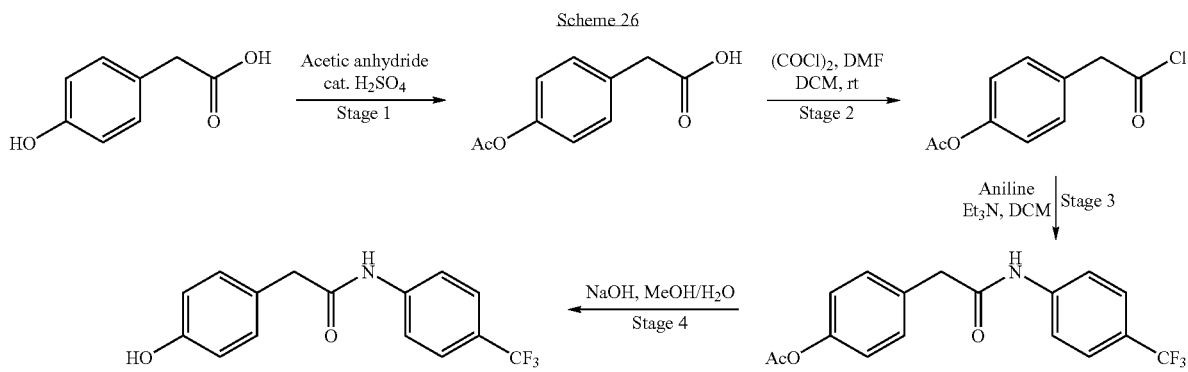

Stage 1-(4-Acetoxy-phenyl)-acetic acid

A solution of (4-hydroxy-phenyl)-acetic acid (5.11 g, 33.6 mmol) and concentrated sulfuric acid (10 drops) in acetic anhydride (20 ml) was heated to 80° C. for 45 minutes. The reaction mixture was poured in water (50 ml) and extracted with DCM (3×50 ml). The combined organic extracts were washed with a saturated aqueous solution of $Na_2CO_3$ (2×50 ml), brine (50 ml), dried ($MgSO_4$), filtered and concentrated under reduced pressure to leave a yellow oil (6.07 g, 93% yield), which was used in the next step without purification.

Stage 2-Acetic acid 4-chlorocarbonylmethyl-phenyl ester

A solution of (4-hydroxy-phenyl)-acetic acid (6.07 g, 31 mmol) and DMF (10 drops) in DCM (20 ml) was cooled to 0° C. and a 2 M solution of oxalyl chloride in DCM (31 ml, 62 mmol, 2.0 eq) was added dropwise over 10 minutes. The reaction mixture was allowed to warm to room temperature, stirred for 2 hours and concentrated under reduced pressure to give the title compound as a yellow oil (6.64 g, 100% yield). This acyl chloride was used without further purification.

Stage 3-Acetic acid 4-[(4-trifluoromethyl-phenylcarbamoyl)-methyl]-phenyl ester To a solution of acetic acid 4-chlorocarbonylmethyl-phenyl ester (950 mg, 4.4 mmol) in DCM (2 ml) was added triethylamine (1.24 ml, 8.9 mmol, 2.0 eq) and 4-trifluoromethyl-phenylamine (1.12 ml, 8.9 mmol, 2.0 eq). The reaction mixture was stirred at room temperature for 30 minutes diluted with DCM (15 ml), washed with 1 N HCl (20 ml), brine (20 ml), dried ($MgSO_4$), filtered and concentrated under reduced pressure to give the title compound as a pale yellow solid (976 mg, 66% yield).
LC/MS: m/z 338 [M+H]$^+$.

Stage 4-2-(4-Hydroxy-phenyl)-N-(4-trifluoromethyl-phenyl)-acetamide

To a solution of acetic acid 4-[(4-trifluoromethyl-phenyl-carbamoyl)-methyl]-phenyl ester (976 mg, 2.9 mmol) in methanol/water (1:1, 20 ml) was added sodium hydroxide (231 mg, 5.8 mmol, 2.0 eq). The reaction mixture was stirred at room temperature for 2 hours, acidified to pH=1 with concentrated HCl and extracted with ethyl acetate (2×20 ml). The combined organic extracts were washed with brine (20 ml), dried ($MgSO_4$), filtered and concentrated under reduced pressure to give the title compound as a yellow solid (760 mg, 89% yield).
LC/MS: m/z 296 [M+H]$^+$.

EXAMPLE 80

(S)-2-Amino-4-[6-methoxy-4-(4-phenylcarbamoyl-methyl-phenoxy)-quinolin-7-yloxy]-butyric acid cyclopentyl ester

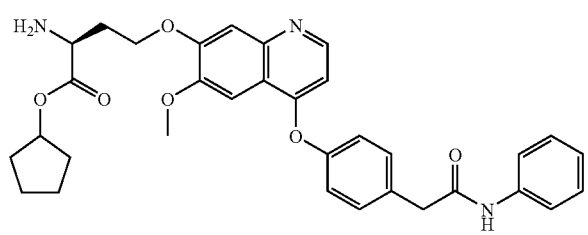

LC/MS: m/z 570 [M+H]$^+$. $^1$H NMR (300 MHz, $CD_3OD$), δ: 8.67 (1H, d, J=6.6 Hz), 7.89 (1H, s), 7.66-7.54 (5H, m), 7.38-7.30 (4H, m), 7.13 (1H, t, J=7.3 Hz), 6.95 (1H, d, J=6.4 Hz), 5.40-5.32 (1H, m), 4.51 (2H, t, J=5.6 Hz), 4.34 (1H, t, J=6.5 Hz), 4.13 (3H, s), 3.83 (2H, s), 2.66 (2H, m), 2.01-1.85 (2H, m), 1.84-1.58 (6H, m).

EXAMPLE 81

(S)-2-Amino-4-[6-methoxy-4-(4-phenylcarbamoyl-methyl-phenoxy)-quinolin-7-yloxy]-butyric acid

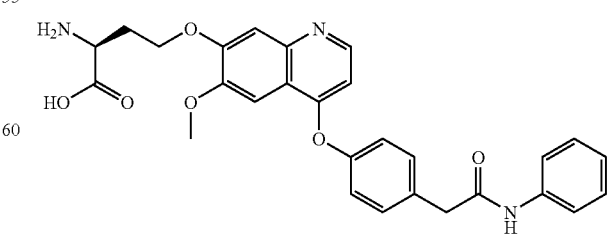

LC/MS: m/z 502 [M+H]$^+$. $^1$H NMR (300 MHz, $CD_3OD$) δ: 8.43 (1H, d, J=4.9 Hz), 7.67 (1H, s), 7.61 (2H, d, J=7.7 Hz), 7.54 (2H, d, J=8.3 Hz), 7.37 (1H, d, J=8.1 Hz), 7.34-7.29 (2H, m), 7.23 (2H, d, J=8.3 Hz), 7.11 (1H, t, J=7.3 Hz), 6.58 (1H, d, J=5.3 Hz), 4.76-4.58 (1H, m), 4.52-4.35 (2H, m), 4.06 (3H, s), 3.79 (2H, s), 2.67-2.53 (1H, m), 2.50-2.37 (1H, m).

EXAMPLE 82

(S)-2-Amino-4-(4-{4-[(2-fluoro-phenylcarbamoyl)-methyl]-phenoxy}-6-methoxy-quinolin-7-yloxy)-butyric acid cyclopentyl ester

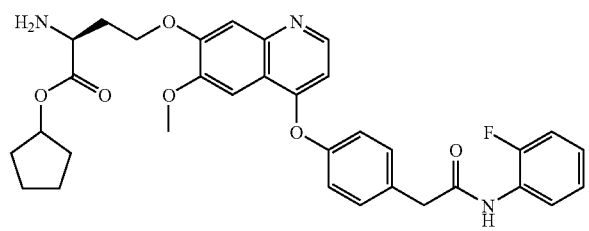

LC/MS: m/z 588 [M+H]$^+$. $^1$H NMR (300 MHz, DMSO-d$_6$) δ: 10.05 (1H, s), 8.69 (1H, d, J=6.0 Hz), 8.48 (2H, br s), 7.94-7.88 (1H, m), 7.68 (1H, s), 7.56-7.54 (3H, m), 7.34-7.24 (3H, m), 7.18-7.13 (2H, m), 6.71 (1H, d, J=6.0 Hz), 5.23-5.18 (1H, m), 4.41-4.30 (1H, m), 4.22 (1H, br s), 4.00 (3H, s), 3.84 (2H, s), 2.44-2.30 (2H, m), 1.90-1.71 (2H, m), 1.69-1.46 (6H, m).

EXAMPLE 83

(S)-2-Amino-4-(4-{4-[(2-fluoro-phenylcarbamoyl)-methyl]-phenoxy}-6-methoxy-quinolin-7-yloxy)-butyric acid

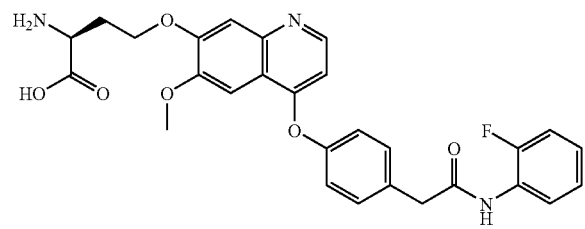

LC/MS: m/z 520 [M+H]$^+$. $^1$H NMR (300 MHz, CD$_3$OD) δ: 8.48 (1H, d, J=6.0 Hz), 7.81-7.77 (1H, m), 7.70 (1H, s), 7.50 (2H, d, J=8.5 Hz), 7.38 (1H, s), 7.22 (2H, d, J=8.5 Hz), 7.10-7.02 (3H, m), 6.73 (1H, d, J=6.0 Hz), 4.48-4.39 (2H, m), 4.00 (3H, s), 3.98-3.91 (1H, m), 3.78 (2H, s), 2.58-2.42 (1H, m), 2.41-2.29 (1H, m)

EXAMPLE 84

(S)-2-Amino-4-(4-{4-[(3-fluoro-phenylcarbamoyl)-methyl]-phenoxy}-6-methoxy-quinolin-7-yloxy)-butyric acid cyclopentyl ester

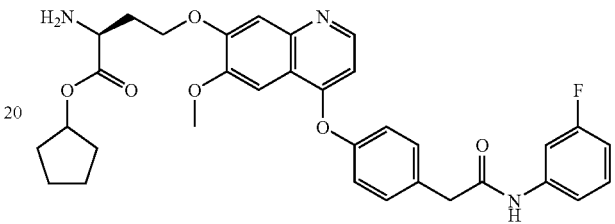

LC/MS: m/z 588 [M+H]$^+$. $^1$H NMR (300 MHz, DMSO-d$_6$) δ: 10.50 (1H, s), 8.72 (1H, d, J=6.0 Hz), 8.48 (2H, br s), 7.70-7.53 (5H, m), 7.37-7.29 (4H, m), 6.95-6.89 (1H, m), 6.74 (1H, d, J=6.0 Hz), 5.30-5.19 (1H, m), 4.40-4.33 (2H, m), 4.21 (1H, br s), 4.01 (3H, s), 3.77 (2H, s), 2.45-2.28 (2H, m), 1.91-1.69 (2H, m), 1.67-1.46 (6H, m).

EXAMPLE 85

(S)-2-Amino-4-(4-{4-[(3-fluoro-phenylcarbamoyl)-methyl]-phenoxy}-6-methoxy-quinolin-7-yloxy)-butyric acid

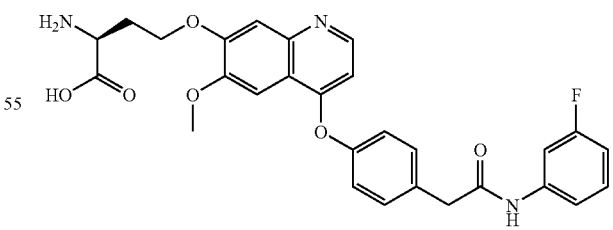

LC/MS: m/z 520 [M+H]$^+$. $^1$H NMR (300 MHz, CD$_3$OD) δ: 8.41 (1H, d, J=5.4 Hz), 7.63-7.57 (2H, m), 7.52 (2H, d, J=8.5 Hz), 7.38 (1H, s), 7.34-7.27 (2H, m), 7.23 (2H, d, J=8.5 Hz), 6.87-6.82 (1H, m), 6.57 (1H, d, J=5.4 Hz), 4.37 (2H, br s), 4.01 (3H, s), 3.61 (2H, s), 3.66-3.53 (1H, s), 2.52-2.38 (1H, m), 2.29-2.10 (1H, m).

EXAMPLE 86

(S)-2-Amino-4-(4-{4-[(4-fluoro-phenylcarbamoyl)-methyl]-phenoxy}-6-methoxy-quinolin-7-yloxy)-butyric acid cyclopentyl ester

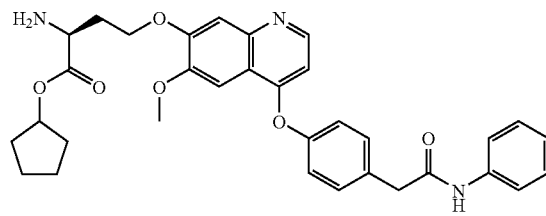

LC/MS: m/z 588 [M+H]$^+$. $^1$H NMR (300 MHz, DMSO-d$_6$) δ: 10.33 (1H, s), 8.68 (1H, d, J=6.3 Hz), 8.46 (2H, br s), 7.67-7.62 (3H, m), 7.55-7.52 (3H, m), 7.33-7.28 (2H, m), 7.19-711 (2H, m), 6.70 (1H, d, J=6.3 Hz), 5.25-5.18 (1H, m), 4.41-4.30 (2H, m), 4.22 (1H, br s), 4.00 (3H, s), 3.74 (2H, s), 2.44-2.38 (2H, m), 1.95-1.71 (2H, m), 1.70-1.48 (6H, m).

EXAMPLE 87

(S)-2-Amino-4-(4-{4-[(4-fluoro-phenylcarbamoyl)-methyl]-phenoxy}-6-methoxy-quinolin-7-yloxy)-butyric acid

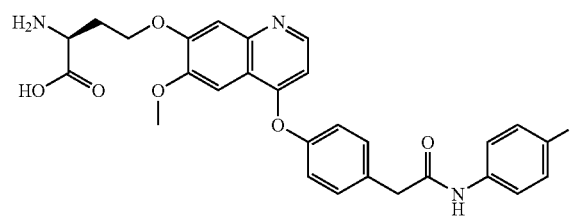

LC/MS: m/z 520 [M+H]$^+$. $^1$H NMR (300 MHz, CD$_3$OD) δ: 8.56 (1H, br s), 7.78 (1H, br s), 7.64-7.50 (4H, m), 7.48 (1H, br s), 7.30 (2H, d, J=8.1 Hz), 7.10-7.04 (2H, m), 6.79 (1H, d, J=5.7 Hz), 4.50 (2H, br s), 4.09 (3H, s), 4.08-3.91 (1H, m), 3.80 (2H, s), 2.70-2.53 (1H, m), 2.52-2.40 (1H, m).

EXAMPLE 88

(S)-2-Amino-4-(4-{4-[(2,4-difluoro-phenylcarbamoyl)-methyl]-phenoxy}-6-methoxy-quinolin-7-yloxy)-butyric acid cyclopentyl ester

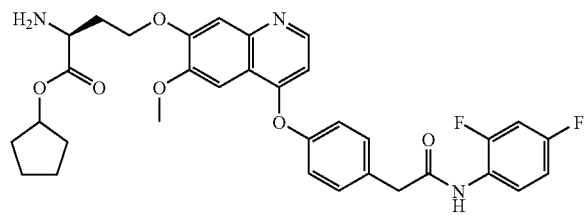

LC/MS: m/z 606 [M+H]$^+$. $^1$H NMR (300 MHz, DMSO-d$_6$) δ 10.06 (1H, s), 8.70 (1H, d, J=6.0 Hz), 8.48 (2H, br s), 7.84 (1H, dd, J=15.0, 6.0 Hz), 7.69 (1H, s), 7.56-7.53 (3H, m), 7.39-7.29 (3H, m), 7.12-7.05 (1H, m), 6.72 (1H, d, J=6.0 Hz), 5.23-5.18 (1H, m), 4.41-4.32 (2H, m), 4.00 (3H, s), 3.81 (2H, s), 2.45-2.38 (2H, m), 1.92-1.71 (2H, m), 1.68-1.47 (6H, m).

EXAMPLE 89

(S)-2-Amino-4-(4-{4-[(2,4-difluoro-phenylcarbamoyl)-methyl]-phenoxy}-6-methoxy-quinolin-7-yloxy)-butyric acid

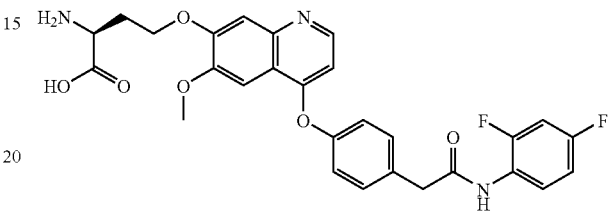

LC/MS: m/z 538 [M+H]$^+$. $^1$H NMR (300 MHz, CD$_3$OD) δ: 8.44 (1H, d, J=5.4 Hz), 7.86-7.79 (1H, m), 7.69 (1H, s), 7.54 (2H, d, J=8.4 Hz), 7.40 (1H, s), 7.24 (2H, d, J=8.4 Hz), 7.09-6.97 (2H, m), 6.60 (1H, d, J=5.4 Hz), 4.45 (2H, br s), 4.06 (3H, s), 3.95-3.89 (1H, m), 3.84 (2H, s), 2.68-2.52 (1H, m), 2.49-2.32 (1H, m).

EXAMPLE 90

(S)-2-Amino-4-(6-methoxy-4-{4-[(4-methoxy-phenylcarbamoyl)-methyl]-phenoxy}-quinolin-7-yloxy)-butyric acid cyclopentyl ester

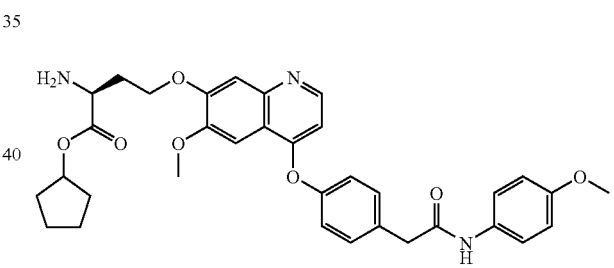

LC/MS: m/z 600 [M+H]$^+$. $^1$H NMR (300 MHz, DMSO-d$_6$) δ: 10.13 (1H, s), 8.70 (1H, d, J=6.0 Hz), 8.47 (2H, br s), 7.68 (1H, s), 7.62-7.41 (5H, m), 7.39-7.23 (2H, m), 6.99-6.68 (2H, m), 6.72 (1H, d, J=6.0 Hz), 5.22 (1H, br s), 4.36 (2H, br s), 4.21 (1H, br s), 4.00 (3H, s), 3.72 (5H, s), 2.42-2.27 (2H, m), 1.96-1.70 (2H, m), 1.68-1.47 (6H, m).

EXAMPLE 91

(S)-2-Amino-4-(6-methoxy-4-{4-[(4-methoxy-phenylcarbamoyl)-methyl]-phenoxy}-quinolin-7-yloxy)-butyric acid

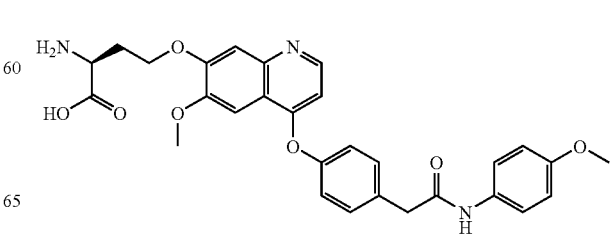

LC/MS: m/z 532 [M+H]⁺. ¹H NMR (300 MHz, CD₃OD) δ: 8.59 (1H, br s), 7.81 (1H, br s), 7.61-7.48 (5H, m), 7.32 (2H, d, J=8.4 Hz), 6.91-6.84 (3H, m), 4.52 (2H, br s), 4.11 (4H, br s), 3.79 (5H, s), 2.66-2.40 (2H, m).

EXAMPLE 92

(S)-2-Amino-4-{6-methoxy-4-[4-(5-phenyl-[1,2,4] oxadiazol-3-yl)-phenoxy]-quinolin-7-yloxy}-butyric acid cyclopentyl ester

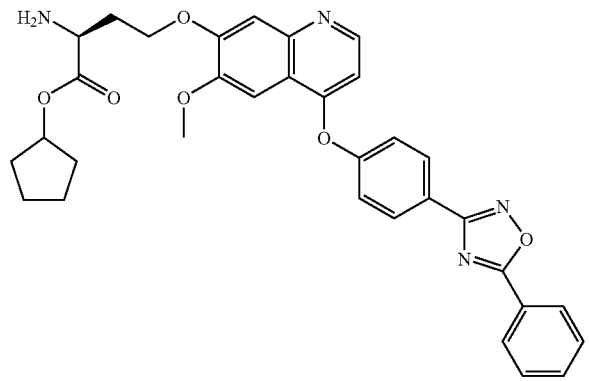

LC/MS purity: 98% (254 nm), m/z 581.3 [M+H]⁺. ¹H NMR (300 MHz, CD₃OD), δ: 8.74 (1H, d, J=6.6 Hz), 8.43 (2H, d, J=8.5 Hz), 8.29-8.23 (2H, m), 7.93 (1H, s), 7.76-7.57 (6H, m), 7.06 (1H, d, J=6.6 Hz), 5.40-5.31 (1H, m), 4.55 (2H, t, J=5.3 Hz), 4.35 (1H, t, J=6.2 Hz), 4.14 (3H, s), 2.65-2.53 (2H,m), 2.02-1.58 (9H, m).

The 4-(5-Phenyl-[1,2,4]oxadiazol-3-yl)-phenol side chain substituent was prepared as described in Scheme 27.

Scheme 27

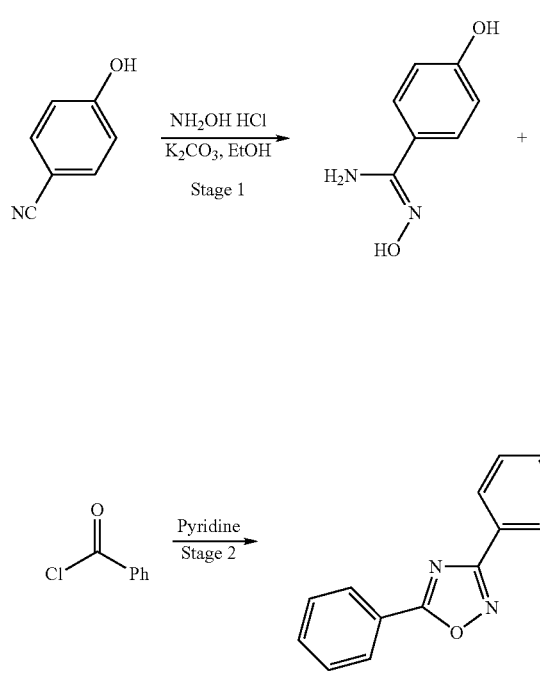

Stage 1-4-N-Dihydroxy-benzamidine

To a solution of 4-cyanophenol (5 g, 42 mmol) in ethanol (150 ml) was added finely divided potassium carbonate (29 g, 5 eq) and hydroxylamine hydrochloride (14 g, 5 eq) The reaction mixture was stirred at reflux overnight. The hot mixture was filtered and the solid was washed with hot ethanol (2×100 ml). The combined filtrates were concentrated under reduced pressure to give the title compound as a light brown solid (6.30 g, 98% yield).

LC/MS: m/z 153 [M+H]⁺.

Stage 2-4-(5-Phenyl-[1,2,4]oxadiazol-3-yl)-phenol

To a solution of 4-N-dihydroxy-benzamidine (7.9 g, 21.7 mmol) in anhydrous pyridine (30 ml) was added benzoyl chloride (6.1 g, 43.7 mmol, 2 eq) at a rate to maintain gentle reflux. The reaction mixture was stirred at reflux for 18 hours. The reaction mixture was cooled to room temperature and pyridine removed under reduced pressure. The residue was dissolved in ethyl acetate and washed with 1M HCl, aqueous NaHCO₃ and brine. The organic phase was dried on magnesium sulphate and the solvent removed under reduced pressure to give 8.0 g of a yellow solid. Purification by column chromatography (50% ethyl acetate in heptane) afforded the title compound as a white solid (1.35 g, 26% yield).

LC/MS: m/z 239 [M+H]⁺. ¹H NMR (300 MHz, CD₃OD), δ: 8.18 (2H, dd, J=1.4, 6.9 Hz), 8.01-7.91 (2H, m), 7.71-7.52 (3H, m), 6.95-6.88 (2H, m).

The following examples were prepared by methods described in Scheme 28 below.

EXAMPLE 93

(S)-2-Amino-4-(6-methoxy-4-{4-[3-(4-trifluoromethyl-phenyl)-ureido]-phenoxy}-quinolin-7-yloxy)-butyric acid cyclopentyl ester

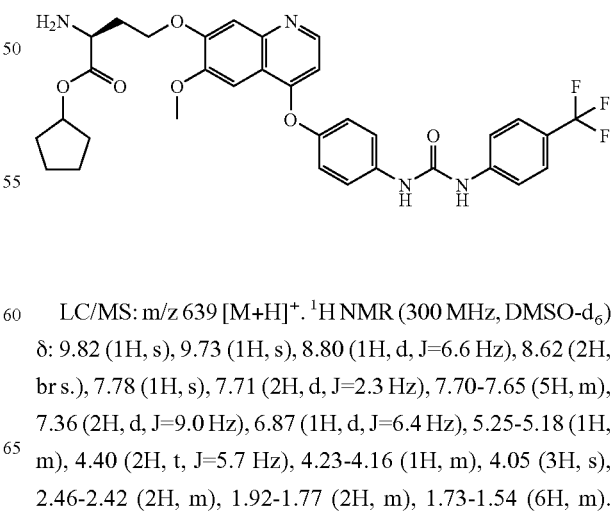

LC/MS: m/z 639 [M+H]⁺. ¹H NMR (300 MHz, DMSO-d₆) δ: 9.82 (1H, s), 9.73 (1H, s), 8.80 (1H, d, J=6.6 Hz), 8.62 (2H, br s.), 7.78 (1H, s), 7.71 (2H, d, J=2.3 Hz), 7.70-7.65 (5H, m), 7.36 (2H, d, J=9.0 Hz), 6.87 (1H, d, J=6.4 Hz), 5.25-5.18 (1H, m), 4.40 (2H, t, J=5.7 Hz), 4.23-4.16 (1H, m), 4.05 (3H, s), 2.46-2.42 (2H, m), 1.92-1.77 (2H, m), 1.73-1.54 (6H, m).

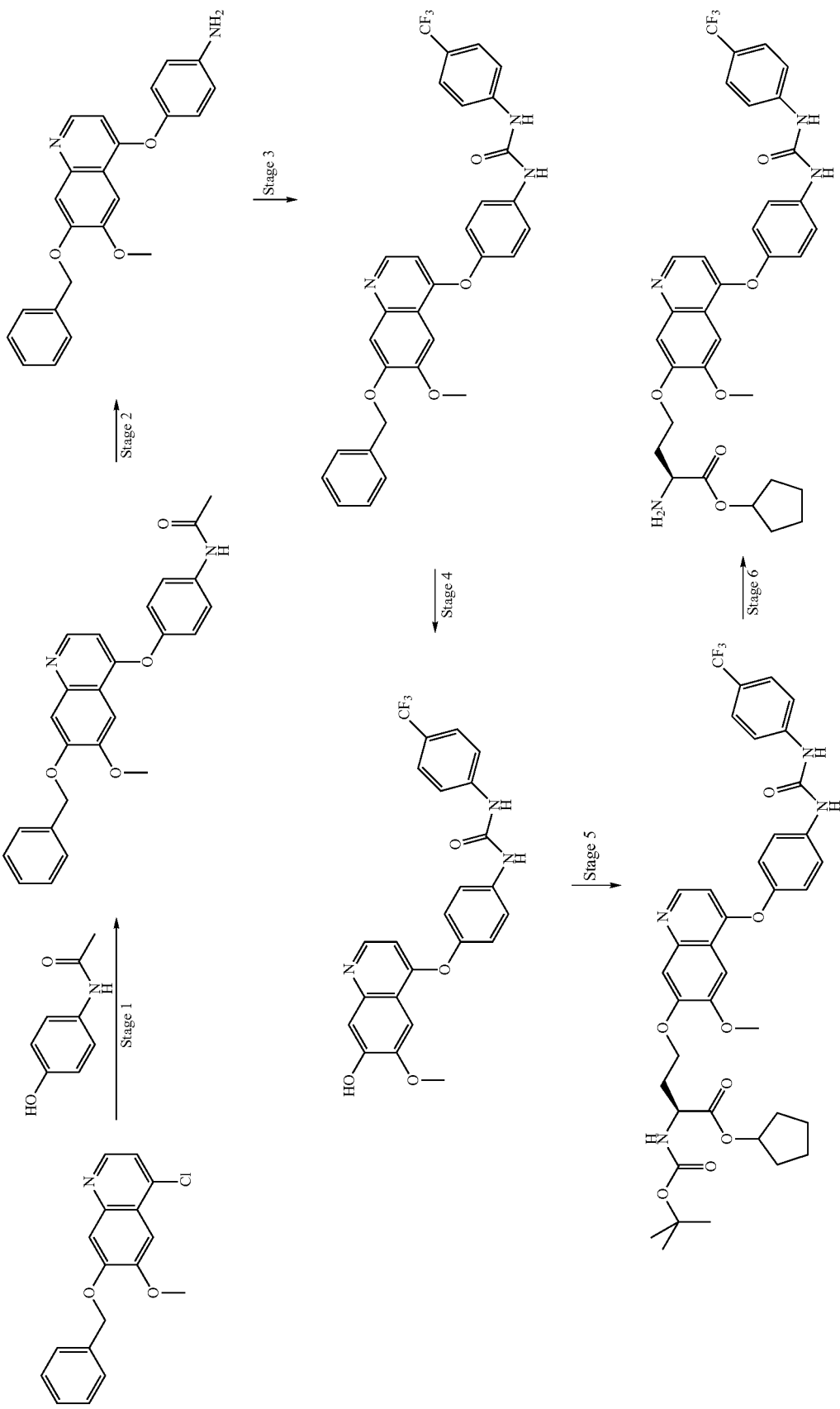
Scheme 28

Stage 1-N-[4-(7-Benzyloxy-6-methoxy-quinolin-4-yloxy)-phenyl]-acetamide

Twelve carousel tubes were charged with 7-benzyloxy-4-chloro-6-methoxy-quinoline (12×2.00 g, 12×6.67 mmol) and N-(4-hydroxy-phenyl)-acetamide (12×3.03 g, 12×20.00 mmol, 3.0 eq) in NMP (12×2.00 ml) and heated under to nitrogen to 150° C. for 2.5 hours. The reaction mixtures were allowed to cool to room temperature, diluted with DCM (12×20 ml). The combined organic solutions were washed with 2N NaOH (3×200 ml), water (200 ml), brine (200 ml), dried ($MgSO_4$), filtered and concentrated under reduced pressure to leave a brown oil. Purification by column chromatography (4% methanol in DCM) afforded the title compound as a beige solid (36.73 g).

LC/MS: m/z 415 $[M+H]^+$. This compound was used without further purification in the next step.

Stage 2-4-(7-Benzyloxy-6-methoxy-quinolin-4-yloxy)-phenylamine

A solution of impure N-[4-(7-benzyloxy-6-methoxy-quinolin-4-yloxy)-phenyl]-acetamide (36.73 g) in methanol (100 ml), water (150 ml) and concentrated HCl (50 ml) was heated to reflux for 6 hours. The reaction mixture was poured in water (500 ml) and basified to pH=12 with 2N NaOH. A precipitate was collected by filtration and taken up in DCM:MeOH (4:1, 1.25 L). The organic solution was washed with water (250 ml), brine (250 ml), dried ($MgSO_4$), filtered and concentrated under reduced pressure to leave a pale brown solid. Purification by column chromatography (2% methanol in DCM) afforded the title compound as an off-white solid (17.44 g, 58% yield over 2 steps).

LC/MS: m/z 373 $[M+H]^+$. $^1$H NMR (300 MHz, $CDCl_3$) δ: 8.45 (1H, d, J=5.4 Hz), 7.62 (1H, s), 7.54 (2H, d, J=7.2 Hz), 7.46-7.31 (4H, m), 7.03-6.98 (2H, m), 6.80-6.75 (2H, m), 6.42 (1H, d, J=5.4 Hz), 5.35 (2H, s), 4.07 (3H, s).

Stage 3-1-[4-(7-Benzyloxy-6-methoxy-quinolin-4-yloxy)-phenyl]-3-(4-trifluoromethyl-phenyl)-urea To a solution of 4-(7-benzyloxy-6-methoxy-quinolin-4-yloxy)-phenylamine (5 g, 13.4 mmol) in DCM (200 ml) was added slowly 4-trifluoromethyl phenylisocyanate (3.76 ml, 26.8 mmol). The solution became instantaneously clear. After 10 min stirring, a white solid had formed. This was collected by filtration and washed with diethyl ether to afford the title compound as a white solid (7.04 g, 94% yield).

LC/MS: m/z 560 $[M+H]^+$. $^1$H NMR (300 MHz, DMSO-$d_6$) δ: 9.15 (1H, s), 8.96 (1H, s), 8.47 (1H, dd, J=1.8, 5.2 Hz), 7.72-7.57 (6H, m), 7.57-7.48 (4H, m), 7.48-7.33 (3H, m), 7.27-7.21 (2H, m), 6.47-6.43 (1H, m), 5.31 (2H, s), 3.96 (3H, s).

Stage 4-1-[4-(7-Hydroxy-6-methoxy-quinolin-4-yloxy)-phenyl]-3-(4-trifluoromethyl-phenyl)-urea A solution of 1-[4-(7-benzyloxy-6-methoxy-quinolin-4-yloxy)-phenyl]-3-(4-trifluoromethyl-phenyl)-urea (7.04 g, 12.58 mmol) in ethanol (200 ml) and cyclohexene (20 ml) was degassed and put under nitrogen three times. Pd/C (1 g) was added and the reaction was refluxed overnight. The Pd was removed by filtration over a small plug of Celite, washing with hot ethanol and DCM. The yellow filtrate was concentrated under reduced pressure. The resulting solid was triturated with diethyl ether (50 ml) to afford the title compound as a white solid (5.12 g, 87% yield).

LC/MS: m/z 470 $[M+H]^+$. $^1$H NMR (300 MHz, DMSO-$d_6$) δ: 10.10 (1H, br s), 9.16 (1H, s), 8.97 (1H, s), 8.41 (1H, d, J=5.3 Hz), 7.71-7.58 (6H, m), 7.50 (1H, s), 7.28 (1H, s), 7.25-7.19 (2H, m), 6.38 (1H, d, J=5.1 Hz), 3.95 (3H, s).

Stage 5-(S)-2-tert-Butoxycarbonylamino-4-{6-methoxy-4-[4-(3-(4-trifluoromethyl-phenyl)-ureido)-phenoxy]-quinolin-7-yloxy}-butyric acid cyclopentyl ester To a solution of 1-[4-(7-hydroxy-6-methoxy-quinolin-4-yloxy)-phenyl]-3-p-tolyl-urea (1.6 g, 3.4 mmol) in DMF (15 ml) were added (S)-4-bromo-2-tert-butoxycarbonylamino-butyric acid cyclopentyl ester (1.54 g, 3.4 mmol) and potassium carbonate (564 mg, 4.1 mmol). The dark brown solution was stirred at 40° C. for 3 days. The DMF was removed under reduced pressure, EtOAc (200 ml) was added and the organic layer was washed with water (300 ml). The emulsion was broken by addition of brine (200 ml). The aqueous layer was extracted again with DCM (500 ml), all organic layers were combined, dried over $MgSO_4$, filtered and concentrated under reduced pressure to give the crude product. This was purified by flash chromatography using 2.5% MeOH in DCM, to give the title compound (1.62 g, 67% yield).

LC/MS: m/z 739 $[M+H]^+$. $^1$H NMR (300 MHz, DMSO-$d_6$) δ: 9.15 (1H, s), 8.96 (1H, s), 8.48 (1H, d, J=5.1 Hz), 7.72-7.58 (6H, m), 7.53 (1H, s), 7.40-7.31 (2H, m), 7.25-7.20 (2H, m), 6.46 (1H, d, J=5.3 Hz), 5.14-5.08 (1H, m), 4.27-4.12 (2H, m), 3.96 (3H, s), 2.28-2.06 (2H, m), 1.84-1.72 (2H, m), 1.66-1.49 (6H, m), 1.39 (9H, s).

Stage 6-(S)-2-Amino-4-{6-methoxy-4-[4-(3-(4-trifluoromethyl-phenyl)-ureido)-phenoxy]-quinolin-7-yloxy}-butyric acid cyclopentyl ester The (S)-2-tert-butoxycarbonylamino-4-{6-methoxy-4-[4-(3-p-tolyl-ureido)-phenoxy]-quinolin-7-yloxy}-butyric acid cyclopentyl ester (1.62 g, 2.19 mmol) was treated with a 4M solution of HCl in dioxane (20 ml) under nitrogen. The reaction was complete after 3 hours stirring at room temperature. The solvent was removed under reduced pressure and the compound was triturated with diethyl ether (20 ml) to afford the title compound as a pale yellow solid (1.37 g, 98% yield).

EXAMPLE 94

(S)-2-Amino-4-(6-methoxy-4-{4-[3-(4-trifluoromethyl-phenyl)-ureido]-phenoxy}-quinolin-7-yloxy)-butyric acid

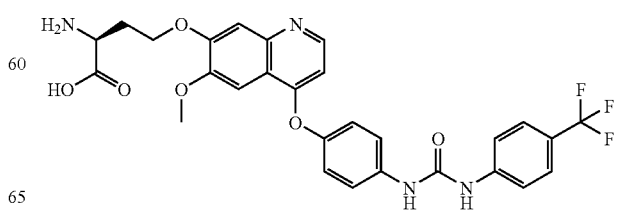

LC/MS: m/z 639 [M+H]⁺. ¹H NMR (300 MHz, DMSO-d₆), δ: 11.16 (1H, br s), 11.06 (1H, br s), 8.19 (1H, d, J=5.3 Hz), 7.80 (2H, d, J=7.2 Hz), 7.59 (4H, d, J=7.7 Hz), 7.53 (1H, s), 7.41 (1H, br s), 6.96 (2H, d, J=8.1 Hz), 5.96 (1H, d, J=4.9 Hz), 4.48-4.35 (2H, m), 3.97 (3H, s), 3.96-3.93 (1H, m), 2.46-2.41 (2H, m), 2.31-2.19 (2H, m).

EXAMPLE 95

(S)-2-Amino-4-{6-methoxy-4-[4-(3-phenyl-ureido)-phenoxy]-quinolin-7-yloxy}-butyric acid cyclopentyl ester

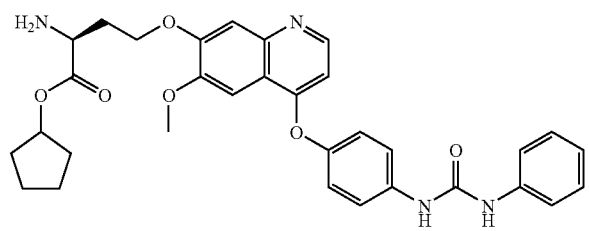

LC/MS: m/z 571 [M+H]⁺. ¹H NMR (300 MHz, DMSO-d₆) δ: 9.55 (1H, s), 9.28 (1H, s), 7.78 (1H, d, J=6.6 Hz), 8.63 (3H, br s), 7.77 (1H, s), 7.70-7.66 (3H, m), 7.48 (2H, d, J=7.5 Hz), 7.38-7.27 (4H, m), 6.98 (1H, t, J=7.3 Hz), 6.85 (1H, d, J=6.3 Hz), 5.22 (1H, t, J=5.7 Hz), 4.46-4.35 (2H, m), 4.25-4.15 (1H, m), 4.04 (3H, s), 2.45-2.35 (2H, m), 1.85-1.50 (8H, m).

EXAMPLE 96

(S)-2-Amino-4-{6-methoxy-4-[4-(3-phenyl-ureido)-phenoxy]-quinolin-7-yloxy}-butyric acid

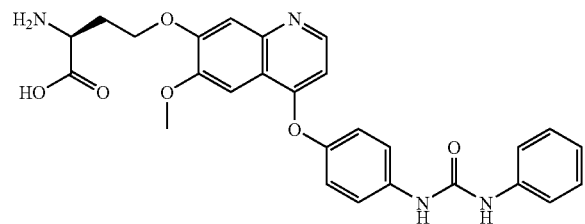

LC/MS: m/z 503 [M+H]⁺. ¹H NMR (300 MHz, DMSO-d₆) δ: 9.30 (1H, s), 9.14 (1H, s), 8.64 (1H, d, J=5.7 Hz), 8.39 (2H, br s), 7.68-7.65 (3H, m), 7.50 (3H, d, J=9.0 Hz), 7.33-7.25 (5H, m), 7.16 (1H, s), 7.00-6.97 (1H, m), 6.66 (1H, d, J=6.0 Hz), 4.37 (2H, t, J=6.0 Hz), 4.20-4.10 (1H, m), 4.01 (3H, s), 2.44-2.31 (2H, m).

EXAMPLE 97

(S)-2-Amino-4-{4-[4-(3-indan-5-yl-ureido)-phenoxy]-6-methoxy-quinolin-7-yloxy}-butyric acid cyclopentyl ester

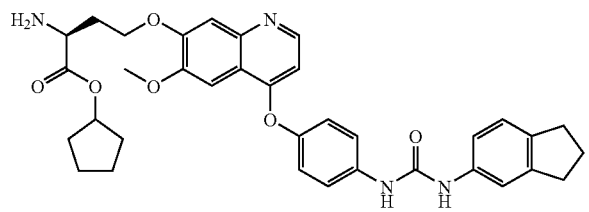

LC/MS purity: 98% (254 nm), m/z 611 [M+H]⁺. ¹H NMR (300 MHz, CD₃OD), δ: 8.69 (1H, d, J=6.8 Hz), 7.89 (1H, s), 7.64-7.72 (2H, m), 7.54 (1H, s), 7.26-7.37 (3H, m), 7.14 (2H, s), 6.96 (1H, d, J=6.6 Hz), 4.53 (2H, t, J=5.6 Hz), 4.34 (1H, t, J=6.5 Hz), 4.13 (3H, s), 3.66 (1H, s), 2.81-2.94 (4H, m), 2.47-2.67 (2H, m), 2.02-2.14 (2H, m), 1.86-1.99 (2H, m), 1.60-1.82 (6H, m).

EXAMPLE 98

(S)-2-Amino-4-{4-[4-(3-indan-5-yl-ureido)-phenoxy]-6-methoxy-quinolin-7-yloxy}-butyric acid

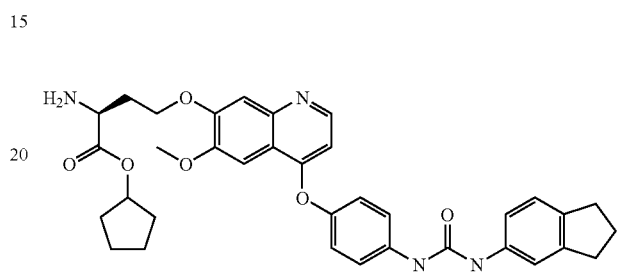

LC/MS purity: 92% (254 nm), m/z 543 [M+H]⁺. ¹H NMR (300 MHz, DMSO-d₆) δ: 8.22 (1H, d, J=5.1 Hz), 7.46-7.56 (5H, m), 7.40 (1H, s), 7.26-7.31 (1H, m), 7.15-7.21 (1H, m), 7.08 (1H, d, J=8.1 Hz), 6.90 (2H, d, J=9.0 Hz), 3.98 (3H, s), 2.74-2.86 (5H, m), 1.53-1.69 (3H, m), 1.23 (2H, s), 0.85 (1H, t, J=6.7 Hz).

Examples 99-108 were prepared as detailed in Scheme 3 using the (R)-4-bromo-2-tert-butoxycarbonylamino-butyric acid cyclopentyl ester at Stage 4.

EXAMPLE 99

(R)-2-Amino-4-[4-(4-benzoylamino-phenoxy)-6-methoxy-quinolin-7-yloxy]-butyric acid cyclopentyl ester

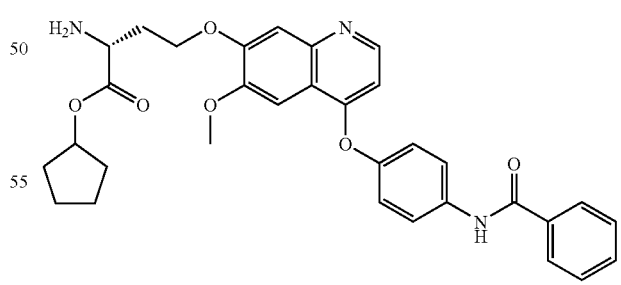

LC/MS purity: 100% (254 nm), m/z 556.3 [M+H]⁺. ¹H NMR (300 MHz, CD₃OD) δ: 8.71 (1H, d, J=6.7 Hz), 8.02-7.94 (4H, m), 7.90 (1H, s), 7.64-7.50 (4H, m), 7.44-7.36 (2H, m), 6.98 (1H, d, J=6.7 Hz), 5.39-5.31 (1H, m) 4.51 (2H, t, J=5.6 Hz), 4.33 (1H, t, J=6.5 Hz), 4.13 (3H, s), 2.66-2.50 (2H, m), 2.01-1.58 (9H, m).

EXAMPLE 100

(R)-2-Amino-4-[4-(4-benzoylamino-phenoxy)-6-methoxy-quinolin-7-yloxy]-butyric acid

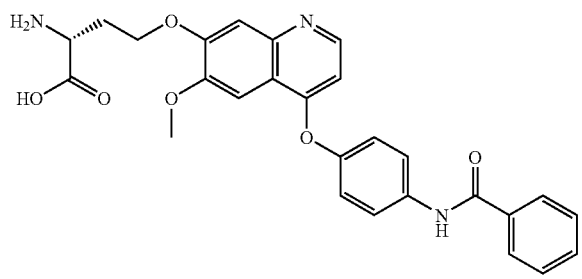

LC/MS purity: 98% (254 nm), m/z 488.2 [M+H]⁺. ¹H NMR (300 MHz, CD₃OD) δ: 8.70 (1H, d, J=6.8 Hz), 8.01-7.94 (4H,m), 7.89 (1H, s), 7.66-7.51 (5H, m), 7.42-7.36 (2H, m), 6.97 (1H, d, J=6.8 Hz), 4.54 (2H, t, J=5.7 Hz), 4.32-4.28 (1H, m), 4.13 (3H, s), 2.71-2.48 (2H, m).

EXAMPLE 101

(R)-2-Amino-4-{6-methoxy-4-[4-(3-phenyl-ureido)-phenoxy]-quinolin-7-yloxy}-butyric acid cyclopentyl ester

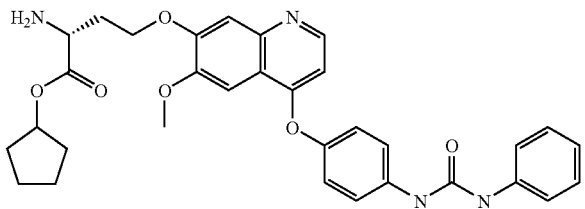

LC/MS purity: 95% (254 nm), m/z 571 [M+H]⁺. ¹H NMR (300 MHz, CD₃OD) δ: 9.54 (1H, s), 9.27 (1H, s), 8.79 (1H, d, J=6.6 Hz), 8.63 (3H, br s), 7.78 (1H, s), 7.71-7.67 (3H, m), 7.48 (1H, d, J=7.5 Hz), 7.36-7.26 (4H, m), 6.98 (1H, t, J=7.3 Hz), 6.87 (1H, d, J=6.6 Hz), 5.25-5.15 (1H, m), 4.42-4.38 (2H, m), 4.25-4.15 (1H, m), 4.05 (3H, s), 2.45-2.40 (2H, m), 1.88-1.79 (2H, m), 1.68-1.55 (6H, m).

EXAMPLE 102

(R)-2-Amino-4-{6-methoxy-4-[4-(3-phenyl-ureido)-phenoxy]-quinolin-7-yloxy}-butyric acid

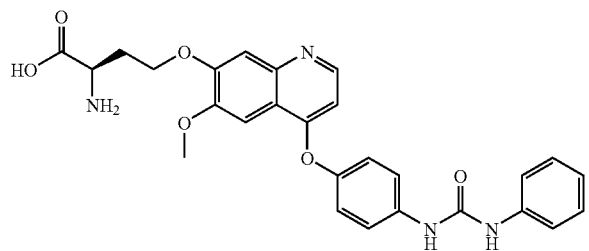

LC/MS purity: 93% (254 nm), m/z 503 [M+H]⁺. ¹H NMR (300 MHz, DMSO-d₆) δ: 10.22 (1H, s), 9.98 (1H, s), 8.37 (1H, d, J=5.1 Hz), 8.32-7.96 (2H, m), 7.57-7.52 (5H, m), 7.42 (1H, s), 7.27 (2H, t, J=8.0 Hz), 7.05 (2H, d, J=9.0 Hz), 6.94 (1H, t, J=7.4 Hz), 6.20 (1H, d, J=5.1 Hz), 4.48-4.31 (2H, m), 3.98 (3H, s), 3.85-3.78 (1H, m), 2.48-2.31 (2H, m)

EXAMPLE 103

(R)-2-Amino-4-{6-methoxy-4-[4-(4-trifluoromethyl-benzoylamino)-phenoxy]-quinolin-7-yloxy}-butyric acid cyclopentyl ester

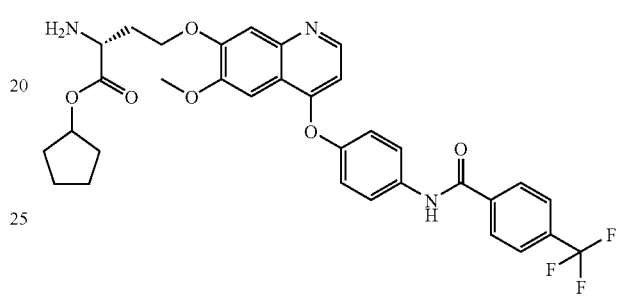

LC/MS purity: 95% (254 nm), m/z 624 [M+H]⁺. ¹H NMR (300 MHz, DMSO-d₆) δ: 10.79 (1H, s), 8.80 (1H, d, J=6.4 Hz), 8.63 (2H, br s), 8.21 (2H, d, J=8.1 Hz), 8.05 (2H, d, J=9.0 Hz), 7.96 (2H, d, J=8.3 Hz), 7.77 (1H, s), 7.71 (1H, s), 7.44 (2H, d, J=9.0 Hz), 6.86 (1H, d, J=6.4 Hz), 5.22 (1H, t, J=5.6 Hz), 4.40 (2H, t, J=5.8 Hz), 4.23-4.16 (1H, m), 4.05 (3H, s), 2.47-2.40 (2H, m), 1.92-1.77 (2H, m), 1.73-1.49 (6H, m).

EXAMPLE 104

(R)-2-Amino-4-(6-methoxy-4-{4-[3-(4-trifluoromethyl-phenyl)-ureido]-phenoxy}-quinolin-7-yloxy)-butyric acid cyclopentyl ester

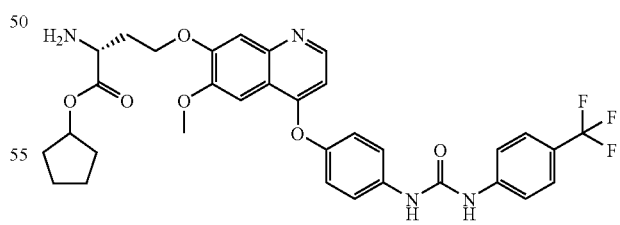

LC/MS purity: 96% (254 nm), m/z 639 [M+H]⁺. ¹H NMR (300 MHz, DMSO-d₆) δ: 9.87 (1H, s), 9.78 (1H, s), 8.80 (1H, d, J=6.6 Hz), 8.64 (2H, s), 7.78 (1H, s), 7.68 (7H, m), 7.36 (2H, d, J=8.7 Hz), 6.88 (1H, d, J=6.6 Hz), 5.22 (1H, s), 4.40 (2H, s), 4.18 (1H, s), 4.05 (3H, s), 2.43 (2H, m), 1.82 (2H, m), 1.60 (6H, m).

EXAMPLE 105

(R)-2-Amino-4-(6-methoxy-4-{4-[3-(4-trifluoromethyl-phenyl)-ureido]-phenoxy}-quinolin-7-yloxy)-butyric acid

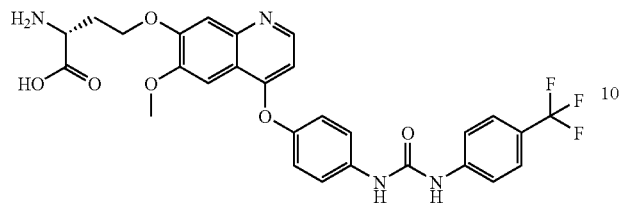

LC/MS purity: 95% (254 nm), m/z 571 [M+H]⁺. $^1$H NMR (300 MHz, DMSO-d$_6$) δ: 10.99 (1H, s), 10.90 (1H, s), 8.17 (1H, d, J=5.1 Hz), 7.72 (2H, d, J=8.1 Hz), 7.54 (2H, d, J=8.4 Hz), 7.49 (1H, s), 7.42 (2H, d, J=9.0 Hz), 7.35 (1H, s), 6.80 (2H, d, J=8.4 Hz), 5.81 (1H, d, J=5.1 Hz), 4.40 (1H, m), 4.30 (1H, m), 3.93 (3H, s), 3.89 (1H, m), 3.66 (1H, m), 2.28 (1H, m).

EXAMPLE 106

(R)-2-Amino-4-{4-[2-fluoro-4-(4-trifluoromethyl-benzoylamino)-phenoxy]-6-methoxy-quinolin-7-yloxy}-butyric acid cyclopentyl ester

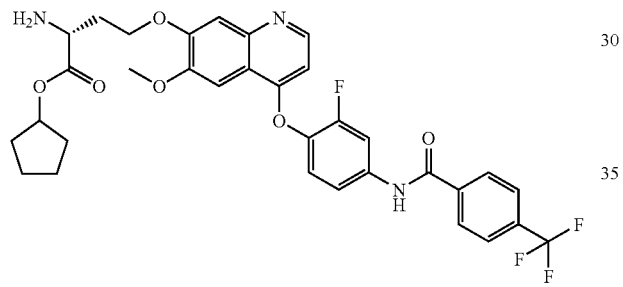

LC/MS purity: 97% (254 nm), m/z 642 [M+H]⁺. $^1$H NMR (300 MHz, CD$_3$OD) δ: 8.78 (1H, d, J=6.6 Hz), 8.17 (2H, d, J=8.1 Hz), 8.11 (1H, dd, J=2.3, 12.8 Hz), 7.94 (1H, s), 7.89 (2H, d, J=8.3 Hz), 7.77-7.70 (1H, m), 7.60-7.53 (2H, m), 7.08 (1H, dd, J=1.0, 6.7, Hz), 5.40-5.33 (1H, m), 4.56 (2H, t, J=5.7 Hz), 4.36 (1H, t, J=6.5 Hz), 4.16 (3H, s), 2.61 (2H, t, J=5.7 Hz), 2.02-1.89 (2H, m), 1.86-1.62 (6H, m).

EXAMPLE 107

(R)-2-Amino-4-{6-methoxy-4-[4-(5-phenyl-[1,2,4]oxadiazol-3-yl)-phenoxy]-quinolin-7-yloxy}-butyric acid cyclopentyl ester

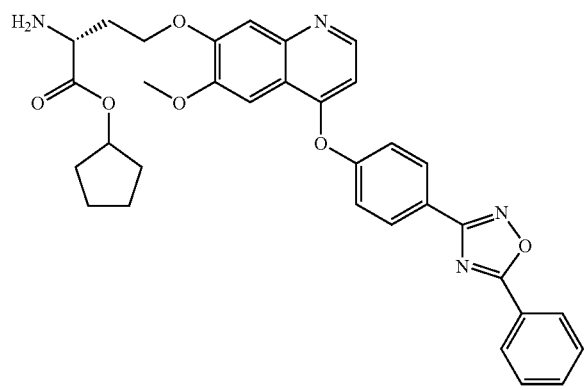

LC/MS purity: 96% (254 nm), m/z 581 [M+H]⁺. $^1$H NMR (300 MHz, CD$_3$OD) δ: 8.75 (1H, d, J=6.8 Hz), 8.43 (2H, d, J=8.7 Hz), 8.30-8.22 (2H, m), 7.93 (1H, s), 7.76-7.56 (6H, m), 7.06 (1H, d, J=6.6 Hz), 5.41-5.31 (1H, m), 4.55 (2H, t, J=5.5 Hz), 4.35 (1H, t, J=6.5 Hz), 4.14 (3H, s), 2.70-2.46 (2H, m), 2.04-1.56 (9H, m).

EXAMPLE 108

(R)-2-Amino-4-(4-{2-fluoro-4-[3-(4-trifluoromethyl-phenyl)-ureido]-phenoxy}-6-methoxy-quinolin-7-yloxy)-butyric acid cyclopentyl ester

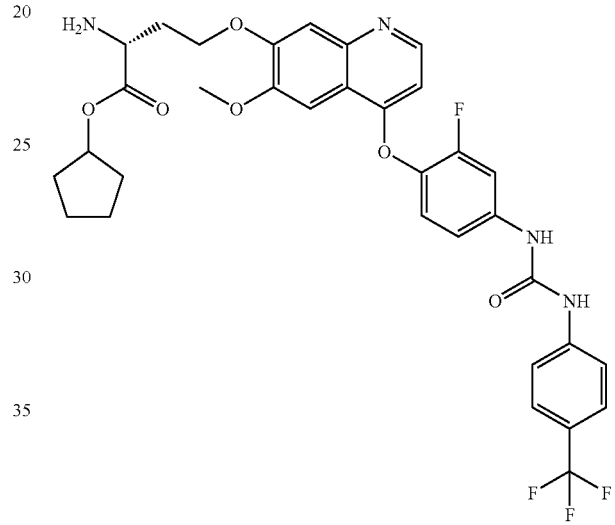

LC/MS purity: 100% (254 nm), m/z 671 [M+H]⁺. $^1$H NMR (300 MHz, DMSO-d$_6$) δ: 10.06 (1H, br s), 9.95 (1H, br s), 8.83 (1H, d, J=4.9 Hz), 8.63 (3H, br s), 7.85 (1H, dd, J=2.3, 13.4 Hz), 7.78 (1H, s), 7.73-7.62 (5H, m), 7.54 (1H, t, J=9.0 Hz), 7.33 (1H, dd, J=1.0, 8.9 Hz), 6.98 (1H, d, J=5.8 Hz), 5.21 (1H, t, J=5.6 Hz), 4.40 (2H, t, J=5.0 Hz), 4.24-4.13 (1H, m), 4.03 (3H, s), 2.43 (2H, d, J=5.3 Hz), 1.93-1.47 (9H, m).

The following examples were prepared by using (S)-5-bromo-2-tert-butoxycarbonylamino-pentanoic acid cyclopentyl ester at Stage 4 in Scheme 3.

The synthesis of (S)-5-bromo-2-tert-butoxycarbonylamino-pentanoic acid cyclopentyl ester is outlined below in Scheme 29. Additional literature references relating to this route can be found within *J. Org. Chem.* 1984, 49, 3527-3534.

Scheme 29

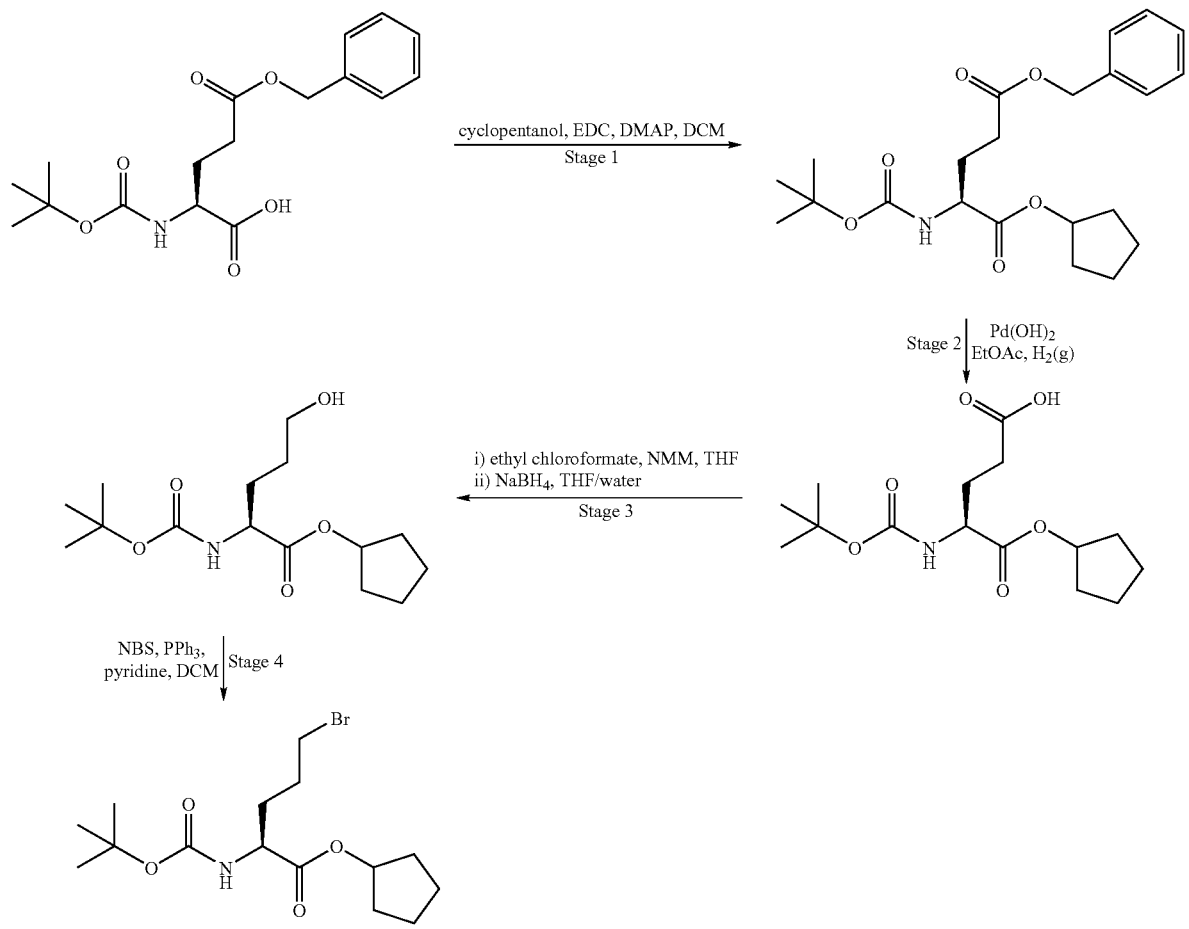

Stage 1-(S)-2-tert-Butoxycarbonylamino-pentanedioic acid 5-benzyl ester 1-cyclopentyl ester

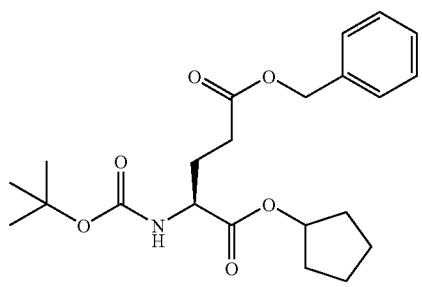

To a solution of Boc-L-Glu(OBzl)-OH (15 g, 44.5 mmol) in dichloromethane (220 ml) in an ice-bath, was added cyclopentanol (4.8 ml, 53.3 mmol, 1.2 eq), EDC (9.4 g, 48.9 mmol, 1.1 eq) and DMAP (543 mg, 4.4 mmol, 0.1 eq). The reaction mixture was allowed to warm to room temperature and stirred for 12 hours for complete reaction. The reaction mixture was diluted with DCM (200 ml) and washed with 1M HCl, 1M $Na_2CO_3$ and brine. The organic layer was then dried over magnesium sulphate and evaporated under reduced pressure. The product was purified by column chromatography using ethyl acetate/heptane (1:4) to afford the title compound as a white solid (12.4 g, 69%).

$^1$H NMR (300 MHz, $CDCl_3$) δ: 7.38 (5H, m), 5.70 (1H, m), 5.10 (2H, s), 5.05 (1H, m), 4.25 (1H, m), 2.47 (2H, m), 2.15 (1H, m), 1.95-1.55 (9H, m), 1.47 (9H, s).

Stage 2-(S)-2-tert-Butoxycarbonylamino-pentanedioic acid 1-cyclopentyl ester

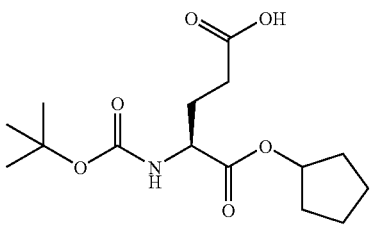

(S)-2-tert-Butoxycarbonylamino-pentanedioic acid 5-benzyl ester 1-cyclopentyl ester (12.4 g, 30.5 mmol) was dissolved in EtOAc (200 ml) and purged with nitrogen before addition of 20% Pd(OH)$_2$ on carbon catalyst (1.3 g). The reaction flask was then purged with hydrogen gas for a period of 5 minutes before leaving under a balloon of hydrogen for 5 hours for complete reaction. The catalyst was removed by filtration, washing with 50 ml EtOAc and the combined filtrates were evaporated under reduced pressure. The title compound was isolated as a clear oil (7.73 g, 85% yield) and required no further purification.

$^1$H NMR (300 MHz, CDCl$_3$) δ: 10.0 (1H, br s), 5.70 (2H, m), 4.28 (1H, m), 2.47 (2H, m), 2.15 (1H, m), 1.95-1.55 (9H, m), 1.47 (9H, s).

Stage 3-(S)-2-tert-Butoxycarbonylamino-5-hydroxy-pentanoic acid cyclopentyl ester

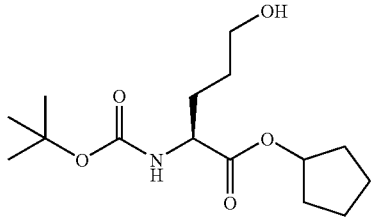

Ethyl chloroformate (2.45 ml, 25.6 mmol, 1.2 eq) was added at −20° C. to a stirred solution of (S)-2-tert-butoxycarbonylamino-pentanedioic acid 1-cyclopentyl ester (6.73 g, 21.4 mmol) and N-methyl morpholine (3.05 ml, 27.8 mmol, 1.3 eq) in THF (50 ml). The reaction mixture became very thick with precipitation of a white solid. The reaction was therefore diluted further with THF (100 ml) to aid mixing and left stirring at −20° C. for 2 hours. The precipitated mass was filtered off and the filtrate was added over a period of 20 minutes to a solution of sodium borohydride (2.43 g, 64.1 mmol, 3 eq) in THF (20 ml) and water (5 ml) at 0° C. The reaction mixture was allowed to stir to room temperature and left for 4 hours for complete reaction. The mixture was acidified to pH 5 with 1M HCl and the THF removed under reduced pressure. The aqueous solution was extracted with EtOAc (3×100 ml) and dried over magnesium sulphate. The product was purified by column chromatography (DCM-5% MeOH/DCM) and isolated as a clear oil (5.0 g, 78% yield).

$^1$H NMR (300 MHz, CDCl$_3$) δ: 5.20 (2H, m), 4.25 (1H, m), 3.65 (2H, m), 2.00-1.57 (12H, m), 1.47 (9H, s).

Stage 4-(S)-5-Bromo-2-tert-butoxycarbonylamino-pentanoic acid cyclopentyl ester

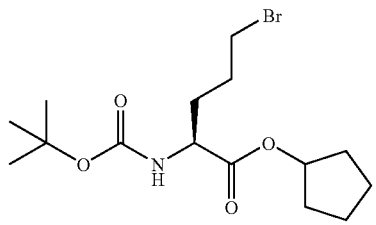

To a slurry of N-bromo succinimide (3.54 g, 19.9 mmol, 3 eq) in DCM (30 ml) was added a solution of triphenyl phosphine (4.87 g, 18.8 mmol, 2.8 eq) in DCM (15 ml). The solution was stirred for a further 5 minutes before addition of pyridine (644 μl, 7.96 mmol, 1.2 eq) and a solution of (S)-2-tert-butoxycarbonylamino-5-hydroxy-pentanoic acid cyclopentyl ester (2.0 g, 6.64 mmol) in DCM (20 ml). The solution was stirred for 18 hours, concentrated in vacuo and the residual solvent azeotroped with toluene (3×30 ml). The residue was triturated with diethyl ether (30 ml) and ethyl acetate: heptane (1:9, 2×30 ml). The combined ether and ethyl acetate/heptane solutions was concentrated onto silica and purified by column chromatography using ethyl acetate/heptane (1:9 to 2:8) to provide the title compound as a clear oil (1.34 g, 55% yield).

$^1$H NMR (300 MHz, CDCl$_3$) δ: 5.25 (1H, m), 5.05 (1H, br d), 3.45 (2H, m), 2.00-1.55 (12H, m), 1.45 (9H, s).

EXAMPLE 109

(S)-2-Amino-5-[4-(4-benzoylamino-phenoxy)-6-methoxy-quinolin-7-yloxy]-pentanoic acid cyclopentyl ester

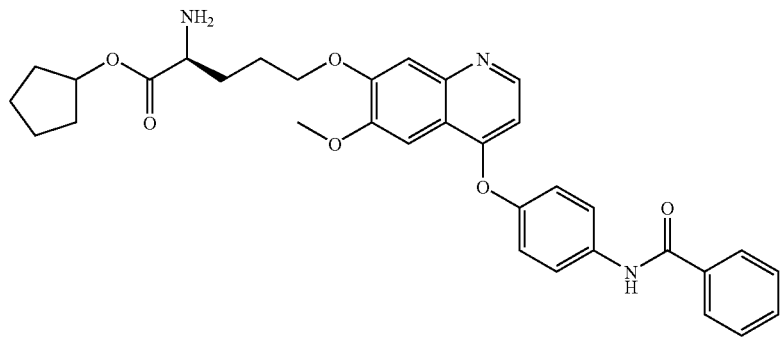

LC/MS purity: 94% (254 nm), m/z 570 [M+H]$^+$. $^1$H NMR (300 MHz, CD$_3$OD) δ: 8.46 (1H, d, J=5.4 Hz), 7.98 (2H, d, J=5.1 Hz), 7.89 (2H, d, J=9.0 Hz), 7.67 (1H, s), 7.65-7.53 (4H, m), 7.38 (1H, s), 7.28 (2H, d, J=9.0 Hz), 6.60 (1H, d, J=5.4 Hz), 5.32-5.28 (1H, m), 4.29-4.27 (2H, m), 4.04 (4H, br s), 2.21-2.03 (4H, m), 2.01-1.79 (2H, m), 1.77-1.54 (6H, m)

EXAMPLE 110

(S)-2-Amino-5-[4-(4-benzoylamino-phenoxy)-6-methoxy-quinolin-7-yloxy]-pentanoic acid

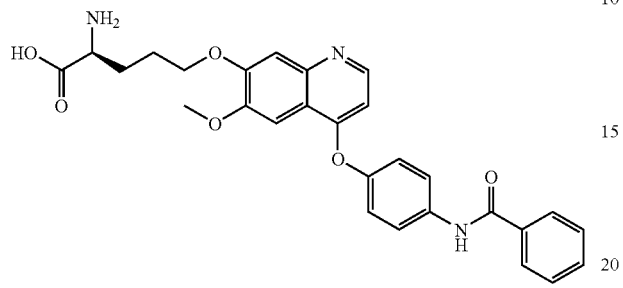

LC/MS purity: 96% (254 nm), m/z 502 [M+H]$^+$. $^1$H NMR (300 MHz, DMSO-d$_6$) δ: 8.50 (1H, d, J=5.2 Hz), 8.06-7.92 (4H, m), 7.65-7.51 (4H, m), 7.44 (1H, s), 7.29 (2H, d, J=8.9 Hz), 6.50 (1H, d, J=5.3 Hz), 4.26-4.14 (2H, m), 3.96 (3H, s), 3.19-3.13 (1H, m), 2.10-1.87 (4H, m).

EXAMPLE 111

(S)-2-Amino-5-{6-methoxy-4-[4-(3-phenyl-ureido)-phenoxy]-quinolin-7-yloxy}-pentanoic acid cyclopentyl ester

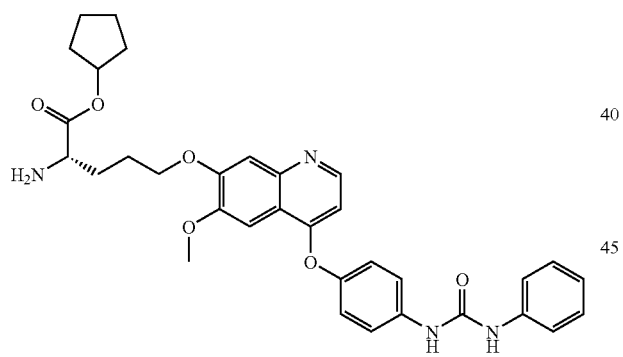

LC/MS purity: 95% (254 nm), m/z 585 [M+H]$^+$. $^1$H NMR (300 MHz, DMSO-d$_6$) δ: 9.57 (1H, s), 9.32 (1H, s), 8.72 (1H, d, J=6.0 Hz), 8.55 (3H, br s), 7.72 (1H, s), 7.67 (2H, d, J=8.7 Hz), 7.48 (1H, d, J=7.8 Hz), 7.40 (1H, s), 7.32-7.23 (4H, m), 7.06 (1H, s), 6.97 (1H, t, J=7.2 Hz), 6.77 (1H, d, J=6.0 Hz), 5.28-5.18 (1H, m), 4.30-4.20 (2H, m), 4.18-4.08 (1H, m), 4.02 (3H, s), 2.10-1.80 (6H, m), 1.75-1.50 (6H, m).

EXAMPLE 112

(S)-2-Amino-5-{6-methoxy-4-[4-(3-phenyl-ureido)-phenoxy]-quinolin-7-yloxy}-pentanoic acid

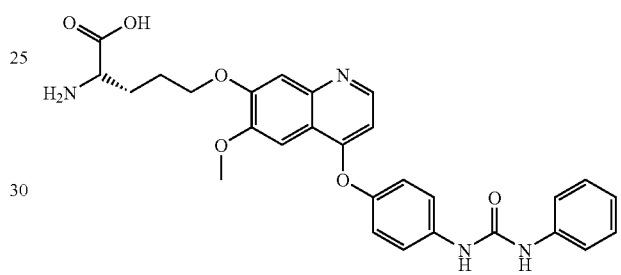

LC/MS purity: 93% (254 nm), m/z 517 [M+H]$^+$. $^1$H NMR (300 MHz, DMSO-d$_6$) δ: 9.95 (1H, s), 6.67 (1H, s), 8.60-8.53 (3H, m), 7.60-7.56 (4H, m), 7.41 (2H, d, J=7.5 Hz), 7.24-7.19 (4H, m), 6.89 (1H, t, J=7.2 Hz), 6.59 (1H, d, J=5.7 Hz), 4.16 (2H, br, s), 3.93 (3H, s), 3.65-3.59 (1H, m), 2.06-1.81 (4H, m).

EXAMPLE 113

(S)-2-Amino-5-(6-methoxy-4-{4-[3-(4-trifluoromethyl-phenyl)-ureido]-phenoxy}-quinolin-7-yloxy)-pentanoic acid cyclopentyl ester

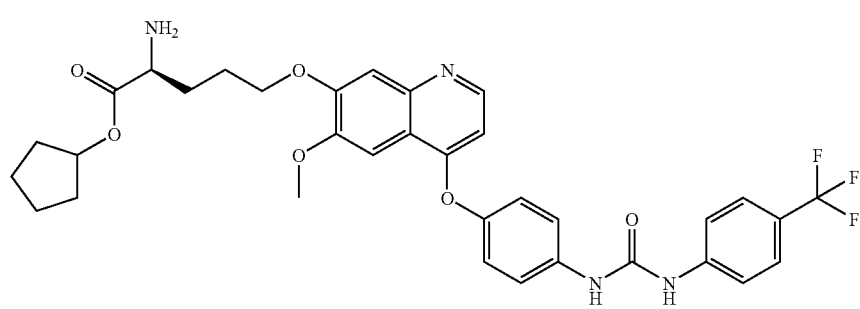

LC/MS purity: 90% (254 nm), m/z 653 [M+H]⁺. ¹H NMR (300 MHz, DMSO-d₆) δ: 9.88 (1H, s), 9.79 (1H, s), 8.79 (1H, d, J=6.6 Hz), 8.55 (2H, s), 7.78 (1H, s), 7.68 (7H, m), 7.36 (2H, d, J=8.7 Hz), 6.87 (1H, d, J=6.6 Hz), 5.23 (1H, m), 4.28 (2H, m), 4.12 (1H, m), 4.05 (3H, s), 2.04 (3H, m), 1.88 (3H, m), 1.63 (6H, m).

EXAMPLE 114

(S)-2-Amino-5-(6-methoxy-4-{4-[3-(4-trifluoromethyl-phenyl)-ureido]-phenoxy}-quinolin-7-yloxy)-pentanoic acid

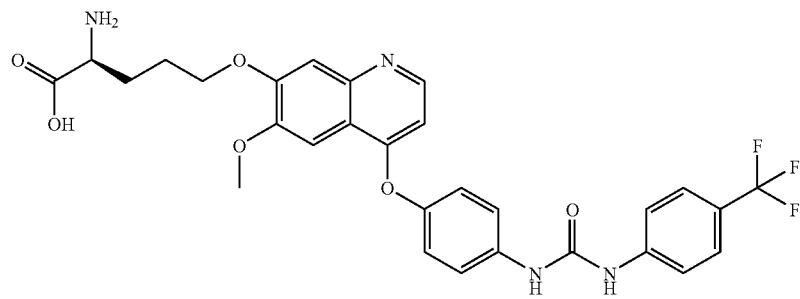

LC/MS purity: 96% (254 nm), m/z 585 [M+H]⁺. ¹H NMR (300 MHz, DMSO-d₆) δ: 8.42 (1H, d, J=5.4 Hz), 7.71 (2H, d, J=8.7 Hz), 7.62 (2H, m), 7.52 (1H, s), 7.36 (3H, br s), 7.02 (2H, d, J=8.1 Hz), 6.39 (1H, d, J=5.4 Hz), 4.14 (2H, br s), 3.94 (3H, s), 2.98 (1H, br s), 1.88-1.66 (4H, m).

The following examples were prepared using the corresponding (R)-5-bromo-2-tert-butoxycarbonylamino-pentanoic acid cyclopentyl ester, the synthesis of which is identical to the (S)-enantiomer shown above in Scheme 29.

EXAMPLE 115

(R)-2-Amino-5-[4-(4-benzoylamino-phenoxy)-6-methoxy-quinolin-7-yloxy]-pentanoic acid cyclopentyl ester

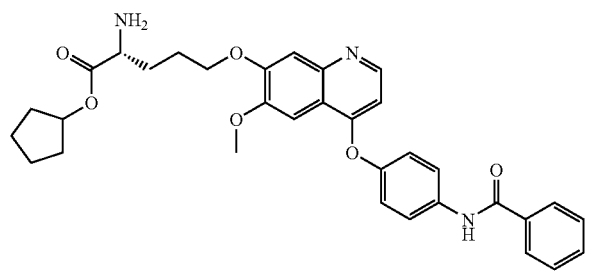

LC/MS purity: 99% (254 nm), m/z 571 [M+H]⁺. ¹H NMR (300 MHz, DMSO-d₆) δ: 10.57 (1H, s), 8.79 (1H, d, J=6.6 Hz), 8.59 (2H, s), 8.03 (4H, m), 7.77 (2H, m), 7.60 (3H, m), 7.43 (2H, d, J=9 Hz), 6.86 (1H, d, J=6.3 Hz), 5.22 (1H, t, J=5.6 Hz), 4.28 (2H, m), 4.12 (1H, m), 4.05 (3H, s), 1.96 (4H, m), 1.86 (2H, m), 1.66 (6H, m).

EXAMPLE 116

(R)-2-Amino-5-[4-(4-benzoylamino-phenoxy)-6-methoxy-quinolin-7-yloxy]-pentanoic acid

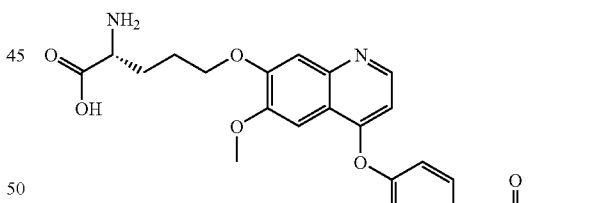

LC/MS purity: 95% (254 nm), m/z 502 [M+H]⁺. ¹H NMR (300 MHz, DMSO-d₆) δ: 8.46 (1H, d, J=5.1 Hz), 8.02 (2H, d, J=6.3 Hz), 7.86 (2H, d, J=8.4 Hz), 7.50 (4H, m), 7.37 (1H, s), 7.19 (2H, d, J=8.1 Hz), 6.46 (1H, d, J=5.1 Hz), 4.13 (2H, t, J=6.0 Hz), 3.34 (3H, s), 2.90 (1H, m), 1.86-1.66 (3H, m), 1.48 (1H, m).

EXAMPLE 117

(R)-2-Amino-5-[4-(4-benzoylamino-phenoxy)-6-methoxy-quinolin-7-yloxy]-pentanoic acid cyclopentyl ester

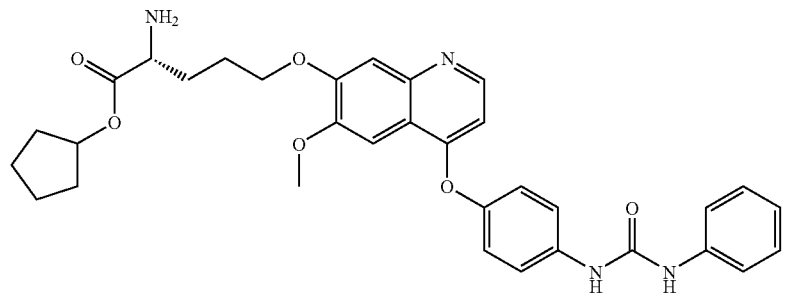

LC/MS purity: 96% (254 nm), m/z 586 [M+H]$^+$. $^1$H NMR (300 MHz, DMSO-d$_6$) δ: 9.58 (1H, s), 9.30 (1H, s), 8.80 (1H, d, J=6.6 Hz), 8.54 (2H, s), 7.78 (1H, s), 7.71 (3H, m), 7.48 (2H, d, J=7.5 Hz), 7.32 (4H, m), 6.98 (1H, t, J=7.4 Hz), 6.88 (1H, d, J=6.6 Hz), 5.22 (1H, m), 4.28 (2H, s), 4.12 (1H, m), 4.05 (3H, s), 1.91 (3H, m), 1.68 (3H, m), 1.58 (6H, m).

EXAMPLE 118

(R)-2-Amino-5-{6-methoxy-4-[4-(3-phenyl-ureido)-phenoxy]-quinolin-7-yloxy}-pentanoic acid

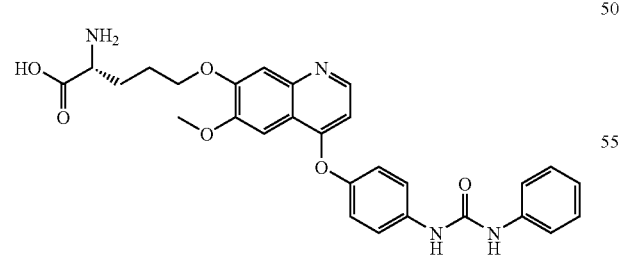

LC/MS purity: 98% (254 nm), m/z 517 [M+H]$^+$. $^1$H NMR (300 MHz, DMSO-d$_6$) δ: 9.89 (1H, s), 9.71 (1H, s), 8.44 (1H, br s), 7.63 (2H, d, J=8.7 Hz), 7.61-7.543 (3H, m), 7.41 (1H, s), 7.27 (2H, t, J=7.8 Hz), 7.16 (2H, d, J=9.0 Hz), 6.95 (1H, t, J=7.4 Hz), 6.42 (1H, d, J=5.1 Hz), 4.19 (2H, br s), 3.94 (3H, s), 3.69 (1H, br s), 2.11-1.86 (4H, m).

EXAMPLE 119

(R)-2-Amino-5-(6-methoxy-4-{4-[3-(4-trifluoromethyl-phenyl)-ureido]-phenoxy}-quinolin-7-yloxy)-pentanoic acid cyclopentyl ester

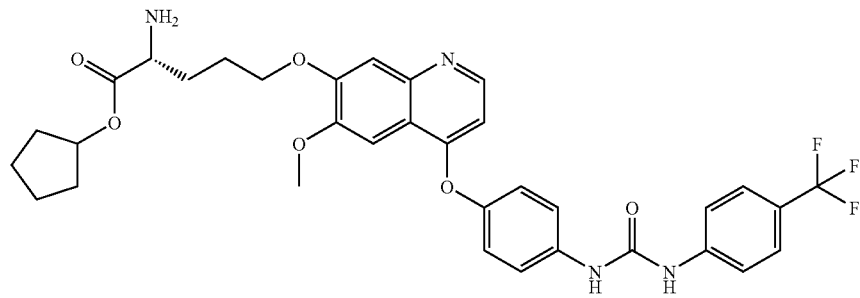

LC/MS purity: 98% (254 nm), m/z 653 [M+H]$^+$. $^1$H NMR (300 MHz, DMSO-d$_6$) δ: 9.72 (1H, s), 9.63 (1H, s), 8.80 (1H, d, J=6.6 Hz), 8.49 (2H, s), 7.78 (1H, s), 7.68 (7H, m), 7.36 (2H, d, J=9 Hz), 6.87 (1H, d, J=6.3 Hz), 5.23 (1H, m), 4.29 (2H, m), 4.13 (1H, m), 4.05 (3H, s), 2.03 (3H, m), 1.87 (3H, m), 1.63 (6H, m).

EXAMPLE 120

(R)-2-Amino-5-(6-methoxy-4-{4-[3-(4-trifluoromethyl-phenyl)-ureido]-phenoxy}-quinolin-7-yloxy)-pentanoic acid

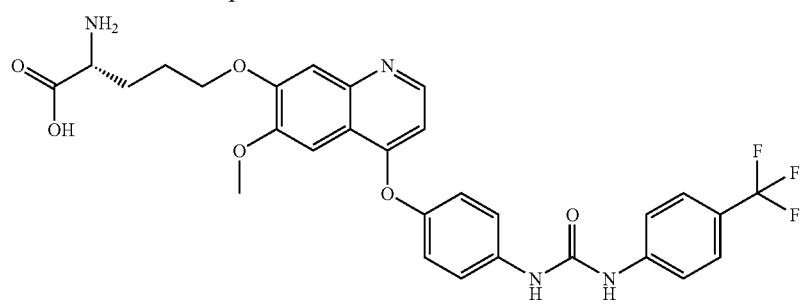

LC/MS purity: 94% (254 nm), m/z 585 [M+H]$^+$. $^1$H NMR (300 MHz, DMSO-d$_6$) δ: 8.33 (1H, m), 7.61 (2H, d, J=8.7 Hz), 7.50 (2H, m), 7.44 (1H, s), 7.28 (1H, s), 7.22 (2H, m), 6.88 (2H, d, J=8.7 Hz), 6.29 (1H, m), 4.07 (2H, m), 3.87 (3H, s), 2.90 (1H, m), 1.76 (2H, m), 1.35 (2H, m).

EXAMPLE 121

(R)-2-Amino-5-(6-methoxy-4-{4-[3-(4-trifluoromethyl-phenyl)-ureido]-phenylsulfanyl}-quinolin-7-yloxy)-pentanoic acid cyclopentyl ester

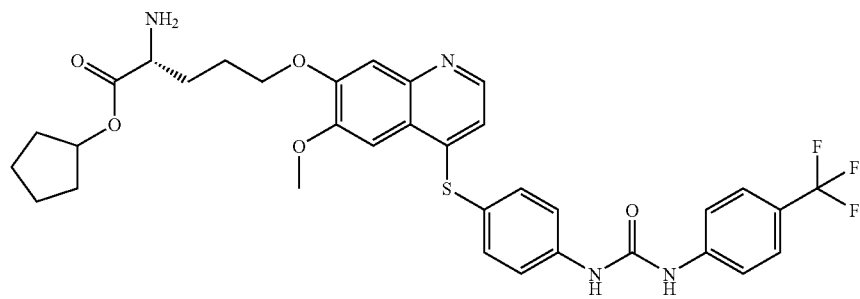

LC/MS purity: 95% (254 nm), m/z 669 [M+H]⁺. ¹H NMR (300 MHz, DMSO-d₆) δ: 9.99 (1H, s), 9.95 (1H, s), 8.59 (1H, d, J=6 Hz), 8.52 (3H, s), 7.77 (2H, d, J=8.4 Hz), 7.67 (7H, m), 7.50 (1H, s), 6.85 (1H, s), 5.22 (1H, m), 4.27 (2H, m), 4.12 (1H, m), 4.05 (3H, s), 2.02 (3H, m), 1.86 (3H, m), 1.67 (6H, m).

EXAMPLE 122

(R)-2-Amino-5-(6-methoxy-4-{4-[3-(4-trifluoromethyl-phenyl)-ureido]-phenylsulfanyl}-quinolin-7-yloxy)-pentanoic acid

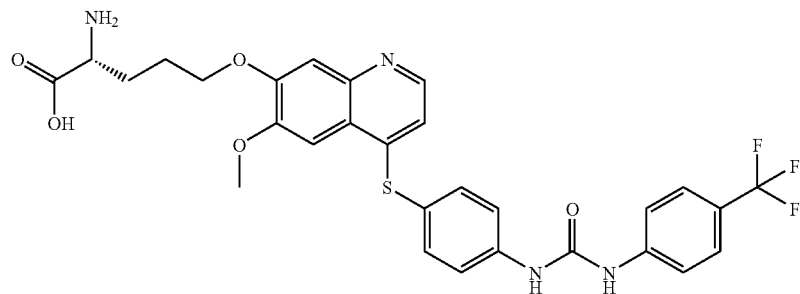

LC/MS purity: 94% (254 nm), m/z 601 [M+H]⁺. ¹H NMR (300 MHz, DMSO-d₆) δ: 8.33 (1H, br s), 7.72-7.68 (4H, m), 7.35-7.30 (6H, m), 6.49 (1H, br s), 4.17-4.13 (2H, m), 3.94 (3H, s), 3.02 (1H, br s), 1.90-1.67 (4H, m).

The synthesis of Example 123 is shown below in Scheme 30.

EXAMPLE 123

(R)-2-Amino-5-(4-{2-fluoro-4-[3-(4-trifluoromethyl-phenyl)-ureido]-phenoxy}-6-methoxy-quinolin-7-yloxy)-pentanoic acid cyclopentyl ester

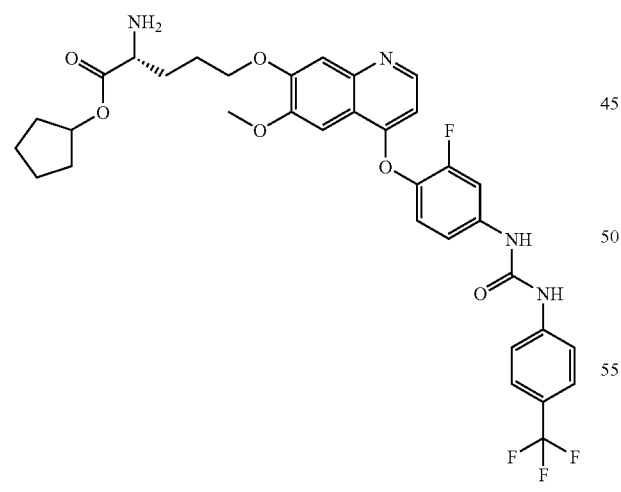

LC/MS purity: 100% (254 nm), m/z 671 [M+H]⁺. ¹H NMR (300 MHz, DMSO-d₆) δ: 10.01 (1H, s), 9.90 (1H, s), 8.81 (1H, d, J=6.2 Hz), 8.59-8.48 (2H, m), 7.86 (1H, d, J=2.4 Hz), 7.82 (1H, d, J=2.3 Hz), 7.73-7.626 (5H, m), 7.53 (1H, t, J=9.0 Hz), 7.34 (1H, dd, J=1.1, 9.0 Hz), 6.96 (1H, d, J=6.2 Hz), 5.22 (1H, t, J=5.7 Hz), 4.28 (2H, br.s.), 4.13 (2H, dd, J=2.0 5.6 Hz), 4.04 (3H, s), 2.10-1.76 (6H, m), 1.75-1.51 (6H, m).

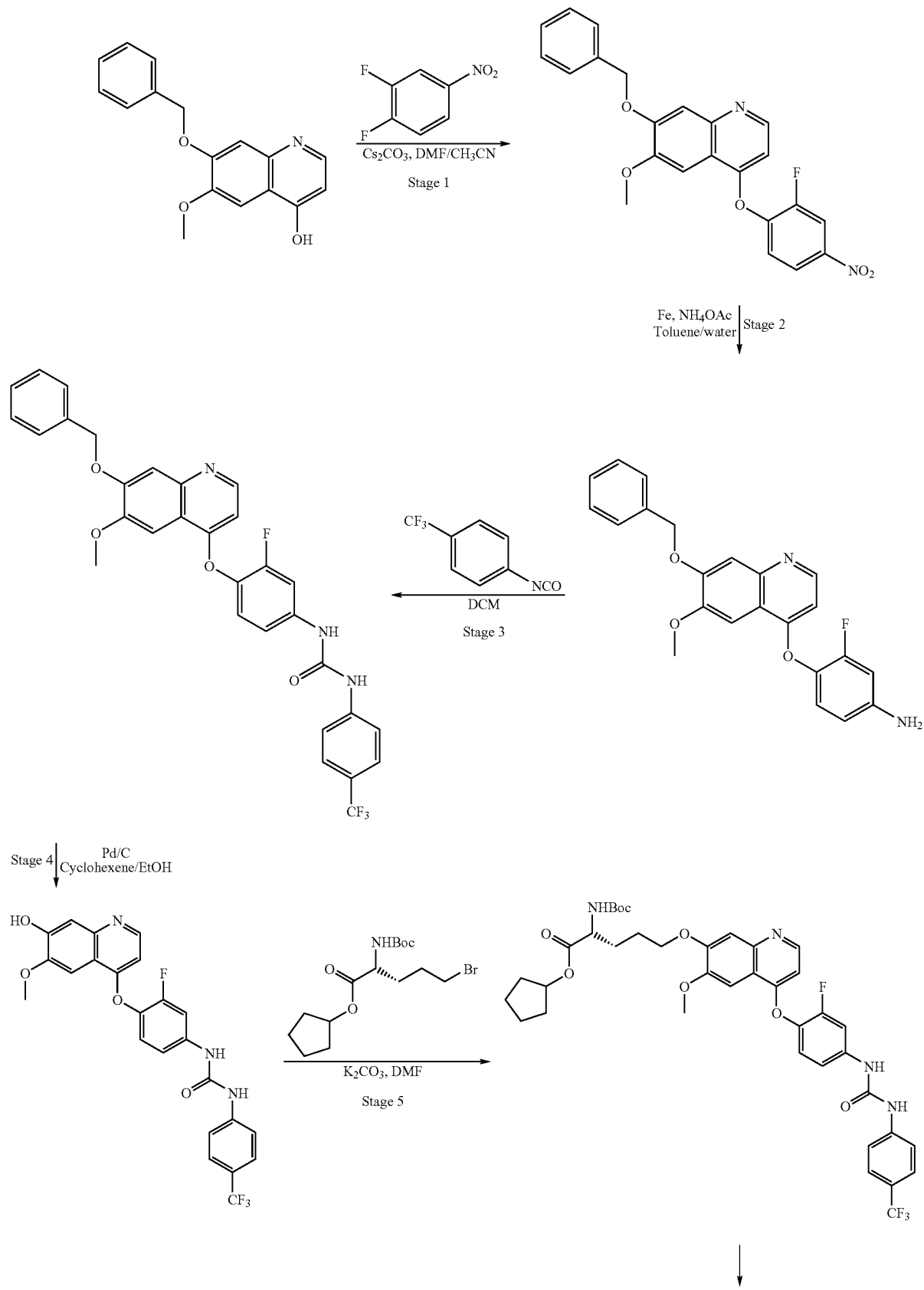
Scheme 30

-continued

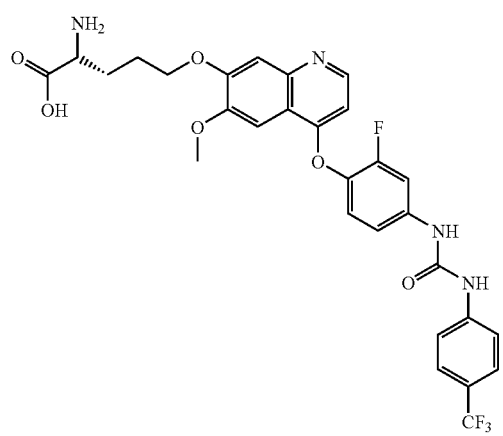
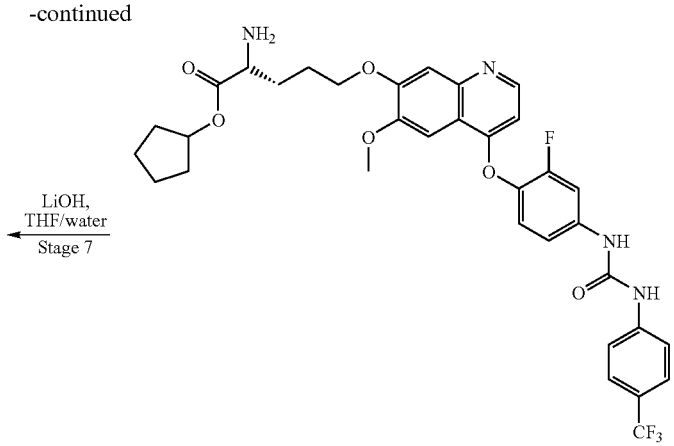

LiOH, THF/water
Stage 7

Stage 1-7-Benzyloxy-4-(2-fluoro-4-nitro-phenoxy)-6-methoxy-quinoline

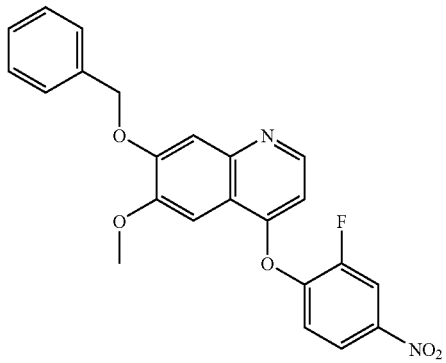

To a solution of 7-benzyloxy-6-methoxy-quinolin-4-ol (1.50 g, 5.33 mmol, 1 eq) in DMF/acetonitrile 1:1 was added cesium carbonate (4.00 g, 10.66 mmol, 2 eq) and the mixture stirred at room temperature for 30 minutes. 1,2-Difluoro-4-nitro-benzene was added over a 10 minutes period and the mixture was stirred at room temperature for 2.5 hours. The solvents were removed under reduced pressure and the residue was partitioned between water and ethyl acetate. The organic layer was washed with brine, and dried over magnesium sulphate. The solvent was removed under reduced pressure to give a dark brown foam. The product was purified by column chromatography using ethyl acetate/heptane to give the title compound (0.70 g, 31% yield).

LC/MS: m/z 421 [M+H]$^+$. $^1$H NMR (300 MHz, CDCl$_3$) δ: 8.57 (1H, d, J=5.3 Hz), 8.23-8.11 (2H, m), 7.55-7.30 (8H, m), 6.55 (1H, dd, J=0.7, 5.2 Hz), 5.35 (2H, s), 4.05 (3H, s).

Stage 2-4-(7-Benzyloxy-6-methoxy-quinolin-4-yloxy)-3-fluoro-phenylamine

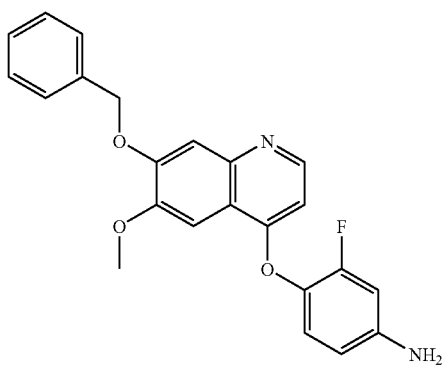

A mixture of 7-benzyloxy-4-(2-fluoro-4-nitro-phenoxy)-6-methoxy-quinoline (0.64 g, 1.53 mmol), iron powder (0.34 g, 6.14 mmol, 4 eq) and ammonium acetate (0.47 g, 6.14 mmol, 4 eq) in toluene/water 1:1 was stirred at reflux for 4.5 hours. The mixture was filtered through a pad of Celite washing with ethyl acetate (15 ml). The organic layer was separated and washed with water (2×15 ml), brine and dried over magnesium sulphate. The solvent was removed under reduced pressure to afford the title compound as a white solid (0.39 g, 65% yield).

LC/MS: m/z 391 [M+H]$^+$.

Stage 3-1-[4-(7-Benzyloxy-6-methoxy-quinolin-4-yloxy)-3-fluoro-phenyl]-3-(4-trifluoromethyl-phenyl)-urea

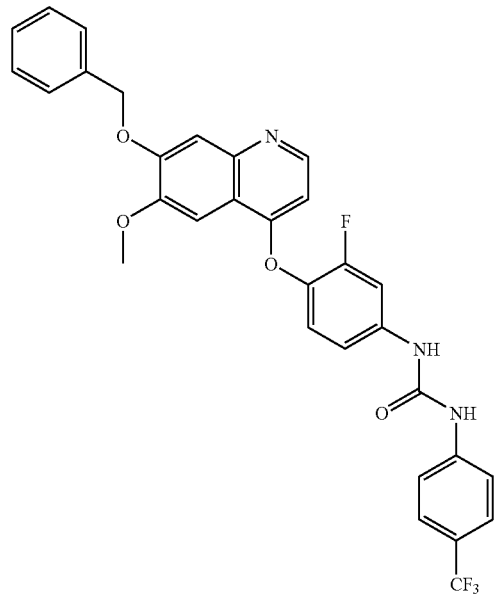

To a solution of 4-(7-benzyloxy-6-methoxy-quinolin-4-yloxy)-3-fluoro-phenylamine (0.20 g, 0.51 mmol, 1 eq) in DCM (30 ml) was added N-(4-trifluoromethyl-phenyl)-formamide (0.073 ml, 0.51 mmol, 1 eq) and the mixture stirred at room temperature for 2.5 hours. The solvent was removed under reduced pressure and the residue triturated in diethyl ether (2×30 ml). The solid was dried under reduced pressure to give the title compound as a white solid. (0.23 g, 79% yield).

LC/MS purity: 95% (254 nm), m/z 578 [M+H]⁺. ¹H NMR (300 MHz, DMSO-d₆), δ: 9.33 (2H, d, J=12.2 Hz), 8.54 (1H, d, J=5.7 Hz), 7.84-7.25 (16H, m), 6.56 (1H, d, J=5.3 Hz), 5.33 (2H, s), 3.98 (3H, s).

Stage 4-1-[3-Fluoro-4-(7-hydroxy-6-methoxy-quinolin-4-yloxy)-phenyl]-3-(4-trifluoromethyl-phenyl)-urea

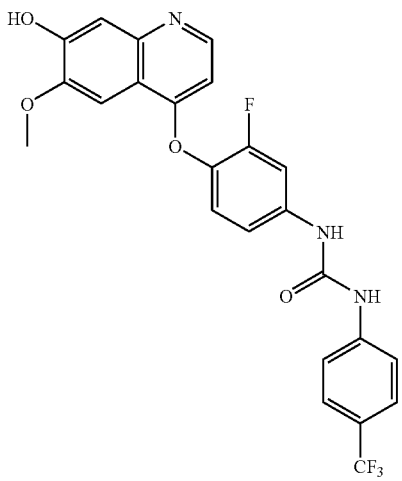

A mixture of 1-[4-(7-Benzyloxy-6-methoxy-quinolin-4-yloxy)-3-fluoro-phenyl]-3-(4-trifluoromethyl-phenyl)-urea (0.23 g, 0.39 mmol) and 10% Pd/C (0.12 g) in 10% cyclohexene/ethanol (30 ml) was heated under reflux overnight. The Pd/C catalyst was filtered through a pad of Celite, washing twice with methanol. The filtrate was concentrated under reduced pressure to give the title compound as a yellow solid (0.17 g, 89% yield).

LC/MS: m/z 488 [M+H]⁺.

Stage 5-(R)-2-tert-Butoxycarbonylamino-5-(4-{2-fluoro-4-[3-(4-trifluoromethyl-phenyl)-ureido]-phenoxy}-6-methoxy-quinolin-7-yloxy)-pentanoic acid cyclopentyl ester

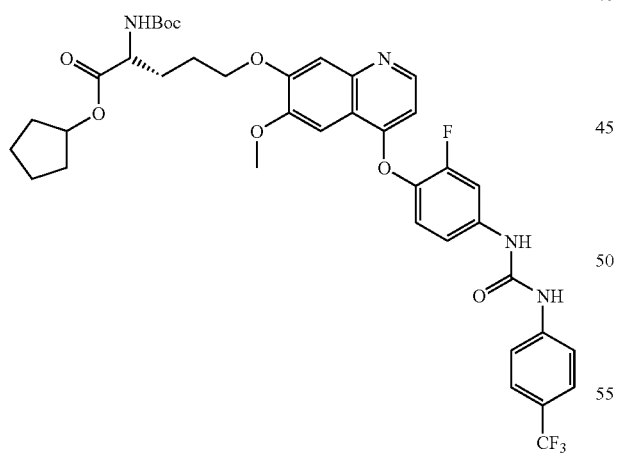

1-[3-Fluoro-4-(7-hydroxy-6-methoxy-quinolin-4-yloxy)-phenyl]-3-(4-trifluoromethyl-phenyl)-urea (0.10 g, 0.20 mmol), (R)-4-bromo-2-tert-butoxycarbonylamino-butyric acid cyclopentyl ester (0.08 g, 0.225 mmol, 1.1 eq) and K₂CO₃ (0.056 g, 0.41 mmol, 2 eq) were dissolved in anhydrous DMF (6 ml) under an atmosphere of nitrogen. The reaction was stirred at 35° C. overnight before the DMF was removed under reduced pressure. The residue was dissolved in DCM and washed with water followed by brine. The organic layer was dried over magnesium sulphate and evaporated under reduced pressure. The product was purified using column chromatography eluting with methanol/DCM to afford the title compound (0.10 g, 66% yield).

LC/MS purity: 95% (254 nm), m/z 771 [M+H]⁺. ¹H NMR (300 MHz, CDCl₃) δ: 8.46 (1H, d, J=5.3 Hz), 8.22 (2H, d, J=4.5 Hz), 7.61-7.51 (6H, m), 7.35 (1H, s), 7.11 (2H, s), 6.40 (1H, d, J=5.3 Hz), 5.35 (1H, d, J=8.1 Hz), 5.23-5.15 (1H, m), 4.36-4.26 (1H, m), 4.12 (2H, t, J=5.0 Hz), 4.02 (3H, s), 2.13-1.54 (13H, m), 1.46 (9H, m).

Stage 6-(R)-2-Amino-5-(4-{2-fluoro-4-[3-(4-trifluoromethyl-phenyl)-ureido]-phenoxy}-6-methoxy-quinolin-7-yloxy)-pentanoic acid cyclopentyl ester

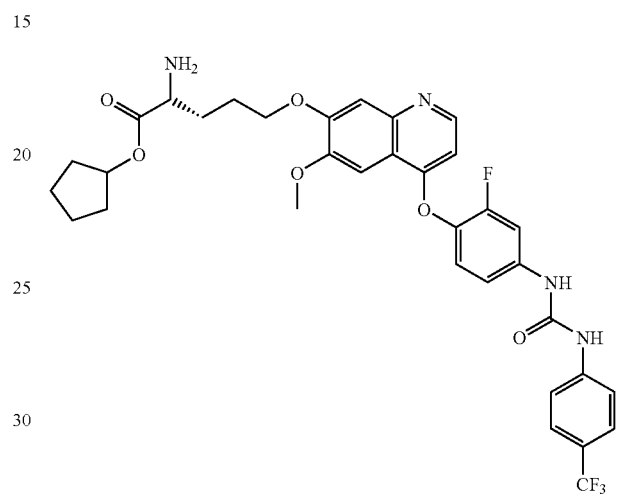

To (S)-2-tert-butoxycarbonylamino-5-(4-{2-fluoro-4-[3-(4-trifluoromethyl-phenyl)-ureido]-phenoxy}-6-methoxy-quinolin-7-yloxy)-pentanoic acid cyclopentyl ester (0.10 g, 0.13 mmol) was added 4N HCl in dioxane (5 ml). The reaction mixture was stirred at room temperature overnight before evaporation under reduced pressure to yield the title compound as a pale yellow solid.

EXAMPLE 124

Stage 7-(R)-2-Amino-5-(4-{2-fluoro-4-[3-(4-trifluoromethyl-phenyl)-ureido]-phenoxy}-6-methoxy-quinolin-7-yloxy)-pentanoic acid

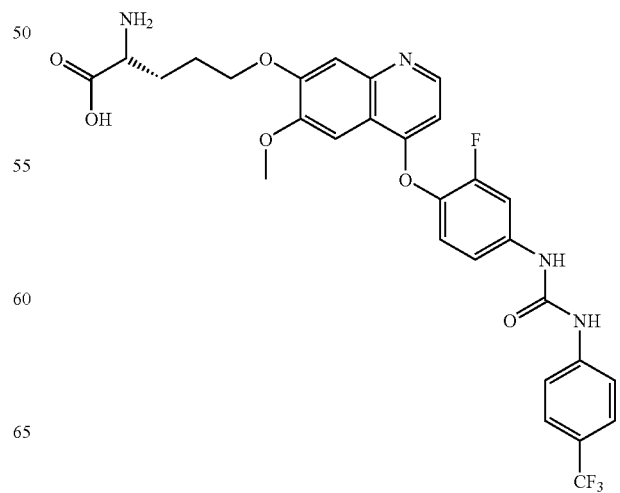

To a solution of (S)-2-amino-5-(4-{2-fluoro-4-[3-(4-trifluoromethyl-phenyl)-ureido]-phenoxy}-6-methoxy-quinolin-7-yloxy)-pentanoic acid cyclopentyl ester (0.05 g 0.07 mmol) in THF (2.5 ml) was added a solution of LiOH (0.08 g, 0.34 mmol, 5 eq) in water (2.5 ml). The reaction mixture was stirred at room temperature overnight. THF was removed under reduced pressure. The aqueous layer was diluted with 2 ml of water and acidified to pH 7 with 1M HCl. The title compound was extracted into n-butanol, and isolated as a white solid (0.05 g).

LC/MS purity: 100% (254 nm), m/z 603 [M+H]$^+$. $^1$H NMR (300 MHz, DMSO-d$_6$) δ: 11.17 (2H, d, J=16.2 Hz), 8.39 (1H, d, J=5.1 Hz), 7.88-7.74 (3H, m), 7.61 (3H, d, J=8.3 Hz), 7.50 (1H, s), 7.42 (1H, brs), 7.30 (1H, d, J=7.9 Hz), 7.12 (1H, t, J=8.9 Hz), 6.31 (1H, d, J=4.9 Hz), 4.22 (2H, brs), 3.93 (3H, s), 3.49 (1H, brs), 2.12-1.83 (4H, m).

EXAMPLE 125

(S)-2-Amino-4-(4-{2-fluoro-4-[3-(4-trifluoromethyl-phenyl)-ureido]-phenoxy}-6-methoxy-quinolin-7-yloxy)-butyric acid cyclopentyl ester

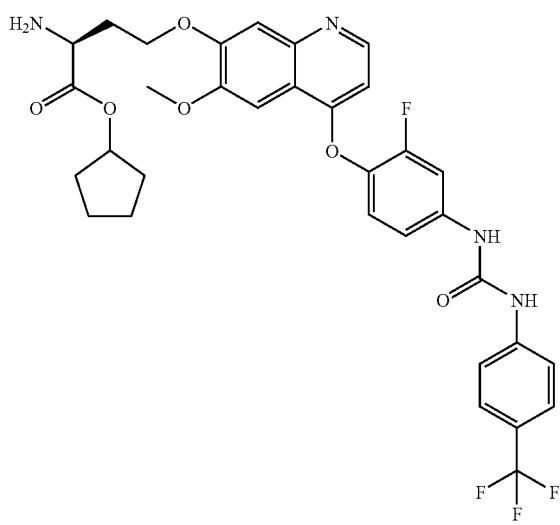

LC/MS purity: 90% (254 nm), m/z 657 [M+H]$^+$. $^1$H NMR (300 MHz, DMSO-d$_6$) δ: 10.07 (1H, s), 9.96 (1H, s), 8.82 (1H, d, J=6.6 Hz), 8.64 (3H, br s), 7.88-7.82 (1H, m), 7.78 (1H, s), 7.71-7.64 (4H, m), 7.54 (1H, t, J=9.0 Hz), 7.34 (1H, d, J=8.7 Hz), 6.98 (1H, d, J=6.3 Hz), 5.24-5.19 (1H, m), 4.45-4.35 (2H, m), 4.26-4.15 (1H, m), 4.05 (3H, s), 2.45-2.40 (2H, m), 1.85-1.50 (8H, m).

EXAMPLE 126

(S)-2-Amino-4-(4-{2-fluoro-4-[3-(4-trifluoromethyl-phenyl)-ureido]-phenoxy}-6-methoxy-quinolin-7-yloxy)-butyric acid

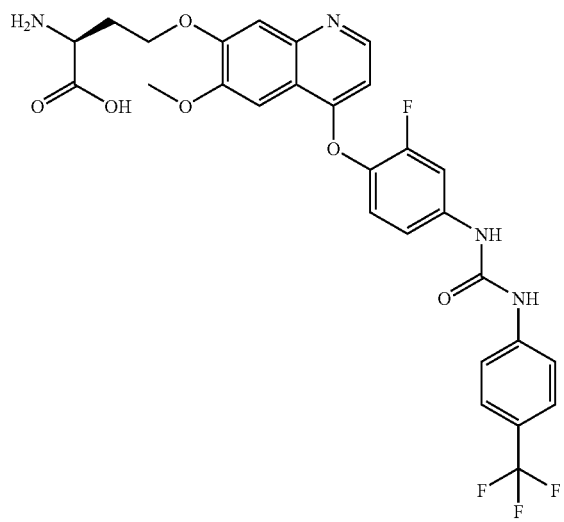

LC/MS purity: 95% (254 nm), m/z 589 [M+H]$^+$. $^1$H NMR (300 MHz, CD$_3$OD) δ: 8.62 (1H, d, J=6.3 Hz), 7.78-7.71 (2H, m), 7.58 (2H, d, J=8.7 Hz), 7.49 (3H, d, J=8.4 Hz), 7.34 (1H, t, J=8.5 Hz), 7.27-7.22 (1H, m), 6.89 (1H, d, J=6.6 Hz), 4.5-4.40 (2H, m), 4.18 (1H, t, J=6.1 Hz), 4.03 (3H, s), 2.60-2.35 (2H, m).

The following examples make use of the 4-(7-benzyloxy-6-methoxy-quinolin-4-yloxy)-3-fluoro-phenylamine intermediate in their synthesis, using the appropriate acid chloride at Stage 3 in Scheme 30.

EXAMPLE 127

(S)-2-Amino-4-{4-[2-fluoro-4-(4-trifluoromethyl-benzoylamino)-phenoxy]-6-methoxy-quinolin-7-yloxy}-butyric acid cyclopentyl ester

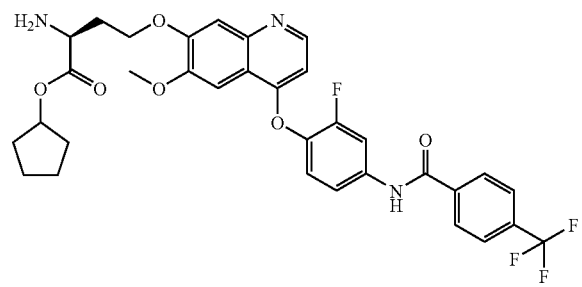

LC/MS purity: 97% (254 nm), m/z 642 [M+H]$^+$. $^1$H NMR (300 MHz, DMSO-d$_6$) δ: 10.87 (1H, s), 8.70 (1H, m), 8.48 (2H, brs), 8.19 (2H, d, J=8.1 Hz), 8.10 (1H, d, J=12.3 Hz), 7.97 (2H, d, J=8.4 Hz), 7.75 (2H, m), 7.58 (2H, m), 6.80 (1H, br s), 5.22 (1H, t, J=5.4 Hz), 4.37 (2H, t, J=4.6 Hz), 4.20 (1H, m), 4.03 (3H, s), 2.27 (2H, m), 1.76-1.93 (2H, m), 1.49-1.72 (6H, m).

EXAMPLE 128

(S)-2-Amino-4-[4-(4-benzoylamino-2-fluoro-phenoxy)-6-methoxy-quinolin-7-yloxy]-butyric acid cyclopentyl ester

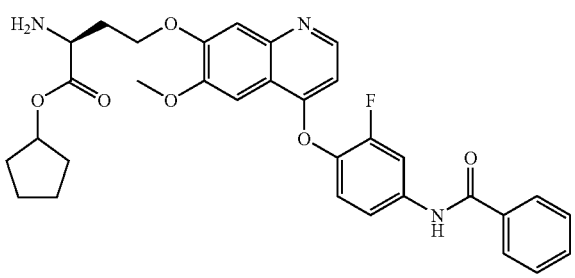

LC/MS purity: 96% (254 nm), m/z 574 [M+H]⁺. ¹H NMR (300 MHz, CD₃OD), δ: 8.76 (1H, d, J=6.8 Hz), 8.09 (1H, dd, J=2.4, 12.9 Hz), 8.01-7.95 (2H, m), 7.91 (1H, s), 7.74-7.68 (2H, m), 7.66-7.59 (1H, m), 7.59-7.49 (3H, m), 7.04 (1H, dd, J=1.0, 6.7 Hz), 5.39-5.32 (1H, m), 4.54 (2H, t, J=5.6 Hz), 4.36 (1H, t, J=6.5 Hz), 4.14 (3H, s), 2.65-2.54 (2H, m), 2.01-1.87 (2H, m), 1.84-1.58 (6H, m).

EXAMPLE 129

(S)-2-Amino-4-[4-(4-benzoylamino-2-fluoro-phenoxy)-6-methoxy-quinolin-7-yloxy]-butyric acid

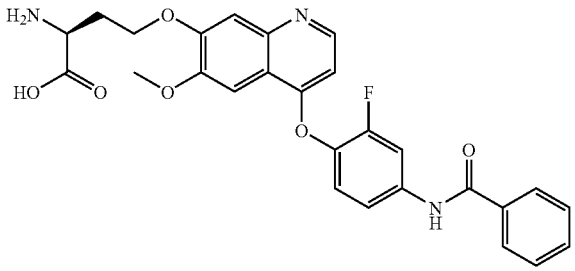

LC/MS purity: 98% (254 nm), m/z 506 [M+H]⁺. ¹H NMR (300 MHz, CD₃OD) δ: 8.76 (1H, d, J=6.6 Hz), 8.09 (1H, dd, J=2.3, 12.8 Hz), 7.99 (2H, d, J=7.9 Hz), 7.91 (1H, s), 7.72 (1H, dd, J=1.3 8.9 Hz), 7.68-7.61 (2H, m), 7.61-7.55 (2H, m), 7.56-7.49 (1H, m), 7.04 (1H, d, J=6.6 Hz), 4.57 (2H, 5.2 Hz), 4.32 (1H, t, J=6.2 Hz), 4.15 (3H, s), 2.74-2.62 (1H, m), 2.62-2.49 (1H, m).

The following example was prepared using the corresponding 1,3-difluoro-4-nitro-benzene at Stage 1 in Scheme 30 above.

EXAMPLE 130

(S)-2-Amino-4-[4-(4-benzoylamino-3-fluoro-phenoxy)-6-methoxy-quinolin-7-yloxy]-butyric acid cyclopentyl ester

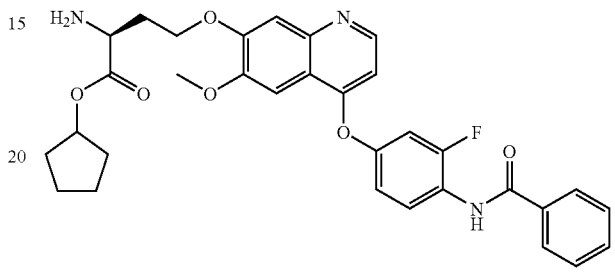

LC/MS purity: 98% (254 nm), m/z 574 [M+H]⁺. ¹H NMR (300 MHz, CD₃OD) δ: 8.77 (1H, s), 8.05-7.96 (3H, m), 7.89 (1H, s), 7.71-7.61 (2H, m), 7.61-7.52 (2H, m), 7.46-7.38 (1H, m), 7.34-7.27 (1H, m), 7.09 (1H, d, J=6.6 Hz), 5.40-5.32 (1H, m), 4.53 (2H, t, J=5.6 Hz), 4.35 (1H, t, J=6.5 Hz), 4.14 (3H, s), 2.65-2.52 (2H, m), 1.94 (2H, s), 1.84-1.61 (6H, m).

EXAMPLE 131

(S)-2-Amino-4-[4-(4-benzoylamino-3-fluoro-phenoxy)-6-methoxy-quinolin-7-yloxy]-butyric acid LC/MS purity: 96% (254 nm), m/z 506 [M+H]⁺. ¹H NMR (300 MHz, CD₃OD) δ: 8.60 (1H, s), 8.04-7.98 (2H, m), 7.92 (1H, t, J=8.6 Hz), 7.73 (1H, s), 7.68-7.61 (1H, m), 7.60-7.52 (2H, m), 7.49-7.43 (1H, m), 7.29 (1H, dd, J=2.4, 10.7 Hz), 7.23-7.17 (1H, m), 6.83 (1H, d, J=4.5 Hz), 4.49 (2H, s), 4.10 (3H, s), 4.03-3.94 (1H, m), 2.67-2.54 (1H, m), 2.47 (1H, s).

The following examples were prepared using 1-fluoro-2-methoxy-4-nitro-benzene at Stage 1 of Scheme 30 above.

EXAMPLE 132

(S)-2-Amino-4-[4-(4-benzoylamino-2-methoxy-phenoxy)-6-methoxy-quinolin-7-yloxy]-butyric acid cyclopentyl ester

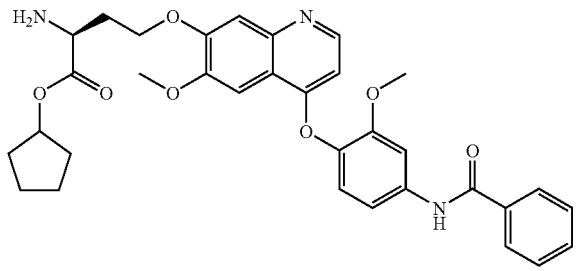

LC/MS purity: 93% (254 nm), m/z 586 [M+H]+. 1H NMR (300 MHz, CD3OD) δ: 8.69 (1H, d, J=6.8 Hz), 8.02-7.96 (2H, m), 7.90 (1H, s), 7.86 (1H, d, J=2.3 Hz), 7.67-7.63 (1H, m), 7.61 (1H, t, J=1.4 Hz), 7.60-7.55 (2H, m), 7.48 (1H, d, J=2.4 Hz), 7.40-7.35 (1H, m), 6.93-6.88 (1H, m), 5.40-5.32 (1H, m), 4.53 (2H, t, J=5.6 Hz), 4.35 (1H, t, J=6.5 Hz), 4.14 (3H, s), 3.83 (3H, s), 2.65-2.53 (2H, m), 2.01-1.86 (2H, m), 1.85-1.58 (6H, m).

EXAMPLE 133

(S)-2-Amino-4-[4-(4-benzoylamino-2-methoxy-phenoxy)-6-methoxy-quinolin-7-yloxy]-butyric acid

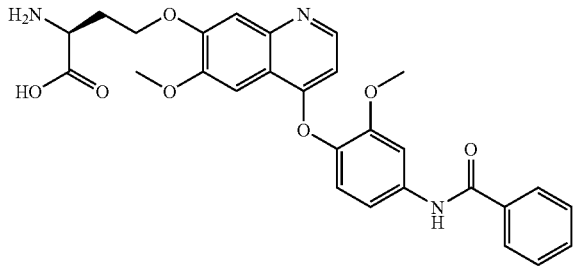

LC/MS purity: 94% (254 nm), m/z 518 [M+H]+. 1H NMR (300 MHz, CD3OD), δ: 8.70-8.66 (1H, m), 8.02-7.97 (2H, m), 7.92-7.89 (1H, m), 7.87 (1H, d, J=2.3 Hz), 7.68-7.53 (4H, m), 7.52-7.46 (1H, m), 7.42-7.35 (1H, m), 6.94-6.88 (1H, m), 4.56 (2H, t, J=5.4 Hz), 4.33 (1H, dd, J=8.5, 7.2 Hz), 4.15 (3H, s), 3.83 (3H, s), 2.74-2.62 (1H, m), 2.62-2.50 (1H, m).

The following example was prepared using 2-fluoro-5-nitro-pyridine at Stage 1 of Scheme 30 above.

EXAMPLE 134

(S)-2-Amino-4-[4-(4-benzoylamino-2-methoxy-phenoxy)-6-methoxy-quinolin-7-yloxy]-butyric acid cyclopentyl ester

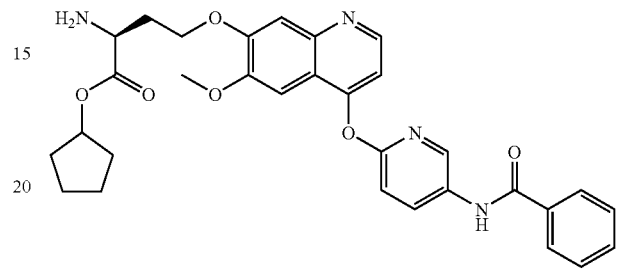

LC/MS purity: 95% (254 nm), m/z 557 [M+H]+. 1H NMR (300 MHz, DMSO-d6) δ: 10.82 (1H, br s), 8.90-8.85 (2H, m), 8.68 (3H, br s), 8.54 (1H, d, J=9.0 Hz), 8.06-8.01 (2H, m), 7.76 (2H, s), 7.68-7.54 (4H, m), 7.27 (1H, d, J=6.6 Hz), 5.25-5.20 (1H, m), 4.46-4.40 (2H, m), 4.25-4.20 (1H, m), 4.04 (3H, s), 2.48-2.44 (2H, m), 1.85-1.55 (8H, m).

Example 135 was prepared by the route shown in Scheme 31.

EXAMPLE 135

(S)-2-Amino-4-{(S)-2-[4-(4-benzoylamino-phenoxy)-6-methoxy-quinolin-7-yloxymethyl]-pyrrolidin-1-yl}-butyric acid cyclopentyl ester

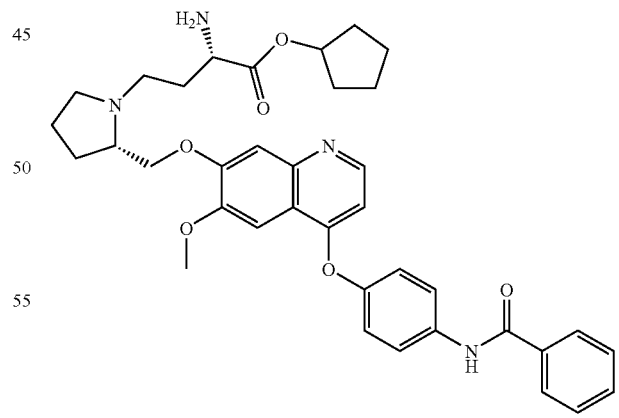

LC/MS purity: 95% (254 nm), m/z 639 [M+H]+. 1H NMR (300 MHz, CD3OD) δ: 8.73 (1H, d, J=6.6 Hz), 8.03-7.90 (5H, m), 7.66-7.50 (4H, m), 7.40 (2H, d, J=8.9 Hz), 7.00 (1H, d, J=6.8 Hz), 5.42-5.31 (1H, m), 4.76 (2H, d, J=5.3 Hz), 4.33-4.19 (2H, m), 4.15 (3H, s), 4.06-3.81 (2H, m), 3.63-3.46 (2H, m), 2.60-2.43 (3H, m), 2.36-1.54 (12H, m).

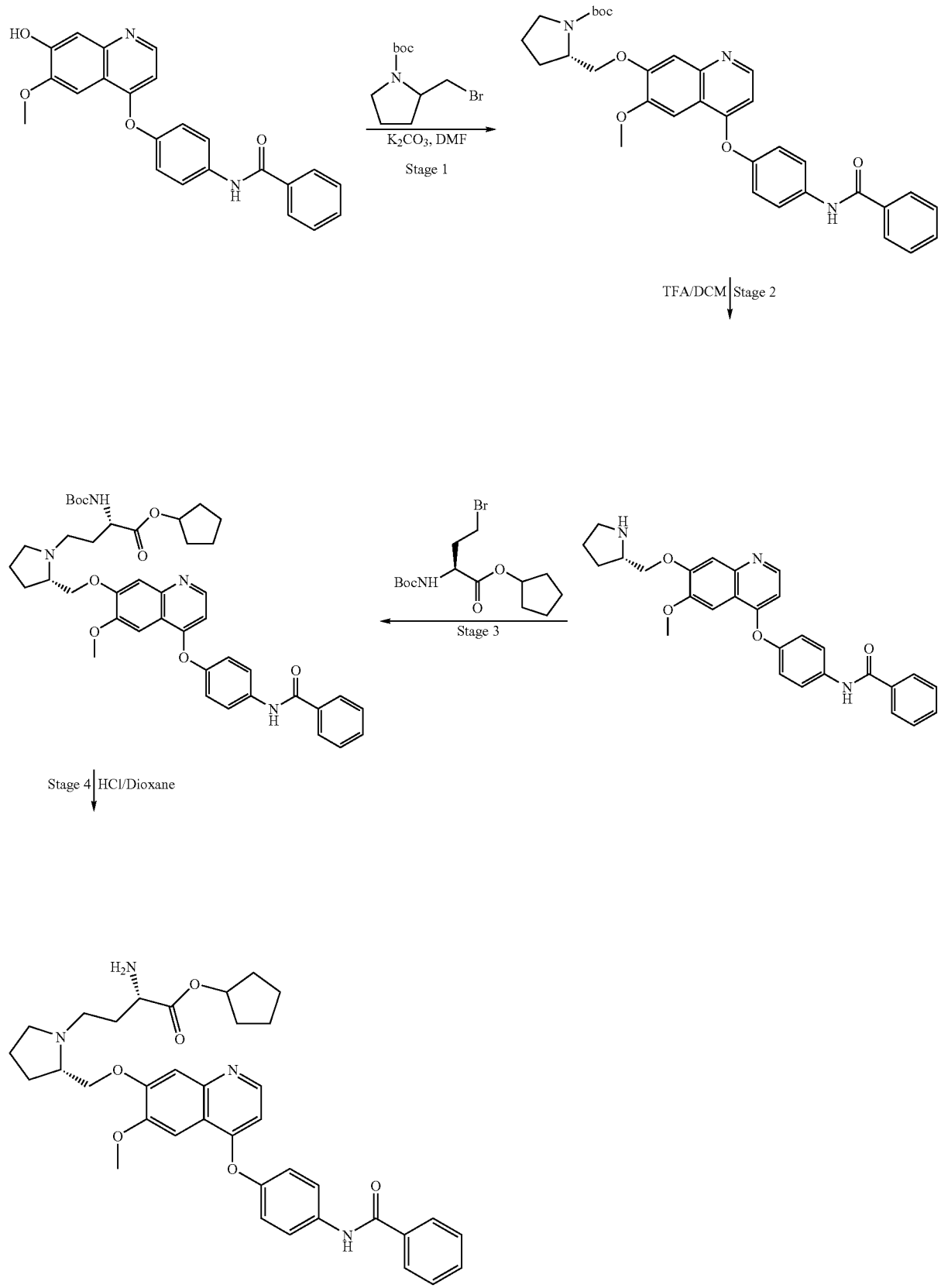

Stage 1-2-[4-(4-Benzoylamino-phenoxy)-6-methoxy-quinolin-7-yloxymethyl]-pyrrolidine-1-carboxylic acid tert-butyl ester

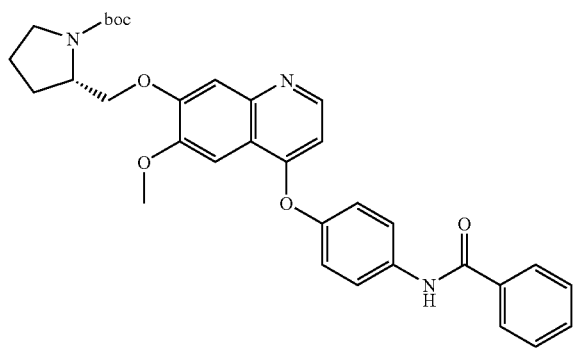

N-[4-(7-Hydroxy-6-methoxy-quinolin-4-yloxy)-phenyl]-benzamide (0.15 g, 0.39 mmol), (S)-2-bromomethyl-pyrrolidine-1-carboxylic acid tert-butyl ester* (0.14 g, 0.43 mmol, 1.1 eq) and $K_2CO_3$ (0.11 g, 0.783 mmol, 2 eq) were dissolved in anhydrous DMF (5 ml) under an atmosphere of nitrogen. The reaction was stirred at 35° C. overnight before the DMF was removed under reduced pressure. The residue was dissolved in DCM and washed with water followed by brine. The organic layer was dried over magnesium sulphate and evaporated under reduced pressure. The product was purified using column chromatography eluting with methanol/DCM to give the title compound, (0.74 g, 33% yield).

LC/MS: m/z 570 [M+H]$^+$.

*The synthesis of (S)-2-bromomethyl-pyrrolidine-1-carboxylic acid tert-butyl ester is outlined in Scheme 32.

Scheme 32

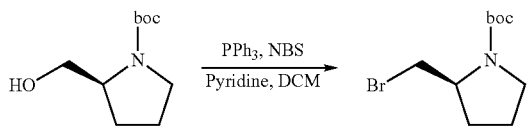

*(S)-2-Bromomethyl-pyrrolidine-1-carboxylic acid tert-butyl ester

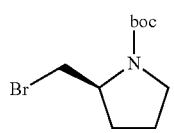

To a solution of N-bromosuccinimide (1.33 g, 7.45 mmol, 3 eq) in DCM (15 ml) was added drop wise a solution of triphenylphosphine (1.82 g, 6.94 mmol, 2.8 eq) in DCM (15 ml). The solution was stirred at room temperature for 15 minutes. Pyridine (0.015 ml, 1.2 eq) was added followed by dropwise addition of (R)-2-hydroxymethyl-pyrrolidine-1-carboxylic acid tert-butyl ester (0.50 g, 2.48 mmol, 1 eq) in DCM (15 ml). The solution was stirred overnight at room temperature. The solvent was removed under reduced pressure. The residue was triturated in diethyl ether (2×50 ml) and 10% ethyl acetate in heptane. The solvents from trituration were combined and concentrated under reduced pressure to give a pale pink solid. The product was purified using column chromatography eluting with ethyl acetate/heptane to give the title compound (0.20 g, 30% yield).

$^1$H NMR (300 MHz, CDCl$_3$) δ: 4.10-4.00 (1H, m), 3.70-3.55 (1H, m), 3.50-3.35 (3H, m), 2.10-1.75 (4H, m), 1.50 (9H, s).

Stage 2-N-{4-[6-Methoxy-7-(pyrrolidin-2-ylmethoxy)-quinolin-4-yloxy]-phenyl}-benzamide

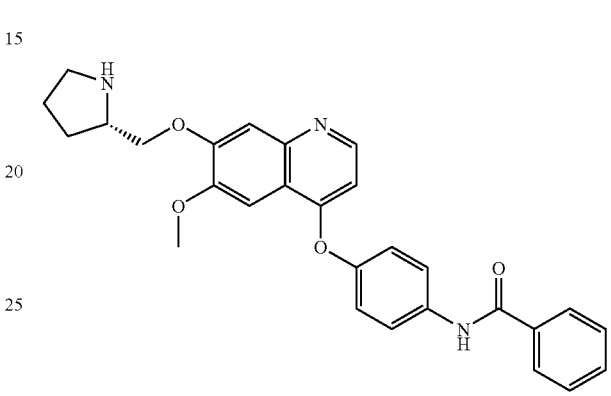

To 2-[4-(4-benzoylamino-phenoxy)-6-methoxy-quinolin-7-yloxymethyl]-pyrrolidine-1-carboxylic acid tert-butyl ester (0.07 g, 0.12 mmol) in DCM (2.5 ml) was added TFA (2.5 ml). The reaction mixture was stirred overnight before evaporation under reduced pressure to yield 0.1 g of the title compound.

LC/MS: m/z 470 [M+H]$^+$.

Stage 3-(S)-4-{2-[4-(4-Benzoylamino-phenoxy)-6-methoxy-quinolin-7 yloxymethyl]-pyrrolidin-1-yl}-2-tert-butoxycarbonylamino-butyric acid cyclopentyl ester

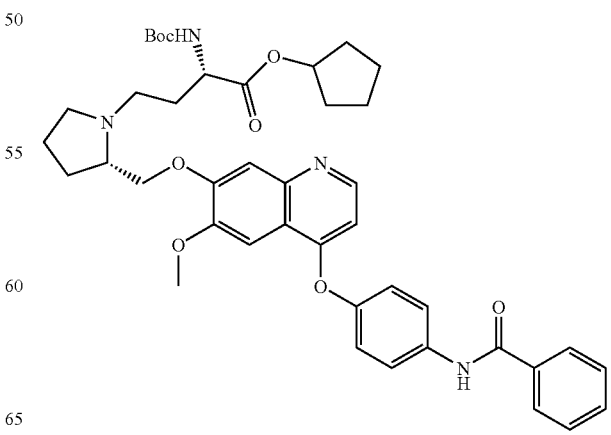

The product from stage 2 (0.11 g, 0.5 mmol), (S)-4-bromo-2-tert butoxycarbonylamino-butyric acid cyclopentyl ester (0.45 g, 0.13 mmol, 1.2 eq) and di-isopropyl ethyl amine (0.06 ml, 0.32 mmol, 3 eq) were dissolved in acetonitrile (10 ml) under an atmosphere of nitrogen. The reaction was stirred at 50° C. for 48 hours before the solvent was removed under reduced pressure. The residue was dissolved in DCM and washed with water followed by brine. The organic layer was dried over magnesium sulphate and evaporated under reduced pressure. The product was purified using column chromatography eluting with methanol/DCM to give the title compound, (0.20 g, 25% yield).
LC/MS: m/z 739 [M+H]+.

mixture was stirred for 5 hours before evaporation under reduced pressure to yield the title compound as a pale yellow solid.

EXAMPLE 136

(S)-2-Amino-4-{4-[4-(4-benzoylamino-phenoxy)-6-methoxy-quinolin-7-yloxymethyl]-piperidin-1-yl}-butyric acid cyclopentyl ester LC/MS purity: 100% (254 nm), m/z 653 [M+H]+. 1H NMR (300 MHz, CD3OD) δ: 10.35 (1H, s), 8.68 (1H, d, J=6.0 Hz),

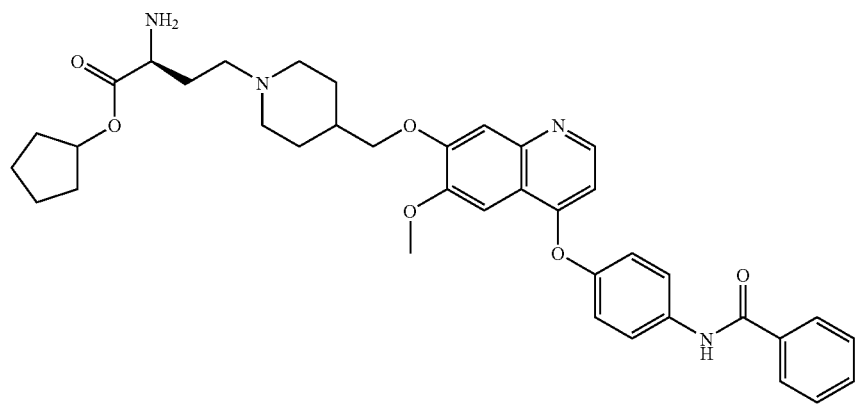

Stage 4-(S)-2-Amino-4-{2-[4-(4-benzoylamino-phenoxy)-6-methoxy-quinolin-7-yloxymethyl]-pyrrolidin-1-yl}-butyric acid cyclopentyl ester 8.02-7.93 (4H, m), 7.87 (1H, s), 7.66-7.47 (4H, m), 7.39 (2H, d, J=8.9 Hz), 6.96 (1H, d, J=6.4 Hz), 5.36 (1H, t, J=5.1 Hz), 4.24 (2H, br s), 4.10 (3H, s), 3.82-3.53 (4H, m), 3.48-3.35 (2H, m), 2.60-2.18 (5H, m), 2.06-1.60 (11H, m).

4-Bromomethyl-piperidine-1-carboxylic acid tert-butyl ester was prepared following the synthetic route described in Scheme 32.

4-Bromomethyl-piperidine-1-carboxylic acid tert-butyl ester

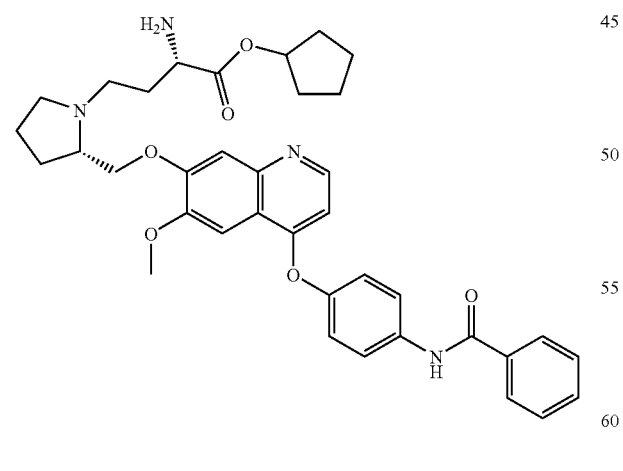

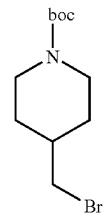

To (S)-4-{2-[4-(4-benzoylamino-phenoxy)-6-methoxy-quinolin-7yloxymethyl]-pyrrolidin-1-yl}-2-tert-butoxycarbonylamino-butyric acid cyclopentyl ester (0.02 g, 0.03 mmol) was added 4N HCl in dioxane (3 ml). The reaction 1H NMR (300 MHz, CDCl3) δ: 4.25-4.15 (2H, m), 3.35-3.25 (2H, m), 2.80-2.60 (2H, m), 1.90-1.80 (3H, m), 1.50 (9H, s), 1.30-1.10 (2H, m).

EXAMPLE 137

(S)-2-Amino-4-{3-[4-(4-benzoylamino-phenoxy)-6-methoxy-quinolin-7-yloxy]-pyrrolidin-1-yl}-butyric acid cyclopentyl ester

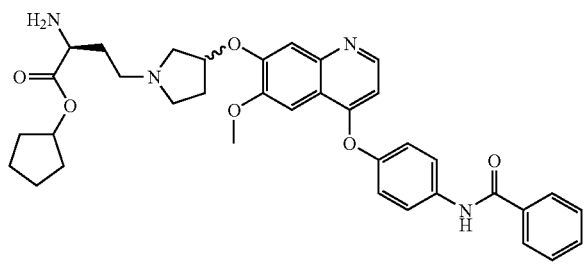

LC/MS purity: 98% (254 nm), m/z 625 [M+H]$^+$. $^1$H NMR (300 MHz, CD$_3$OD) δ: 12.00 (0.5H, br s), 11.3 (0.5H, br s), 10.57 (1H, s), 8.9-8.6 (4H, m), 8.1-7.95 (4H, m), 7.92-7.84 (1H, m), 7.82 (1H, s), 7.66-7.54 (3H, m), 7.42 (2H, d, J=8.7 Hz), 6.89 (1H, d, J=6.0 Hz), 5.45-5.35 (1H, m), 5.30-5.15 (1H, m), 4.30-4.15 (2H, m), 4.06 (3H, s), 3.90-3.60 (6H, m), 2.40-2.15 (4H, m), 1.90-1.50 (9H, m).

EXAMPLE 138

(S)-2-Amino-4-[4-(4-benzylamino-phenoxy)-6-methoxy-quinolin-7-yloxy]-butyric acid cyclopentyl ester

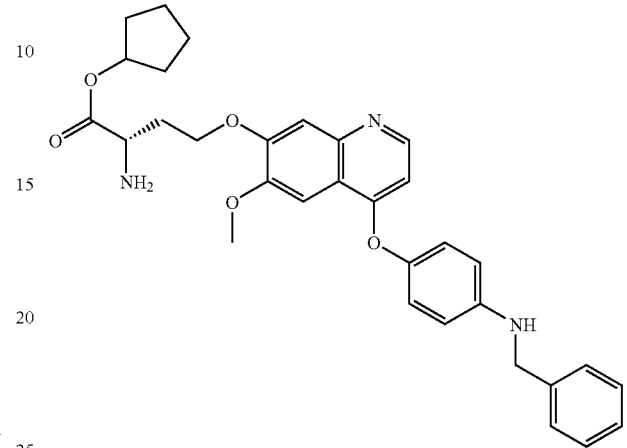

LC/MS purity: 98% (254 nm), m/z 542.3 [M+H]$^+$. $^1$H NMR (300 MHz, DMSO-d$_6$) δ: 8.78 (1H, d, J=6.7 Hz), 8.59-8.42 (2H, m), 7.72 (1H, s), 7.59 (1H, s), 7.44-7.31 (4H, m), 7.30-7.21 (1H, m), 7.08 (2H, d, J=9.0 Hz), 6.81 (1H, d, J=6.6 Hz), 6.74 (2H, d, J=8.9 Hz), 5.25-5.16 (1H, m), 4.36 (2H, dd), 4.31 (2H, s), 4.24-4.14 (1H, m), 4.02 (3H, s), 2.45-2.34 (2H, m), 1.93-1.44 (9H, m).

The synthesis of Example 138 is shown below in Scheme 33. The key intermediate is the N-[4-(7-hydroxy-6-methoxy-quinolin-4-yloxy)-phenyl]-benzamide, the synthesis of which is already described in Scheme 2.

Scheme 33

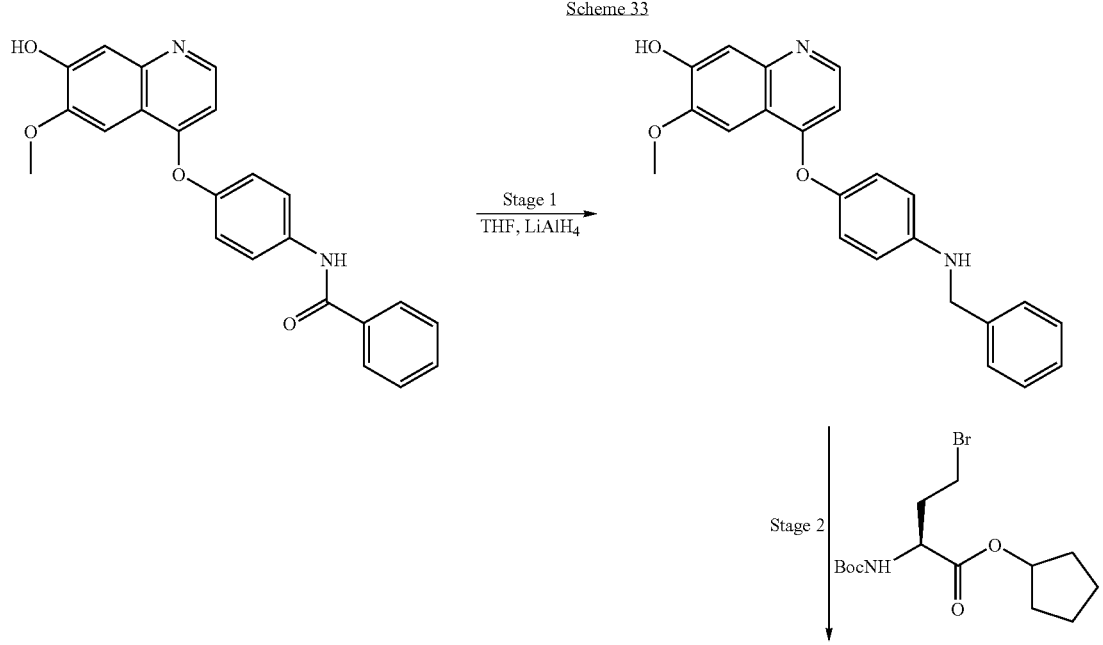

-continued

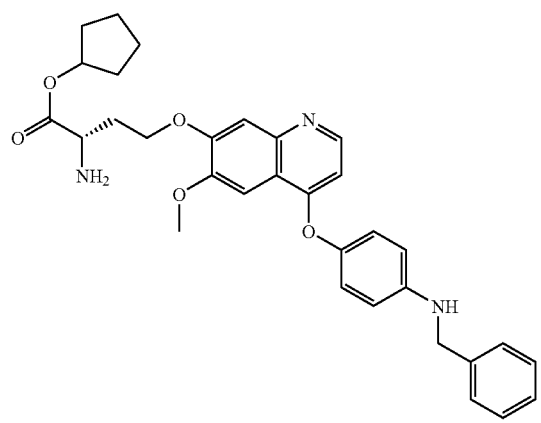

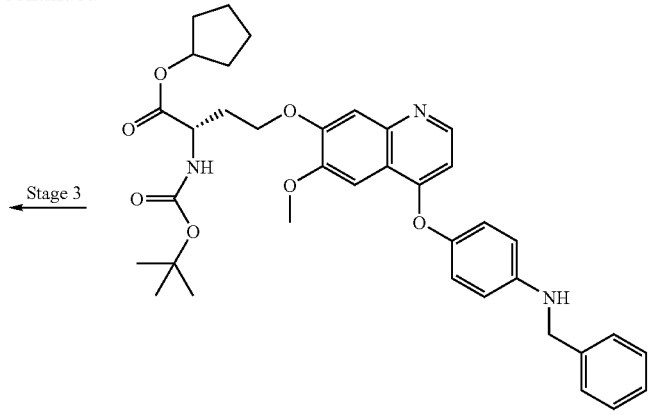

Stage 3

Stage 1-4-(4-Benzylamino-phenoxy)-6-methoxy-quinolin-7-ol

A solution of N-[4-(7-hydroxy-6-methoxy-quinolin-4-yloxy)-phenyl]-benzamide (60 mg, 0, 155 mmol) in anhydrous THF (2 ml) was cooled to 0° C. under a nitrogen atmosphere. 2M LiAlH$_4$ in THF was then added (0.46 ml, 0.23 mmol) and the reaction allowed to warm to room temperature before heating to 65° C. for complete reaction. The crude reaction mixture was cooled and quenched with 1M HCl solution and the product extracted with EtOAc. The combined EtOAc layers were washed further with brine and dried over magnesium sulphate. The product was isolated after evaporation of the EtOAc to give a yellow solid (60 mg) which was taken forward without further purification.

LC/MS purity: 95% (254 nm), m/z 373 [M+H]$^+$.

Stage 2-(S)-4-[4-(4-Benzylamino-phenoxy)-6-methoxy-quinolin-7-yloxy]-2-tert-butoxycarbonylamino-butyric acid cyclopentyl ester A mixture of 4-(4-benzylamino-phenoxy)-6-methoxy-quinolin-7-ol (60 mg, 0.16 mmol), (S)-4-bromo-2-tert-butoxycarbonylamino-butyric acid cyclopentyl ester* (62 mg, 1.18 mmol, 1.1 eq) and potassium carbonate (44 mg, 0.32 mmol, 2 eq) in anhydrous DMF (10 ml) was stirred at 35° C. under an atmosphere of nitrogen for 20 hours. The DMF was removed under reduced pressure and the crude residue dissolved in DCM and washed with water (2×50 ml) and brine (50 ml), dried (MgSO$_4$), filtered and concentrated under reduced pressure to leave a yellow solid (100 mg). Purification by column chromatography (5% methanol/DCM) afforded the title compound as a clear wax (70 mg, 68% yield).

LC/MS purity: 96% (254 nm), m/z 642 [M+H]$^+$. $^1$H NMR (300 MHz, DMSO-d$_6$) δ: 8.42 (1H, d, J=5.3 Hz), 7.50 (1H, s), 7.29-7.43 (6H, m), 7.21-7.28 (1H, m), 6.93-7.02 (2H, m), 6.68 (2H, d, J=9.0 Hz), 6.32-6.40 (2H, m), 5.10 (1H, t, J=5.5 Hz), 4.29 (2H, d, J=5.8 Hz), 4.09-4.24 (3H, m), 3.93 (3H, m), 2.01-2.32 (2H, m), 1.70-1.88 (2H, m), 1.47-1.66 (7H, m), 1.32-1.41 (10H, m).

Stage 3-(S)-2-Amino-4-[4-(4-benzylamino-phenoxy)-6-methoxy-quinolin-7-yloxy]-butyric acid cyclopentyl ester (S)-4-[4-(4-Benzylamino-phenoxy)-6-methoxy-quinolin-7-yloxy]-2-tert-butoxycarbonylamino-butyric acid cyclopentyl ester (62 mg, 0.097 mmol) was dissolved in TFA/DCM (1:1, 5 ml) and left to stir at room temperature for 2 hours for complete reaction. The reaction mixture was evaporated to dryness and the product was isolated as the TFA salt (40 mg).

EXAMPLE 139
(S)-2-Amino-4-[4-(4-benzylamino-phenoxy)-6-methoxy-quinolin-7-yloxy]-butyric acid

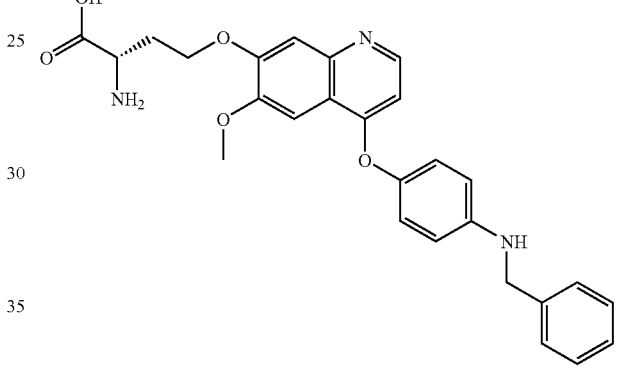

LC/MS purity: 98% (254 nm), m/z 542.3 [M+H]$^+$. $^1$H NMR (300 MHz, CD$_3$OD), δ: 8.62 (1H, d, J=6.6 Hz), 7.83 (1H, s), 7.56 (1H, s), 7.43-7.18 (6H, m), 7.05 (2H, d, J=8.9 Hz), 6.88 (1H, d, J=6.8 Hz), 6.82-6.75 (2H, m), 4.52 (2H, t, J=5.3 Hz), 4.37 (2H, m), 4.28 (1H, t, J=6.2 Hz), 4.09 (3H, s), 2.72-2.44 (2H, m).

The synthesis of Example 140 is shown below in Scheme 34.

EXAMPLE 140
(S)-2-Amino-4-{6-methoxy-4-[4-(2-oxo-2-phenyl-ethyl)-phenoxy]-quinolin-7-yloxy}-butyric acid cyclopentyl ester

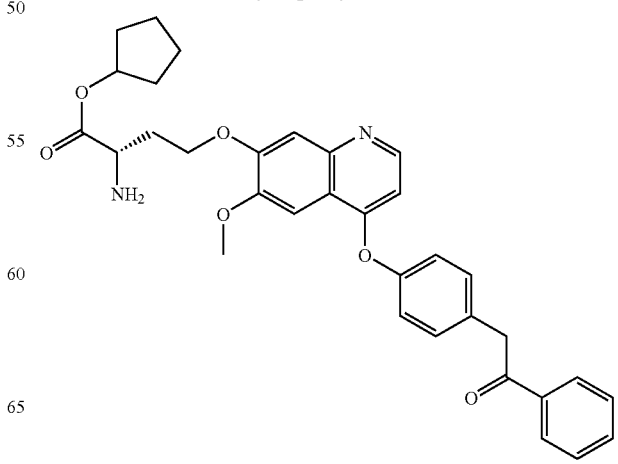

189
LC/MS purity: 98% (254 nm), m/z 556 [M+H]+. ¹H NMR (300 MHz, CD₃OD) δ: 8.68 (1H, d, J=6.6 Hz), 8.16-8.08 (2H, m), 7.88 (1H, s), 7.71-7.60 (2H, m), 7.59-7.49 (4H, m), 7.38-
190
7.29 (2H, m), 6.97 (1H, d, J=6.6 Hz), 5.39-5.30 (1H, m), 4.56-4.47 (4H, m), 4.33 (1H, t, J=6.4 Hz), 4.11 (3H, s), 2.67-2.49 (2H, m), 2.02-1.54 (9H, m).
Scheme 34
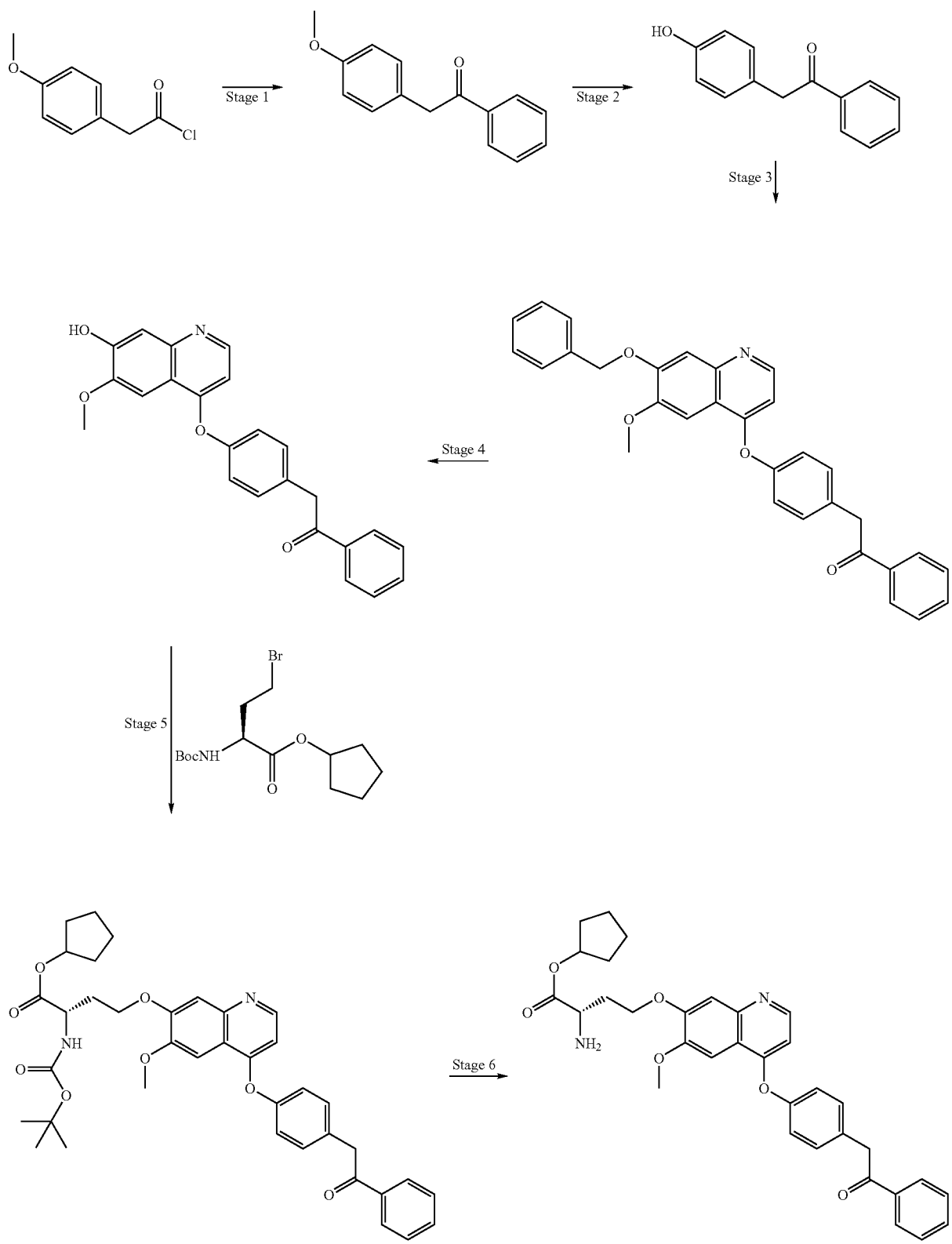

Stage 1-2-(4-Methoxy-phenyl)-1-phenyl-ethanone

To a solution of 4-methoxyphenyl acetyl chloride (3.0 g, 16.3 mmol) in THF (10 ml) at −78° C. was added a 1M solution of phenyl magnesium chloride in THF (16.25 ml, 16.25 mmol). The reaction was allowed to warm to room temperature and stirred for 1 hour. To the crude mixture was added water (20 ml) and the aqueous solution was extracted with diethyl ether (2×50 ml). The combined organic extracts were washed with 1M NaOH solution before drying over magnesium sulphate. The crude residue was purified by column chromatography (2:8 EtOAc:Heptane) and the product was isolated as a white solid (1.3 g, 50% yield).

LC/MS: m/z 227 [M+H]$^+$.

Stage 2-2-(4-Hydroxy-phenyl)-1-phenyl-ethanone 2-(4-Methoxy-phenyl)-1-phenyl-ethanone (544 mg, 2.4 mmol) was dissolved in 48% HBr solution (6 ml) and the reaction heated to 120° C. for 1 hour. The reaction was then cooled to room temperature and a solution of potassium hydroxide added to adjust the pH to 7. The aqueous layer was extracted with EtOAc (2×100 ml) and the combined organic layers washed further with brine before drying over magnesium sulphate. The solvent was removed under reduced pressure to give the product as a yellow oil (103 mg, 37% yield).

LC/MS: m/z 213 [M+H]$^+$.

Stage 3-2-[4-(7-Benzyloxy-6-methoxy-quinolin-4-yloxy)-phenyl]-1-phenyl-ethanone 7-Benzyloxy-4-chloro-6-methoxy-quinoline (200 mg, 0.67 mmol) and 2-(4-hydroxy-phenyl)-1-phenyl-ethanone (425 mg, 2.0 mmol) were dissolved in DMF (1 ml) and heated to 145° C. for 5 hours. The DMF was removed under reduced pressure and the crude residue dissolved in DCM, washing with 5% NaOH solution and then brine. The DCM layer was dried over magnesium sulphate and concentrated under reduced pressure. The product was purified by column chromatography (DCM-3% MeOH/DCM afford the title compound as a yellow wax (68 mg, 21% yield).

LC/MS: m/z 476 [M+H]$^+$.

Stage 4-2-[4-(7-Hydroxy-6-methoxy-quinolin-4-yloxy)-phenyl]-1-phenyl-ethanone 2-[4-(7-Benzyloxy-6-methoxy-quinolin-4-yloxy)-phenyl]-1-phenyl-ethanone (64 mg, 0.13 mmol) was dissolved in 10% cyclohexene/ethanol (25 ml) and Pd/C catalyst (40 mg) added under an inert atmosphere. The reaction mixture was heated to reflux for 2 hours for complete reaction. The solution was cooled to room temperature and the catalyst filtered off. The filtrate was evaporated to dryness to give the title product as a yellow solid (36 mg, 68% yield).

LC/MS: m/z 386 [M+H]$^+$.

Stage 5-(S)-2-tert-Butoxycarbonylamino-4-{6-methoxy-4-[4-(2-oxo-2-phenyl-ethyl)-phenoxy]-quinolin-7-yloxy}-butyric acid cyclopentyl ester A mixture of 2-[4-(7-hydroxy-6-methoxy-quinolin-4-yloxy)-phenyl]-1-phenyl-ethanone (35 mg, 0.09 mmol), (S)-4-bromo-2-tert-butoxycarbonylamino-butyric acid cyclopentyl ester* (35 mg, 0.099 mmol, 1.1 eq) and potassium carbonate (25 mg, 0.182 mmol, 2 eq) in anhydrous DMF (10 ml) was stirred at 35° C. under an atmosphere of nitrogen for 20 hours. The DMF was removed under reduced pressure and the crude residue dissolved in DCM and washed with water (2×50 ml) and brine (50 ml), dried (MgSO$_4$), filtered and concentrated under reduced pressure to leave a yellow solid (61 mg). Purification by column chromatography (5% methanol/DCM) afforded the title compound as a clear wax (35 mg, 71% yield).

LC/MS: m/z 655 [M+H]$^+$.

Stage 6-(S)-2-Amino-4-{6-methoxy-4-[4-(2-oxo-2-phenyl-ethyl)-phenoxy]-quinolin-7-yloxy}-butyric acid cyclopentyl ester (S)-2-tert-Butoxycarbonylamino-4-{6-methoxy-4-[4-(2-oxo-2-phenyl-ethyl)-phenoxy]-quinolin-7-yloxy}-butyric acid cyclopentyl ester (35 mg, 0.053 mmol) was dissolved in TFA/DCM (1:1, 5 ml) and left to stir at room temperature for 2 hours for complete reaction. The reaction mixture was evaporated to dryness and the product was purified by preparative HPLC to give the title compound (11 mg).

Example 141 was prepared by using N-(4-hydroxy-benzyl)-benzamide at Stage 3 of Scheme 34 above. This can be conveniently prepared by reaction of 4-Hydroxybenzylamine with benzoyl chloride under traditional conditions already described therein.

EXAMPLE 141

(S)-2-Amino-4-{4-[4-(benzoylamino-methyl)-phenoxy]-6-methoxy-quinolin-7-yloxy}-butyric acid cyclopentyl ester

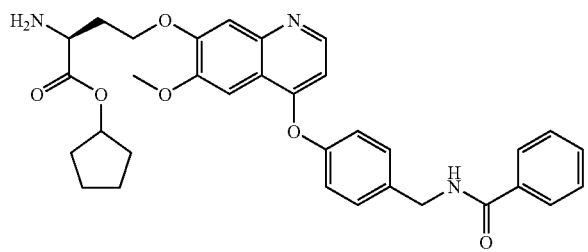

LC/MS purity: 97% (254 nm), m/z 570 [M+H]$^+$. $^1$H NMR (300 MHz, CD$_3$OD) δ: 8.67 (1H, d, J=6.7 Hz), 7.92-7.85 (3H,m), 7.66-7.45 (6H,m), 7.35 (2H, d, J=8.6 Hz), 6.92 (1H, d, J=6.7 Hz), 5.39-5.30 (1H, m), 4.67 (2H, s), 4.50 (2H, t, J=5.6 Hz), 4.33 (1H, t, J=6.5 Hz), 4.11 (3H, s), 2.67-2.46 (2H, m), 2.01 (9H, m).

EXAMPLE 142

(S)-2-Amino-4-{4-[4-(benzoylamino-methyl)-phenoxy]-6-methoxy-quinolin-7-yloxy}-butyric acid

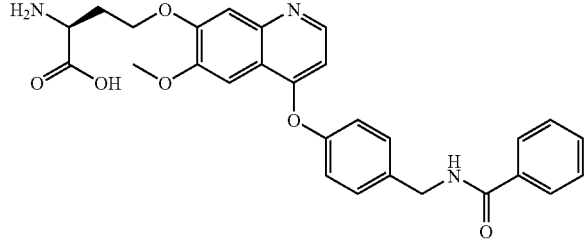

LC/MS purity: 98% (254 nm), m/z 502 [M+H]$^+$. $^1$H NMR (300 MHz, CD$_3$OD) δ: 8.66 (1H, d, J=6.7 Hz), 7.94-7.84 (3H, m), 7.66-7.44 (6H, m), 7.35 (2H, d, J=8.6 Hz), 6.90 (1H, d, J=6.8 Hz), 4.67 (2H, s), 4.53 (2H, t, J=5.5 Hz), 4.37-4.27 (1H, m), 4.11 (3H, s), 2.75-2.41 (2H, m).

EXAMPLE 143

(S)-2-Amino-4-[6-methoxy-4-(5-methyl-1H-pyrazol-3-ylamino)-2-phenylsulfanyl-quinazolin-7-yloxy]-butyric acid cyclopentyl ester

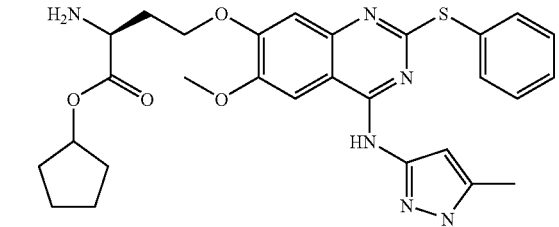

LC/MS: m/z 549 [M+H]$^+$. $^1$H NMR (300 MHz, CD$_3$OD) δ: 7.90 (1H, s), 7.69-7.63 (2H, m), 7.60 (1H, d, J=7.3 Hz), 7.55-7.47 (2H, m), 7.07 (1H, s), 5.32 (1H, s), 5.28-5.20 (1H, m), 4.37 (2H, t, J=5.3 Hz), 4.22 (1H, t, J=6.4 Hz), 3.95 (3H, s), 2.45 (2H, t, J=5.9 Hz), 2.07 (3H, s), 1.84 (2H, d, J=5.8 Hz), 1.71-1.51 (6H, m).

The synthesis of example 143 is shown below in Scheme 35.

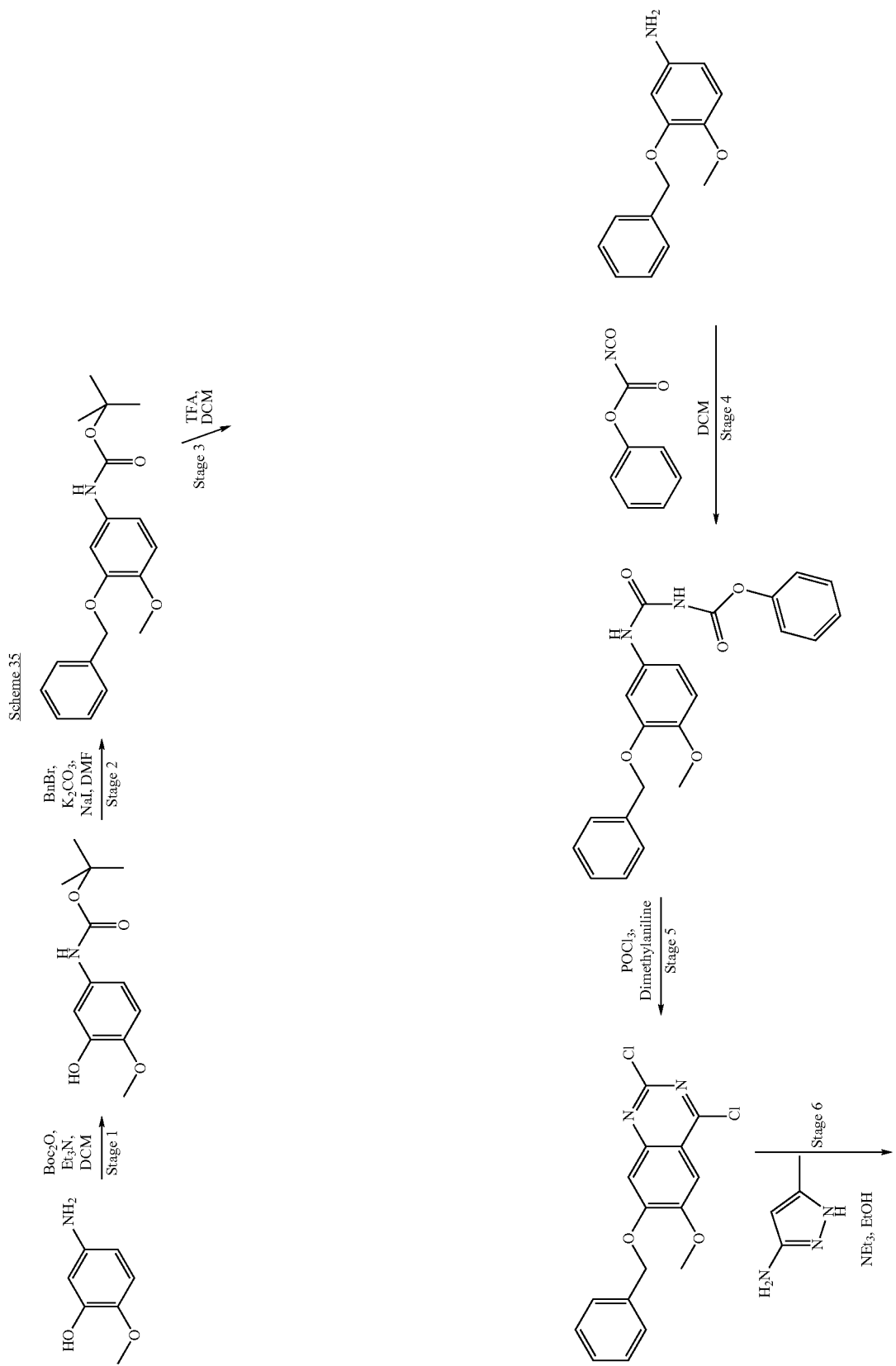

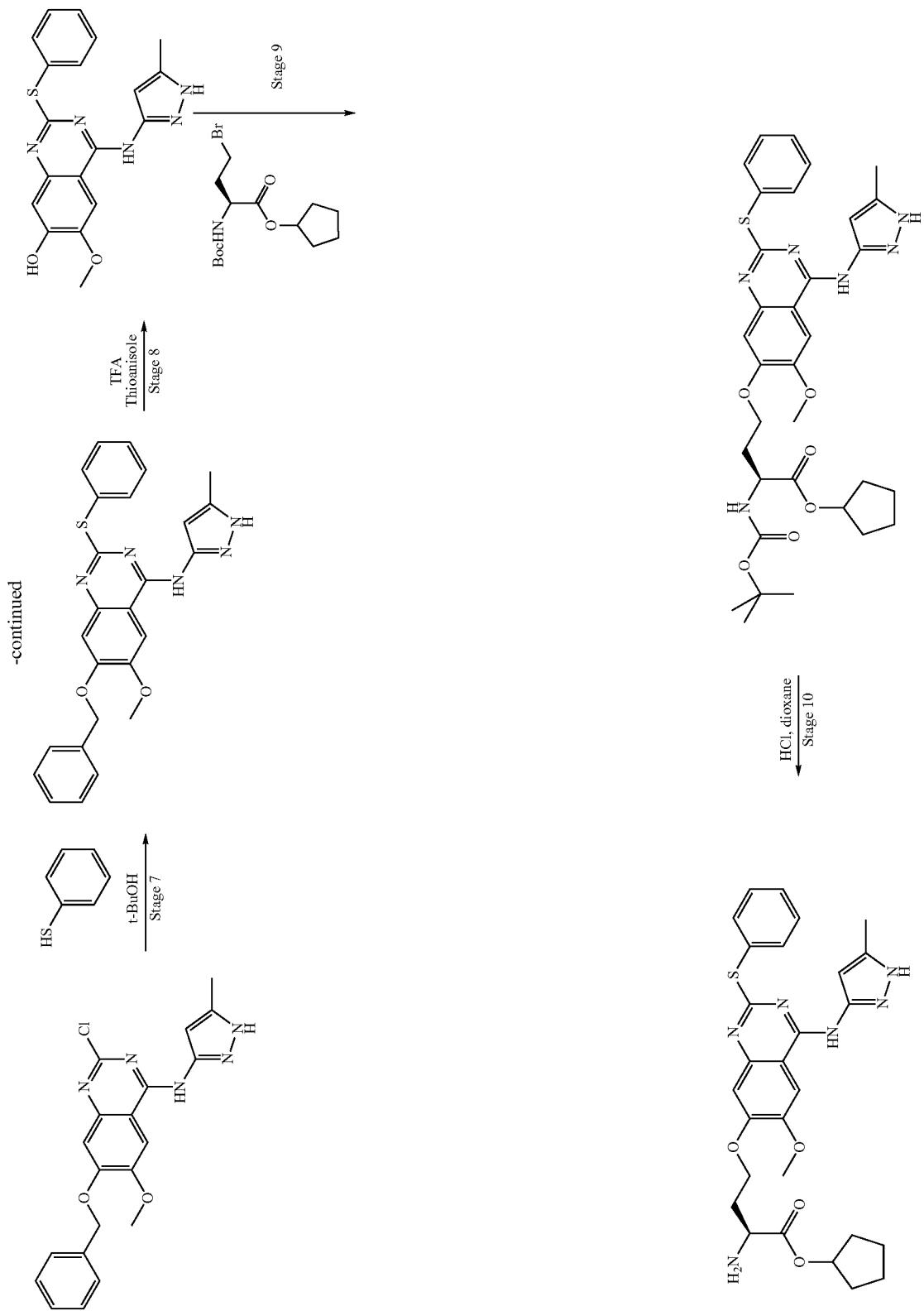

Stages 1 to 5 were performed as described in *Bioorg. Med. Chem. Lett.* 1998, 8, 2891-2896.

Stage 6-(7-Benzyloxy-2-chloro-6-methoxy-quinazolin-4-yl)-(5-methyl-1H-pyrazol-3-yl)-amine To a solution of 7-benzyloxy-2,4-dichloro-6-methoxyquinazoline (620 mg, 1.85 mmol) and 3-amino-5-methylpyrazole (180 mg, 1.85 mmol) in ethanol (10 ml) was added triethylamine (258 µL, 1.85 mmol) and the reaction was heated for 10 min. at 110° C. under microwave irradiation. The solid formed was collected by filtration, washed with cold ethanol and triturated with Et$_2$O and heptane to give the title compound as a white solid (300 mg, 41% yield)

LC/MS: m/z 396/398 [M+H]$^+$.

Stage 7-(7-Benzyloxy-6-methoxy-2-phenylsulfanyl-quinazolin-4-yl)-(5-methyl-1H-pyrazol-3-yl)-amine To a solution of (7-benzyloxy-2-chloro-6-methoxy-quinazolin-4-yl)-(5-methyl-1H-pyrazol-3-yl)-amine (300 mg, 0.76 mmol) in tert-butanol (10 ml) was added thiophenol (389 µL, 3.79 mmol) and the reaction was heated for 10 min. at 140° C. under microwave irradiation. The slightly yellow solid was collected by filtration. It was then suspended in EtOH/H$_2$O ⅓ (4 ml) and K$_2$CO$_3$ (100 mg) was added. The suspension was stirred at room temperature for 2 hours. The white solid was collected by filtration and dried under vacuum to afford the title compound (222 mg, 62% yield).

LC/MS: m/z 470 [M+H]$^+$.

Stage 8-6-Methoxy-4-(5-methyl-1H-pyrazol-3-ylamino)-2-phenylsulfanyl-quinazolin-7-ol The (7-benzyloxy-6-methoxy-2-phenylsulfanyl-quinazolin-4-yl)-(5-methyl-1H-pyrazol-3-yl)-amine (222 mg, 0.47 mmol) was treated with TFA (5 ml) and thioanisole (0.5 ml) for 3 hours at 80° C. The reaction mixture was concentrated under high vacuum to remove most of the thioanisole present. The compound was used without any further purification.

LC/MS: m/z 380 [M+H]$^+$.

Stage 9-(S)-2-tert-Butoxycarbonylamino-4-[6-methoxy-4-(5-methyl-1H-pyrazol-3-ylamino)-2-phenylsulfanyl-quinazolin-7-yloxy]-butyric acid cyclopentyl ester To a solution of 6-methoxy-4-(5-methyl-1H-pyrazol-3-ylamino)-2-phenylsulfanyl-quinazolin-7-ol (70 mg, 0.18 mmol) in DMF (2 ml) were added (S)-4-bromo-2-tert-butoxycarbonylamino-butyric acid cyclopentyl ester (65 mg, 0.18 mmol) and K$_2$CO$_3$ (31 mg, 0.22 mmol) and the reaction mixture was stirred for 3 days at 40° C. under nitrogen. The DMF was removed under reduced pressure, the crude was diluted into EtOAc, washed with sat. NaHCO$_3$ and brine, dried over MgSO$_4$, filtered and concentrated under reduced pressure to give a light brown solid. DCM (+1 drop of MeOH) was added and a white solid crashed out, which was collected by filtration to give the pure product (47 mg, 39% yield)

$^1$H NMR (300 MHz, CD$_3$OD) δ: 7.72-7.68 (2H, m), 7.62 (1H, s), 7.58-7.49 (3H, m), 7.36-7.24 (1H, m), 7.00 (1H, s), 5.24-5.17 (1H, m), 4.44-4.37 (1H, m), 4.32-4.24 (1H, m), 4.21-4.12 (1H, m), 4.01 (3H, s), 2.44-2.30 (2H, m), 2.14 (3H, s), 1.89-1.78 (2H, m), 1.75-1.56 (6H, m), 1.46 (9H, s).

LC/MS: m/z 649 [M+H]$^+$.

Stage 10-(S)-2-Amino-4-[6-methoxy-4-(5-methyl-1H-pyrazol-3-ylamino)-2-phenylsulfanyl-quinazolin-7-yloxy]-butyric acid cyclopentyl ester To (S)-2-tert-butoxycarbonylamino-4-[6-methoxy-4-(5-methyl-1H-pyrazol-3-ylamino)-2-phenylsulfanyl-quinazolin-7-yloxy]-butyric acid cyclopentyl ester (47 mg, 0.07 mmol) was added a 4M solution of HCl in 1,4-dioxane (8 ml) and the reaction mixture was stirred at room temperature under nitrogen atmosphere for 2 hours. The crude was concentrated under reduced pressure to give afford the title compound as a white solid (30 mg, 78% yield).

Measurement of Biological Activity

Aurora-A Enzyme Assay

The ability of compounds to inhibit Aurora-A activity was measured using a simple microplate assay for Aurora-A activity, also suitable for high-throughput screening. In brief, γ-$^{33}$P-ATP and Aurora-A were incubated in a myelin basic protein (MBP)-coated Flashplate® to generate a scintillation signal. The plates were formatted to contain the inhibitor, controls, positive control (staurosporin) and blanks. After incubation at 37° C. for 1 hour and a subsequent wash procedure, the plates were read on a TopCount-NXT™.

The 384-well basic Flashplate® and the γ-$^{33}$P-ATP were obtained from PerkinElmer Life Sciences, Boston, Mass.

IC50 values were determined by non-linear regression analysis, after fitting the data point results to the equation for sigmoidal dose response with variable slope (% activity against log concentration of compound), using Graphpad Prism software.

Full experimental procedure for this assay can be found within the following reference: Sun, C *Journal of Biomolecular Screening* 9(5), 2004, 391.

The Aurora-B enzyme assay follows the identical protocol as Aurora-A.

IC50 results were allocated to one of 3 ranges as follows:
Range A: IC50<2000 nM,
Range B: IC50 from 2000 nM to 5000 nM;
and Range C: IC50>5000 nM.
NT=Not tested Cell Inhibition Assay The corresponding cancer cell lines (U937, HCT 116 and HUT) growing in log phase were harvested and seeded at 1000 cells/well (200 ul final volume) into 96-well tissue culture plates. Following 24 h of cell growth cells were treated with compounds (final concentration of 20 uM). Plates were then re-incubated for a further 72 h before a sulphorhodamine B (SRB) cell viability assay was conducted according to Skehan 1990 J Natl Canc Inst 82, 1107-1112.

Data were expressed as a percentage inhibition of the control, measured in the absence of inhibitor, as follows: —

% inhibition=100−(($S^i/S^o$)×100)

where $S^i$ is the signal in the presence of inhibitor and $S^o$ is the signal in the presence of DMSO.

IC50 values were determined by non-linear regression analysis, after fitting the results of eight data points to the equation for sigmoidal dose response with variable slope (% activity against log concentration of compound), using Graphpad Prism software.

IC50 results were allocated to one of 3 ranges as follows:
Range A: IC50<1000 nM,
Range B: IC50 from 1000 nM to 5000 nM;
and Range C: IC50>5000 nM.
NT=Not tested
Results Table

Results Table

| Example Number | Inhibitor Activity vs Aurora-A | Inhibitor Activity vs Aurora-B | Inhibitor Activity vs U937 cell line | Inhibitor Activity vs HCT 116 cell line | Inhibitor Activity vs HUT cell line |
|---|---|---|---|---|---|
| 1 | B | C | A | A | B |
| 2 | B | B | A | A | A |
| 3 | A | A | NT | NT | NT |
| 4 | A | A | NT | NT | NT |
| 5 | NT | NT | B | C | B |
| 6 | NT | NT | NT | NT | NT |
| 7 | NT | NT | B | C | B |
| 8 | NT | NT | NT | NT | NT |
| 9 | NT | NT | B | C | C |
| 10 | NT | NT | NT | NT | NT |
| 11 | NT | NT | B | B | B |
| 12 | NT | NT | B | C | C |
| 13 | NT | NT | NT | NT | NT |
| 14 | NT | NT | A | B | B |
| 15 | B | C | B | B | B |
| 16 | C | B | NT | NT | NT |
| 17 | NT | NT | NT | NT | NT |
| 18 | A | C | A | A | A |
| 19 | A | A | NT | NT | NT |
| 20 | C | C | A | A | A |
| 21 | B | B | NT | NT | NT |
| 22 | NT | NT | B | C | C |
| 23 | NT | C | NT | NT | NT |
| 24 | NT | NT | C | C | C |
| 25 | NT | NT | B | B | B |
| 26 | A | B | NT | NT | NT |
| 27 | C | NT | B | B | A |
| 28 | C | NT | A | C | B |
| 29 | NT | C | A | A | A |
| 30 | B | B | NT | NT | NT |
| 31 | NT | NT | C | C | C |
| 32 | C | C | B | C | B |
| 33 | NT | NT | B | C | B |
| 34 | NT | NT | B | C | B |
| 35 | NT | C | A | B | B |
| 36 | A | B | NT | NT | NT |
| 37 | NT | NT | A | B | B |
| 38 | NT | NT | A | B | B |
| 39 | NT | NT | B | C | C |
| 40 | NT | NT | A | B | B |
| 41 | NT | NT | B | B | B |
| 42 | NT | B | A | A | A |
| 43 | A | A | NT | NT | NT |
| 44 | NT | NT | A | C | B |
| 45 | NT | NT | A | B | A |
| 46 | NT | NT | A | A | A |
| 47 | NT | NT | A | A | A |
| 48 | NT | NT | A | A | A |
| 49 | NT | NT | A | A | A |
| 50 | B | B | A | A | A |
| 51 | NT | NT | A | A | A |
| 52 | NT | NT | A | A | A |
| 53 | NT | A | A | A | A |
| 54 | A | A | NT | NT | NT |
| 55 | B | B | A | A | A |
| 56 | NT | A | NT | NT | NT |
| 57 | NT | B | A | B | B |
| 58 | C | A | NT | NT | NT |
| 59 | NT | C | A | B | B |
| 60 | C | C | NT | NT | NT |
| 61 | NT | NT | A | A | A |
| 62 | B | A | NT | NT | NT |
| 63 | NT | NT | A | A | A |
| 64 | B | A | NT | NT | NT |
| 65 | NT | NT | A | A | A |
| 66 | NT | NT | A | A | A |
| 67 | A | A | NT | NT | NT |
| 68 | NT | NT | A | A | A |
| 69 | B | A | NT | NT | NT |
| 70 | NT | NT | A | A | A |
| 71 | NT | B | NT | NT | NT |
| 72 | NT | NT | A | A | A |
| 73 | NT | NT | B | C | B |

-continued

Results Table

| Example Number | Inhibitor Activity vs Aurora-A | Inhibitor Activity vs Aurora-B | Inhibitor Activity vs U937 cell line | Inhibitor Activity vs HCT 116 cell line | Inhibitor Activity vs HUT cell line |
|---|---|---|---|---|---|
| 74 | NT | B | NT | NT | NT |
| 75 | NT | NT | A | A | A |
| 76 | A | A | NT | NT | NT |
| 77 | NT | C | B | C | B |
| 78 | B | B | NT | NT | NT |
| 79 | NT | NT | A | A | A |
| 80 | NT | NT | A | A | A |
| 81 | B | B | NT | NT | NT |
| 82 | NT | NT | A | A | A |
| 83 | B | A | NT | NT | NT |
| 84 | NT | NT | A | A | A |
| 85 | B | A | NT | NT | NT |
| 86 | NT | NT | A | A | A |
| 87 | C | A | NT | NT | NT |
| 88 | NT | NT | A | A | A |
| 89 | C | A | NT | NT | NT |
| 90 | NT | NT | A | A | A |
| 91 | B | A | NT | NT | NT |
| 92 | NT | NT | C | C | C |
| 93 | A | B | A | A | A |
| 94 | A | A | NT | NT | NT |
| 95 | B | B | A | A | A |
| 96 | A | A | NT | NT | NT |
| 97 | NT | NT | A | A | A |
| 98 | NT | NT | NT | NT | NT |
| 99 | B | B | A | A | A |
| 100 | B | A | NT | NT | NT |
| 101 | B | A | A | A | A |
| 102 | A | A | NT | NT | NT |
| 103 | NT | NT | A | A | A |
| 104 | NT | NT | A | A | A |
| 105 | A | A | NT | NT | NT |
| 106 | NT | NT | A | A | A |
| 107 | NT | NT | C | C | C |
| 108 | NT | NT | A | A | A |
| 109 | B | B | A | A | A |
| 110 | A | A | NT | NT | NT |
| 111 | B | B | A | A | A |
| 112 | A | A | NT | NT | NT |
| 113 | NT | NT | A | A | A |
| 114 | A | A | NT | NT | NT |
| 115 | B | B | A | A | A |
| 116 | A | A | NT | NT | NT |
| 117 | NT | NT | A | A | A |
| 118 | A | A | NT | NT | NT |
| 119 | A | A | A | A | A |
| 120 | A | A | NT | NT | NT |
| 121 | NT | NT | A | A | A |
| 122 | A | A | NT | NT | NT |
| 123 | NT | NT | A | A | A |
| 124 | A | A | NT | NT | NT |
| 125 | B | B | A | A | A |
| 126 | A | A | NT | NT | NT |
| 127 | NT | NT | A | A | A |
| 128 | NT | B | A | A | A |
| 129 | A | A | NT | NT | NT |
| 130 | NT | NT | A | A | A |
| 131 | C | B | NT | NT | NT |
| 132 | NT | NT | A | B | B |
| 133 | B | B | NT | NT | NT |
| 134 | NT | NT | A | A | A |
| 135 | NT | NT | A | B | B |
| 136 | NT | NT | A | A | A |
| 137 | NT | NT | A | B | A |
| 138 | NT | NT | A | B | A |
| 139 | B | B | NT | NT | NT |
| 140 | NT | NT | A | B | A |
| 141 | NT | NT | A | A | A |
| 142 | B | A | NT | NT | NT |
| 143 | NT | NT | B | C | B |

Broken Cell Carboxy esterase Assay

Preparation of Cell Extract

U937 or Hct116 tumour cells (~109 were washed in 4 volumes of Dulbeccos PBS (~1 liter) and pelleted at 160 g for 10 mins at 4° C. This was repeated twice and the final cell pellet was then resuspended in 35 ml of cold homogenising buffer (Trizma 10 mM, NaCl 130 mM, $CaCl_2$ 0.5 mM PH 7.0) at 25° C. Homogenates were prepared by nitrogen cavitation (700 psi for 50 min at 4° C.). The homogenate was kept on ice and supplemented with a cocktail of inhibitors designed to give final concentrations of Leupeptin 1 μM Aprotinin 0.1 μM

E64 8 μM

Pepstatin 1.5 μM

Bestatin 162 μM

Chymostatin 33 μM

After clarification of the cell homogenate by centrifugation at 360 rpm for 10 min, the resulting supernatant was used as a source of esterase activity and could be stored at −80° C. until required.

Measurement of ester Cleavage

Hydrolysis of ester to the corresponding carboxylic acid can be measured using this cell extract. To this effect cell extract (~30 ug/total assay volume of 0.5 ml) was incubated at 37° C. in a Tris-HCl 25 mM, 125 mM NaCl, buffer, PH 7.5 at 25° C. At zero time the relevant ester (substrate), at a final concentration of 2.5 μM was then added and samples incubated at 37° C. for the appropriate time (Usually zero or 80 minutes). Reactions were stopped by the addition of 3× volumes of Acetonitrile. For zero time samples the acetonitrile was added prior to the ester compound. After centrifugation at 12000 g for 5 minutes, samples were analysed for the parent ester and its corresponding carboxylic acid at room temperature by LCMS (Sciex API 3000, HP1100 binary pump, CTC PAL). Chromatographic conditions used were based on an AcCN (75×2.1 mm) column and a mobile phase of 5-95% acetonitrile in water/0.1% formic acid.

The invention claimed is:

1. A compound of formula (IA) or (IB), or a salt, or N-oxide thereof:

(IA)

R—$L^1$—$Y^1$—O, quinoline ring with $R_6$O substituent, linked through O to phenyl ring A, then N($R^B$)—$L^2$—[B]$_r$—H (IB)

$R_6$O, quinoline ring, R—$L^1$—$Y^1$—O substituent, linked through O to phenyl ring A, then N($R^B$)—$L^2$—[B]$_r$—H wherein $Y^1$ is a bond, or —C(=O);

$L^1$ is a divalent radical of formula -(Alk$^1$)$_m$(Q$^1$)$_n$(Alk$^2$)$_p$- wherein m, n and p are independently 0 or 1, $Q^1$ is (i) an optionally substituted divalent mono- or bicyclic carbocyclic or heterocyclic radical having 5-13 ring members, or (ii), in the case where p is 0, a divalent radical of formula -$Q^2$-$X^2$— wherein $X^2$ is —O—, —S— or NR$^A$— wherein R$^A$ is hydrogen or optionally substituted $C_1$-$C_3$ alkyl, and $Q^2$ is an optionally substituted divalent mono- or bicyclic carbocyclic or heterocyclic radical having 5-13 ring members, Alk$^1$ and Alk$^2$ independently represent optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radicals which may optionally contain or terminate in an ether (—O—), thioether (—S—) or amino (—NR$^A$—) link wherein R$^A$ is hydrogen or optionally substituted $C_1$-$C_3$ alkyl;

$R_6$ is $C_1$-$C_4$ alkyl;

$R^B$ hydrogen or $C_1$-$C_3$ alkyl;

each $L^2$ independently represents a radical of formula *—Z-(AlK$^4$)$_b$- wherein the bond marked * is directly connected to the nitrogen atom and wherein b is 0 or 1;

Alk$^4$ independently represents optionally substituted divalent $C_3$-$C_7$ cycloalkyl radicals, or optionally substituted straight or branched, $C_1$-$C_6$ alkylene, $C_2$-$C_6$ alkenylene, or $C_2$-$C_6$ alkynylene radical which may optionally contain or terminate in an ether (—O—), thioether (—S—) or amino (—NR$^A$—) link wherein R$^A$ is hydrogen or optionally substituted $C_1$-$C_3$ alkyl;

Z represents a —CO—, —SO$_2$—, *—CONR$^B$—, or *—CSNR$^B$— radical, wherein the bond marked * is directly connected to the nitrogen atom;

r is 0 or 1; and ring A is an optionally substituted 1,4-phenylene ring; and ring B is a mono- or bi-cyclic carbocyclic or heterocyclic ring or ring system having up to 12 ring atoms;

R is a radical of formula (X) or (Y):

(X)

$R_4$—N($R_4^1$)—CH($R_1$)—

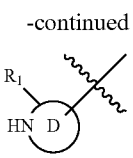
(Y)

wherein
R₁ is an ester group of formula —(C=O)OR₉ which is hydrolysable by one or more intracellular carboxylesterase enzymes to a carboxylic acid group wherein R₉ is
(i) R₇R₈CH— wherein R₇ is optionally substituted (C₁-C₃)alkyl-(Z¹)ₐ—(C₁-C₃)alkyl- or C₂-C₃)alkenyl-(Z¹)ₐ—(C₁-C₃)alkyl- wherein a is 0 or 1 and Z¹ is —O—, —S—, or —NH—, and R₈ is hydrogen or (C₁-C₃)alkyl- or R₇ and R₈ taken together with the carbon to which they are attached form an optionally substituted C₃-C₇ cycloalkyl ring or an optionally substituted heterocyclic ring of 5- or 6-ring atoms; or
(ii) optionally substituted phenyl or monocyclic heterocyclic having 5 or 6 ring atoms;

R₄ is hydrogen; or optionally substituted C₁-C₆ alkyl, C₃-C₇ cycloalkyl, aryl, aryl(C₁-C₆ alkyl)-, heteroaryl, heteroaryl(C₁-C₆ alkyl)-, —(C=O)R₃, —(C=O)OR₃, or —(C=O)NR₃ wherein R₃ is hydrogen or optionally substituted (C₁-C₆)alkyl, C₃-C₇ cycloalkyl, aryl, aryl (C₁-C₆ alkyl)-, heteroaryl, or heteroaryl(C₁-C₆ alkyl)-;

R₄¹ is hydrogen or optionally substituted C₁-C₆ alkyl; and

D is a monocyclic heterocyclic ring of 5 or 6 ring atoms wherein R₁ is linked to a ring carbon adjacent the ring nitrogen shown, and ring D is optionally fused to a second carbocyclic or heterocyclic ring of 5 or 6 ring atoms in which case the bond shown intersected by a wavy line may be from a ring atom in said second ring.

2. A compound as claimed in claim 1 wherein R₆ is methyl.
3. A compound as claimed in claim 1 wherein ring A is 1,4 phenylene or 1,4 phenylene substituted in the 2 or 3 position by fluoro or methoxy.
4. A compound as claimed in claim 1 wherein ring B, when present, is selected from cyclopropyl or optionally substituted 1,4-phenylene, 1,3-phenylene, 2- or 3-thienyl, 1,2,4-oxadiazol-3-yl, indanyl, indenyl, pyridyl, pyrimidinyl or pyrazinyl.
5. A compound as claimed in claim 1 wherein, in L² Alk⁴ when present is methylene (—CH₂—).
6. A compound as claimed in claim 1 wherein, in L², Z is *—C(=O)NH— or —C(=O)—.
7. A compound as claimed in claim 6 wherein, in L² b is 0.
8. A compound as claimed in claim 1 which has the formula (IC):

(IC)

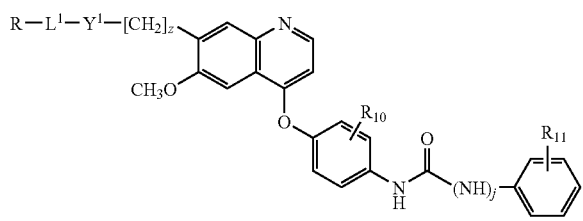

wherein j is 0 or 1; R₁₀ and R₁₁ independently represent hydrogen or one or more substituents in their respective rings selected from fluoro, chloro, methyl, methoxy trifluoromethyl and trifluoromethoxy; and R, L¹, and Y¹ are as defined in claim 1.

9. A compound as claimed in claim 8 wherein R₁₀ represents hydrogen or a single fluoro substituent, and R₁₁, represents hydrogen or one or two substituents selected from fluoro, chloro, methyl, methoxy trifluoromethyl and trifluoromethoxy.

10. A compound as claimed in claim 1 wherein Y¹ is a bond; in the radical L¹, Alk¹ and Alk², when present, are selected from —CH₂—, —CH₂CH₂—, —CH₂CH₂CH₂—, and divalent cyclopropyl, cyclopentyl and cyclohexyl radicals; and Q when present is a divalent phenyl radical or a mono-, or bi-cyclic heteroaryl radical having 5 to 13 ring members.

11. A compound as claimed in claim 1 wherein the radical -L¹-Y¹—O— is selected from, —CH₂C(O)O—, —CH₂CH₂C(O)O—, —CH₂O, —CH₂CH₂O—, —CH₂CH₂CH₂O—,

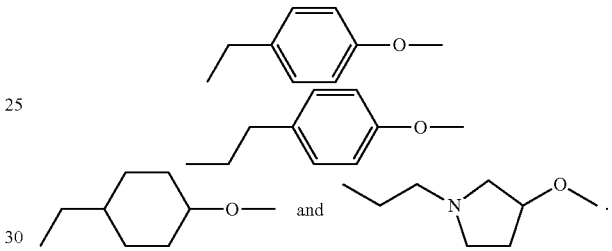

12. A compound as claimed in claim 1 which has the formula (ID):

(ID)

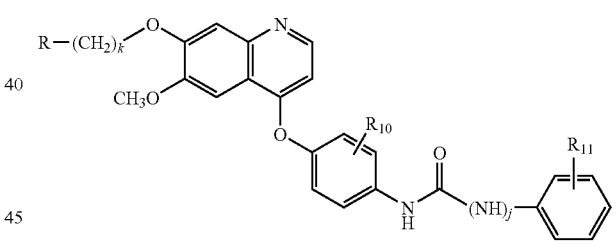

wherein j is 0 or 1; R₁₀ and R₁₁ independently represent hydrogen or one or more substituents in their respective rings selected from fluoro, chloro, methyl, methoxy trifluoromethyl and trifluoromethoxy; k is 1, 2 or 3; and R is as defined in claim 1.

13. A compound as claimed in claim 12 wherein R₁₀ represents hydrogen or a single fluoro substituent, and R₁₁ represents hydrogen or one or two substituents selected from fluoro, chloro, methyl, methoxy trifluoromethyl and trifluoromethoxy.

14. A compound as claimed in claim 1 wherein R₉ is methyl, ethyl, n- or iso-propyl, n- or sec-butyl, t-butyl, cyclopentyl, cyclohexyl, allyl, phenyl, benzyl, 2-, 3- or 4-pyridylmethyl, N-methylpiperidin-4-yl, tetrahydrofuran-3-yl or methoxyethyl.

15. A compound as claimed in claim 1 wherein R is a group of formula (X); R₄ is hydrogen, —(C=O)R₃, —(C=O)OR₃, or —(C=O)NHR₃ wherein R₃ is hydrogen or optionally substituted (C₁-C₆)alkyl; and R₄¹ is hydrogen or methyl, ethyl, n-or isopropyl.

16. A compound as claimed claim 15 wherein $R_4$ and $R_4^1$ are each hydrogen.

17. A compound as claimed in claim 1 wherein R is a group of formula (Y) wherein ring or ring system D is selected from the following:

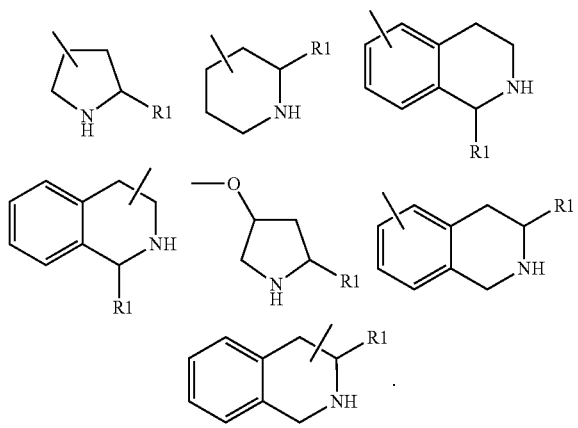

18. A compound which has the formula (IE):

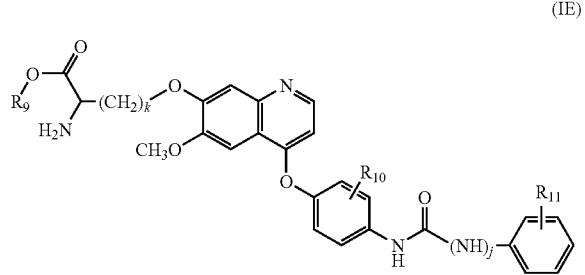

(IE)

wherein j is 0 or 1; $R_{10}$ and $R_{11}$ independently represent hydrogen or one or more substituents in their respective rings selected from fluoro, chloro, methyl, methoxy trifluoromethyl and trifluoromethoxy; k is 1, 2 or 3; and $R_9$ is methyl, ethyl, n- or iso-propyl, n- or sec-butyl, t-butyl, cyclopentyl, cyclohexyl, allyl, phenyl, benzyl, 2-, 3- or 4-pyridylmethyl, N-methylpiperidin-4-yl, tetrahydrofuran-3-yl or methoxyethyl.

19. A compound as claimed in claim 18 wherein $R_{10}$ represents hydrogen or a single fluoro substituent, and $R_{11}$ represents hydrogen or one or two substituents selected from fluoro, chloro, methyl, methoxy trifluoromethyl and trifluoromethoxy.

20. A compound selected from the group consisting of:
(S)-2-Amino-4-[4-(4-benzoylamino-phenoxy)-6-methoxy-quinolin-7-yloxy]-butyric acid cyclopentyl ester
(R)-2-Amino-5-(6-methoxy-4-{4-[3-(4-trifluoromethyl-phenyl)-ureido]-phenoxy}quinolin-7-yloxy)-pentanoic acid cyclopentyl ester
(R)-2-Amino-5-[4-(4-benzoylamino-phenoxy)-6-methoxy-quinolin-7-yloxy]-pentanoic acid cyclopentyl ester
(S)-2-Amino-4-{6-methoxy-4-[4-(3-phenyl-ureido)-phenoxy]-quinolin-7-yloxy}butyric acid cyclopentyl ester
(R)-2-Amino-4-[4-(4-benzoylamino-phenoxy)-6-methoxy-quinolin-7-yloxy]-butyric acid cyclopentyl ester
(S)-2-Amino-4-{4-2-fluoro-4-[3-(4-trifluoromethyl-phenyl)-ureido]-phenoxy}-6-methoxy-quinolin-7-yloxy)-butyric acid cyclopentyl ester
(R)-2-Amino-4-(6-methoxy-4-{4-[3-(4-trifluoromethyl-phenyl)-ureido]-phenoxy}-quinolin-7-yloxy)-butyric acid cyclopentyl ester
(S)-2-Amino-5-[4-(4-benzoylamino-phenoxy)-6-methoxy-quinolin-7-yloxy]-pentanoic acid cyclopentyl ester
(S)-2-Amino-4-{4-[4-(4-chloro-benzoylamino)-phenoxy]-6-methoxy-quinolin-7-yloxy}-butyric acid cyclopentyl ester
and salts, N-oxides thereof.

21. A pharmaceutical composition comprising a compound as claimed in claim 1, together with a pharmaceutically acceptable carrier.

* * * * *